(12) United States Patent
Stock et al.

(10) Patent No.: US 10,314,802 B2
(45) Date of Patent: *Jun. 11, 2019

(54) ISOPRENYL COMPOUNDS AND METHODS THEREOF

(71) Applicant: Signum Biosciences, Inc., Monmouth Junction, NJ (US)

(72) Inventors: Jeffry B. Stock, Princeton, NJ (US); Maxwell Stock, Boulder, CO (US); Keshava Rapole, Edison, NJ (US); Seung-Yub Lee, Princeton, NJ (US); Michael Voronkov, Pennington, NJ (US); Eduardo Perez, Somerset, NJ (US); Joel Gordon, Princeton Junction, NJ (US); Shuyi Chen, Somerset, NJ (US); Jinglong Chen, Newark, NJ (US)

(73) Assignee: Signum Biosciences, Inc., Monmouth Junction, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/665,922

(22) Filed: Aug. 1, 2017

(65) Prior Publication Data

US 2017/0368011 A1     Dec. 28, 2017

Related U.S. Application Data

(63) Continuation of application No. 15/151,221, filed on May 10, 2016, now Pat. No. 9,744,147, which is a continuation of application No. 13/760,627, filed on Feb. 6, 2013, now Pat. No. 9,376,383, which is a continuation of application No. 12/616,781, filed on Nov. 12, 2009, now Pat. No. 8,372,884.

(60) Provisional application No. 61/113,498, filed on Nov. 11, 2008.

(51) Int. Cl.

| A61K 31/197 | (2006.01) |
|---|---|
| A61K 9/00 | (2006.01) |
| C07C 323/59 | (2006.01) |
| C07C 335/08 | (2006.01) |
| C07C 243/34 | (2006.01) |
| C07C 321/18 | (2006.01) |
| C07D 209/18 | (2006.01) |
| C07D 209/48 | (2006.01) |
| C07D 217/26 | (2006.01) |
| C07D 295/145 | (2006.01) |
| C07D 307/54 | (2006.01) |
| C07D 333/24 | (2006.01) |
| C07D 207/16 | (2006.01) |
| C07D 243/34 | (2006.01) |

(52) U.S. Cl.
CPC .......... *A61K 31/197* (2013.01); *A61K 9/0014* (2013.01); *C07C 243/34* (2013.01); *C07C 321/18* (2013.01); *C07C 323/59* (2013.01); *C07C 335/08* (2013.01); *C07D 207/16* (2013.01); *C07D 209/18* (2013.01); *C07D 209/48* (2013.01); *C07D 217/26* (2013.01); *C07D 243/34* (2013.01); *C07D 295/145* (2013.01); *C07D 307/54* (2013.01); *C07D 333/24* (2013.01); C07C 2601/02 (2017.05); C07C 2601/14 (2017.05)

(58) Field of Classification Search
CPC .. A61K 31/197; A61K 9/0014; C07D 207/16; C07C 323/59
See application file for complete search history.

(56) References Cited

U.S. PATENT DOCUMENTS

| 4,603,011 A | 7/1986 | Roy et al. |
|---|---|---|
| 4,622,417 A | 11/1986 | Barnett et al. |
| 5,043,268 A | 8/1991 | Stock |
| 5,202,456 A | 4/1993 | Rando |
| 5,491,164 A | 2/1996 | deSolms et al. |

(Continued)

FOREIGN PATENT DOCUMENTS

| WO | 00/00469 | 1/2000 |
|---|---|---|
| WO | 2004/087064 | 10/2004 |

(Continued)

OTHER PUBLICATIONS

Gordon et al, Journal of Investigative Dermatology, Topical N-acetyl-S-farnesyl-L-cysteine Inhibits Mouse Skin Inflammation, and Unlike Dexamethasone, its Effects Are Restricted to the Application Site, 2008, 128(3), pp. 643-654. (Year: 2008).*

(Continued)

*Primary Examiner* — Paul A Zucker

(74) *Attorney, Agent, or Firm* — McCarter & English, LLP; Peter Tu, Esq.; Maneesh Gulati, Esq.

(57) ABSTRACT

Among other things, the present invention provides novel isoprenyl compounds capable of effectively modulating inflammatory responses and pharmaceutical, cosmetic, cosmeceutical and topical compositions comprising these isoprenyl compounds. Anti-inflammatory compounds of the present invention are useful in treating or preventing diseases or conditions associated with inflammation. Proinflammatory compounds of the present invention are useful in treating or preventing diseases or conditions associated with suppression of inflammatory responses. Thus, the present invention also provides methods useful in the treatment or prevention of diseases or conditions associated with inflammation as well as methods useful in the treatment or prevention of diseases or conditions associated with suppression of inflammatory responses.

60 Claims, 14 Drawing Sheets

(56) References Cited

U.S. PATENT DOCUMENTS

| | | | |
|---|---|---|---|
| 5,571,687 | A | 11/1996 | Casey et al. |
| 5,965,539 | A | 10/1999 | Sebti et al. |
| 6,015,877 | A | 1/2000 | Rando |
| 6,251,882 | B1 | 6/2001 | Uckun et al. |
| 7,745,589 | B1 * | 6/2010 | Spielmann ............. C07K 16/44 424/175.1 |
| 8,372,884 | B2 | 2/2013 | Stock et al. |
| 8,461,204 | B2 * | 6/2013 | Stock .................... A61K 31/197 514/562 |
| 9,376,383 | B2 | 6/2016 | Stock et al. |
| 9,744,147 | B2 * | 8/2017 | Stock .................... C07C 323/59 |
| 2003/0158117 | A1 | 8/2003 | Vertesy et al. |
| 2007/0004803 | A1 | 1/2007 | Gibbs et al. |
| 2009/0192332 | A1 | 7/2009 | Rapole et al. |

FOREIGN PATENT DOCUMENTS

| | | |
|---|---|---|
| WO | 2006/135894 | 12/2006 |
| WO | 2009/073665 | 6/2009 |
| WO | 2009/102997 | 8/2009 |
| WO | 2010/056778 | 5/2010 |
| WO | 2010/090845 | 8/2010 |

OTHER PUBLICATIONS

Ding J et al: "Farnesyl-L-Cysteine Analogs Can Inhibit or Initiate Superoxide Release by Human Neutrophils", Journal of Biological Chemistry, The American Society for Biochemistry and Molecular Biology, Inc, US, vol. 269, No. 24, Jun. 17, 1994 (Jun. 17, 1994), pp. 16837-16844, XP001151963, ISSN: 0021-9258.

Supplementary European Search Report dated Jun. 8, 2012 issued for European Application/Patent No. 09826691.9-2117/2362866 PCT/US2009/064077.

Tan et al, The Journal of Biological Chemistry, Identifying the Recognition Unit of G Protein Methylation, 266(17), pp. 10719-10722, Jun. 18, 1991.

International Search Report for International Application No. PCT/US09/64077, dated Jan. 15, 2010.

Written Opinion of the International Searching Authority for International Patent Application No. PCT/US09/64077, dated Jan. 15, 2010.

Zhang et al., The Journal of Biological Chemistry, Characterization of Prenylcysteines That Interact with P-glycoprotein and Inhibit Drug Transport in Tumor Cells, 1995, 270(39), pp. 22859-22865.

Dugan et al. Biology of Reproduction, Changes in Protein Prenylation and Prenyltransferase Activity in the Rat Seminiferous Epithelium During Early Stages of Spermatogenesis, 1995, 53, pp. 958-973.

Winter-Vann et al., Nature, Post-prenylation-processing Enzymes as New Targets in Oncogenesis, May 2005, vol. 5, pp. 405-412.

International Preliminary Report on Patentability for International Application No. PCT/US2009/064077 dated May 17, 2011.

International Search Report for International Application No. PCT/US2010/021544 dated Jun. 16, 2010.

Written Opinion of the International Search Authority for International Application No. PCT/US2010/021544 dated Jun. 16, 2010.

International Preliminary Report on Patentability for International Application No. PCT/US2010/021544 dated Jul. 26, 2011.

Perez-Sala; "Protein Isoprenylation in biology and disease: general overview and perspectives from studies with genetically engineered animals," Frontiers in Bioscience 12; May 1, 2007; pp. 4456-4472.

Perrey et al.; "Cystein Chloromethyl and Diazomethyl Ketone Derivatives with Potent Anti-Leukemic Activity"; Bioorganic & Medical Chemistry Letters 10; (2000); pp. 547-549.

Pillinger et al.; "Characterization of a Plasma Membrane-associated Prenylcysteine-directed alpha Carboxyl Methyltransferase in Human Neutrophils"; The Journal of Biological Chemistry; vol. 269, No. 2; 1994; pp. 1486-1492.

Desrosiers et al.; "Modulation of Rho and Cystoskeletal Protein Attachment to Membranes by a Prenylcysteine Analog"; The Journal of Biological Chemistry; vol. 275, No. 20, 2000; pp. 14949-14957.

Denis, D. et al.; "Synthesis and Biological Activities of Leukotriene F4 and Leukotriene F4 Sulfone," Prostaglandins, 1982, vol. 24, No. 6, pp. 801-813.

Tan, E.W. et al.; "Heteroatom Requirements for Substrate Recognition by GTP-Binding Protein Methyltransferase," The Journal of the American Chemical Society, 1991, vol. 113, No. 16, pp. 6299-6300.

Donelson, J. L. et al.; "Amide-substituted farnesylcysteine analogs as inhibitors of human isoprenylcysteine carboxyl methyltransferase," Bioorganic and Medicinal Chemistry Letters, 2006, vol. 16, No. 16, pp. 4420-4423.

Troutman, J.M. et al.; "Tools to Analyze Protein Farnesylation in Cells," Bioconjugate Chemistry, 2005, vol. 16, No. 5, pp. 1209-1217.

Kamiya, Y., et al., "Metabolites of Mating Pheromone, Rhodotorucine A, by a Cells of Rhodosporidium toruloides", Biochemical and Biophysical Research Communications, 1980, vol. 94, No. 3, pp. 855-860.

Liu, X.-H, et al., "Antigenic Prenylated Peptide Conjugates and Polyclonal Antibodies to Detect Protein Prenylation", Bioconjugate Chemistry, 2004, vol. 15, No. 2, pp. 270-277.

Epstein, W. W., et al, "Identification of Prenylcysteines and Prenylated Proteins by Formation of .Substituted Naphthopyrans", Journal of Organic Chemistry, 1996, vol. 61, No. 15. pp. 4890-4893.

Sakagami, Y., et al., "Peptidal Sex Hormones Inducing Conjugation Tube Formation in Compatible Mating-type Cells of Tremella mesenterica", Science, 1981, vol. 212, No. 4502, pp. 1525-1527.

Pachamuthu, K., et al., "Reversed Approach to S-Farnesylation and S-Palmitoylation: Application to an Efficient Synthesis of the C-Terminus of Lipidated Human N-Ras Hexapeptide", Journal of Organic Chemistry, 2005, vol. 70, No. 9, pp. 3720-3723.

Stober, P., et al., "Synthesis of Characteristic Lipopeptides of the Human N-Ras Protein and Their Evaluation as Possible Inhibitors of Protein Farnesyl Transferase", Bioorganic and Medicinal Chemistry, 1997, vol. 5, No. 1, pp. 75-83.

Xie, H., et al., "Synthesis and Biological Evaluation of the Geometric Farnesylated Analogs of the a-Factor Mating Peptide of *Saccharomyces cerevisiae*", Journal of Organic Chemistry, 2000, vol. 65, No. 25, pp. 8552-8563.

Xue, C.-B., et al., "Synthesis of S-alkyl and C-terminal analogs of the *Saccharomyces cerevisiae* a-factor. Influence of temperature on the stability of Fmoc and OFm groups toward HF", International Journal of Peptide and Protein Research, 1991, vol. 37, No. 6, pp. 476-486.

Brunsveld, L., et al., "Synthesis of Functionalized Rab GTPases by a Combination of Solution- or Solid-Phase Lipopeptide Synthesis with Expressed Protein Ligation", Chemistry—A European Journal, 2005, vol. 11, No. 9, pp. 2756-2772.

Zhang, H., et al., "Photoreceptor cGMP Phosphodiesterase 5 Subunit (PDE 6) Functions as a Prenyl-binding Protein", Journal of Biological Chemistry, 2004, vol. 279, No. 1, pp. 407-413.

Oboh, 0. T., et al, "Liver Prenylated Methylated Protein Methyl Esterase Is the Same Enzyme as Sus scrofa Carboxylesterase", Journal of Biochemical and Molecular Toxicology, 2008, vol. 22, No. 1, pp. 51-62.

Lamango, N. S., et al., "Liver Prenylated Methylated Protein Methyl Esterase Is an Organophosphate-Sensitive Enzyme", Journal of Biochemical and Molecular Toxicology, 2005, vol. 19, No. 5, pp. 347-357.

Kuhn, K., et al., "Synthesis of Functional Ras Lipoproteins and Fluorescent Derivaties", Journal of the American Chemical Society, 2001, vol. 123, No. 6, pp. 1023-1035.

Wang, D.-Y., et al., "A possible antimalarial action mode of qinghaosu (artemisinin) series compounds. Alkylation of reduced glutathione by C-centered primary radicals produced from antimalarial compound qinghaosu and 12-(2,4-dimethoxyphenyl)-12-deoxoqinghaosu", Chemical Communications, 2000, No. 22, pp. 2193-2194.

Thomas Baumert, et al., "Ethanol-Induced Inhibition of Leukotriene Degradatino by x-oxidation", European Journal of Biochemistry, 1989, vol. 182, pp. 223-229.

(56) References Cited

OTHER PUBLICATIONS

Berge et al., Pharmaceutical salts. J Pharm Sci. Jan. 1977;66(1):1-19.

* cited by examiner

Figure 1
| Compound Number | Structure | % Inhibition ||| Dose |
| --- | --- | --- | --- | --- | --- |
| | | Edema | MPO | Erythema | |
| A | 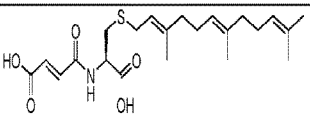 | 58.18 ± 13.02 | 78.39 ± 9.71 | 41.1 ± 13.84 | 0.2 mg/20 µL |
| | | 77.52 ± 10.21 | 93.24 ± 1.3 | - | 0.8 mg/20 µL |
| B | 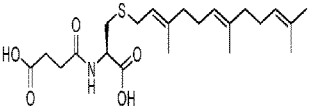 | 42.56 ± 5.86 | 53.91 ± 2.02 | - | 0.2 mg/20 µL |
| | | 61.13 ± 16.31 | 82.78 ± 7.91 | - | 0.8 mg/20 µL |
| C | 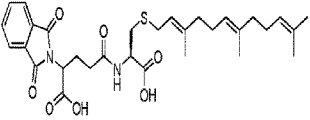 | 37.29 ± 12.51 | 62.65 ± 11.93 | - | 0.2 mg/20 µL |
| | | 76.84 ± 8.7 | 89.12 ± 7.13 | - | 0.8 mg/20 µL |
| D | 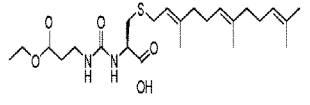 | 35.87 ± 6.25 | 54.28 ± 9.16 | 30.03 ± 7.16 | 0.2 mg/20 µL |
| | | - | - | - | - |
| E | 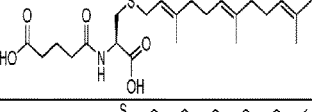 | 29.47 ± 9.8 | 61.6 ± 5.76 | 31.8 ± 3.53 | 0.2 mg/20 µL |
| | | - | - | - | - |
| F | 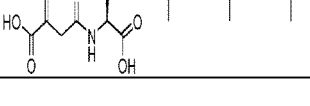 | 29.37 ± 7.41 | 53.27 ± 18.26 | 25.17 ± 9.97 | 0.2 mg/20 µL |
| | | - | - | - | - |

Figure 1 (cont.)
| | Structure | | | | |
|---|---|---|---|---|---|
| G | 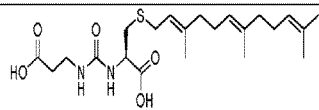 | 16.55± 7.95 | 33.70 ± 3.80 | 15.85 ± 1.65 | 0.2 mg/20 µL |
| | | - | - | - | - |
| H | 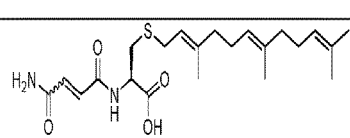 | 59.54±12.41 | (-)10.49±36.67 | 43.32±12.82 | 0.2 mg/20 µL |
| | | - | - | - | - |
| I | 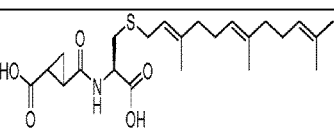 | 68.28 ± 6.15 | 60.44 ± 14.12 | 38.88 ± 10.14 | 0.2 mg/20 µL |
| | | - | - | - | - |
| J | 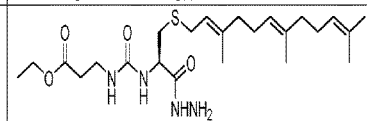 | 43.82 ± 2.79 | 51.75 ± 6.31 | 36.5 ± 6.86 | 0.2 mg/20 µL |
| | | - | - | - | - |
| K | 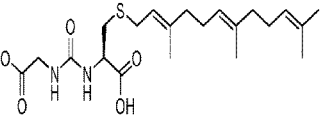 | 12.86 ± 13.79 | - | 5.93 ± 1.2 | 0.2 mg/20 µL |
| | | - | - | - | - |
| L | 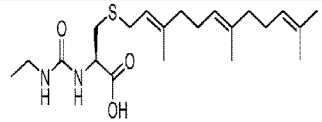 | 11.10 ± 8.75 | 11.37 ± 13.29 | (-)1.80 ± 2.06 | 0.2 mg/20 µL |
| | | - | - | - | - |
| M | 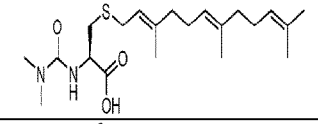 | 27.91 ± 12.46 | 24.68 ± 25.44 | 42.39 ± 23.0 | 0.2 mg/20 µL |
| | | - | - | - | - |
| AFC | 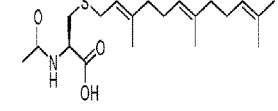 | (-)2.574 ± 19.68 | 2.025 ± 25.49 | (-)6.87 ± 7.37 | 0.2 mg/20 µL |
| | | 37.58 ± 5.57 | 66.42 ± 5.65 | 31.95 ± 15.14 | 0.8 mg/20 mL |

Figure 2
| Compound | Structure | M.W. | ED$_{50}$ value (μg/ear)[a] | | |
|---|---|---|---|---|---|
| | | | Edema | Erythema | MPO |
| A | 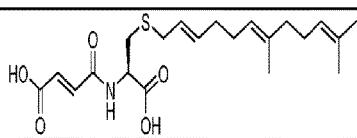 | 423.57 | 180 ± 11 | 109 ± 21 | 264 ± 12 |
| B | 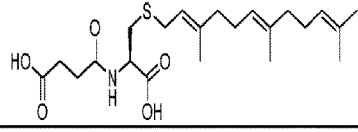 | 425.22 | 452 ± 11 | 106 ± 21 | 377 ± 12 |
| AFC | 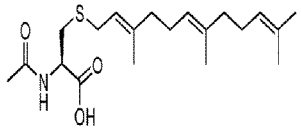 | 367.55 | 553 ± 20 | 651 ± 54 | 1342 ± 349 |
[a] 5 concentrations were tested on the same day (1 concentration/6 mice) for each compound. Compound A and compound B were tested in duplicate and AFC was tested in quadruplicate.

Figure 3

| Compound Number | Activity Range |
|---|---|
| A; B; C; E; I; N-22; N-23; N-24; N-26; N-21; N-33; N-34; N-37; N-38; N-40; N-55; N-59; N-61; N-62; N-70; N-73; N-80; N-81; N-82; N-83; N-87; N-91; N-95; N-97; N-96; N-39; N-3. | 1 |
| D; F; G; H; J; K; L; M; N-1; N-2; N-3; N-4; N-5; N-6; N-7; N-9; N-10; N-11; N-12; N-13; N-14;s N-15; N-16; N-17; N-19; N-20; N-29; N-36; N-41; N-42; N-43; N-44; N-45; N-46; N-47; N-48; N-49; N-50; N-51; N-52; N-53; N-54; N-56; N-57; N-58; N-60; N-63; N-64; N-65; N-66; N-67; N-68; N-69; N-71; N-72; N-74; N-75; N-76; N-78; N-84; N-85; N-88; N-89; N-90; N-92; N-93; N-94; and N-98. | 2 |
| N-8; N-18; N-27; N-28; N-25; N-30; N-32; N-77; N-79; N-86. | 3 |

Activity Range 1 is > 60% (Active Anti-inflammatory)
Activity Range 2 is 0 – 60% (Moderately active anti-inflammtory)
Activity Range 3 is < 0% (Proinflammatory)
*Activity is Percent Inhibition in MPO activity assay

ISOPRENYL COMPOUNDS AND METHODS THEREOF

RELATED APPLICATIONS

This application is a continuation of U.S. patent application Ser. No. 15/151,221 filed on May 10, 2016, now U.S. Pat. No. 9,744,147, which is a continuation of U.S. patent application Ser. No. 13/760,627 filed on Feb. 6, 2013, now U.S. Pat. No. 9,376,383, which is a continuation of U.S. patent application Ser. No. 12/616,781 filed on Nov. 12, 2009, now U.S. Pat. No. 8,372,884, which claims priority from U.S. Provisional Patent Application No. 61/113,498 filed on Nov. 11, 2008, the entire disclosures of each of the aforementioned applications are incorporated herein by reference.

GOVERNMENT LICENSE RIGHTS

This invention was made with government support under SBIR grants 1R43AI062034-01A2 and R44AI062034 awarded by National Institutes of Health. The government has certain rights in the invention.

BACKGROUND

Inflammation often is a bodily response to infection or injury in which cells involved in detoxification and repair are mobilized to the compromised site by inflammatory mediators. Such infection or injury can be a result of acute or chronic disease, disorders, conditions or trauma, or of environmental conditions or aging. Examples include diseases, disorders, syndromes, conditions and injuries of the cardiovascular, digestive, integumentary, muscular, nervous, reproductive, respiratory and urinary systems, as well as, diseases, disorders, syndromes, conditions and injuries of tissue and cartilage such as atherosclerosis, irritable bowel syndrome, psoriasis, tendonitis, Alzheimer's disease and vascular dementia, multiple sclerosis, diabetes, endometriosis, asthma and kidney failure. Treatment of inflammatory diseases or disorders with traditional anti-inflammatory drugs, e.g., corticosteroids and non-steroidal anti-inflammatory drugs ("NSAIDS") can cause multiple side effects, e.g., appetite and weight gain, excess sweating, high blood pressure, nausea, vomiting, diarrhea, etc.

SUMMARY

The present invention provides, among other things, certain compounds that are structurally related to N-acetyl-S-farnesyl-L-cysteine ("AFC").

In some embodiments, the present invention provides a compound of Formula I:

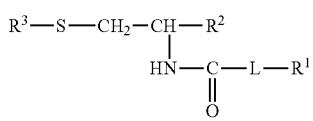

or a pharmaceutically acceptable salt thereof, wherein:
L is a bivalent, branched or unbranched, saturated or unsaturated, $C_2$-$C_6$ hydrocarbon chain wherein one or more methylene units of L is independently replaced by —O—, —S—, —NH—, —C(O)—, —C(=CH$_2$)—, or $C_3$-$C_6$ cycloalkylene, wherein L is optionally substituted by one or more groups selected from halogen, phenyl, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5-to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur;
$R^1$ is hydrogen, —OH or —OR, wherein each R is independently hydrogen or an optionally substituted group selected from $C_{1-6}$ aliphatic or $C_{1-6}$ heteroaliphatic;
$R^2$ is —C(O)X, wherein X is independently R, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted group selected from $C_{1-6}$ aliphatic or $C_{1-6}$ heteroaliphatic; and
$R^3$ is a substituted or unsubstituted, branched or unbranched, saturated or unsaturated, $C_{10}$-$C_{25}$ aliphatic.

In some embodiments, the present invention provides a compound of Formula I':

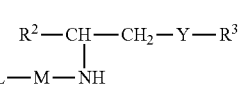

or a pharmaceutically acceptable salt thereof, wherein:
L is a bivalent, branched or unbranched, saturated or unsaturated, $C_2$-$C_6$ hydrocarbon chain wherein one or more methylene units of L is independently replaced by —O—, —S—, —NH—, —C(O)—, —CF$_2$—, —C(=CH$_2$)—, —CH=CH—, or an optionally substituted arylene, heteroarylene, $C_3$-$C_6$ cycloalkylene, $C_3$-$C_6$ heterocycloalkylene, or an 8-10-membered bicyclic heterocyclic moiety,
and wherein L is optionally substituted by one or more groups selected from halogen, $C_1$-$C_6$ alkyl, phenyl, biphenyl, -benzyl, —CH$_2$-phenol, —CH(phenyl)$_2$, —OH, —NH$_2$, —NHC(O)CH$_3$, —NHC(O)NHCH$_2$CH$_3$, —C(O)NH$_2$, —C(O)NHCH$_2$CH$_3$, —CH$_2$C(O)OCH$_2$phenyl, —(CH$_2$)$_2$SCH$_3$, —(CH$_2$)$_2$C(O)NH$_2$, —(CH$_2$)$_2$C(O)OH, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5-to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur;
M is —C(O)—, —C(S), or —SO$_2$—;
$R^1$ is hydrogen, F, CF$_3$, $C_1$-$C_4$ alkyl, —OH, —C(O)CH$_3$, —NH(OR), —NR$_2$, —NHNR$_2$, —SO$_2$R, —NH-phenyl, —SO$_2$-phenyl, -phenyl-NO$_2$, or —OR, wherein each R is independently hydrogen, oxygen, or an optionally substituted group selected from $C_{1-6}$ aliphatic or $C_{1-6}$ heteroaliphatic;
$R^2$ is —C(O)X, wherein X is independently R, —C(O)NHNH$_2$, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted group selected from $C_{1-6}$ aliphatic or $C_{1-6}$ heteroaliphatic; and $R^3$ is a substituted or unsubstituted, branched or unbranched, saturated or unsaturated, $C_{10}$-$C_{25}$ aliphatic; and Y is —O—, —N—, —S—, —Se—, —S(O)—, —S(=N)—, —SO$_2$—, —Se(O)—, or —Se(O)$_2$—.

In some embodiments, compounds of Formulae I and/or I' are provided with the proviso that L and $R^1$ cannot together be $C_1$-$C_3$ unsubstituted non-halogenated alkyl.

In certain embodiments, the present invention provides a compound of Formula Ia,

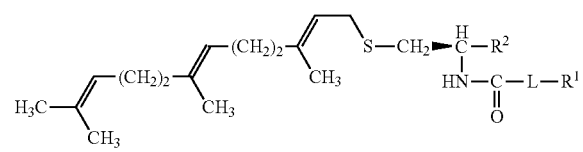

Ia or a pharmaceutically acceptable salt thereof, wherein:

L is a bivalent, branched or unbranched, saturated or unsaturated, $C_2$-$C_6$ hydrocarbon chain wherein one or more methylene units of L is independently replaced by —O—, —S—, —NH—, —C(O)—, —C(=CH$_2$)—, or $C_3$-$C_6$ cycloalkylene, wherein L is optionally substituted by one or more groups selected from halogen, phenyl, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5-to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur;

$R^1$ is hydrogen, —OH or —OR, wherein each R is independently hydrogen or an optionally substituted group selected from $C_{1-6}$ aliphatic or $C_{1-6}$ heteroaliphatic; and $R^2$ is —C(O)X, wherein X is independently R, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted group selected from $C_{1-6}$ aliphatic or $C_{1-6}$ heteroaliphatic.

In some embodiments, treatment of inflammatory diseases or disorders is achieved using compounds of the present invention.

In some embodiments, treatment of inflammatory diseases or disorders is achieved using provided compounds without having the side effects of corticosteroids or NSAIDS.

The present invention encompasses the finding that certain isoprenyl compounds have surprising and desirable characteristics as compared with other compounds and/or N-acetyl-S-farnesyl-L-cysteine ("AFC"). For example, the present disclosure illustrates that certain isoprenyl compounds show surprising inhibition of edema, erythema and dermal neutrophil infiltration, as measured by inhibition of MPO (myeloperoxidase), when compared to AFC.

In some embodiments, the present invention provides compounds that modulate the G-protein signaling cascade. In some embodiments, the present invention provides compounds that modulate inflammatory pathways. In certain embodiments, the inflammatory pathway is associated with G-protein pathways (e.g., purinergic receptor-mediated). In certain embodiments, the inflammatory pathway is associated with non G-protein pathways (e.g., PPAR-mediated, Toll-like receptor-mediated, and TNF-alpha receptor-mediated). In certain embodiments, isoprenyl compounds of the present invention modulate the levels of inflammatory mediators (e.g., cytokines). In certain embodiments, isoprenyl compounds of the present invention demonstrate surprising inhibition of pro-inflammatory cytokines (e.g., IL-1α, IL-1β, IL-2, IL-3, IL-4, IL-5, IL-6, IL-7, IL-8, IL-9, IL-10, IL-11, IL-12/IL-23 p40, IL13, IL-17, IL-18, TGF-β, IFN-γ, GM-CSF, Groα, MCP-1 and TNF-α).

In some embodiments, isoprenyl compounds of the present invention exhibit anti-oxidant activity.

In some embodiments, isoprenyl compounds of the present invention demonstrate surprising inhibition of helper T-lymphocyte infiltration and accumulation.

In some embodiments, isoprenyl compounds of the present invention show surprising inhibition of oxidative burst response from neutrophils.

In some embodiments, compounds provided by the present invention have the structure set forth in Formulae I, I', and/or Ia herein. Certain particular embodiments are described in more detail below.

The present invention also provides compositions containing compounds described herein, methods of preparing such compounds and/or compositions, and methods of using such compounds and/or compositions.

In some embodiments, the present invention provides compositions for treating or preventing inflammation comprising at least one isoprenyl compound, a carrier and optionally an additional active ingredient.

In some embodiments, the present invention provides topical compositions for treating or preventing a skin disease or condition, comprising at least one isoprenyl compound, a carrier and optionally an additional active ingredient, formulated for topical administration. In certain embodiments, provided herein are topical compositions for promoting healthy skin in a subject comprising at least one isoprenyl compound, a carrier and optionally an additional active ingredient.

In some embodiments, the present invention provides compositions for treating or preventing conditions associated with suppression of inflammatory responses comprising at least one isoprenyl compound, a carrier and optionally, an additional active ingredient.

In some embodiments, the present invention provides uses of provided compounds and/or compositions in the treatment of inflammation. In certain embodiments, the present invention provides uses of provided compounds and/or compositions in the treatment of diseases that may benefit from inhibition of infiltration and activation of inflammatory cells (e.g. neutrophils, lymphocytes, monocytes, mast cells), and/or inhibition of expression and activation of cell surface adhesion molecules (e.g. VCAM-1 and ICAM-1) in endothelial and inflammatory cells. In some embodiments, such includes treating or lessening the severity of inflammatory diseases or disorders selected from inflammation (acute or chronic), inflammation associated with spinal cord injury to promote nerve regeneration, inhibition of rejection of genetically engineered cells by the immune system during in vivo gene therapy, asthma, autoimmune diseases, and chronic obstructive pulmonary disease (COPD) (e.g., emphysema, chronic bronchitis and small airways disease, etc.), inflammatory responses of the immune system, skin diseases (e.g., reducing acute skin irritation for patients suffering from rosacea, atopic dermatitis, seborrheic dermatitis, psoriasis), irritable bowel syndrome (e.g., Chron's disease and ulcerative colitis, etc.), neurodegenerative disorders (e.g., Parkinson's disease, Alzheimer's disease, Huntington's disease, Dementia pugilistica, Pick's disease, Guam parkinsonism dementia complex, Fronto-temporal dementia, Cortico-basal degeneration, Pallido-pontal-nigral degeneration, Progressive supranuclear palsy, Dementia with Lewy bodies (DLB), and multiple system atrophy (MSA)).

In some embodiments, the present invention provides uses of provided compounds and/or compositions in medicine, for example, in the treatment or prevention of diseases or conditions associated with suppression of inflammatory responses. In certain embodiments, provided herein are methods for treating or preventing a disease or condition associated with suppression of inflammatory responses, methods comprising steps of administering an effective amount of a composition comprising at least one isoprenyl compound, a carrier and optionally an additional active ingredient.

In some embodiments, the present invention provides methods for treating or preventing diseases in a subject that may benefit from the modulation of levels of inflammatory mediators such as cytokines comprising provided compounds and/or compositions. In certain embodiments, the present invention provides methods for treating or preventing diseases in a subject that may benefit from the inhibition of infiltration and accumulation of helper-T lymphocytes comprising provided compounds and/or compositions. In certain embodiments, the present invention provides methods for treating or preventing diseases in a subject that may benefit from the inhibition of ICMT comprising provided compounds and/or compositions. In certain embodiments, the present invention provides methods for treating or preventing diseases in a subject that may benefit from inhibition of oxidative burst response from neutrophils comprising provided compounds and/or compositions.

In some embodiments, provided herein are methods for treating or preventing skin conditions, said methods comprising the step of topically applying onto a surface of a subject, including a human, in need thereof, an effective amount of a composition comprising at least one isoprenyl compound, a carrier and optionally an additional active ingredient. In certain embodiments, provided herein are methods of promoting healthy skin, said methods comprising the step of topically applying onto a surface of a subject, including a human, in need thereof, an effective amount of a composition comprising at least one isoprenyl compound, a carrier and optionally an additional active ingredient.

In certain embodiments, the present invention provides methods for treating or preventing inflammation in a subject, methods comprising the step of administering an effective amount of a composition comprising at least one isoprenyl compound, a carrier and optionally an additional active ingredient.

In some embodiments, provided compounds are compared to AFC. In some embodiments, provided compounds have superior activity to AFC.

While the present specification illustrates certain particular provided compounds, various other compounds and/or compositions as described herein would be known to those skilled in the art made aware of this disclosure. As described more fully below, in the accompanying figures, examples and descriptions, a related object of this disclosure includes various compounds and/or compositions, the choice as to which can be determined as desirable for a specific end use application.

Definitions

"Activating Agent": As used herein, the term "activating agent" refers to a coupling agent. Exemplary activating agents include, but are not limited to: benzotriazol-1-yl-oxy-tris-(dimethylamino)-phosphonium hexafluorphosphate (BOP), N,N'-carbonyldiimidazole (CDI), N,N'-dicyclohhexylcarbodiimide (DCC), N,N'-diisopropylcarbodiimide (DIC), 3-(diethoxyphosphoryloxy)-1,2,3-benzotriazin-4-(3H)-one (DIC), 3-(diethoxyphosphoryloxy)-1,2,3-benzotriazin-4-(3H)-one (DEPBT), N-ethyl-N'-(3-dimethylaminopropyl)carbodiimide hydrochloride (EDC), 2-(1H-benzotriazol-1-yl)-1,1,3,3-tetramethyluronoium hexafluorphosphate (HBTU), 2-(3,4-dihydro-4-oxo-1,2,3-benzotriazin-3-yl)-N,N,N',N'-tetramethyluronium hexafluorophosphate (HDBTU), 2-(mercaptobenzothiazol)-N,N,N',N'-tetramethyluronium hexafluorophosphate (HMTU), 2-(endo-5-norbornene-2,3-dicarboxymido)-1,1,3,3-tetramethyluronium hexafluorophosphate (HNTU), 1-hydroxibenzotriazol monohydrate (HOBt*H2O), 1-hydroxy-1H-1,2,3-Triazole-4-carboxylate (HOCt), N-hydroxy-5-norbornene-2,3-dicarboxylimide (HONB), 3-hydroxy-3,4-dihydro-4-oxo-1,2,3-benzotriazine (HOOBt), S-(1-oxido-2-pyridyl)-thio-N,N,N',N'-tetramethyluronium hexafluorophosphate (HOTT), O-succinimidyl-1,3-dimethylpropyleneuronium hexafluorophosphate (HPD-OSu), S-(1-oxo-2-pyridyl)-thio-1,3-dimethylpropyleneuronium hexafluorophosphate (HPTDP), O-(1,2-dihydro-2-oxo-pyridyl]-N,N,N',N'-tetramethyluronium hexafluorophosphate (HPTU), 2-succinimido-1,1,3,3-tetramethyluronium hexafluorophosphate (HSTU), 4-(4,6-dimethoxy-1,3,5-triazin-2-yl)-4-morpholinium tetrafluoroborate (MMTM), 1-(mesitylene-2-sulfonyl)-3-nitro-1,2,4-triazole (MSNT), pentafluorphenol-tetramethyluronium hexafluorophosphate (PFTU), tris-n-propan-phosphonic acid anhydride (50% in AcOEt) (PPAA/AcOEt), tris-n-propan-phosphonic acid anhydride (50% in DMF) (PPAA/DMF), 2-(1H-benzotriazole-1-yl)-1,1,3,3-tetramethyluronium tetrafluoroborate (TBTU), N,N,N',N'-tetramethylchloroformamidinium-hexafluorophosphate (TCFH), N,N,N',N'-tetramethylfluoroformamidinium hexafluorophosphate (TFFH), 2-(endo-5-norbornene-2,3-dicarboxymido)-1,1,3,3-tetramethyluronium tetrafluoroborate (TNTU), S-(1-oxo-2-pyridyl)-thio-N,N,N',N'-tetramethyluronium tetrafluoroborate (TOTT), O-succinimidyl-1,3-dimethylpropyleneuronium tetrafluoroborate (TPD-OSu), S-(1-oxo-2-pyridyl)-thio-1,3-dimethylpropyleneuronium tetrafluoroborate (TPTDP), O-(1,2-dihydro-2-oxo-pyridyl]-N,N,N',N'-tetramethyluronium tetrafluoroborate (TPTU), or N,N,N',N'-tetramethyl-O-(succinimidyl)uronium tetrafluoroborate (TSTU), and combinations thereof.

"N-acetyl-S-farnesyl-L-cysteine compound" or an "AFC compound": As used herein, an "N-acetyl-S-farnesyl-L-cysteine compound" (or an "AFC compound"), as used herein, is a small molecule compound that is structurally related to N-acetyl-S-farnesyl-L-cysteine (AFC). In some embodiments, an AFC compound as provided herein has a structure set forth in Formulae I and/or I'. In some embodiments, an AFC compound may also be referred to as an "Isoprenyl Compound."

"Acyl": As used herein, the term "acyl" refers to a radical formed from an organic acid by removal of a hydroxyl group.

"Additional active ingredient": As used herein, the phrase "additional active ingredient" refers to an agent, other than an isoprenyl compound that exerts a pharmacological, dermatological or any other beneficial activity. It is to be understood that "other beneficial activity" may be one that is only perceived as such by the subject using the inventive compositions. Typically, an additional active ingredient, as that term is used herein, refers to a pharmaceutically active agent that is administered in combination with an isoprenyl compound of the present invention.

"Aliphatic": The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, cycloalkynyl moieties. Thus, as used herein, the term "alkyl" includes straight, branched and cyclic alkyl groups (see below). An analogous convention applies to other generic terms such as "alkenyl", "alkynyl", and the like. Furthermore, as used herein, the terms "alkyl", "alkenyl", "alkynyl", and the like encompass both substituted and unsubstituted groups. In some embodiments, an aliphatic group contains 1-25 aliphatic carbon atoms. In some embodiments, an aliphatic group contains from 1 to 25, from 1 to 24, from 1 to 23, from 1 to 22, from 1 to 21, from 1 to 20, from 1 to 19, from 1 to 18, from 1 to 17, from 1 to 16, from 1 to 15, from 1 to 14, from 1 to 13, from 1 to 12, from 1 to 11, from 1 to 10, from 1 to 9, from 1 to 8, from 1 to 7, from 1 to 6, from 1 to 5, from 1 to 4, from 1 to 3, from 1 to 2, from 2 to 3, or 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, 20 to 21, 21 to 22, 22 to 23, 23 to 24, or 24 to 25 aliphatic carbon atoms. In certain embodiments, as used herein, "lower alkyl" is used to indicate those alkyl groups (cyclic, acyclic, substituted, unsubstituted, branched, or unbranched) having 1-6 carbon atoms. In some embodiments, wherein a portion of a term such as alkyl, alkenyl, alkynyl, cycloalkyl, cycloalkenyl, cycloalkynyl is used within a different generic term (e.g., dialkylamino, alkoxy, alkylthio, alkylamino), then it is understood that an analogous convention applies with respect to the number of carbon atoms present.

"Alkenyl": As used herein, the term "alkenyl" denotes a substituted or unsubstituted, monovalent group derived from a straight- or branched-chain hydrocarbon moiety containing at least one carbon-carbon double bond by removal of a single hydrogen atom. In some embodiments, the alkenyl group contains 1-25 aliphatic carbon atoms. In certain embodiments, an alkenyl group employed in the invention contains 10-25 carbon atoms. In certain embodiments, an alkenyl group employed in the invention contains 10-20 carbon atoms. In certain embodiments, an alkenyl group employed in the invention contains 10-15 carbon atoms. In certain embodiments, an alkenyl group employed contains 10 carbon atoms. In certain embodiments, an alkenyl group employed contains 15 carbon atoms. In certain embodiments, an alkenyl group employed contains 20 carbon atoms. Alkenyl groups include, for example, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, polyunsaturated alkenes including octadec-9,12-dienyl, octadec-9,12,15-trienyl, eicos-5,8,11,14-tetraenyl, farnesyl, geranyl, and geranylgeranyl, C-20 phytyl, and the like.

"Alkenylene": The term "alkenylene" refers to a bivalent, substituted or unsubstituted, alkenyl group. A substituted alkenylene chain is a polymethylene group containing at least one double bond in which one or more hydrogen atoms are replaced with a substituent. Suitable substituents include those described herein for a substituted aliphatic group.

"Alkyl": As used herein, the term "alkyl" means substituted or unsubstituted, saturated, straight- or branched-chain hydrocarbon radicals derived from an aliphatic moiety by removal of a single hydrogen atom. In some embodiments, the alkyl group contains 1-25 aliphatic carbon atoms. In certain embodiments, an alkyl group employed in the invention contains 10-25 carbon atoms. In certain embodiments, an alkyl group employed in the invention contains 10-20 carbon atoms. In certain embodiments, an alkyl group employed in the invention contains 15-20 carbon atoms. In certain embodiments, an alkyl group employed contains 10 carbon atoms. In certain embodiments, an alkyl group employed contains 15 carbon atoms. In certain embodiments, an alkyl group employed contains 20 carbon atoms. In certain embodiments, an alkyl group employed in the invention contains 1-3 carbon atoms. In certain embodiments, an alkyl group employed contains 1-2 carbon atoms. In certain embodiments, an alkyl group contains 1 carbon atom. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, tridecyl, tetradecyl, pentadecyl, hexadecyl, heptadecyl, octadecyl, nonadecyl, eicosyl, heneicosyl, docosyl, tricosyl, teteracosyl, pentacosyl, and the like.

"Alkylamino": The term "alkylamino" refers to a substituted or unsubstituted group having the structure —NHR', wherein R' is aliphatic, as defined herein. In certain embodiments, the aliphatic group contains 1-20 aliphatic carbon atoms. In some embodiments, the aliphatic group contains 1-10 aliphatic carbon atoms. In some embodiments, the aliphatic group employed in the invention contains 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

"Alkylene": The term "alkylene" refers to a bivalent substituted or unsubstituted alkyl group. Unless otherwise specified, the alkylene group contains 1-25 aliphatic carbon atoms. An "alkylene chain" is a polymethylene group, i.e., —(CH$_2$)$_n$—, wherein n is a positive integer, preferably from 1 to 6, from 1 to 5, from 1 to 4, from 1 to 3, from 1 to 2, from 2 to 3, or 3 to 4, 4 to 5, 5 to 6. A substituted alkylene chain is a polymethylene group in which one or more methylene hydrogen atoms are replaced with a substituent. Suitable substituents include those described herein for a substituted aliphatic group.

"Alkynyl": As used herein, the term "alkynyl" denotes a substituted or unsubstituted monovalent group derived from a straight- or branched-chain hydrocarbon moiety containing at least one carbon-carbon triple bond by removal of a single hydrogen atom. In certain embodiments, an alkynyl group employed in the invention contains 10-25 carbon atoms. In certain embodiments, an alkynyl group employed in the invention contains 10-20 carbon atoms. In certain embodiments, an alkynyl group employed contains 10 carbon atoms. In certain embodiments, an alkynyl group employed contains 15 carbon atoms. In certain embodiments, an alkynyl group employed contains 20 carbon atoms. In certain embodiments, an alkynyl group employed in the invention contains 2-3 carbon atoms. In certain embodiments, an alkynyl group employed contains 2 carbon atoms. In certain embodiments, an alkynyl group employed contains 3 carbon atoms. Representative alkynyl groups include, but are not limited to, ethynyl, 2-propynyl (propargyl), 1-propynyl, and the like.

"Alkoxy", or "Alkylthio": The term "alkoxy", or "alkylthio" as used herein refers to a substituted or unsubstituted alkyl group, as previously defined, attached to the parent molecule through an oxygen atom or through a sulfur atom. In certain embodiments, the "alk" or "alkyl" portion of an "alkoxy" or "alkylthio" group contains 1-10 aliphatic carbon atoms. In yet other embodiments, the "alk" or "alkyl" portion of an "alkoxy" or "alkylthio" group employed in the present invention contains 1-8 aliphatic carbon atoms. In still other embodiments, the "alk" or "alkyl" portion of an "alkoxy" or "alkylthio" group contains 1-6 aliphatic carbon atoms. In yet other embodiments, the "alk" or "alkyl" portion of an "alkoxy" or "alkylthio" group contains 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl groups include, but are not limited to, methylthio, ethylthio, propylthio, isopropylthio, n-butylthio, and the like.

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal. In some embodiments, the term animal is used to refer to veterinary animals (e.g., fowl, cows, pigs, horses, etc.).

"Aralkylene" refers to a divalent group of formula —$R^a$—$Ar^a$— where $R^a$ is an "alkylene" as defined herein, and $Ar^a$ is an "arylene" as defined herein (i.e., an alkylene is bonded to an arylene).

"Anti-dandruff agent": As used herein, the term "anti-dandruff agent" is an agent that reduces, eliminates or prevents a scurf from forming on skin, especially of the scalp, that comes off in small white or grayish scales. Exemplary anti-dandruff ingredients usable in context of the present invention include, without limitation, butoconazole, climbazole, coal tar, clotrimazole, dichlorophenyl imidazolodioxalan, imidazoles (e.g., fluconazole, ketoconazole, itraconazole, miconazole, miconazolenitrite, povidone-iodine, sulconazole, tioconazole), salicylic acid, selenium sulfide, shale oil and the like (e.g., sulfonated shale oil), sulfur, zinc pyrithione, and the like, and any possible stereo isomers thereof such as anthralin, piroctone olamine (Octopirox), selenium sulfide, and ciclopiroxolamine, and combinations thereof.

"Antihistamine agent": As used herein, the term "antihistamine agent" is an agent that counteracts histamine in the body and that is used for treating allergic reactions (such as hay fever) and cold symptoms. Non-limiting examples of antihistamines usable in context of the present invention include astemizole, brompheniramine, chlorpheniramine, clemastine, dexchlorpheniramine, diphenhydramine, loratadine, piperidines, piperazines, promethazine, terfenadine and tripolidine and combinations thereof.

"Anti-irritant": The term "anti-irritant", as used herein, is an agent that prevents or reduces soreness, roughness, or inflammation of a bodily part (e.g., skin). Presently known anti-irritants can be divided into water-soluble anti-irritants and water-insoluble anti-irritants. Representative examples of such compositions are described, for example, in U.S. Pat. No. 5,482,710, which is herein incorporated by reference. Suitable anti-irritants that can be used in the context of the present invention include, for example, steroidal and non steroidal anti-inflammatory agents or other materials such as allantoin, aloe vera, alpha-bisabolol, caffeine, chamomile, cola nitida extract, green tea extract, glycyrrhizic acid, licorice extract, tea tree oil, or other xanthines, and combinations thereof.

"Anti-oxidant agent": As used herein, the term "anti-oxidant agent" is an agent that inhibits oxidation or reactions promoted by oxygen or peroxides. Non-limiting examples of anti-oxidants that are usable in the context of the present invention include amines (e.g., N,N-diethylhydroxylamine, amino-guanidine), arginine pilolate, ascorbic acid (vitamin C) and its salts, ascorbyl esters of fatty acids, ascorbic acid and the like (e.g., magnesium ascorbyl phosphate, sodium ascorbyl phosphate, ascorbyl sorbate), bioflavonoids, butylated hydroxy benzoic acids and their salts, curcumin, dihydroxy fumaric acid and its salts, gallic acid and its alkyl esters (e.g., propyl gallate, uric acid and its salts and alkyl esters), glycine pidolate, grape skin/seed extracts, 6-hydroxy-2,5,7,8-tetramethylchroman-2-carboxylic acid (commercially available under the tradename Trolox®), lipoic acid, lysine, melanin, methionine, nordihydroguaiaretic acid, proline, rosemary extracts, silymarin, sorbic acid and its salts, sulfhydryl compounds (e.g., glutathione), superoxide dismutase, tea extracts, tocopherol acetate, tocopherol (vitamin E), tocopherol sorbate, and other esters of tocopherol and combinations thereof.

"Antipruritic agents": As used herein, the term "antipruritic agent" as used herein, is an agent that reduces, eliminates or prevents itching. Suitable antipruritic agents include, without limitation, methdilazine and trimeprazine, and combinations thereof.

"Anti-skin atrophy actives": As used herein, the term "anti-skin atrophy active" is an agent that is effective in replenishing or rejuvenating the epidermal layer by promoting or maintaining the natural process of desquamation. Examples of antiwrinkle and antiskin atrophy actives which can be used in context of the present invention include alpha-hydroxy acids (e.g. glycolic acid, and lactic acid), lipoic acid, lysophosphatidic acid, phytic acid, retinoic acid, its prodrugs, isomers (e.g., cis and trans) and analogues thereof, salicylic acid and the like, sclerosing agents or sclerosants, skin peel agents (e.g., phenol and the like), sulfur-containing D and L amino acids and the like and related salts, (e.g., N-acetyl derivatives, such as N-acetyl L-cysteine), and thiols (e.g. ethane thiol).

"Anesthetic agents": The term "anesthetic agent" as used herein is an agent that results in a reduction or loss of sensation. Non-limiting examples of anesthetic drugs that are suitable for use in the context of the present invention include pharmaceutically acceptable salts of bupivacaine, chlorprocaine, cocaine, dibucaine, dyclonine, etidocaine, hexylcaine, ketamine, lidocaine, mepivacaine, phenol, pramoxine, procaine, and tetracaine.

"Aryl" and "Heteroaryl": In general, the terms "aryl" and "heteroaryl" refer to substituted or unsubstituted aromatic groups or moieties. In some embodiments, the terms "aryl" and "heteroaryl" may be used in the context of a different moiety name (e.g., "arylalkyl", "aralkylene", "aryloxy", "heteroaryloxy" or "heteroarylalkyl"). In some embodiments, an "aryl" and/or "heteroaryl" refer to stable mono- or polycyclic, heterocyclic, polycyclic, and polyheterocyclic unsaturated moieties wherein at least one ring in the system is aromatic. In some embodiments, an "aryl" and/or "heteroaryl" ring system contains three to seven ring members. In some embodiments, an "aryl" and/or "heteroaryl" contain 3-14 carbon atoms. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. It will be appreciated that aryl and heteroaryl groups can be unsubstituted or substituted, wherein substitution includes replacement of one, two, three, or more of the hydrogen atoms thereon independently with any one or more of the moieties (e.g., "substituents") provided herein.

"Arylene" and "Heteroarylene": The term "arylene" refers to an unsubstituted or substituted divalent group that is carbocyclic and aromatic. In some embodiments, rings in an arylene group are fused to one another. In some embodiments rings in an arylene group are not fused, but are nonetheless connected. In some embodiments, an arylene group includes some fused rings and some connected rings. In some embodiments, an arylene group includes aromatic rings. In some embodiments, an arylene group includes non-aromatic rings. In some embodiments, an arylene group includes some aromatic rings and some non-aromatic rings. In some embodiments, the arylene group has up to 5 rings, up to 4 rings, up to 3 rings, up to 2 rings, or one aromatic ring. For example, the arylene group can be phenylene. Exemplary arylene groups include any of the "aryl" moieties listed herein with the understanding that divalency is required to arrive at a corresponding "arylene" group from an "aryl" group. Exemplary substituents of "arylene" groups include replacement of one, two, three, or more of the hydrogen atoms thereon independently with any one or more of the moieties applicable for "aryl" and "heteroaryl," as defined herein. It will be appreciated by one skilled in the art that a carbon ring atom of an "arylene" can be replaced by one, two or three heteroatoms independently selected from S, O, and N while the remaining ring atoms are carbon, the divalent group being joined to the rest of the molecule via any two ring atoms, to form a "heteroarylene". Exemplary "heteroarylene" groups include any of the "heteroaryl" moieties listed herein with the understanding that divalency is required to arrive at a corresponding "heteroarylene" group from a "heteroaryl" group.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Astringent": As used herein, the term "astringent" is an agent that draws together or constricts body tissues and is effective in stopping the flow of blood or other secretions. In some embodiments, an astringent coagulate blood, and therefore can be used to arrest hemorrhage. In some embodiments, an astringent promotes healing, toughens skin and/or to decreases sweating. In some embodiments astringents are protein precipitants. Typically, astringents have low cell penetrability such that their action is limited to the cell surface and/or interstitial spaces. In some embodiments, astringent action is accompanied by contraction and wrinkling of tissues to which astringents are applied. In some embodiments, application of astringents is accompanied by blanching of recipient tissue. In some embodiments, astringents include one or more agents such as aluminum, bismuth, iron, manganese, zinc. Alternatively and/or additionally, such agents can be provided in any of a variety of forms including, for example, pharmaceutically acceptable salt forms.

"Bivalent, branched or unbranched, saturated or unsaturated, $C_2$-$C_6$ (e.g., $C_2$, $C_3$, $C_4$, $C_5$, or $C_6$) hydrocarbon chain": As used herein, the term "bivalent, branched or unbranched, saturated or unsaturated, $C_2$-$C_6$ (e.g., $C_2$, $C_3$, $C_4$, $C_5$, or $C_6$) hydrocarbon chain", refers to bivalent alkylene, alkenylene, and alkynylene chains that are straight or branched as defined herein.

"Carrier": The term "carrier" is used in accordance with its art-understood meaning, to refer to a material that is included in a pharmaceutical composition but does not abrogate the biological activity of pharmaceutically active agent(s) that are also included within the composition. Typically, carriers have very low toxicity to the animal to which such compositions are to be administered. In some embodiments, carriers are inert. In some embodiments, carriers are affirmatively beneficial (e.g., providing pharmaceutical and/or cosmetic benefits). In some embodiments, isoprenyl compounds of Formulae I, I' and/or Ia, act as acceptable carriers. In some embodiments, AFC acts as an acceptable carrier. In some embodiments, the term "carrier" when used in the pharmaceutical context (e.g., pharmaceutically acceptable carrier) means that an agent is present in a composition but does not abrogate the biological activity of another agent(s) present in a composition. In some embodiments, the term "carrier" when used in a cosmetic context (e.g., cosmetically acceptable carrier) means that an agent is present in a composition but does not but does not abrogate the biological activity and/or aesthetic effect of another agent(s) present in a composition. In some embodiments, a cosmetically acceptable carrier is used to topically administer cosmetics with which isoprenyl compounds of the present invention will remain stable and bioavailable. It will be understood that "cosmetically acceptable carriers" and "carriers" as defined herein are similar, if not often identical, in nature. In some embodiments, the term "carrier" when used in a cosmeceutical context (e.g., cosmeceutical carrier) means that an agent is present in a composition but does not abrogate the biological activity and aesthetic effect of another agent(s) present in a composition.

"Caustic agents": As used herein, the term "caustic agent" is an agent that is capable of destroying or eating away epithelial tissue by chemical action. Caustic agents can be used to remove dead skin cells. For example, beta-hydroxy acids, naturally derived acids with a strong kerolytic effect, are useful for problem skin or peeling.

"Chelating Agent": The term "chelating agent" as used herein, is an agent that binds to a metal ion such as calcium ($Ca^{2+}$), magnesium ($Mg^{2+}$) and copper ($Cu^{2+}$), forming a metal complex known as a chelate. In some embodiments, a chelating agent is a ligand. In some embodiments, a chelating agent is an atom. In some embodiments, a chelating agent is an ion. In some embodiments, a pharmaceutical composition may contain a chelating agent (e.g., a mild agent, such as, ethylenediaminetetraacetic acid ("EDTA"), EDTA derivatives, or combinations thereof). In some embodiments, a chelating agent enhances a preservative or preservative system of the composition.

"Colorants": As used herein, the term "colorant" refers to pigments and/or dyes or a combination thereof, that are used to change hair color as cosmetic benefit requires. In some embodiments, pigments included in "colorants" include, but are not limited to, iron oxides, and titanium oxides. In some embodiments, dyes included in "colorants" include D&C approved colorants, FD&C approved colorants, and those approved for use in Europe and Japan. See Marmion, D. M., Handbook of US Colorants for Food, Drugs, Cosmetics, and Medical Devices, 3rd ed, 1991 herein incorporated by reference.

"Compatible": The term "compatible" as used herein means that the components of such a composition are capable of being combined with each other in a manner such that there is no interaction that would substantially reduce the efficacy of the composition under ordinary use conditions.

"Demulcent": As used herein, the term "demulcent" is an agent used to primarily alleviate irritation, particularly mucous membranes or abraded tissues. Exemplary demulcents include acacia, agar, alginates, mucilages, benzoin, carbomer, gelatin, glycerin, gums, hydroxyethyl cellulose, hydroxypropyl cellulose, hydroxypropyl methylcellulose, hydrogels, dextrins, starches, certain sugars, and polymeric polyhydric glycols, propylene glycol, sodium alginate, tragacanth, and combinations thereof.

"Deodorant agent": As used herein, the term "deodorant agent" refers to a substance for inhibiting or masking perspiration or other bodily odors. Representative examples of deodorant agents that are usable in the context of the present invention include, without limitation, quaternary ammonium compounds such as benzethonium chloride, cetyl pyridinium chloride, cetyl-trimethylammonium bromide, diisobutyl phenoxy ethoxy ethyl dimethyl benzyl ammonium chloride, lauroyl sarcosine, sodium aluminum chlorohydroxy lactate, sodium N-lauryl sarcosine, sodium N-palmlthyl sarcosine, N-myristoyl glycine, potassium N-lauryl sarcosine, stearyl, trimethyl ammonium chloride, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts (e.g. as the alkali metal carbonates and bicarbonates, ammonium and tetraalkylammonium carbonates and bicarbonates, especially the sodium and potassium salts) or combination thereof.

"Dialkylamino": The term "dialkylamino" refers to a group having the structure —NRR', wherein R and R' are each an aliphatic group, as defined herein. R and R' may be the same or different in a dialkyamino moiety. In certain embodiments, the aliphatic group contains 1-20 aliphatic carbon atoms. In some embodiments, the aliphatic group contains 1-10 aliphatic carbon atoms. In yet other embodiments, the aliphatic groups employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of dialkylamino groups include, but are not limited to, dimethylamino, methyl ethylamino, diethylamino, methylpropylamino, di(n-propyl) amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

"Effective amount": In general, the "effective amount" of an active agent (e.g., a therapeutic agent, composition, and/or formulation) refers to an amount sufficient to elicit the desired biological response. In some embodiments, a therapeutically effective amount of a substance is an amount that is sufficient, when administered to a subject suffering from or susceptible to a disease, disorder, and/or condition, to treat, diagnose, prevent, and/or delay the onset of one or more symptoms of the disease, disorder, and/or condition. As will be appreciated by those of ordinary skill in this art, and effective amount of a substance may vary depending on such factors as the desired biological endpoint, the substance to be delivered, the pharmacokinetics of the compound, the target cell or tissue, the disease being treated, the mode of administration, and the patient, etc. For example, the effective amount of a composition and/or formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. Those of ordinary skill in the art will appreciate that, commonly, a therapeutically effective amount will be administered over a series of individual doses. In some embodiments, the term "effective amount" when used in a pharmaceutical context (e.g., pharmaceutically effective amount) means that an agent is present in an amount sufficient to achieve a desired therapeutic effect. In some embodiments, the term "effective amount" when used in a cosmetic context (e.g., cosmetically effective amount) means that an agent is present in an amount sufficient to achieve an aesthetic effect. In some embodiments, the term "effective amount" when used in a cosmeceutical context (e.g., cosmeceutically effective amount) means that an agent is present in an amount sufficient to achieve a therapeutic and/or aesthetic effect.

"Emollients": As used herein, the term "emollients" refers to an agent that increases tissue moisture content, thereby rendering skin softer and more pliable. Increased moisture content in the skin can be achieved by preventing water loss with an occlusive water-immiscible barrier, by increasing the water-holding capacity in the skin with humectants, or by altering the desquamation of the outermost skin layer, the stratum corneum. In some embodiments, "emollients" are typically bland, fatty or oleaginous materials which can be applied locally, particularly to the skin. Useful emollients include cetyl alcohol, glycerin, hydrophilic petrolatum, isopropyl myristate, lanolin, mineral oil, myristyl alcohol, oleyl alcohol, paraffin, petrolatum, spermaceti, vegetable oils, waxes, white ointment, white petroleum, yellow ointment or combinations thereof.

"Emulsifier": The term "emulsifier" as used herein promotes formation and stabilization of an emulsion. Suitable emulsifiers may be finely divided solids, natural materials, or synthetic materials. Natural emulsifying agents may be derived from either animal or vegetable sources. Those from animal sources include casein, cholesterol, egg yolk, gelatin, or wool fat or combinations thereof. Those from vegetable sources include acacia, chondrus, pectin or tragacanth or combinations thereof. Vegetable sources specifically from cellulose derivatives include carboxymethyl cellulose and methyl cellulose to increase the viscosity. Finely divided emulsifiers include aluminum hydroxide, bentonite, magnesium hydroxide, or magnesium trisylicate. Synthetic agents include anionic, cationic or nonionic agents, and include benzalkonium chloride, polyethylene glycol 400 monostearate, sodium lauryl sulfate, or combinations thereof.

"Enantiomerically enriched" and "Enantioenriched": As used herein, the terms "enantiomerically enriched" and "enantioenriched" denote that one enantiomer is enriched with respect to other enantiomers of the same compound in a composition. For example, when a compound is substantially in the R-form or the S-form with respect to a particular chiral center, the compound may be considered to have an enantiomeric excess (ee) for that form. In some embodiments, a composition is considered "enriched" when one enantiomer is present in at least 75% ee in the composition. In certain embodiments, the terms denote that one enantiomer is present in at least 80% ee, 85% ee, 90% ee, 95% ee, 97.5% ee, or more. In some embodiments, a composition is considered "enantiomerically pure" or "enantiopure" when one enantiomer is present with an ee of at least about 90%, with respect to other enantiomers. In some embodiments, a composition is considered "enantiomerically pure" or "enantiopure" when one enantiomer is present with an ee of at least about 95%, with respect to other enantiomer(s) present in the composition. In some embodiments, a composition is considered "enantiomerically pure" or "enantiopure" when one enantiomer is present with an ee of at least about 97.5%, with respect to other enantiomer(s) present in the composition. In some embodiments, a composition is considered "enantiomerically pure" or "enantiopure" when one enantiomer is present with an ee of at least about 99%, with respect to other enantiomer(s) present in the composition.

"Fragrance": As used herein, the term "fragrance" refers to an agent having a pleasant aroma. Suitable fragrances include, but are not limited to, camphor synthetic, chamomile, clove oil, *eucalyptus* oil, lavender, peppermint oil, and the like.

"G-protein mediated condition": The term "G-protein mediated condition", as used herein means any disease or other deleterious condition for which the appearance, incidence, and/or severity of one or more symptoms correlates with changes in a G-protein signaling cascade. In some embodiments, one or more symptoms of the disease or condition is caused by a defect or alteration in G-protein signaling.

"Hair Conditioning Agents": As used herein, the term "hair conditioning agent" refers to an agent that is suitable for use in conditioning hair (e.g., so as to further improve the condition of the hair). In some embodiments, representative hair conditioning agents include, for example, one or more alkoxylated alcohols, alkoxylated amides, alkoxylated carboxylic acids, cationic surfactants, collagens, dimethicone polyols, esters (e.g., glyceryl esters), halogenated quaternary ammonium compounds, keratins, modified silicones, proteins, polymeric ethers, quaternary ammonium compounds, or sorbitan derivatives, or combinations thereof.

"Halo" and "Halogen": The terms "halo" and "halogen" as used herein refer to an atom selected from fluorine, chlorine, bromine, and iodine.

"Heteroaliphatic": The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties (e.g., "substituents") described herein.

"Heteroatom": As used herein, the term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR_x$ (as in N-substituted pyrrolidinyl)).

"Heterocycle" or "Heterocyclyl": As used herein, the terms "heterocycle", "heterocyclyl", "heterocyclic radical", and "heterocyclic ring" are used interchangeably and refer to a stable 3-to 7-membered monocyclic or 7-10-membered bicyclic heterocyclic moiety that is either saturated or partially unsaturated, and having, in addition to carbon atoms, one or more, preferably one to four heteroatoms independently selected from nitrogen, oxygen, or sulfur. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or $NR_x$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. In certain embodiments, one or more carbon atoms may be substituted with an oxo group in the heterocyclyl ring. Examples of such groups include, without limitation, an isoindolin-1,3-dione moiety. A heterocyclyl group may be mono- or bicyclic. The term "heterocyclylalkyl" refers to an alkyl group substituted by a heterocyclyl, wherein the alkyl and heterocyclyl portions independently are optionally substituted.

"Hormone": As used herein, the term "hormone" refers to natural substances produced by organs of the body that travel by blood to trigger activity in other locations or their synthetic analogs. Suitable hormones for use in the context of the present invention include, but are not limited to, calciferol (Vitamin $D_3$) and its products, androgens, estrogens and progesterones.

"Hydrocarbon": The term "hydrocarbon", as used herein, refers to any chemical group comprising hydrogen and carbon. In some embodiments, a hydrocarbon consists of hydrogen and carbon. A hydrocarbon may be substituted or unsubstituted. A hydrocarbon may be unsaturated, saturated, branched, unbranched, cyclic, or polycyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions. As used herein, a "bivalent hydrocarbon" refers to alkylene, alkenylene, or alkynylene, etc.

"Hypopigmenting agents": As used herein, the term "hypopigmenting agents" refers to substances capable of depigmenting the skin. Suitable hypopigmenting agents include hydroquinones, mequinol, and various protease inhibitors including serine protease inhibitors, active soy and retinoic acid.

"In combination": As used herein, the phrase "in combination" refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination".

"Independently selected": The term "independently selected" is used herein to indicate that the R groups can be identical or different.

"Irritant": As used herein, the term "irritant" is a material that acts locally on the skin to induce, based on irritant concentration, hyperemia, inflammation, and desiccation. Irritant agents include, but are not limited to, alcohol, aromatic ammonia spirits, benzoin tincture, camphor capsicum, and coal tar extracts. In some embodiments, the irritant is a rubefacient.

"Isoprenyl compound": As used herein, a "isoprenyl compound" is a small molecule compound that is structurally related to N-acetyl-S-farnesyl-L-cysteine (AFC) and has the following structure:

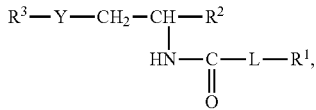

wherein L, R¹, R², R³, and Y are as defined herein. In certain embodiments, an isoprenyl compound has the structure set forth in Formula I:

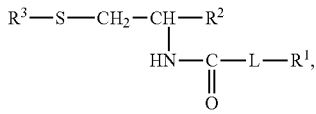

wherein L, R¹, R², R³, and Y are as defined herein. In certain embodiments, an isoprenyl compound has the structure set forth in Formula Ia:

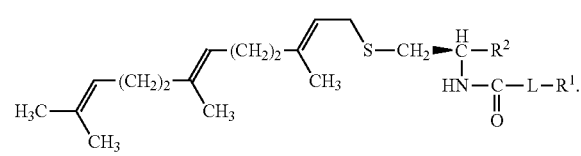

In certain embodiments, an isoprenyl compound has the structure set forth in Formula I':

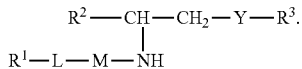

In certain embodiments, an isoprenyl compound is (4-((R)-1-carboxy-2-((2E,6E)-3,7,11-trimethyldodeca-2,6,10-trienylthio)ethylamino)-4-oxobutanoic acid). In certain embodiments, an isoprenyl compound is ((E)-4-((R)-1-carboxy-2-((2E,6E)-3,7,11-trimethyldodeca-2,6,10-trienylthio)ethylamino)-4-oxobut-2-enoic acid). In certain embodiments, an isoprenyl compound is (4-((R)-1-carboxy-2-((2E,6E)-3,7,11-trimethyldodeca-2,6,10-trienylthio)ethylamino)-2-methylene-4-oxobutanoic acid). In certain embodiments an isoprenyl compound is (5-((R)-1-carboxy-2-((2E,6E)-3,7,11-trimethyldodeca-2,6,10-trienylthio)ethylamino)-5-oxopentanoic acid). In certain embodiments, an isoprenyl compound is 5-((R)-1-carboxy-2-((2E,6E)-3,7,11-trimethyldodeca-2,6,10-trienylthio)ethylamino)-2-(1,3-dioxoisoindolin-2-yl)-5-oxopentanoic acid). In certain embodiments, an isoprenyl compound is ((R,14E,18E)-15,19,23-trimethyl-4,8-dioxo-3-oxa-12-thia-7,9-diazatetracosa-14,18,22-triene-10-carboxylic acid). In certain embodiments, an isoprenyl compound is ((R)-2-(3-(2-carboxyethyl)ureido)-3-((2E,6E)-3,7,11-trimethyldodeca-2,6,10-trienylthio)propanoic acid).

"Modulate": The term "modulate" refers to change in a parameter (e.g., a change in a binding interaction or an activity, etc.). Modulation can refer to an increase or a decrease in the parameter (e.g., an increase or decrease in binding, an increase or decrease in activity, etc.).

"Modulator": The term "modulator" refers to an agent that alters level and/or activity of its target in an inflammatory pathway. In some embodiments, a modulator alters interaction between a protein in an inflammatory pathway and one or more other entities. In some embodiments, a modulator alters interaction between a protein in an inflammatory pathway and a substrate. Determination of whether an agent is a modulator can be performed directly or indirectly. Determination of whether an agent modulates an interaction can be performed directly, e.g., using an assay that detects the interaction between a protein in an inflammatory pathway and a substrate. Determination of whether an agent modulates an interaction can be performed with a technique that indirectly detects modulation, e.g., a technique that detects a biological activity that is downstream of, and dependent on, the protein-substrate interaction. In certain embodiments, inflammatory pathways are G-protein-mediated (e.g., purinergic receptor-mediated). In certain embodiments, inflammatory pathways are non G-protein-mediated (e.g., PPAR-mediated, Toll-like receptor-mediated, and TNF-alpha receptor-mediated).

"Moisturizing agent": As used herein a "moisturizing agent" is a substance that adds or restores moisture to the skin. Representative examples of moisturizing or humectant agents that are usable in the present invention include, without limitation, acetamide monoethanolamine urazole, aloe vera in any of its variety of forms (e.g., aloe vera gel), allantoin, guanidine, glycolic acid and glycolate salts (e.g. ammonium salt and quaternary alkyl ammonium salt), hyaluronic acid, lactamide monoethanolamine, polyethylene glycols, polyhydroxy alcohols (e.g., sorbitol, glycerol, hexanetriol, propylene glycol, butylene glycol, hexylene glycol and the like), sugars and starches, sugar and starch derivatives (e.g., alkoxylated glucose), and any combination thereof.

"Non-steroidal anti-inflammatory agents": As used herein, the term "non-steroidal anti-inflammatory agents" refers to a large group of agents that are aspirin-like in their action, including acetaminophen, Advil®, Aleve®, ibuprofen, naproxen sodium and Tylenol®. Additional examples of non-steroidal anti-inflammatory agents that are usable in the context of the present invention include, without limitation, acetic acid derivatives (e.g., acematacin, clindanac, diclofenac, felbinac, fenclofenac, fentiazac, furofenac, indomethacin, isoxepac, ketorolac, oxepinac, sulindac, tiopinac, tolmetin, zidometacin and zomepirac), benorylate, diflunisal, disalcid, fenamates (e.g., flufenamic, meclofenamic, mefenamic, niflumic and tolfenamic acids), fendosal, oxicams (e.g., CP-14,304, isoxicam, piroxicam, sudoxicarn, and tenoxicam), propionic acid derivatives (e.g., alminoprofen, benoxaprofen, carprofen, fenbufen, fenoprofen, flurbiprofen, ibuprofen, indopropfen, ketoprofen, miroprofen, naproxen, oxaprozin, pirprofen, pranoprofen, suprofen, tiaprofenic and tioxaprofen), pyrazoles (e.g., azapropazone, feprazone, oxyphenbutazone, phenylbutazone and trimethazone), safapryn, solprin, trilisate.

"Partially Unsaturated": As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

"Penetration enhancer" and "pharmaceutically acceptable penetration enhancer": The term "penetration enhancer" and "pharmaceutically acceptable penetration enhancer" as used herein is a non-toxic agent that improves bioavailability of a topical composition. In some embodiments, a penetration enhancer is known to accelerate the delivery of a substance through the skin (e.g., disrupting the barrier function of the skin without compromising its barrier effects on microorganisms and toxins). Typically, a penetration enhancer is selected to be non-toxic to skin of the intended recipient (e.g., human). A penetration enhancer is also desirably compatible with any pharmaceutically active agent with which it is administered. Representative penetration enhancers include, for example, and without limitation, such agents as 1-substituted azacycloheptane-2-ones (e.g., 1-n-dodecyl-cyclazacycloheptan-2-one, available under the trademark Azone® from Whitby Research Incorporated, Richmond, Va.), dipolar-aprotic solvents (e.g., N,N-dimethylacetamide ("DMA"), decylmethylsulfoxide ("$C_{10}$ MSO"), dimethyl formamide ("DMF"), dimethylsulfoxide ("DMSO") and N-methyl-2-pyrrolidone ("NMP")), phospholipids (e.g., allantoin, fatty acid alcohols, lecithin, alcohols including glycerols such as polyethylene glycol monolaurate ("PGML"), glycerol monolaurate ("GML"), urazole, and the like). Penetration enhancer also can be a vegetable oil, such as, but not limited to, corn oil, cottonseed oil, safflower oil, and olive oil. Additional penetration enhancers generally can be found in Remington: The Science and Practice of Pharmacy, 20$^{th}$ ed. (Gennaro, A. R., et al., eds.) Lippincott Williams & Wilkins: Philadelphia (2000), which is incorporated herein by reference.

"pH adjusting agent": As used herein, the term "pH adjusting agent" as used herein is an agent that imparts suitable pH characteristics to compositions provided herein, (e.g., a substantially neutral pH), the pH of which depends on the specific utilization of the composition. In some embodiments, as the pH of skin is 5.5, it may be desireable to formulate compositions for topical skin application (to avoid irritation) having a pH value in a range of from about 4.0 to about 7.0, or in a range of from about 5.0 and 6.0, or about 5.5, or substantially 5.5. Suitable pH adjusting agents include, for example, but are not limited to, one or more adipic acids, buffers, citric acids, calcium hydroxides, glycines, magnesium aluminometasilicates, or combinations thereof.

"Pharmaceutically acceptable salt": The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 66: 1-19, 1977; incorporated herein by reference. Such salts can be prepared in situ during the final isolation and purification of the compounds of the invention, or separately (e.g., by reacting the free base functionality with a suitable organic or inorganic acid). Alternatively or additionally, salts may form during formulation of a compound. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

"Pharmaceutically acceptable ester": The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include formates, acetates, propionates, butyrates, acrylates, and ethylsuccinates. In certain embodiments, the esters are cleaved by enzymes such as esterases.

"Pharmaceutically acceptable prodrugs": The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Preservative": As used herein, the term "preservative" has its art-understood meaning and refers to an agent that protects against undesirable chemical modifications of one or more components in a composition (e.g., protection against an undesirable chemical modification of an active ingredient). Suitable preservatives for use in the compositions of the present invention include, but are not limited to, one or more alkanols, disodium EDTA, EDTA salts, EDTA fatty acid conjugates, isothioazolinone, parabens such as methylparaben and propylparaben, polypropylene glycols, sorbates, urea derivatives such as diazolindinyl urea, or combinations thereof.

"Propellant": As used herein, the term "propellant" refers to an agent that propels the delivery of a composition in, e.g., a vaporized, aerosol nebulized, or spray form. Propellants often are used in metered-dose inhalers for the treatment of asthma and other respiratory disorders and for systemic treatments such as insulin for diabetes. Propellants also are used, for example, in nasal inhalers for treatment of allergic rhinitis, topical sprays, oral sprays, and other aerosol applications. An example of such propellants, without limitation, are the Dymel® pharmaceutical propellants manufactured by DuPont™. (Wilmington, Del.).

"Protecting Group": One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis (4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1, 1,3,3-tetramethylbutyl)phenoxyacetate, 2,4-bis(1, 1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1, 1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzo suberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chloro salicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzene sulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide, phenyl urea, ethylurea and cyclopropyl sulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

"Protective": As used herein, the term "protective" refers to an agent that isolates exposed surface of skin or other membrane from harmful or annoying stimuli. Exemplary protectives include dusting powders, adsorbents, mechanical protective agents, and plasters. Mechanical protectives are generally either collodions or plasters, and include, for example aluminum hydroxide gel, collodium, dimethicone, petrolatum gauze, absorbable gelatin film, absorbable gelatin sponge, zinc gelatin, kaolin, lanolin, anhydrous lanolin, mineral oil, mineral oil emulsion, mineral oil light, olive oil, peanut oil, petrolatum, silicones, hydrocolloids and the like. In some embodiments, a protective includes an adherent, continuous film that may be flexible or semi-rigid depending on the materials and the formulations as well as the manner in which they are applied. In some embodiments, a "protective" may be a "demulscent" as described herein.

"Racemic": As used herein, a racemic mixture means about 50% of one enantiomer and about 50% of its corresponding enantiomer relative to all chiral centers in a molecule. Compounds of the present invention may encompass enantiomerically pure, enantiomerically enriched, and racemic mixtures.

"Rubefacient": As used herein, the term "rubefacient" is an agent that induces hyperemia, wherein hyperemia means an increased amount of blood in a body part or organ. Rubefaction, which is induced by rubefacients, results from increased circulation to an injured area and is accompanied by a feeling of comfort, warmth, itching and hyperesthesia.

"Sclerosant": As used herein, the term "sclerosant" is an agent (e.g., chemical irritant) that is injected into a vein in sclerotherapy. Exemplary sclerosants include laureth 9 and ethanolamine oleate, morrhuate sodium, sodium tetradecyl sulfate.

"Skin Irritant": As used herein, the term "skin irritant" refers to a compound that, when applied to skin or a skin equivalents, elicits a cellular response characterized by the expression of an "irritant responsive gene." Examples of known skin irritants include, but are not limited to, sodium dodecyl sulfate ("SDS"), calcipotriol, and trans-retinoic acid. The term "skin irritant" is also intended to encompass unknown or suspected irritants, including but not limited to, those containing in some pharmaceuticals, cosmetics, and consumer products.

"Small Molecule": As used herein, the term "small molecule" refers to an organic compound either synthesized in the laboratory or found in nature. Typically, a small molecule is characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, the inventive compounds incorporated herein.

"Solubilizing agent": As used herein, the term "solubilizing agent" are those substances that enable solutes to dissolve. Representative examples of solubilizing agents that are usable in the context of the present invention include, without limitation, complex-forming solubilizers (e.g., citric acid, ethylenediamine-tetraacetate, sodium meta-phosphate, succinic acid, urea, cyclodextrin, polyvinylpyrrolidone, diethylammonium-ortho-benzoate, etc.), n-alkyl amine n-oxides, micelle-forming solubilizers (e.g., TWEEN®, including TWEEN 80®), organic solvents (e.g., acetone, phospholipids and cyclodextrins), polyoxamers, polyoxyethylene n-alkyl ethers, and polyoxyethylene sorbitan fatty acid ester.

"Steroidal anti-inflammatory agent": As used herein, the term "steroidal anti-inflammatory agent", refers to any one of numerous compounds containing a 17-carbon 4-ring system and includes the sterols, various hormones (as anabolic steroids), and glycosides. Representative examples of steroidal anti-inflammatory drugs include, without limitation, cortico steroids such as alpha-methyl dexamethasone, amcinafel, amcinafide, beclomethasone dipropionates, beclomethasone dipropionate, betamethasone and the balance of its esters, chloroprednisone, chloroprednisone acetate, clescinolone, clobetasol valerate, clocortelone, cortisone, cortodoxone, desonide, desoxycorticosterone acetate, desoxymethasone, dexamethasone, dexamethasone-phosphate, dichlorisone, dichlorisone, diflorasone diacetate, diflucortolone valerate, difluorosone diacetate, diflurosone diacetate, diflurprednate, fluadrenolone, flucetonide, fluclorolone acetonide, flucloronide, flucortine butylesters, fludrocortisone, fludrocortisone, fludrocortisone, flumethasone pivalate, flunisolide, fluocinonide, fluocortolone, fluoromethalone, fluosinolone acetonide, fluperolone, fluprednidene (fluprednylidene) acetate, fluprednisolone, fluradrenolone acetonide, fluradrenolone, flurandrenolone, halcinonide, hydrocortamate, hydrocortisone acetate, hydrocortisone butyrate, hydrocortisone valerate, hydrocortisone cyclopentylpropionate, hydrocortisone, hydroxyltriamcinolone, medrysone, meprednisone, methylprednisolone, paramethasone, prednisolone, prednisone, triamcinolone acetonide, triamcinolone, and combinations thereof.

"Substituted": It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of inflammatory diseases and/or disorders, e.g., in the modulation of a G-protein signaling cascade.

Some examples of substituents of aliphatic and other moieties of compounds provided by the present invention include, but are not limited to aliphatic; heteroaliphatic; aryl (e.g., phenyl); heteroaryl; arylalkyl; heteroarylalkyl; alkoxy; aryloxy; arylthio, heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$;

—C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

"Stable": As used herein, the term "stable" preferably refers to the state of maintaining integrity of a compound over a period of time (e.g., during manufacture and/or storage).

"Substantially free of": As used herein, the term "substantially free of", when used to describe a material or compound, means that the material or compound lacks a significant or detectable amount of a designated substance. In some embodiments, the designated substance is present at a level not more than about 1%, 2%, 3%, 4% or 5% (w/w or v/v) of the material or compound.

"Surfactants": As used herein, the term "surfactant" is a surface-active substance, such as a detergent. Suitable surfactants for use with the inventive compositions include, but are not limited to, sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isothionates, glycerylether sulfonates, sulfosuccinates and combinations thereof. More particularly, an anionic surfactant is selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

"Sun screening agent": As used herein, a "sun screening agent" refers to an agent, when topically applied, absorbs or reflects some of the sun's ultraviolet radiation on skin exposed to sunlight, and therefore helps protect against sunburn. In some embodiments, a sun screening agent absorbed in the skin may lead to an increase in reactive oxygen species. Representative examples of sun screening agents usable in the present invention include, without limitation, p-aminobenzoic acid and its salts and derivatives thereof (p-dimethylaminobenzoic acid; ethyl, glyceryl, and isobutyl esters;); anthranilates (i.e., o-amino-benzoates; benzyl, cyclohexenyl, linalyl, menthyl, methyl, phenyl, phenylethyl, and terpinyl esters); benzophenones (i.e., hydroxy- or methoxy-substituted benzophenones such as benzoresorcinol, butylmethoxydibenzoylmethane, 2,2'-dihydroxy-4,4'-dimethoxybenzophenone, etocrylene, 4-isopropyldibenzoylmethane, dioxybenzone, 3-4'-methylbenzylidene-boman-2-one, octabenzone, octocrylene, oxybenzene, sulisobenzone, and 2,2',4,4'-tetrahydroxybenzophenone); (butyl carbotol) (6-propyl piperonyl) ether; cinnamic acid derivatives (alpha.-phenyl cinnamonitrile; butyl cinnamoyl pyruvate; benzyl and methyl esters); diazoles (2-acetyl-3-bromoindazole, aryl benzothiazoles, methyl naphthoxazole, and phenyl benzoxazole); dibenzylacetone; dihydroxycinnamic acid derivatives (methylaceto-umbelliferone, methylumbelliferone, umbelliferone); di-hydroxynaphthoic acid and its salts; hydrocarbons (diphenylbutadiene, and stilbene); hydroquinone; o- and p-hydroxybiphenyldisulfonates; coumarin derivatives (3-phenyl, 7-hydroxy, and 7-methyl,); naphtholsulfonates (sodium salts of 2-naphthol-3,6-disulfonic and of 2-naphthol-6,8-disulfonic acids); quinine salts (bisulfate, chloride, oleate, sulfate and tannate); quinoline derivatives (8-hydroxyquinoline salts, and 2-phenylquinoline); salicylates (amyl, benzyl, di-propylene glycol, glyceryl, menthyl, octyl, and phenyl esters); tannic acid and its derivatives (e.g., hexaethylether); trihydroxy-cinnamic acid derivatives (daphnetin, daphnin, esculetin, esculin, methylesculetin; and the glucosides); and uric and violuric acids; and combinations thereof.

"Thickeners": As used herein, the term "thickener" refers to agents that make a composition more dense or viscous in consistency. Suitable thickeners that can be used in the context of the present invention include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids, anionic polymers, and their alkali salts and mixtures thereof.

"Thio": As used herein, the term "thio" used alone or as part of a larger moiety as in "alkylthio", "arylthio", "heteroalkylthio", or "heteroarylthio" refers to replacement of an oxygen. For example, "alkylthio" refers to an alkyl group, as previously defined, attached to the parent molecule through a sulfur atom. Similarly, "arylthio" refers to an aryl group, as previously defined, attached to the parent molecule through a sulfur molecule. Similarly, "heteroalkylthio" refers to a heteroalkyl group, as previously defined, attached to the parent molecule through a sulfur molecule, etc.

"Treat," "treating" and "treatment": As used herein, the terms "treat," "treating" and "treatment," contemplate an action that occurs while a patient is suffering from or susceptible to a specified disease, disorder or condition, which delays onset of and/or reduces the frequency or severity of one or more symptoms or features of the disease disorder or condition. Thus, "treat", "treating", and "treatment" refer to any type of treatment that imparts a benefit to a subject afflicted with a disease, disorder or condition, including improvement in the condition of the subject (e.g., in one or more symptoms), delay in the progression of the disease, disorder or condition, prevention or delay of the onset of the disease, disorder or condition, etc.

Unit dosage form: The expression "unit dosage form" as used herein refers to a physically discrete unit of a provided formulation appropriate for the subject to be treated. It will be understood, however, that the total daily usage of provided formulation will be decided by the attending physician within the scope of sound medical judgment. The specific effective dose level for any particular subject or organism may depend upon a variety of factors including the disorder being treated and the severity of the disorder; activity of specific active agent employed; specific formulation employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts. In some embodiments, a unit dosage form contains an amount of a therapeutically active agent appropriate for use in a therapeutic regimen (i.e., in a regimen that delivers a therapeutically effective amount of an agent). In some embodiments, such a unit dosage form may be considered to contain a "therapeutically effective amount" of an agent even if a single dose would not be expected to be effective.

"Unsaturated": As used herein, the term "unsaturated" means that a moiety has one or more units of unsaturation.

"Vitamin": As used herein, the term "vitamin" refers to any of various organic substances essential in minute quantities to the nutrition of most animals act especially as coenzymes and precursors of coenzymes in the regulation of metabolic processes. Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

BRIEF DESCRIPTION OF THE DRAWING

FIG. 1 is a table depicting % inhibition determined from an edema assay, an erythema assay, and myeloperoxidase ("MPO") assay for compound A, compound B, compound C, compound D, compound E, compound F, compound G and AFC.

FIG. 2 is a table depicting $ED_{50}$ results (μg/ear) obtained for AFC, Compound A and Compound B using an edema assay, an erythema assay, and myeloperoxidase ("MPO") assay, as described infra.

FIG. 3 is a table summarizing activity ranges determined from an MPO activity assay for exemplary compounds in Table 1.

DETAILED DESCRIPTION OF CERTAIN EMBODIMENTS

1. Description of Exemplary Compounds

Figures 4A, 4B:
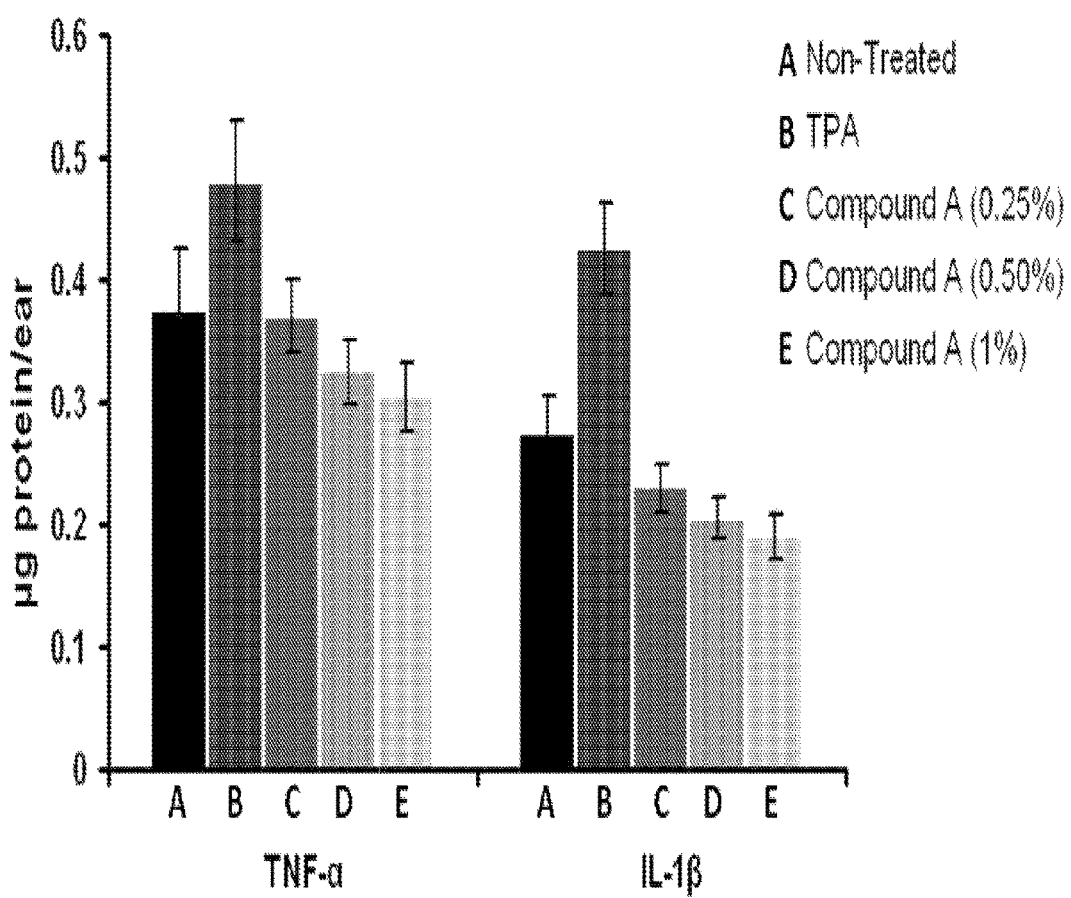
FIG. 4A and FIG. 4B are bar graphs depicting $ED_{50}$ results (μg/ear) obtained for Compound A, demonstrating that administering Compound A at 0.25%, 0.50% and 1.0% dosage levels results in an inhibition in TNF-α (FIG. 4A panel) and IL-1β (FIG. 4B panel) levels, as determined using a TPA mouse ear inflammation model.

Compounds provided by the present invention include those described generally above, and are further illustrated by all classes, subclasses and species of each of these compounds disclosed herein.

According to one aspect, the present invention provides compounds of Formula:

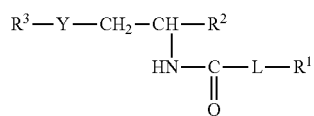

or a pharmaceutically acceptable salt thereof, wherein:

L is a bivalent, branched or unbranched, saturated or unsaturated, $C_2$-$C_6$ hydrocarbon chain wherein one or more methylene units of L is independently replaced by —O—, —S—, —NH—, —C(O)—, —C(=$CH_2$)—, or $C_3$-$C_6$ cycloalkylene, wherein L is optionally substituted by one or more groups selected from halogen, phenyl, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, or a 5-to 7-membered monocyclic or 7-10 membered bicyclic heterocyclyl ring having 1-2 heteroatoms independently selected from nitrogen, oxygen, or sulfur;

$R^1$ is hydrogen, —OH or —OR, wherein each R is independently hydrogen, an optionally substituted group selected from $C_{1-6}$ aliphatic or $C_{1-6}$ heteroaliphatic, —NHR, —NH(OR), —$ONH_2$, or —$NR_2$;

$R^2$ is —C(O)X, wherein X is independently R, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted group selected from $C_{1-6}$ aliphatic or $C_{1-6}$ heteroaliphatic;

$R^3$ is a substituted or unsubstituted, branched or unbranched, saturated or unsaturated, $C_{10}$-$C_{25}$ aliphatic; and Y is —O—, —N—, —S—, —Se—, —S(O)—, —S(=N)—, —$SO_2$—, —Se(O)—, or —Se(O)$_2$—.

In some embodiments, compounds of the above-described Formula are provided with the proviso that L and R¹ cannot together be $C_1$-$C_3$ unsubstituted non-halogenated alkyl.

In some embodiments, the present invention provides a compound of Formula I':

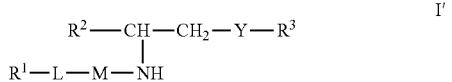

I' or a pharmaceutically acceptable salt thereof, wherein:

L is a bivalent, branched or unbranched, saturated or unsaturated, $C_2$-$C_6$ hydrocarbon chain wherein one or more methylene units of L is independently replaced by —O—, —S—, —NH—, —C(O)—, —CF$_2$—, —C(=CH$_2$)—, —CH=CH—, or an optionally substituted arylene, heteroarylene, $C_3$-$C_6$ cycloalkylene, $C_3$-$C_6$ heterocycloalkylene, or an 8-10-membered bicyclic heterocyclic moiety, and wherein L is optionally substituted by one or more groups selected from halogen, $C_1$-$C_6$ alkyl, phenyl, biphenyl, -benzyl, —CH$_2$-phenol, —CH(phenyl)$_2$, —OH, —NH$_2$, —NHC(O)CH$_3$, —NHC(O)NHCH$_2$CH$_3$, —C(O)NH$_2$, —C(O)NHCH$_2$CH$_3$, —CH$_2$C(O)OCH$_2$phenyl, —(CH$_2$)$_2$SCH$_3$, —(CH$_2$)$_2$C(O)NH$_2$, —(CH$_2$)$_2$C(O)OH, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5-to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur;

M is —C(O)—, —C(S)—, or —SO$_2$—;

R¹ is hydrogen, F, CF$_3$, $C_1$-$C_4$ alkyl, —OH, —C(O)CH$_3$, —NH(OR), —NR$_2$, —NHNR$_2$, —SO$_2$R, —NH-phenyl, —SO$_2$-phenyl, -phenyl-NO$_2$, or —OR, wherein each R is independently hydrogen, oxygen, or an optionally substituted group selected from $C_{1-6}$ aliphatic or $C_{1-6}$ heteroaliphatic;

R² is —C(O)X, wherein X is independently R, —C(O)NHNH$_2$, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted group selected from $C_{1-6}$ aliphatic or $C_{1-6}$ heteroaliphatic; and R³ is a substituted or unsubstituted, branched or unbranched, saturated or unsaturated, $C_{10}$-$C_{25}$ aliphatic; and Y is —O—, —N—, —S—, —Se—, —S(O)—, —S(=N)—, —SO$_2$—, —Se(O)—, or —Se(O)$_2$—.

In some embodiments, compounds of Formula I' are provided with the proviso that L and R¹ cannot together be $C_1$-$C_3$ unsubstituted non-halogenated alkyl.

According to one aspect, the present invention provides compounds of Formula I,

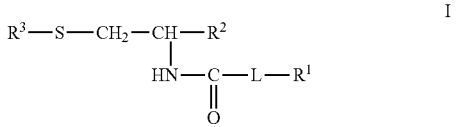

I or a pharmaceutically acceptable salt thereof, wherein:

L is a bivalent, branched or unbranched, saturated or unsaturated, $C_2$-$C_6$ hydrocarbon chain wherein one or more methylene units of L is independently replaced by —O—, —S—, —NH—, —C(O)—, —C(=CH$_2$)—, or $C_3$-$C_6$ cycloalkylene, wherein L is optionally substituted by one or more groups selected from halogen, phenyl, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, or a 5-to 7-membered monocyclic or 7-10 membered bicyclic heterocyclyl ring having 1-2 heteroatoms independently selected from nitrogen, oxygen, or sulfur;

R¹ is hydrogen, —OH or —OR, wherein each R is independently hydrogen or an optionally substituted group selected from $C_{1-6}$ aliphatic or $C_{1-6}$ heteroaliphatic;

R² is —C(O)X, wherein X is independently R, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted group selected from $C_{1-6}$ aliphatic or $C_{1-6}$ heteroaliphatic; and R³ is a substituted or unsubstituted, branched or unbranched, saturated or unsaturated, $C_{10}$-$C_{25}$ aliphatic.

According to another aspect, the present invention provides compounds of Formula I,

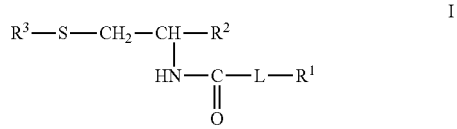

I or a pharmaceutically acceptable salt thereof, wherein:

L is a bivalent, branched or unbranched, saturated or unsaturated, $C_2$-$C_6$ hydrocarbon chain wherein one or more methylene units of L is independently replaced by —O—, —S—, —NH—, —C(O)—, —C(=CH$_2$)—, or $C_3$-$C_6$ cycloalkylene, wherein L is optionally substituted by one or more groups selected from halogen, phenyl, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5-to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur;

R¹ is hydrogen, —OH or —OR, wherein each R is independently hydrogen or an optionally substituted group selected from $C_{1-6}$ aliphatic or $C_{1-6}$ heteroaliphatic;

R² is —C(O)X, wherein X is independently R, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted $C_{1-6}$ aliphatic; and R³ is a substituted or unsubstituted, branched or unbranched, saturated or unsaturated, $C_{10}$-$C_{25}$ aliphatic.

In certain embodiments, the present invention provides a compound of Formula Ia,

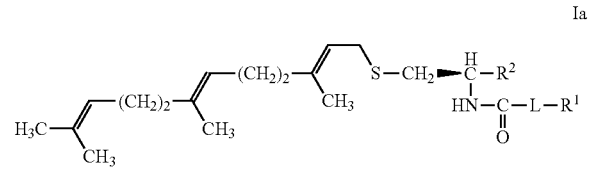

or a pharmaceutically acceptable salt thereof, wherein:

L is a bivalent, branched or unbranched, saturated or unsaturated, $C_2$-$C_6$ hydrocarbon chain wherein one or more methylene units of L is independently replaced by —O—, —S—, —NH—, C(O)—, —C(=CH$_2$)—, or $C_3$-$C_6$ cycloalkylene, wherein L is optionally substituted by one or more groups selected from halogen, phenyl, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5- to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur;

$R^1$ is hydrogen, —OH or —OR, wherein each R is independently hydrogen or an optionally substituted group selected from $C_{1-6}$ aliphatic or $C_{1-6}$ heteroaliphatic; and $R^2$ is —C(O)X, wherein X is independently R, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted group selected from $C_{1-6}$ aliphatic or $C_{1-6}$ heteroaliphatic.

As defined generally above, the L group of Formulae I, and/or I' is a bivalent, branched or unbranched, saturated or unsaturated, $C_2$-$C_6$ hydrocarbon chain wherein one or more methylene units of L is independently replaced by —O—, —S—, —NH—, —C(O)—, —CF$_2$—, —C(=CH$_2$)—, —CH=CH—, or an optionally substituted arylene, heteroarylene, $C_3$-$C_6$ cycloalkylene, $C_3$-$C_6$ heterocycloalkylene, or an 8-10-membered bicyclic heterocyclic moiety, and wherein L is optionally substituted by one or more groups selected from halogen, $C_1$-$C_6$ alkyl, phenyl, biphenyl, -benzyl, —CH$_2$-phenol, —CH(phenyl)$_2$, —OH, —NH$_2$, —NHC(O)CH$_3$, —NHC(O)NHCH$_2$CH$_3$, —C(O)NH$_2$, —C(O)NHCH$_2$CH$_3$, —CH$_2$C(O)OCH$_2$phenyl, —(CH$_2$)$_2$SCH$_3$, —(CH$_2$)$_2$C(O)NH$_2$, —(CH$_2$)$_2$C(O)OH, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5- to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur.

Particular embodiments of different moieties/groups included in compounds of the present invention are discussed in more detail below. Those of ordinary skill in the art will appreciate that, unless otherwise indicated, each embodiment of each individual moiety or group may be independently combined with each embodiment of each other individual moiety or group in compounds of the present invention.

1. L Group Embodiments

In certain embodiments, L is a bivalent, branched or unbranched, saturated or unsaturated, $C_{2-6}$ hydrocarbon chain wherein methylene unit(s) of L is/are are independently replaced by —O—, —S—, —NH—, —C(O)—, —CF$_2$—, —C(=CH$_2$)—, —CH=CH—, or an optionally substituted arylene, heteroarylene, $C_3$-$C_6$ cycloalkylene, $C_3$-$C_6$ heterocycloalkylene, or an 8-10-membered bicyclic heterocyclic moiety, and wherein L is optionally substituted by one or more groups selected from halogen, $C_1$-$C_6$ alkyl, phenyl, —CH$_2$(phenyl), —CH$_2$-phenol, —CH(phenyl)$_2$, —NH$_2$, —NHC(O)CH$_3$, —NHC(O)NHCH$_2$CH$_3$, —C(O)NH$_2$, —C(O)NHCH$_2$CH$_3$, —CH$_2$C(O)OCH$_2$phenyl, —(CH$_2$)$_2$SCH$_3$, —(CH$_2$)$_2$C(O)NH$_2$, —(CH$_2$)$_2$C(O)OH, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5- to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur.

One skilled in the art will appreciate that any number of individual methylene units within $C_{2-6}$ hydrocarbon chains may be replaced, as appropriate, by individual moietie(s) according to the present invention. One skilled in the art will also appreciate that such individual moieties, relative to one another, may be present in any combination or subcombination within $C_{2-6}$ hydrocarbon chains.

Exemplary L groups with varied numbers of moieties replacing individual methylene units within a $C_2$, $C_3$, $C_4$, $C_5$, or $C_6$ hydrocarbon chain, and various combinations and subcombinations thereof, are described below.

(i) $C_2$ Hydrocarbon L Groups

In certain embodiments, L is a bivalent, branched or unbranched, saturated or unsaturated, $C_2$ hydrocarbon chain wherein one or more methylene units of L is independently replaced by —O—, —S—, —NH—, —C(O)—, —CF$_2$—, —C(=CH$_2$)—, —CH=CH—, or an optionally substituted arylene, heteroarylene, $C_3$-$C_6$ cycloalkylene, $C_3$-$C_6$ heterocycloalkylene, or an 8-10-membered bicyclic heterocyclic moiety.

In certain embodiments, L is selected from a bivalent, branched or unbranched, saturated or unsaturated, $C_2$ hydrocarbon chain wherein one or more methylene units of L is independently replaced by —NH—, —O—, —C(O)—, —CH=CH—, $C_3$-$C_6$ cycloalkylene, $C_3$-$C_6$ heterocycloalkylene, 8-10-membered bicyclic heterocyclic moiety, an optionally substituted arylene and optionally substituted heteroarylene, and wherein L is optionally substituted by one or more groups selected from halogen, substituted or unsubstituted $C_1$-$C_6$ alkyl, and —NHC(O)CH$_3$.

In certain embodiments, L is a bivalent, branched or unbranched, saturated or unsaturated, $C_2$ hydrocarbon chain wherein one methylene unit is replaced by —NH—. In certain embodiments, the L group is —NH(CH$_3$)—. In certain embodiments, L is a $C_2$ hydrocarbon chain wherein one methylene unit of L is replaced by —NH— and further substituted by —CH$_3$. In certain embodiments, the L group is —N(CH$_3$)CH$_2$—. In certain embodiments, L is a $C_2$ hydrocarbon chain wherein one methylene unit of L is substituted. In certain embodiments, a methylene unit of L is substituted with —NHC(O)CH$_3$. In certain embodiments, the L group is —CH[NHC(O)CH₃]CH₂—. In certain embodiments, L is a C₂ hydrocarbon chain wherein one methylene unit of L is replaced by —O—. In certain embodiments, the L group is —OCH₂—. In certain embodiments, L is a C₂ hydrocarbon chain wherein one methylene unit of L is replaced by —C(O)—. In certain embodiments, the L group is —CH₂C(O)—. In certain embodiments, L is a C₂ hydrocarbon chain wherein one methylene unit of L is replaced by —O— and one methylene unit of L is replaced by —C(O)—. In certain embodiments, the L group is —OC(O)—. In certain embodiments, the methylene unit —NH— is substituted. In certain embodiments, the —NH— is optionally substituted. In certain embodiments, the —NH— is substituted with —CH₃, to form —N(CH₃)—. In certain embodiments, L is a C₂ hydrocarbon chain wherein one methylene unit of L is replaced by —N(CH₃)—. In certain embodiments, the L group is —CH₂N(CH₃)—. In certain embodiments, L is a C₂ hydrocarbon chain containing a —CH=CH— moiety. In certain embodiments, L is —CH=CH—. In certain embodiments, L is a C₂ hydrocarbon chain wherein one methylene unit of L is replaced by a C₃-C₆ cycloalkylene. In certain embodiments, L is a C₂ hydrocarbon chain wherein one methylene unit of L is replaced by a —C(O)— and one methylene unit is replaced by a C₃-C₆ cycloalkylene. In certain embodiments, the C₃-C₆ cycloalkylene is a C₃ cycloalkylene. In certain embodiments, the L group is

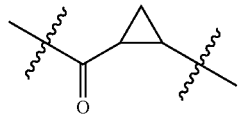

In certain embodiments, the L group is

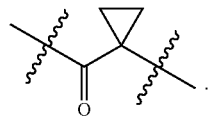 [SMILES: *C(=O)C1(*)CC1]

In certain embodiments, the C₃-C₆ cycloalkylene is a C₄ cycloalkylene. In certain embodiments, the C₃-C₆ cycloalkylene is a C₅ cycloalkylene. In certain embodiments, the C₃-C₆ cycloalkylene is a C₆ cycloalkylene. In certain embodiments, the L group is

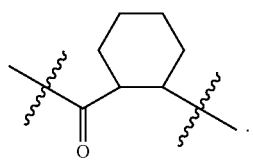 [SMILES: *C(=O)C1CCCCC1*]

In certain embodiments, L is a bivalent, branched or unbranched, saturated or unsaturated, C₂ hydrocarbon chain wherein one methylene unit is replaced by —C(O)— and one methylene unit is replaced by a C₃-C₆ heterocycloalkylene. In certain embodiments, the L group is

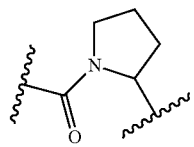

In certain embodiments, L is a C₂ hydrocarbon chain wherein one methylene unit of L is replaced by a 10-membered bicyclic heterocyclic moiety. In certain embodiments, the 10-membered bicyclic heterocyclic moiety has one heteroatom. In certain embodiments, the heteroatom is nitrogen. In certain embodiments, the L group is

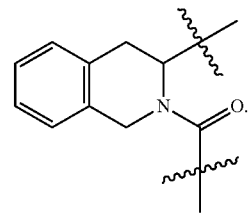 [SMILES: *C(=O)N1Cc2ccccc2CC1*]

In certain embodiments, L is a C₂ hydrocarbon chain wherein one methylene unit of L is replaced by an optionally substituted arylene. In certain embodiments, the L group is

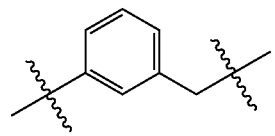

In certain embodiments, L is a C₂ hydrocarbon chain wherein one methylene unit of L is replaced by an optionally substituted arylene and one unit of L is replaced by —NH—. In certain embodiments, the L group is

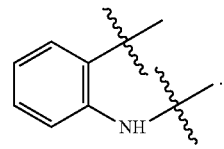 [SMILES: *Nc1ccccc1*]

In certain embodiments, L is a C₂ hydrocarbon chain wherein one methylene unit of L is replaced by an optionally substituted arylene and one unit of L is replaced by —C(O)—. In certain embodiments, the L group is

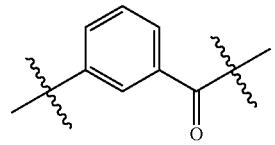

In certain embodiments, the arylene is substituted. In certain embodiments, the arylene is a hydroxy-substituted phenylene. In certain embodiments, the L group is

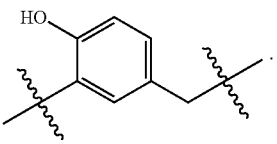 [SMILES: *Cc1ccc(O)c(*)c1]

In certain embodiments, L is a C$_2$ hydrocarbon chain wherein one methylene unit of L is replaced by an optionally substituted heteroarylene. In certain embodiments, the heteroarylene is thiophenyl. In certain embodiments, the heteroarylene is furanyl. In certain embodiments, the heteroarylene is indolyl. In certain embodiments, the L group is

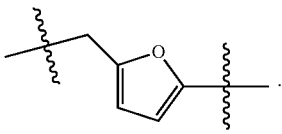

In certain embodiments, the L group is

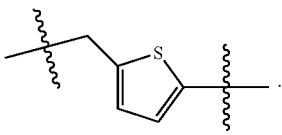 [SMILES: *Cc1ccc(*)o1]

In certain embodiments, the L group is

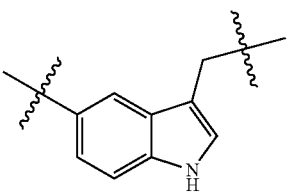

In certain embodiments, L is a C$_2$ hydrocarbon chain wherein one methylene unit of L is replaced by —NH—. In certain embodiments, the L group is —CH$_2$NH—. In certain embodiments, the L group is —(CH$_2$)$_2$NO$_2$ and no R$^1$ group is present.

(ii) C$_3$ Hydrocarbon L Groups

In certain embodiments, L is a bivalent, branched or unbranched, saturated or unsaturated, C$_3$ hydrocarbon chain wherein one or more methylene units of L is independently replaced by —O—, —S—, —NH—, —C(O)—, —CF$_2$—, —C(=CH$_2$)—, —CH=CH—, or an optionally substituted arylene, heteroarylene, C$_3$-C$_6$ cycloalkylene, C$_3$-C$_6$ heterocycloalkylene, or an 8-10-membered bicyclic heterocyclic moiety.

In certain embodiments, L is selected from a bivalent, branched or unbranched, saturated or unsaturated, C$_3$ hydrocarbon chain wherein one or more methylene units of L is independently replaced by —NH—, —O—, —C(O)—, —CF$_2$—, —C(=CH$_2$)—, —CH=CH—, C$_3$-C$_6$ cycloalkylene, 8-10-membered bicyclic heterocyclic moiety, an optionally substituted arylene and optionally substituted heteroarylene, and wherein L is optionally substituted by one or more groups selected from halogen, substituted or unsubstituted C$_1$-C$_6$ alkyl, -phenyl, —CH(phenyl)$_2$, —CH$_2$(phenyl), —NHC(O)CH$_3$, and NHC(O)NHCH$_2$CH$_3$.

In certain embodiments, L is a C$_3$ hydrocarbon chain wherein one methylene unit of L is replaced by —C(O)—. In certain embodiments, the L group is —CH$_2$CH$_2$C(O)—. In certain embodiments, L is a C$_3$ hydrocarbon chain wherein one methylene unit of L is replaced by —C(O)— and one methylene unit is replaced by —NH—. In certain embodiments, the L group is —C(O)CH$_2$NH—. In certain embodiments, the L group is —CH$_2$NHC(O)—. In certain embodiments, L is a C$_3$ hydrocarbon chain wherein one methylene unit of L is replaced by —C(O)—, one methylene unit is replaced by —NH— and one methylene unit is substituted by C$_{1-6}$ alkyl. In certain embodiments, the L group is —CH[(CH$_2$)$_3$CH$_3$]NHC(O)—. In certain embodiments, L is a C$_3$ hydrocarbon chain wherein one methylene unit of L is replaced by —C(O)— and one methylene unit is replaced by —O—. In certain embodiments, the L group is —CH$_2$OC(O)—. In certain embodiments, L is a C$_3$ hydrocarbon chain wherein one methylene unit of L is replaced by —C(O)—, one methylene unit is replaced by —NH— and one methylene is optionally substituted by —CH$_3$, —(CH$_3$)(CH$_3$) (i.e., dimethyl) or —CH$_2$CH$_3$. In certain embodiments, the L group is —C(O)NHC(CH$_3$)—. In certain embodiments, the L group is —C(O)NHCH (CH$_2$CH$_3$)—. In certain embodiments, the L group is —C(O)NHCH[CH$_2$CH(CH$_3$)(CH$_3$)]—. In certain embodiments, L is a C$_3$ hydrocarbon chain wherein one methylene unit of L is replaced by —C(O)— and one or two methylene units are optionally substituted by —CH$_3$. In certain embodiments, the L group is —CH$_2$CH(CH$_3$)C(O)—. In certain embodiments, the L group is —CH(CH$_3$)CH$_2$C(O)—. In certain embodiments, the L group is —CH(CH$_3$)CH(CH$_3$)C(O)—. In certain embodiments, L is a C$_3$ hydrocarbon chain wherein one methylene unit of L is replaced by —C(O)— and one methylene is optionally substituted by —(CH$_3$)(CH$_3$) (i.e., dimethyl). In certain embodiments, the L group is —CH$_2$C[(CH$_3$)(CH$_3$)]C(O)— (i.e., a C$_3$ hydrocarbon chain containing a 3,3-dimethyl substituted methylene). In certain embodiments, the L group is —C[(CH$_3$)(CH$_3$)]CH$_2$C(O)— (i.e., a C$_3$ hydrocarbon chain containing a 2,2-dimethyl substituted methylene). In certain embodiments, L is a C$_3$ hydrocarbon chain wherein one methylene unit of L is replaced by —C(O)— and one methylene is optionally substituted by —NHC(O)(CH$_3$). In certain embodiments, the L group is —CH$_2$CH[NHC(O)CH$_3$]C(O)—. In certain embodiments, L is a C$_3$ hydrocarbon chain wherein one methylene unit of L is replaced by —C(O)—, one methylene unit is replaced by —NH— and one methylene is optionally substituted by —CH(CH$_3$)$_2$. In certain embodiments, the L group is —C(O)NHCH[CH(CH$_3$)(CH$_3$)]—. In certain embodiments, the L group is —C(O)NHCH$_2$—. In certain embodiments, L is a C$_3$ hydrocarbon chain wherein one methylene unit of L is replaced by —C(O)—, one methylene unit is replaced by —O—. In certain embodiments, the L group is —CH$_2$OC (O)—. In certain embodiments, L is a C$_3$ hydrocarbon chain wherein one or two methylene units of L are replaced by —C(O)—. In certain embodiments, the L group is —CH$_2$CH$_2$C(O)—. In certain embodiments, the L group is —C(O)CH$_2$C(O)—. In certain embodiments, L is a C$_3$ hydrocarbon chain wherein one methylene unit of L is replaced by —NH—. In certain embodiments, the L group is —CH$_2$CH$_2$NH—. In certain embodiments, L is a C$_3$ hydrocarbon chain wherein one methylene unit of L is replaced by —O—. In certain embodiments, the L group is —CH₂OCH₂—. In certain embodiments, L is a C₃ hydrocarbon chain wherein one methylene unit of L is replaced by —C(=CH₂)—. In certain embodiments, L is a C₃ hydrocarbon chain wherein one methylene unit of L is replaced by —C(=CH₂)— and one methylene unit is replaced by —C(O)—. One of ordinary skill in the art will recognize that such a —C(=CH₂)— may exist within the hydrocarbon chain backbone or may be "exo" to the backbone chain thus forming and alkylidene group. By way of example, such an L group having a —C=CH₂— within the hydrocarbon chain includes —CH=CHC(O)— or —CH=CHC(O)O—. By way of example, such an L group having a substituted —C=CH₂— within the hydrocarbon chain includes —CH=C(CH₃)C(O)—, —CH=C(phenyl)-C(O)—. and —CH=CHCF₂. By way of example, such an L group having an alkylidene branched chain includes —CH₂C(=CH₂)C(O)—. In certain embodiments, L is a C₃ hydrocarbon chain wherein one methylene unit of L is replaced by —C(O)— and one methylene unit is substituted by phenyl. In certain embodiments, the L group is —CH₂CH(phenyl)C(O)—. In certain embodiments, the L group is —CH(phenyl)CH₂C(O)—. In certain embodiments, L is a C₃ hydrocarbon chain wherein one methylene unit of L is replaced by —C(O)— and one methylene unit is substituted by —NHC(O)NHCH₂CH₃. In certain embodiments, the L group is —CH₂CH[NHC(O)NHCH₂CH₃]C(O)—. In certain embodiments, L is a C₃ hydrocarbon chain wherein one methylene unit of L is replaced by —C(O)—, one methylene unit is replaced by —NH— and one methylene unit is substituted by phenyl or —CH(phenyl)₂. In certain embodiments, the L group is —C(O)NHCH(phenyl)-. In certain embodiments, the L group is —C(O)NHCH[CH(phenyl)₂]—. In certain embodiments, L is a C₃ hydrocarbon chain wherein one methylene unit of L is replaced by —C(O)—, one methylene unit is replaced by —NH—, and one methylene unit is substituted by benzyl. In certain embodiments, the L group is —C(O)NHCH[CH₂(phenyl)]-. In certain embodiments, L is a C₃ hydrocarbon chain wherein one methylene unit of L is replaced by —CF₂—. In certain embodiments, the L group is —(CH₂)₂CF₂—. In certain embodiments, L is a C₃ hydrocarbon chain wherein one methylene unit of L is replaced by a C₃-C₆ cycloalkylene. In certain embodiments, the L group is

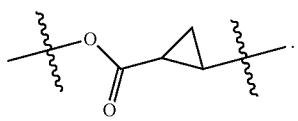 [SMILES: *OC(=O)C1CC1* ; "."]

In certain embodiments, L is a C₃ hydrocarbon chain wherein one methylene unit of L is replaced by —C(O)—, one methylene unit is replaced by —NH— and one methylene unit is replaced by a C₃-C₆ cycloalkylene. In certain embodiments, the L group is

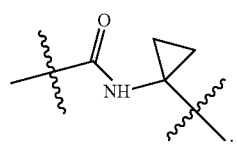 [SMILES: *C(=O)NC1(*)CC1 ; "."]

In certain embodiments, L is a C₃ hydrocarbon chain wherein one methylene unit of L is replace by —C(O)—, one methylene unit is replaced by —NH— and one methylene unit is further substituted with a C₃-C₆ alkyl group. In certain embodiments, the C₃-C₆ alkyl group is C₃-C₆ cycloalkyl. In certain embodiments, the L group is

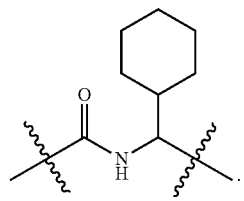 [SMILES: *C(=O)NC(*)C1CCCCC1 ; "."]

In certain embodiments, L is a C₃ hydrocarbon chain wherein one methylene unit of L is replaced by an optionally substituted arylene. In certain embodiments, L is a C₃ hydrocarbon chain wherein one methylene unit of L is replaced by —O— and one methylene unit is replaced by an optionally substituted arylene. In certain embodiments, the arylene is phenylene. In certain embodiments, the L group is

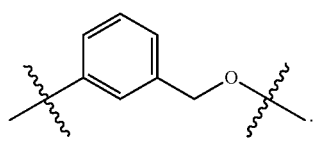 [SMILES: *OCc1cccc(*)c1 ; "."]

In certain embodiments, the arylene is a substituted. In certain embodiments, the arylene is a hydroxy-substituted phenylene. In certain embodiments, the L group is

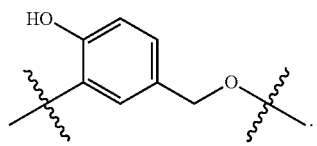 [SMILES: *OCc1ccc(O)c(*)c1 ; "."]

In certain embodiments, L is a C₃ hydrocarbon chain wherein one methylene unit of L is replaced by an optionally substituted heteroarylene. In certain embodiments, the heteroarylene is thiophenyl. In certain embodiments, the heteroarylene is furanyl. In certain embodiments, the heteroarylene is indolyl. In certain embodiments, the L group is

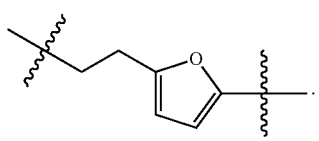 [SMILES: *CCc1ccc(*)o1 ; "."]

In certain embodiments, the L group is

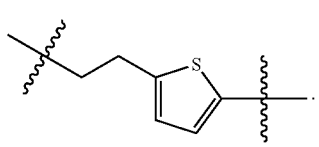 [SMILES: *CCc1ccc(*)s1 ; "."]

In certain embodiments, the L group is

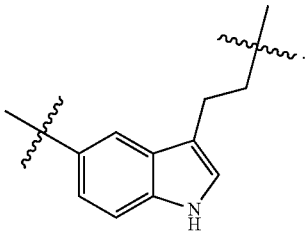 [SMILES: *CCc1c[nH]c2ccc(*)cc12 ; "."]

In certain embodiments, the L group is

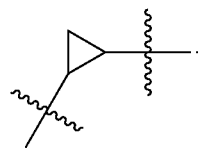 [SMILES: *C1CC1* ; "."]

(iv) C₄ Hydrocarbon L Groups

In certain embodiments, L is a bivalent, branched or unbranched, saturated or unsaturated, C₄ hydrocarbon chain wherein one or more methylene units of L is independently replaced by —O—, —S—, —NH—, —C(O)—, —CF₂—, —C(=CH₂)—, —CH=CH—, or an optionally substituted arylene, heteroarylene, C₃-C₆ cycloalkylene, C₃-C₆ heterocycloalkylene, or an 8-10-membered bicyclic heterocyclic moiety.

In certain embodiments, L is selected from a bivalent, branched or unbranched, saturated or unsaturated, C₄ hydrocarbon chain wherein one or more methylene units of L is independently replaced by —NH—, —O—, —C(O)—, —C(=CH₂)—, —CH=CH—, C₃-C₆ cycloalkylene, 8-10-membered bicyclic heterocyclic moiety, an optionally substituted arylene and optionally substituted heteroarylene, and wherein L is optionally substituted by one or more groups selected from halogen, and substituted or unsubstituted C₁-C₆ alkyl.

In certain embodiments, L is a bivalent, branched or unbranched, saturated or unsaturated C₄ hydrocarbon chain wherein one or more methylene units of L is independently replaced by —NH—, —C(O)—, or a C₃-C₆ cycloalkylene. In certain embodiments, L is a C₄ hydrocarbon chain wherein one methylene unit of L is replaced by —C(O)—. In certain embodiments, L is —CH₂CH₂CH₂C(O)—. In certain embodiments, L is —CH(CH₃)CH₂C(O)—. In certain embodiments, L is a C₄ hydrocarbon chain wherein two methylene units of L are replaced by —C(O)—. In certain embodiments, the L group is —C(O)CH₂CH₂C(O)—. In certain embodiments, the L group is —C(O)CH₂CH(CH₃)—. In certain embodiments, the L group is —C(O)CH(CH₃)CH₂—. In certain embodiments, the L group is. In certain embodiments, L is a C₄ hydrocarbon chain wherein one methylene unit of L is replaced by —C(O)—, one methylene unit is replaced by —NH— and one methylene unit is substituted by —NH₂. In certain embodiments, the L group is —(CH₂)₂C(O)NH—. In certain embodiments, L is a C₄ hydrocarbon chain wherein one methylene unit of L is replaced by a C₃-C₆ cycloalkylene. In certain embodiments, L is

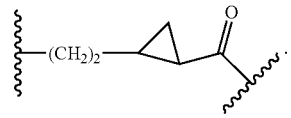

In certain embodiments, L is a C₄ hydrocarbon chain wherein one methylene unit of L is replaced by an —O—, one methylene unit of L is replaced by a C₃-C₆ cycloalkylene wherein the C₃-C₆ cycloalkylene is further substituted by a C₁-C₆ alkyl group. In certain embodiments, the L group is

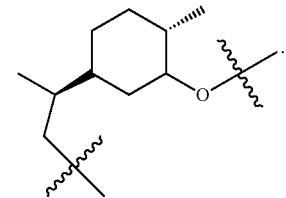 [SMILES: *C[C@@H](C)C1CC[C@H](C)C(O*)C1 ; "."]

In certain embodiments, L is a C₄ hydrocarbon chain wherein one methylene unit of L is replaced by —C(O)— and wherein L is substituted by an 8-10 membered bicyclic heteroaryl ring having 1-4 heteroatoms. Exemplary such rings include 1,3-dioxoisoindolinyl. In certain embodiments, the L group is

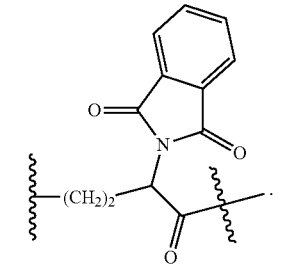

In certain embodiments, L is a C₄ hydrocarbon chain wherein one methylene unit of L is replaced by —C(O)— and one methylene unit is replaced by —NH—. In certain embodiments, L is —NH(CH₂)₂C(O)—. In certain embodiments, the L group is —C(O)NH(CH₂)₂—. In certain embodiments, the L group is —NHC(O)(CH₂)₂—. In certain embodiments, L is a C₄ hydrocarbon chain wherein one methylene unit of L is replaced by —C(O)—, one methylene unit is replaced by —NH—, and one methylene is substituted by —OH. In certain embodiments, the L group is —C(O)NHCH[CH₂(OH)]—. In certain embodiments, L is a C₄ hydrocarbon chain wherein one methylene unit of L is replaced by —C(O)—, one methylene unit is replaced by —NH— and one methylene unit is substituted by —CH₃, —CH₂CH₃, —(CH₂)₃CH₃, —(CH₃)₂, —CH[(CH₃)(CH₃)], —CH₂CH[(CH₃)(CH₃)] or

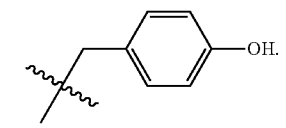 [SMILES: *Cc1ccc(O)cc1]

In certain embodiments, the L group is —CH₂C(O)NHCH (CH₃)—. In certain embodiments, the L group is —CH₂C(O)NHCH[CH(CH₃)(CH₃)]—. In certain embodiments, the L group is —CH₂C(O)NHCH(CH₂CH₃)—. In certain embodiments, the L group is —CH₂C(O)NHCH[CH₂CH (CH₃)(CH₃)]—. In certain embodiments, the L group is

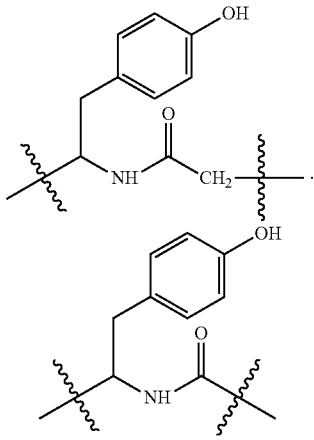

In certain embodiments, L is —CH[(CH₂)₃CH₃]NHC(O)CH₂—. In certain embodiments, L is a C₄ hydrocarbon chain wherein one methylene unit of L is replaced by —C(O)— and one methylene unit is replaced by —O—. In certain embodiments, L is —C(O)O(CH₂)₂—. In certain embodiments, the C₄ hydrocarbon chain is an alkenylene. In certain embodiments, L is —CH=CHC(O)NH—. In certain embodiments, L is a C₄ hydrocarbon chain wherein one methylene unit of L is replaced by an optionally substituted arylene. In certain embodiments, the arylene is phenylene. In certain embodiments, the arylene is a substituted. In certain embodiments, the arylene is a substituted phenylene. In (v) C₅ Hydrocarbon L Groups In certain embodiments, L is a bivalent, branched or unbranched, saturated or unsaturated, C₅ hydrocarbon chain wherein one or more methylene units of L is independently replaced by —O—, —S—, —NH—, —C(O)—, —CF₂—, —C(=CH₂)—, —CH=CH—, or an optionally substituted arylene, heteroarylene, C₃-C₆ cycloalkylene, C₃-C₆ heterocycloalkylene, or an 8-10-membered bicyclic heterocyclic moiety.

In certain embodiments, L is a bivalent, branched or unbranched, saturated or unsaturated, C₅ hydrocarbon chain wherein one or more methylene units of L is independently replaced by —NH—, —O—, —C(O)—, and an optionally substituted arylene, and wherein L is optionally substituted by one or more groups selected from substituted or unsubstituted C₁-C₆ alkyl, and —CH₂C(O)OH.

In certain embodiments, L is a C₅ hydrocarbon chain wherein one methylene unit of L is replaced by —C(O)—. In certain embodiments, the L group is —CH(CH₃)CH (CH₃)C(O)—. In certain embodiments, the L group is —CH₂C[(CH₃)(CH₃)]C(O)—. In certain embodiments, the L group is —C[(CH₃)(CH₃)]CH₂C(O)—. In certain embodiments, L is a C₅ hydrocarbon chain wherein one methylene unit of L is replaced by —C(O)— and one methylene unit is replaced by —NH—. In certain embodiments, L is —C(O)NH(CH₂)₃—. In certain embodiments, L is —(CH₂)₂NHC(O)CH₂—. In certain embodiments, L is a C₅ hydrocarbon chain wherein two methylene units of L are replaced by —C(O)— and one methylene unit is replaced by —NH—. In certain embodiments, L is —(CH₂)₂C(O)NHNH—. In certain embodiments, L is a C₅ hydrocarbon chain wherein one methylene unit of L is replaced by —O—. In certain embodiments, the L group is —OC[(CH₃)(CH₃)]CH₂—. In certain embodiments, L is a C₅ hydrocarbon chain wherein one methylene unit of L is replaced by —C(O)— and one methylene unit is replaced by —O—. In certain embodiments, the L group is —CH₂C(O)OCH₂CH₂—In certain embodiments, L is a C₅ hydrocarbon chain wherein one methylene unit of L is replaced by —C(O)—, one methylene unit is replaced by —NH—, and one methylene is substituted by —OH. In certain embodiments, the L group is —C(O)NHCH[CH(CH₃)(OH)]—. In certain embodiments, L is a C₅ hydrocarbon chain wherein one or two methylene units of L are replaced by —C(O)—, one methylene unit is replaced by —NH—,and one methylene unit is substituted with —OH. In certain embodiments, the L group is —C(O)NHCH[CH₂C(O)OH]—. In certain embodiments, L is a C₅ hydrocarbon chain wherein one methylene unit of L is replaced by an optionally substituted arylene. In certain embodiments, the arylene is phenylene. In certain embodiments, the arylene is a substituted. In certain embodiments, the arylene is a substituted phenylene.

(iv) C₆ Hydrocarbon L Groups

In certain embodiments, L is a bivalent, branched or unbranched, saturated or unsaturated, C₆ hydrocarbon chain wherein one or more methylene units of L is independently replaced by —O—, —S—, —NH—, —C(O)—, —CF₂—, —C(=CH₂)—, —CH=CH—, or an optionally substituted arylene, heteroarylene, C₃-C₆ cycloalkylene, C₃-C₆ heterocycloalkylene, or an 8-10-membered bicyclic heterocyclic moiety.

In certain embodiments, L is a bivalent, branched or unbranched, saturated or unsaturated, C₆ hydrocarbon chain wherein one or more methylene units of L is independently replaced by —NH—, —O—, —C(O)—, —C(=CH₂)—, —CH=CH—, C₃-C₆ cycloalkylene, 8-10-membered bicyclic heterocyclic moiety, an optionally substituted arylene and optionally substituted heteroarylene, and wherein L is optionally substituted by one or more groups selected from halogen, substituted or unsubstituted C₁-C₆ alkyl, —CH₂CH₂C(O)OH, —(CH₂)₂C(O)NH₂, —C(O)NH₂, —NHC(O)CH₃, —(CH₂)₂SCH₃, —(CH₂)₃NHC(O)NH₂, —(CH₂)₂C(O)OCH₂-phenyl, —NHC(O)NHCH₂CH₃ and a 5- to 7-membered monocyclic having 1-2 heteroatoms independently selected from nitrogen, oxygen, or sulfur.

In certain embodiments, L is a C₆ hydrocarbon chain wherein one methylene unit of L is replaced by —NH—. In certain embodiments, the L group is —CH[CH(CH₃)(CH₂CH₃)]NH—. In certain embodiments, L is a C₆ hydrocarbon chain wherein one methylene unit of L is replaced by —C(O)— and one methylene unit is replaced by —O—. In certain embodiments, the L group is —CH₂CH₂C(O)OCH₂CH₂—In certain embodiments, L is a C₆ hydrocarbon chain wherein one or two methylene units of L are replaced by —C(O)—, one methylene unit is replaced by —NH— and one methylene unit is substituted by —OH. In certain embodiments, the L group is —C(O)NHCH[CH₂CH₂C(O)OH]—. In certain embodiments, L is a C₆ hydrocarbon chain wherein one methylene unit of L is replaced by —C(O)— and one or two methylene units are replaced by —NH—. In certain embodiments, L is —CH₂C(O)NH(CH₂)₃—. In certain embodiments, L is —CH[(CH₂)₂C(O)NH₂]NH—. In certain embodiments, the L group is C(O)NHCH[CH(CH₃)(CH₃)]—. In certain embodiments, the L group is C(O)NHCH[CH(CH₃)(CH₃)]—. In certain embodiments, L is a C₆ hydrocarbon chain wherein two methylene units of L are replaced by —C(O)— and one methylene unit is replaced by —NH— and one methylene unit is substituted by —NH₂ or —C(O)NHCH₂CH₃. In certain embodiments, the L group is —C(O)NHCH[(CH₂)₂C(O)NH₂]—. In certain embodiments, the L group is —C(O)NHCH[C(O)NH₂](CH₂)₂—. In certain embodiments, the L group is —(CH₂)₂CH[NHC(O)NHCH₂CH₃]C(O)NH—. In certain embodiments, L is a C₆ hydrocarbon chain wherein one methylene unit of L is replaced by —C(O)—, one methylene unit is replaced by —NH—, one methylene unit is replaced by —S— which is further substituted by a C₁₋₆ alkyl. In certain embodiments, the L group is —C(O)NHCH[(CH₂)₂SCH₃]—. In certain embodiments, L is a C₆ hydrocarbon chain wherein one methylene unit of L is replaced by —C(O)—, one methylene unit is replaced by —NH—, and one methylene unit is replaced by —O—. In certain embodiments, the L group is —NHCH₂C(O)OCH₂CH₂—. In certain embodiments, L is a C₆ hydrocarbon chain wherein one methylene unit of L is replaced by —C(O)— and one methylene unit is replaced by —NH—, and one methylene unit is further substituted by a C₁₋₆ alkyl. In certain embodiments, the L group is —C(O)NHCH[CH₂CH(CH₃)₂]—. In certain embodiments, the L group is —C(O)NHCH[CH(CH₃)(CH₂CH₃)]—. In certain embodiments, the L group is —C(O)NHCH[CH(CH₃)(CH₂CH₃)]—. In certain embodiments, L is a C₆ hydrocarbon chain wherein one or two methylene units of L are replaced by —C(O)— and one methylene unit is replaced by —NH—. In certain embodiments, the L group is —CH₂CH[NHC(O)CH₃]C(O)—. In certain embodiments, the L group is —CH₂CH[NHC(O)CH₃]C(O)—. In certain embodiments, L is a C₆ hydrocarbon chain wherein one or two methylene units of L are replaced by —C(O)—, one methylene unit is replaced by —NH—, one methylene unit is replaced by —O— and one methylene unit is substituted with —OCH₂-phenyl. In certain embodiments, the L group is —C(O)NH—CH[(CH₂)₂C(O)OCH₂-phenyl]-. In certain embodiments, L is a C₆ hydrocarbon chain wherein one or two methylene units of L are replaced by —NH— and one methylene unit is substituted with —C(O)NH₂. In certain embodiments, the L group is —CH[(CH₂)₃NHC(O)NH₂]NH—. In certain embodiments, the L group is —(CH₂)₂CH[C(O)NH₂]NH—. In certain embodiments, L is a C₆ hydrocarbon chain wherein one methylene unit of L is replaced by —NH—, one methylene unit is replaced by —C(O)— and one methylene unit is substituted with —C(O)NH₂. In certain embodiments, L is a C₆ hydrocarbon chain wherein two methylene units of L are replaced by —C(O)—, one methylene unit is replaced by —NH—, one methylene unit is replaced by —O— and one methylene substituted with —NHCH₂CH₃. In certain embodiments, the L group is —CH₂CH[NHC(O)NHCH₂CH₃]C(O)O—. In certain embodiments, L is a C₆ hydrocarbon chain wherein one methylene unit of L is replaced by an optionally substituted arylene. In certain embodiments, the arylene is phenylene. In certain embodiments, the arylene is a substituted. In certain embodiments, the arylene is a substituted phenylene. In certain embodiments, L is a C₆ hydrocarbon chain wherein one methylene unit of L is replaced by —NH—, one methylene unit is replaced by —C(O)—, one methylene unit is substituted by a morpholine ring and one methylene unit is further substituted by a —CH₃ group. In certain embodiments, the L group is —C(O)[morpholino]NHCH[CH(CH₃)(CH₂)]—. In certain embodiments, it will further be appreciated that the -L-R¹ moiety of a compound of Formulae I, and/or I' is —C(O)[morpholino]NHCH[CH(CH₃)(CH₂CH₃)]—, wherein R¹ is a —CH₃.

In summary, a list of Exemplary L groups include —NHCH₂—, —N(CH₃)—, —CH₂CH₂C(O)—, —CH=CHC(O)—, —CH=CHC(O)O—, —NHCH₂C(O)—, —NH(CH₂)₂C(O)—, —CH₂C(=CH₂)C(O)—, —CH₂CH₂CH₂C(O)—,

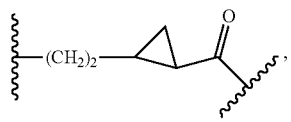

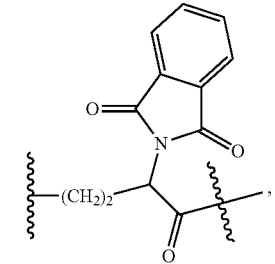

—NHCH₂CH₂C(O)—, —CH₂CH₂C(O)OCH₂CH₂—, —C(O)CH₂C(O)—, —C(O)CH₂CH₂C(O)—, —NH(CH₃)—, —N(CH₃)CH₂—, —CH[NHC(O)CH₃]CH₂—, —OCH₂—, —CH₂C(O)—, —OC(O)—, —N(CH₃)—, —N(CH₃)—. —CH₂N(CH₃)—, —CH=CH—,

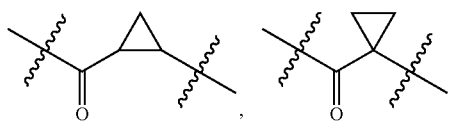

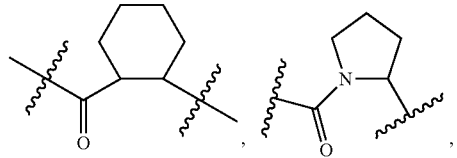

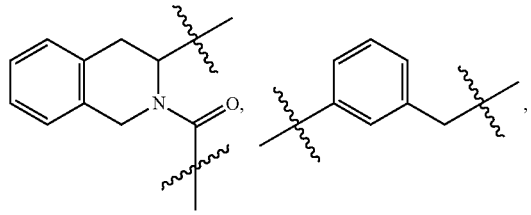

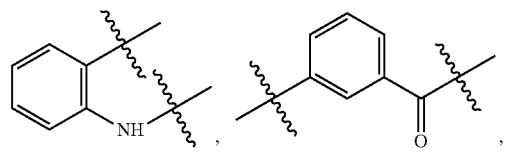

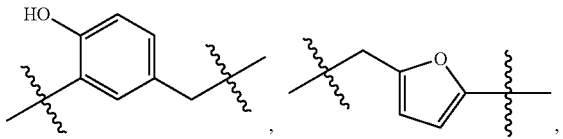

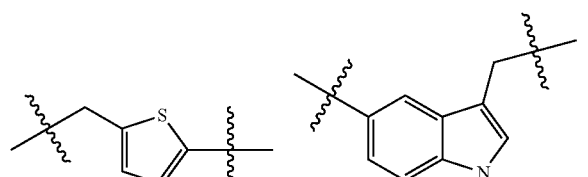

—CH$_2$NH—, —(CH$_2$)$_2$NO$_2$, —CH$_2$CH$_2$C(O)—, —C(O)CH$_2$NH—, —CH$_2$NHC(O)—, —CH[(CH$_2$)$_3$CH$_3$]NHC(O)—, —CH$_2$OC(O)—, —C(O)NHC(CH$_3$)—, —C(O)NHCH(CH$_2$CH$_3$)—, —C(O)NHCH[CH$_2$CH(CH$_3$)(CH$_3$)]—, —CH$_2$CH(CH$_3$)C(O)—, —CH(CH$_3$)CH$_2$C(O)—, —CH(CH$_3$)CH(CH$_3$)C(O)—, —CH$_2$C[(CH$_3$)(CH$_3$)]C(O)—, —C[(CH$_3$)(CH$_3$)]CH$_2$C(O)—, —NHC(O)(CH$_3$), —CH$_2$CH[NHC(O)CH$_3$]C(O)—, —C(O)NHCH[CH(CH$_3$)(CH$_3$)]—, —C(O)NHCH$_2$—, —CH$_2$OC(O)—, —CH$_2$CH$_2$C(O)—, —C(O)CH$_2$C(O)—, —CH$_2$CH$_2$NH—, —CH$_2$OCH$_2$—, —CH=CHC(O)—, or —CH=CHC(O)O—, —CH=C(CH$_3$)C(O)—, —CH=C(phenyl)-C(O)—, —CH=CHCF$_2$, —CH$_2$C(=CH$_2$)C(O)—, —CH$_2$CH(phenyl)C(O)—, —CH(phenyl)CH$_2$C(O)—, —NHC(O)NHCH$_2$CH$_3$, —CH$_2$CH[NHC(O)NHCH$_2$CH$_3$]C(O)—, —C(O)NHCH(phenyl)-, —C(O)NHCH[CH(phenyl)$_2$]—, —C(O)NHCH[CH$_2$(phenyl)]-, —(CH$_2$)$_2$CF$_2$—, C$_3$-C$_6$ cycloalkylene,

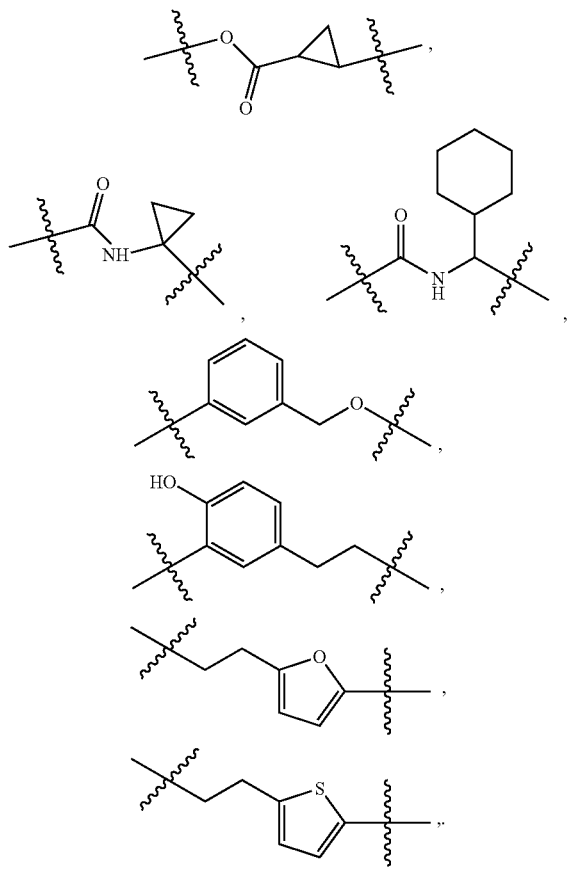

—CH$_2$CH$_2$CH$_2$C(O)—, —CH(CH$_3$)CH$_2$C(O)—, —C(O)CH$_2$CH$_2$C(O)—, —C(O)CH$_2$CH(CH$_3$)—, —C(O)CH(CH$_3$)CH$_2$—, —(CH$_2$)$_2$C(O)NH—,

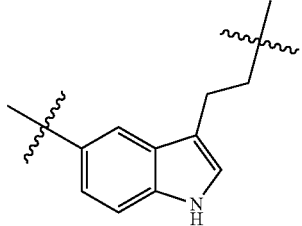

1,3-dioxoisoindolinyl,

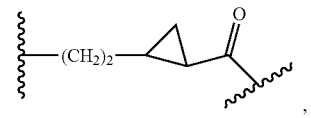

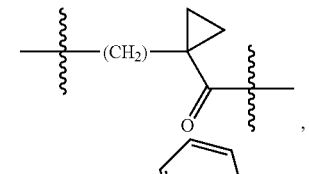

—NH(CH$_2$)$_2$C(O)—, —C(O)NH(CH$_2$)$_2$—, —NHC(O)(CH$_2$)$_2$—, —C(O)NHCH[CH$_2$(OH)]—, —CH$_2$C(O)NHCH(CH$_3$)—, —CH$_2$C(O)NHCH[CH(CH$_3$)(CH$_3$)]—, —CH$_2$C(O)NHCH(CH$_2$CH$_3$)—, —CH$_2$C(O)NHCH[CH$_2$CH(CH$_3$)(CH$_3$)]—,

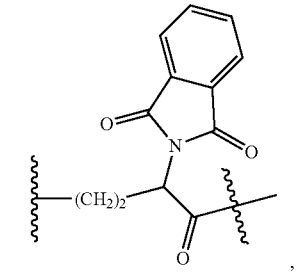

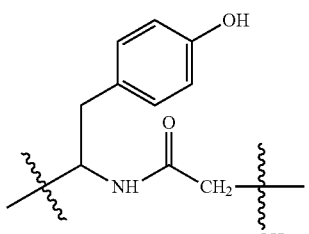

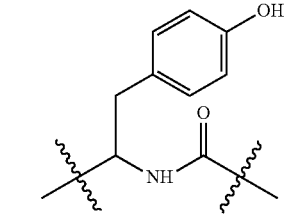

—CH[(CH₂)₃CH₃]NHC(O)CH₂—, —C(O)O(CH₂)₂—, —CH=CHC(O)NH—, —CH(CH₃)CH(CH₃)C(O)—, —CH₂C[—(CH₃)(CH₃)]C(O)—, —C[CH₃)(CH₃)]CH₂C(O)—, —C(O)NH(CH₂)₃—, —(CH₂)₂NHC(O)CH₂—, —(CH₂)₂C(O)NHNH—, I—OC[CH₃)(CH₃)]CH₂—, —CH₂C(O)OCH₂CH₂—, —C(O)NHCH[CH(CH₃)(OH)]—, —C(O)NHCH[CH₂C(O)OH]—, —CH[CH(CH₃)(CH₂CH₃)]NH—, —CH₂CH₂C(O)OCH₂CH₂, —C(O)NHCH[CH₂CH₂C(O)OH]—, —CH₂C(O)NH(CH₂)₃—, —CH[(CH₂)₂C(O)NH₂]NH—, —C(O)NHCH[CH(CH₃)(CH₃)]—, —C(O)NHCH[CH(CH₃)(CH₃)]—, —C(O)NHCH[(CH₂)₂C(O)NH₂]—, —C(O)NHCH[C(O)NH₂](CH₂)₂—, —(CH₂)₂CH[NHC(O)NHCH₂CH₃]C(O)NH—, —C(O)NHCH[(CH₂)₂SCH₃]—, —NHCH₂C(O)OCH₂CH₂—, —C(O)NHCH[CH₂CH(CH₃)₂]—, —C(O)NHCH[CH(CH₃)(CH₂CH₃)]—. —C(O)NHCH[CH(CH₃)(CH₂CH₃)]—, —CH₂CH[NHC(O)CH₃]C(O)—, —CH₂CH[NHC(O)CH₃]C(O)—, —C(O)NH—CH[(CH₂)₂C(O)OCH₂-phenyl], —CH[(CH₂)₃NHC(O)NH₂]NH—, —(CH₂)₂CH[C(O)NH₂]NH—, —(CH₂)₂CH[C(O)NH₂]NHC(O)CH₃—, —CH₂CH[NHC(O)NHCH₂CH₃]C(O)O— and —C(O)[morpholino]NHCH[CH(CH₃)(CH₂)]—.

ii. $R^1$ Group Embodiments

As defined generally above, the $R^1$ group of Formulae I, and/or I' is $R^1$ is hydrogen, F, CF₃, C₁-C₄ alkyl, —OH, —C(O)CH₃, —NH(OR), —NR₂, —NHNR₂, —SO₂R, —NH-phenyl, —SO₂— phenyl, -phenyl-NO₂, or —OR, wherein each R is independently hydrogen, oxygen, or an optionally substituted group selected from $C_{1-6}$ aliphatic or $C_{1-6}$ heteroaliphatic.

Exemplary $R^1$ groups include: hydrogen, —F, —CF₃, —CH₃, —OH, —C(O)CH₃, —C(O)CF₃, —NH₂, —NH₂NH₂, —NHCH₂CH₃, —SO₂-methyl,

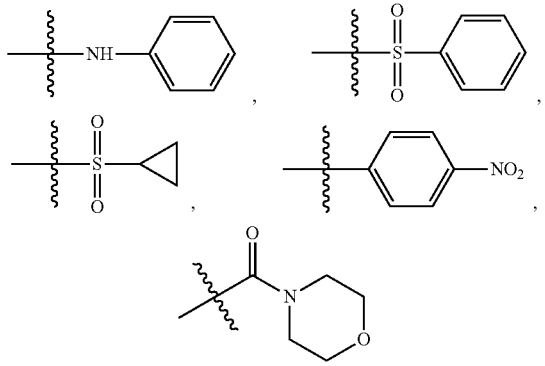

or —OR, wherein each R is independently hydrogen or an optionally substituted group selected from $C_{1-6}$ aliphatic or $C_{1-6}$ heteroaliphatic.

In certain embodiments, $R^1$ is hydrogen. In certain embodiments, $R^1$ is F. In certain embodiments, $R^1$ is CF₃. In certain embodiments, $R^1$ is C₁-C₄ alkyl. In certain embodiments, $R^1$ is —CH₃. In certain embodiments, $R^1$ is methyl. In certain embodiments, $R^1$ is —OH. In certain embodiments, $R^1$ is —C(O)CH₃. In certain embodiments, $R^1$ is —C(O)CF₃. In certain embodiments, $R^1$ is —NH₂. In certain embodiments, $R^1$ is —NH₂NH₂. In certain embodiments, $R^1$ is —NHCH₂CH₃. In certain embodiments, $R^1$ is —SO₂-methyl. In certain embodiments, $R^1$ is

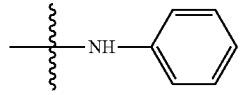

In certain embodiments, $R^1$ is

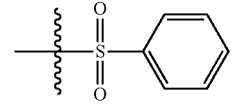

In certain embodiments, $R^1$ is

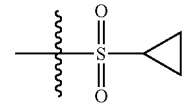

In certain embodiments, $R^1$ is

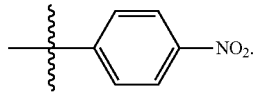

In certain embodiments, $R^1$ is —OR. In certain embodiments, $R^1$ is —OR, wherein R is an optionally substituted $C_{1-6}$ aliphatic. In certain embodiments, $R^1$ is —OCH₂CH₃. In certain embodiments, $R^1$ is —NHR, wherein R is as defined herein. In certain embodiments, $R^1$ is —NH(OR), wherein R is as defined herein. In certain embodiments, $R^1$ is —ONH₂. In certain embodiments, $R^1$ is —NR₂, wherein R is as defined herein.

iii. $R^2$ Group Embodiments

As defined generally above, the $R^2$ group of Formulae I and/or I' is $R^2$ is —C(O)X, wherein X is independently R, —C(O)NHNH₂, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted group selected from $C_{1-6}$ aliphatic or $C_{1-6}$ heteroaliphatic. In certain embodiments, $R^2$ is —C(O)X, wherein X is selected from R, —OR, hydrazine, or a hydrogen. In certain embodiments, $R^2$ is —C(O)X. In certain embodiments, $R^2$ is —C(O)H. In certain embodiments, $R^2$ is —C(O)OH. In certain embodiments, $R^2$ is —C(O)OR. In certain embodiments, $R^2$ is —C(O)NHNH₂.

iv. $R^3$ Group Embodiments

As defined generally above, the $R^3$ group of Formulae I and/or I' is a substituted or unsubstituted, branched or unbranched, saturated or unsaturated, $C_{10}$-$C_{25}$ aliphatic. In certain embodiments, $R^3$ is a substituted or unsubstituted, branched or unbranched $C_{10}$-$C_{15}$ aliphatic. In certain embodiments, $R^3$ is a substituted or unsubstituted, branched or unbranched $C_{10}$-$C_{15}$ alkenyl. In certain embodiments, $R^3$ is a substituted or unsubstituted, branched or unbranched $C_{10}$-$C_{12}$ aliphatic. In certain embodiments, $R^3$ is a substituted or unsubstituted, branched or unbranched $C_{12}$ aliphatic. In certain embodiments, $R^3$ is an unsubstituted, branched $C_{12}$ aliphatic. In certain embodiments, $R^3$ is a substituted, branched $C_{12}$ aliphatic. In certain embodiments, $R^3$ is a branched $C_{12}$ alkenyl group. In certain embodiments, $R^3$ is —$CH_2CH=C(CH_3)CH_2CH_2CH=C(CH_3)CH_2CH_2CH=C(CH_3)(CH_3)$. In certain embodiments, $R^3$ is a substituted, branched $C_{15}$ aliphatic. In certain embodiments, $R^3$ is a branched $C_{15}$ alkenyl group. In certain embodiments, $R^3$ is —$CH_2CH=C(CH_3)CH_2CH_2CH=C(CH_3)CH_2CH_2CH=C(CH_3)(CH_3)$. In certain embodiments, $R^3$ is a substituted, branched $C_{16}$ aliphatic. In certain embodiments, $R^3$ is a branched $C_{16}$ alkenyl group. In certain embodiments, $R^3$ is —$CH_2CH=C(CH_3)CH_2CH_2CH_2CH(CH_3)\ CH_2CH_2CH_2CH(CH_3)CH_2CH_2CH_2CH(CH_3)(CH_3)$. In certain embodiments, $R^3$ is a substituted, branched $C_{20}$ aliphatic. In certain embodiments, $R^3$ is a branched $C_{20}$ alkenyl group. In certain embodiments, $R^3$ is $CH_2CH=C(CH_3)CH_2CH_2CH_2CH(CH_3)$ $CH_2CH_2CH_2CH(CH_3)$ $CH_2CH_2CH_2CH(CH_3)(CH_3)$.

v. Y Group Embodiments

As defined generally above, the Y group is —O—, —N—, —S—, —Se—, —S(O)—, —S(=N)—, —S(O)$_2$—, —Se(O)—, —Se(O)$_2$—, or —C(=S)—In certain embodiments, Y is —S—. In certain embodiments, Y is —O—. In certain embodiments, Y is —N—. In certain embodiments, Y is —Se—. In certain embodiments, Y is —S(O)—. In certain embodiments, Y is —S(=N)—. In certain embodiments, Y is —S(O)$_2$—. In certain embodiments, Y is —Se(O)—. In certain embodiments, Y is —Se(O)$_2$—.

6. Stereochemistry Embodiments

As described herein, compounds may comprise one or more chiral centers, and thus can exist in various stereoisomeric forms, e.g., enantiomers, diastereomers, or geometric isomers). Thus, inventive compounds and pharmaceutical compositions thereof may be in the form of a racemic compound, an individual enantiomer (e.g., enantiomerically pure), an individual diastereomer (e.g., diastereomerically pure), an individual geometric isomer (e.g., geometrically pure), or may be in the form of a mixture of stereoisomers. In certain embodiments, compounds of the present invention are racemic compounds. In certain embodiments, compounds of the present invention are enantioenriched compounds. In certain embodiments, compounds of the present invention are diasteriomerically enriched compounds. In certain embodiments, wherein one or more double bonds is present, compounds of the present invention may be geometrically enriched compounds. In certain embodiments, compounds of the present invention are provided such that 75% of the preparation is of the same enantiomer or diastereomer. In certain embodiments, compounds of the present invention are provided such that at least 80%, 90%, 95%, or 97.5% of the preparation is of the same enantiomer or diastereomer. In certain embodiments, compounds of the present invention are provided such the preparation consists of a single enantiomer or diastereomer to the limits of detection (i.e., "enantiopure").

It will be apparent to one skilled in the art that each chiral center in a provided compound can be present in an (R)-configuration or in an (S)-configuration. In addition, where stereoisomeric forms of provided compounds may exist, such forms may be present in any ratio relative to one another. One skilled in the art will further understand that ratios of stereoisomers may vary according to methods by which such compounds are prepared. Exemplary ratios provided herein are meant to illustrate the present invention, and are not meant to limit the present invention.

With respect to geometric isomerism, the present invention contemplates both E and Z isomers wherein there exists one or more double bonds, unless otherwise indicated. In some embodiments, the invention encompasses compounds as a single geometric isomer substantially free of other geometric isomers and alternatively, as mixtures of various isomers, e.g., racemic mixtures of E and Z isomers. In addition to the above-mentioned compounds per se, this invention also encompasses pharmaceutically acceptable derivatives of these compounds and compositions comprising one or more compounds of the invention and one or more pharmaceutically acceptable excipients or additives.

Where a stereoisomer is preferred, it may, in some embodiments be provided substantially free of other stereoisomers, as defined herein. According to certain embodiments, the present invention provides compounds of Formulae I, I', and/or Ia substantially free of other stereoisomers.

Enantiomeric and stereoisomeric mixtures may be resolved into their component enantiomers or stereoisomers by well known methods, such as chiral-phase gas chromatography, chiral-phase high performance liquid chromatography, crystallizing a compound as a chiral salt complex, or crystallizing a compound in a chiral solvent or by enzymatic resolution of a compound, its precursor or its derivative. Enantiomers and stereoisomers may also be obtained from stereomerically or enantiomerically pure intermediates, reagents, and catalysts by well-known asymmetric synthetic methods.

Additionally, unless otherwise stated, the present invention encompasses compounds that differ from those explicitly depicted herein only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, the $R^1$ group of I, I', and/or Ia comprises one or more deuterium atoms. In certain embodiments, the $R^2$ group of I, I', and/or Ia comprises one or more deuterium atoms. In certain embodiments, the $R^3$ group of I, I', and/or Ia comprises one or more deuterium atoms. Mixtures of isomeric forms may be separated and/or purified by techniques as would be known to one skilled in this art, including but not limited to column chromatography.

As described generally above, the present invention provides a compound of Formulae I, I', and/or Ia, having a stereochemistry as depicted in Formula 1a and/or 1b:

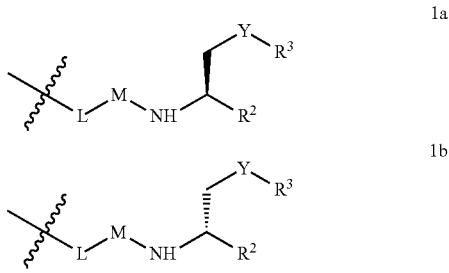

or a pharmaceutically, acceptable salt thereof, wherein each variable is defined above and in classes and subclasses described above and herein.

It will be appreciated that for each racemic compound disclosed herein, individual enantiomers are also contemplated. For example, one of skill in the art would understand that compound N-54 as depicted below:

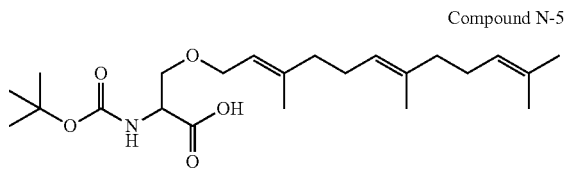

Compound N-54 also contemplates each of its enantiomers:

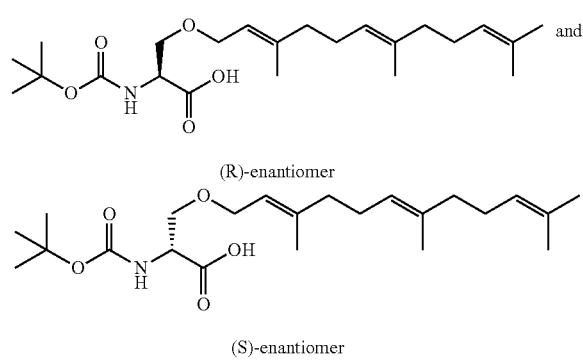

(R)-enantiomer (S)-enantiomer

I. L Group Stereochemistry and $R^3$ Group Stereochemistry

Exemplary L group and $R^3$ group stereochemistry of the present invention are described below. It will be appreciated that all combinations of embodiments, as described herein, are contemplated. In some embodiments, the present invention provides a compound having any combination of one of the L groups and one of the $R^3$ group described below. It will further be appreciated that wherein a specific L group or $R^3$ group is described generally without specifying stereochemistry, the present invention contemplates all embodiments of stereochemistry associated with that group.

A. L Group Stereochemistry

General Definition of L Group

As generally described above and herein, L is a bivalent, branched or unbranched, saturated or unsaturated, $C_2$-$C_6$ hydrocarbon chain wherein one or more methylene units of L is independently replaced by —O—, —S—, —NH—, —C(O)—, —CF$_2$—, —C(=CH$_2$)—, —CH=CH—, or an optionally substituted arylene, heteroarylene, $C_3$-$C_6$ cycloalkylene, $C_3$-$C_6$ heterocycloalkylene, or an 8-10-membered bicyclic heterocyclic moiety, and wherein L is optionally substituted by one or more groups selected from halogen, $C_1$-$C_6$ alkyl, phenyl, biphenyl, -benzyl, —CH$_2$-phenol, —CH(phenyl)$_2$, —OH, —NH$_2$, —NHC(O)CH$_3$, —NHC(O)NHCH$_2$CH$_3$, —C(O)NH$_2$, —C(O)NHCH$_2$CH$_3$, —CH$_2$C(O)OCH$_2$phenyl, —(CH$_2$)$_2$SCH$_3$, —(CH$_2$)$_2$C(O)NH$_2$, —(CH$_2$)$_2$C(O)OH, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5- to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur.

One Chiral Center (i.e., No Chiral Centers in L)

In some embodiments, a compound of Formula I or Formula I', having stereochemistry as depicted in Formula 1a or 1b, contains no chiral centers in the $C_{2-6}$ hydrocarbon chain of L. Exemplary such compounds include, for instance, Compound A [(R)-enantiomer; Example 2] and corresponding (S)-enantiomer.

Two Chiral Centers (i.e., One Chiral Center in L)

In some embodiments, a compound of Formula I or Formula I', having stereochemistry as depicted in Formula 1a or 1b, contains one chiral center in the $C_{2-6}$ hydrocarbon chain of L. In certain embodiments, a chiral center in the $C_{2-6}$ hydrocarbon chain of L is at $C_2$. In certain embodiments, a chiral center in the $C_{2-6}$ hydrocarbon chain of L is at $C_3$. In certain embodiments, a chiral center in the $C_{2-6}$ hydrocarbon chain of L is at $C_4$. In certain embodiments, a chiral center in the $C_{2-6}$ hydrocarbon chain of L is at $C_5$. In certain embodiments, a chiral center in the $C_{2-6}$ hydrocarbon chain of L is at $C_6$. One of skill in the art would recognize that a chiral center in the $C_{2-6}$ hydrocarbon chain of L may be present in either the (R) or (S) configuration. In certain embodiments, a chiral center in the $C_{2-6}$ hydrocarbon chain of L is enantiopure or enantioenriched in the (R) configuration. In certain embodiments, a chiral center in the $C_{2-6}$ hydrocarbon chain of L is enantiopure or enantioenriched in the (S) configuration. In certain embodiments, a chiral center in the $C_{2-6}$ hydrocarbon chain of L is present in approximately a 1:1 molar ratio of (R) to (S).

Exemplary stereochemistry present within an L group containing one chiral center in the $C_{2-6}$ hydrocarbon chain of a compound of Formula I or Formula I', and having stereochemistry as depicted in Formula 1a or 1b, are as depicted below in Formulae 1l-(i), 1l-(ii), 1l-(iii), 1l-(iv), 1l-(v) and/or 1l-(vi):

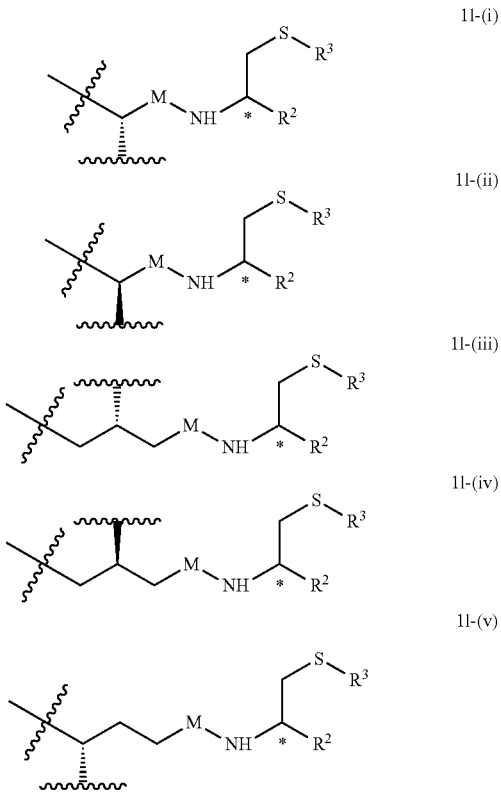

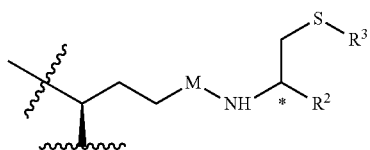

Exemplary compounds having stereochemistry as depicted in Formulae 1l-(v) and 1l-(vi) above for the L group, include: Compound C-2 (Example 5b), Compound N-55 (Example 9), Compound N-57 (Example 11), Compound N-58 (Example 12), Compound N-8 (Example 14), Compound N-3 (Example 15), Compound N-5 (Example 17), Compound N-9 (Example 20), Compound N-12 (Example 21), Compound N-60 (Example 23), Compound N-50 (Example 24), Compound N-63 (Example 29), Compound N-66 (Example 34), Compound N-71 (Example 46), Compound N-91, and Compound N-92.

In certain embodiments, compounds of the present invention, having stereochemistry as depicted in Formula 1a, are provided such that compounds containing an L group of Formula 1l-(i) and compounds containing an L group of Formula 1l-(ii) are present in a 1:1 molar ratio. Exemplary such compounds include Compound C (Example 5 and Example 5a), Compound N-2, Compound N-18, Compound N-31 (Example 62), Compound N-34 (Example 41a), Compound N-37, Compound N-40 (Example 32), Compound N-41 (Example 33), Compound N-46 (Example 35), Compound N-47, Compound N-61 (Example 27), Compound N-64 (Example 30), Compound N-65 (Example 31), Compound N-77 (Example 65), Compound N-89, Compound N-93, and Compound N-94.

In certain embodiments, compounds of the present invention, having stereochemistry as depicted in Formula 1b, are provided such that compounds containing an L group of Formula 1l-(i) and compounds containing an L group of Formula 1l-(ii) are present in a 1:1 molar ratio.

In certain embodiments, compounds of the present invention, having stereochemistry as depicted in Formula 1a, are provided such that compounds containing an L group of Formula 1l-(iii) and compounds containing an L group of Formula 1l-(iv) are present in a 1:1 molar ratio. Exemplary such compounds include Compound N-36; Compound N-78 (Example 66); and Compound N-32 (Example 67).

In certain embodiments, compounds of the present invention, having stereochemistry as depicted in Formula 1b, are provided such that compounds containing an L group of Formula 1l-(iii) and compounds containing an L group of Formula 1l-(iv) are present in a 1:1 molar ratio.

In certain embodiments, compounds of the present invention, having stereochemistry as depicted in Formula 1a, are provided such that compounds containing an L group of Formula 1l-(v) and compounds containing an L group of Formula 1l-(vi) are present in a 1:1 molar ratio. Exemplary compounds of this type include Compound N-88 and Compound N-95.

In certain embodiments, compounds of the present invention, having stereochemistry as depicted in Formula 1b, are provided such that compounds containing an L group of Formula 1l-(v) and compounds containing an L group of Formula 1l-(vi) are present in a 1:1 molar ratio.

Three Chiral Centers (i.e., Two Chiral Center in L)

In certain embodiments, a compound of Formula I or Formula I', having stereochemistry as depicted in Formula 1a or 1b, contains two chiral centers in the $C_{2-6}$ hydrocarbon chain of L. In certain embodiments, two chiral centers in the $C_{2-6}$ hydrocarbon chain of L are at $C_1$ and $C_2$. In certain embodiments, two chiral centers in the $C_{2-6}$ hydrocarbon chain of L are at $C_1$ and $C_3$. In certain embodiments, two chiral centers in the $C_{2-6}$ hydrocarbon chain of L are at $C_1$ and $C_4$. In certain embodiments, two chiral centers in the $C_{2-6}$ hydrocarbon chain of L are at $C_1$ and $C_5$. In certain embodiments, two chiral centers in the $C_{2-6}$ hydrocarbon chain of L are at $C_1$ and $C_6$. In certain embodiments, two chiral centers in the $C_{2-6}$ hydrocarbon chain of L are at $C_2$ and $C_3$. In certain embodiments, two chiral centers in the $C_{2-6}$ hydrocarbon chain of L are at $C_2$ and $C_4$. In certain embodiments, two chiral centers in the $C_{2-6}$ hydrocarbon chain of L are at $C_2$ and $C_5$. In certain embodiments, two chiral centers in the $C_{2-6}$ hydrocarbon chain of L are at $C_2$ and $C_6$. In certain embodiments, two chiral centers in the $C_{2-6}$ hydrocarbon chain of L are at $C_3$ and $C_4$. In certain embodiments, two chiral centers in the $C_{2-6}$ hydrocarbon chain of L are at $C_3$ and $C_5$. In certain embodiments, two chiral centers in the $C_{2-6}$ hydrocarbon chain of L are at $C_3$ and $C_6$. In certain embodiments, two chiral centers in the $C_{2-6}$ hydrocarbon chain of L are at $C_4$ and $C_5$. In certain embodiments, two chiral centers in the $C_{2-6}$ hydrocarbon chain of L are at $C_4$ and $C_6$. In certain embodiments, two chiral centers in the $C_{2-6}$ hydrocarbon chain of L are at $C_5$ and $C_6$.

Exemplary stereochemistry present within an L group containing two chiral centers in the $C_{2-6}$ hydrocarbon chain of a compound of Formula I or Formula I', and having a stereochemistry as depicted in Formula 1a or 1b, are as depicted below in Formulae 2l-(i), 2l-(ii), 2l-(iii), and 2l-(iv):

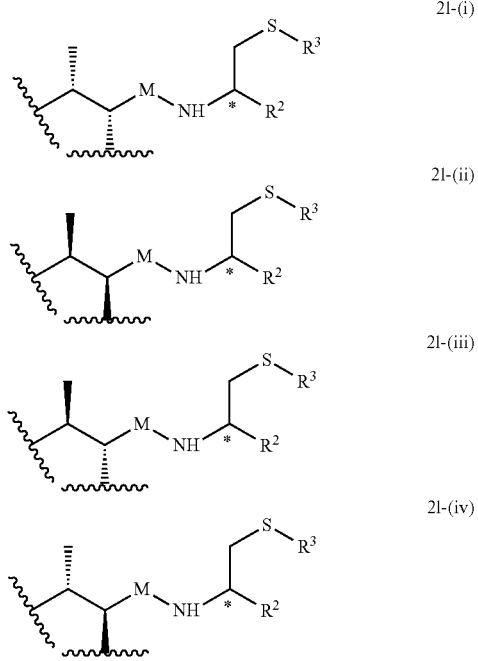

One of skill in the art would recognize that either of the two chiral centers in the $C_{2-6}$ hydrocarbon chain of L may be present in an (R) or (S) configuration. In certain embodiments, both chiral centers in the $C_{2-6}$ hydrocarbon chain of L are in an (R) configuration. In certain embodiments, both chiral centers in the $C_{2-6}$ hydrocarbon chain of L are in an (S) configuration. In certain embodiments, one chiral center in the $C_{2-6}$ hydrocarbon chain of L is present in an (R) configuration and a second chiral center in the $C_{2-6}$ hydrocarbon chain of L is present in an (S) configuration.

In certain embodiments, compounds of Formula I and/or Formula I', having stereochemistry as depicted in Formula 1a and/or 1b, are provided such that at least one of two chiral centers in the $C_{2-6}$ hydrocarbon chain of L is enantiopure or enantioenriched in an (R) or (S) configuration.

In certain embodiments, compounds of Formula I and/or Formula I', having stereochemistry as depicted in Formula 1a and/or 1b, are provided such that both chiral centers in the $C_{2-6}$ hydrocarbon chain of L are independently enantiopure or enantioenriched in an (R) or (S) configuration.

In certain embodiments, compounds of Formula I and/or Formula I', having stereochemistry as depicted in Formula 1a and/or 1b, are provided such that one of the two chiral centers in the $C_{2-6}$ hydrocarbon chain of L is enantiopure or enantioenriched in an (R) or (S) configuration, while the other chiral center in the $C_{2-6}$ hydrocarbon chain of L is present as a racemate.

In certain embodiments, compounds of Formula I and/or Formula I', having stereochemistry as depicted in Formula 1a and/or 1b, are provided such that both chiral centers in the $C_{2-6}$ hydrocarbon chain of L are present as racemates.

In some embodiments, wherein compounds of the present invention are provided as a mixture of one or more stereoisomers, all possible stereoisomers of L are present. In some embodiments, wherein compounds of the present invention are provided as a mixture of stereoisomers, a mixture may contain two stereoisomers present in a ratio of about 20:1, 18:1, 16:1, 14:1, 12:1, 10:1, 9:1, 8:1, 7:1, 6:1, 5:1, 4:1, 3:1, 2:1, or 1:1.

B. $R^3$ Group Stereochemistry

As described generally above and herein, $R^3$ is a substituted or unsubstituted, branched or unbranched, saturated or unsaturated $C_{10}$-$C_{25}$ aliphatic.

In some embodiments, $R^3$ of Formula I or Formula I', having stereochemistry as depicted in Formula 1a or 1b, is of Formula 1r:

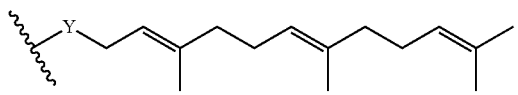

In some embodiments, $R^3$ of Formula I or Formula I', having stereochemistry as depicted in Formula 1a or 1b, is of general Formula 2r:

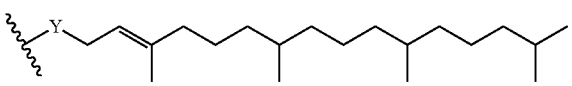

In certain embodiments, $R^3$ of Formula I or Formula I', having a stereochemistry as depicted in Formula 1a or 1b, is of Formula 2r, wherein 2r is of any of Formulae 2r-(i), 2r-(ii), 2r-(iii), or 2r-(iv):

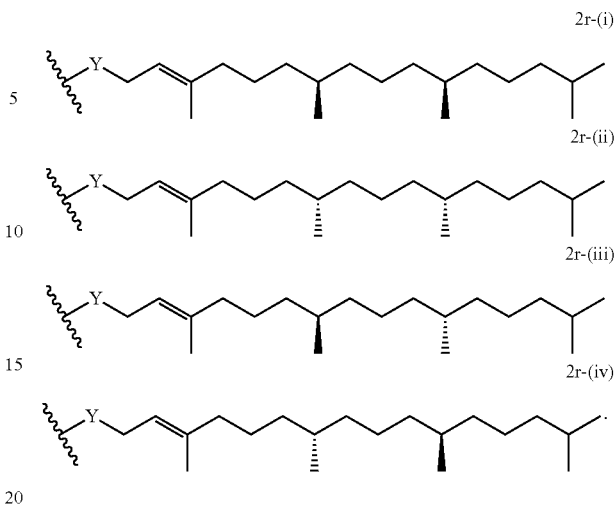

In certain embodiments, compounds of Formula I and/or Formula I', having stereochemistry as depicted in Formula 1a and/or 1b, are provided such that at least one of two chiral centers in $R^3$ is enantiopure or enantioenriched in an (R) or (S) configuration.

In certain embodiments, compounds of Formula I and/or Formula I', having stereochemistry as depicted in Formula 1a and/or 1b, are provided such that two chiral centers in $R^3$ are independently enantiopure or enantioenriched in an (R) or (S) configuration.

In certain embodiments, compounds of Formula I and/or Formula I', having stereochemistry as depicted in Formula 1a and/or 1b, are provided such that a first chiral center in $R^3$ is enantiopure or enantioenriched in an (R) or (S) configuration, while a second chiral center in $R^3$ is present as the racemate.

In certain embodiments, compounds of Formula I and/or Formula I', having stereochemistry as depicted in Formula 1a and/or 1b, are provided such that two chiral centers in $R^3$ are present as racemates.

In some embodiments, wherein $R^3$ is of Formula 2r depicted above, compounds of Formula I and/or Formula I', having stereochemistry as depicted in Formula 1a and/or 1b, are provided such that all possible stereoisomers of Formula 2r are present, three stereoisomers of formula 2r are present, two stereoisomers of Formula 2r are present, or one stereoisomer of Formula 2r is present.

In certain embodiments, wherein $R^3$ is of Formula 2r depicted above, compounds of Formula I and/or Formula I', having stereochemistry as depicted in Formula 1a and/or 1b, are provided such that only compounds containing stereochemistry as depicted in 2r-(i) and 2r-(ii) are present.

In certain embodiments, wherein $R^3$ is of Formula 2r depicted above, compounds of Formula I and/or Formula I', having stereochemistry as depicted in Formula 1a and/or 1b, are provided such that only compounds containing stereochemistry as depicted in 2r-(iii) and 2r-(iv) are present.

In certain embodiments, wherein $R^3$ is of Formula 2r depicted above, compounds of Formula I and/or Formula I', having stereochemistry as depicted in Formula 1a and/or 1b, are provided such that compounds containing stereochemistry as depicted in 2r-(i) and 2r-(ii) are present in a 1:1 ratio. In certain embodiments, wherein $R^3$ is of Formula 2r depicted above, compounds of Formula I and/or Formula I', having stereochemistry as depicted in Formula 1a and/or 1b, are provided such that compounds containing stereochemistry as depicted in 2r-(i) and 2r-(ii) are not present in a 1:1 ratio.

In certain embodiments, wherein $R^3$ is of Formula 2r depicted above, compounds of Formula I and/or Formula I', having stereochemistry as depicted in Formula 1a and/or 1b, are provided such that compounds containing stereochemistry as depicted in 2r-(iii) and 2r-(iv) are present in a 1:1 ratio. In certain embodiments, wherein $R^3$ is of Formula 2r depicted above, compounds of Formula I and/or Formula I', having stereochemistry as depicted in Formula 1a and/or 1b, are provided such that compounds containing stereochemistry as depicted in 2r-(iii) and 2r-(iv) are not present in a 1:1 ratio.

In certain embodiments, wherein $R^3$ is of Formula 2r depicted above, compounds of Formula I and/or Formula I', having stereochemistry as depicted in Formula 1a and/or 1b, are provided such that compounds containing stereochemistry as depicted in 2r-(i) and 2r-(ii) are present in a 1:1 ratio and compounds containing stereochemistry as depicted in 2r-(iii) and 2r-(iv) are present in a 1:1 ratio. In certain embodiments, wherein $R^3$ is of Formula 2r depicted above, compounds of Formula I and/or Formula I', having stereochemistry as depicted in Formula 1a and/or 1b, are provided such that compounds containing stereochemistry as depicted in 2r-(i) and 2r-(ii) are present in a 1:1 ratio and compounds containing stereochemistry as depicted in 2r-(iii) and 2r-(iv) are not present in a 1:1 ratio. In certain embodiments, wherein $R^3$ is of Formula 2r depicted above, compounds of Formula I and/or Formula I', having stereochemistry as depicted in Formula 1a and/or 1b, are provided such that compounds containing stereochemistry as depicted in 2r-(i) and 2r-(ii) are not present in a 1:1 ratio and compounds containing stereochemistry as depicted in 2r-(iii) and 2r-(iv) are present in a 1:1 ratio.

In certain embodiments, wherein $R^3$ is of Formula 2r depicted above, and wherein compounds of the invention are provided such that stereochemical configurations depicted in each of 2r-(i), 2r-(ii), 2r-(iii), and 2r-(iv) are present, the ratio of the sum of compounds containing stereochemistry as depicted in 2r-(i) and 2r-(ii) [i.e., the total amount of compounds wherein $R^3$ is present in either an (R,R) or (S,S) "cis" configuration] to the sum of compounds containing stereochemistry as depicted in 2r-(iii) and 2r-(iv) [i.e., the total amount of compounds wherein $R^3$ is present in either an (R,S) or (S,R) "trans" configuration] is about 20:1, 18:1, 16:1, 14:1, 12:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:12, 1:14, 1:16, 1:18, or 1:20. In certain embodiments, the ratio of the sum of compounds containing stereochemistry as depicted in 2r-(i) and 2r-(ii) to the sum of compounds containing stereochemistry as depicted in 2r-(iii) and 2r-(iv) is 3:7. In certain embodiments, the ratio of the sum of compounds containing stereochemistry as depicted in 2r-(i) and 2r-(ii) to the sum of compounds containing stereochemistry as depicted in 2r-(iii) and 2r-(iv) is 1:2. In certain embodiments, the ratio of the sum of compounds containing stereochemistry as depicted in 2r-(i) and 2r-(ii) to the sum of compounds containing stereochemistry as depicted in 2r-(iii) and 2r-(iv) is 1:1. Exemplary such provided compounds are found in Example 72 (Compound N-53) and Example 73 (Compound N-48).

II. Exemplary Combinations of L and $R^3$

It will be appreciated that all combinations of the above embodiments of L and $R^3$ are contemplated and that the invention is not limited to those described herein. It will further be appreciated that wherein a specific L group or $R^3$ group is described generally without specifying stereochemistry, the present invention contemplates all embodiments of stereochemistry associated with that group. Exemplary combinations of L and $R^3$ embodiments are described below.

Combinations Wherein L Contains No Chiral Centers

In some embodiments, the present invention provides compounds of Formula I and/or Formula I', having stereochemistry as depicted in Formula 1a and/or 1b, wherein L is a $C_{2-6}$ hydrocarbon chain containing no chiral centers, and wherein $R^3$ is of Formula 1r and/or 2r.

In some embodiments, the present invention provides compounds of Formula I and/or Formula I', having stereochemistry as depicted in Formula 1a and/or 1b, wherein L is a $C_{2-6}$ hydrocarbon chain containing no chiral centers, and wherein $R^3$ is of Formula 1r.

In some embodiments, the present invention provides compounds of Formula I and/or Formula I', having stereochemistry as depicted in Formula 1a and/or 1b, wherein L is a $C_{2-6}$ hydrocarbon chain containing no chiral centers, and wherein $R^3$ is of Formula 2r.

In some embodiments, the present invention provides a compound of Formula I or Formula I', having stereochemistry as depicted in Formula 1a, wherein L is a $C_{2-6}$ hydrocarbon chain containing no chiral centers, and wherein $R^3$ is of Formula 1r.

In some embodiments, the present invention provides a compound of Formula I or Formula I', having stereochemistry as depicted in Formula 1b, wherein L is a $C_{2-6}$ hydrocarbon chain containing no chiral centers, and wherein $R^3$ is of Formula 1r.

In some embodiments, the present invention provides compounds of Formula I or Formula I', having stereochemistry as depicted in Formula 1a, wherein L is a $C_{2-6}$ hydrocarbon chain containing no chiral centers, and wherein $R^3$ is of Formula 2r. In certain embodiments wherein L and $R^3$ are as described above, 2r is present as a mixture of compounds containing stereochemistry as depicted in 2r-(i) and 2r-(ii). In certain embodiments wherein L and $R^3$ are as described above, 2r is present as a mixture of compounds containing stereochemistry as depicted in 2r-(iii) and 2r-(iv). In certain embodiments wherein L and $R^3$ are as described above, 2r is present as a mixture of compounds containing stereochemistry as depicted in 2r-(i), 2r-(ii), 2r-(iii) and 2r-(iv). In certain embodiments wherein L and $R^3$ are as described above, 2r is present as a compound containing stereochemistry as depicted in 2r-(i), 2r-(ii), 2r-(iii) or 2r-(iv). In certain embodiments, wherein L and $R^3$ are as described above, the ratio of the sum of compounds containing stereochemistry as depicted in 2r-(i) and 2r-(ii) to the sum of compounds containing stereochemistry as depicted in 2r-(iii) and 2r-(iv) is about 20:1, 18:1, 16:1, 14:1, 12:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:12, 1:14, 1:16, 1:18, or 1:20. In certain embodiments, wherein L and $R^3$ are as described above, the ratio of the sum of compounds containing stereochemistry as depicted in 2r-(i) and 2r-(ii) to the sum of compounds containing stereochemistry as depicted in 2r-(iii) and 2r-(iv) is about 3:7. In certain embodiments, wherein L and $R^3$ are as described above, the ratio of the sum of compounds containing stereochemistry as depicted in 2r-(i) and 2r-(ii) to the sum of compounds containing stereochemistry as depicted in 2r-(iii) and 2r-(iv) is 1:2. In certain embodiments, wherein L and $R^3$ are as described above, the ratio of the sum of compounds containing stereochemistry as depicted in 2r-(i) and 2r-(ii) to the sum of compounds containing stereochemistry as depicted in 2r-(iii) and 2r-(iv) is 1:1.

In some embodiments, the present invention provides a compound of Formula I or Formula I', having stereochemistry as depicted in Formula 1b, wherein L is a $C_{2-6}$ hydrocarbon chain containing no chiral centers, and wherein $R^3$ is of Formula 2r.

Combinations Wherein L Contains One Chiral Center

In some embodiments, the present invention provides compounds of Formula I and/or Formula I', having stereochemistry as depicted in Formula 1a and/or 1b, wherein L is a $C_{2-6}$ hydrocarbon chain containing a chiral center, and wherein $R^3$ is of Formula 1r and/or 2r.

In some embodiments, the present invention provides a compound of Formula I or Formula I', having stereochemistry as depicted in Formula 1a, wherein L is a $C_{2-6}$ hydrocarbon chain containing a chiral center, and wherein $R^3$ is of Formula 1r. In certain embodiments, wherein $R^3$ is as described above, L is a $C_{2-6}$ hydrocarbon chain containing a chiral center in the (R) configuration at $C_1$, $C_2$, or $C_3$. In certain embodiments, wherein $R^3$ is as described above, L is a $C_{2-6}$ hydrocarbon chain containing a chiral center in the (S) configuration at $C_1$, $C_2$, or $C_3$. In certain embodiments, the invention provides compounds wherein $R^3$ is as described above and L is a $C_{2-6}$ hydrocarbon chain containing a chiral center present in approximately a 1:1 molar ratio of (R) to (S).

In some embodiments, the present invention provides a compound of Formula I or Formula I', having stereochemistry as depicted in Formula 1b, wherein L is a $C_{2-6}$ hydrocarbon chain containing a chiral center, and wherein $R^3$ is of Formula 1r.

In some embodiments, the present invention provides a compound of Formula I or Formula I', having stereochemistry as depicted in Formula 1a, wherein L is a $C_{2-6}$ hydrocarbon chain containing a chiral center, and wherein $R^3$ is of Formula 2r.

In some embodiments, the present invention provides a compound of Formula I or Formula I', having stereochemistry as depicted in Formula 1b, wherein L is a $C_{2-6}$ hydrocarbon chain containing a chiral center, and wherein $R^3$ is of Formula 2r.

Combinations Wherein L Contains Two Chiral Centers

In some embodiments, the present invention provides compounds of Formula I and/or Formula I', having stereochemistry as depicted in Formula 1a and/or 1b, wherein L is a $C_{2-6}$ hydrocarbon chain containing two chiral centers, and wherein $R^3$ is of Formula 1r and/or 2r.

In some embodiments, the present invention provides a compound of Formula I or Formula I', having stereochemistry as depicted in Formula 1a, wherein L is a $C_{2-6}$ hydrocarbon chain containing two chiral centers, and wherein $R^3$ is of Formula 1r. In certain embodiments wherein $R^3$ and L are as described above, the two chiral centers in the $C_{2-6}$ hydrocarbon chain are at $C_1$ and $C_2$, wherein at least one of the two chiral centers is racemic. In certain embodiments, wherein $R^3$ and L are as described above, the two chiral centers in the $C_{2-6}$ hydrocarbon chain are at $C_1$ and $C_3$, wherein at least one of the two chiral centers is racemic. In certain embodiments, wherein $R^3$ and L are as described above, the two chiral centers in the $C_{2-6}$ hydrocarbon chain are at $C_2$ and $C_3$, wherein at least one of the two chiral centers is racemic. In certain embodiments, wherein $R^3$ and L are as described above, the two chiral centers in the $C_{2-6}$ hydrocarbon chain are at $C_1$ and $C_2$, wherein both chiral centers are independently enantiopure. In certain embodiments, wherein $R^3$ and L are as described above, the two chiral centers in the $C_{2-6}$ hydrocarbon chain are at $C_1$ and $C_3$, wherein both chiral centers are independently enantiopure. In certain embodiments, wherein $R^3$ and L are as described above, the two chiral centers in the $C_{2-6}$ hydrocarbon chain are at $C_2$ and $C_3$, wherein both chiral centers are independently enantiopure. In certain embodiments, wherein $R^3$ and L are as described above, compounds are provided such that all possible stereoisomers of L are present.

In some embodiments, the present invention provides a compound of Formula I or Formula I', having stereochemistry as depicted in Formula 1b, wherein L is a $C_{2-6}$ hydrocarbon chain containing two chiral centers, and wherein $R^3$ is of Formula 1r.

In some embodiments, the present invention provides a compound of Formula I or Formula I', having stereochemistry as depicted in Formula 1a, wherein L is a $C_{2-6}$ hydrocarbon chain containing two chiral centers, and wherein $R^3$ is of Formula 2r. In some embodiments, the present invention provides a compound of Formula I or Formula I', having stereochemistry as depicted in Formula 1b, wherein L is a $C_{2-6}$ hydrocarbon chain containing two chiral centers, and wherein $R^3$ is of Formula 2r.

7. Regiochemistry Embodiments

In some embodiments, compounds of the present invention are provided as a mixture of one or more regioisomers (e.g., with respect to "L"). One of skill in the art will appreciate that all stereochemistry embodiments described herein are contemplated with respect to regioisomers and/or regioisomeric mixtures. In certain embodiments, regioisomeric mixtures contain two regioisomers present in a ratio of about 20:1, 18:1, 16:1, 14:1, 12:1, 10:1, 9:1, 8:1, 7:1, 6:1, 5:1, 4:1, 3:1, 2:1, or 1:1. In certain embodiments, one or more regioisomers may be present in one or more stereoisomeric forms, as described above.

It will apparent to one skilled in the art that regioisomeric mixtures of compounds may contain one or more regioisomers present in any ratio relative to one another.

Exemplary such regioisomeric mixtures described herein include: (1) Example 60, wherein a composition contains a mixture of Compound N-28: Compound N-27 in a ratio of about 7:3, wherein the chiral carbon present in each of Compound N-28 and Compound N-27 is present in an (R) configuration (i.e., enantiopure). In certain embodiments, the present invention also contemplates the chiral carbon of Compound N-28 and Compound N-27 in an (S) configuration; (2) Example 28, wherein a composition contains a mixture of Compound N-34:Compound N-33 in a ratio of about 6:4, wherein Compound N-34 is present as an (R)(R) enantiomer and as an (S)(R) enantiomer in a ratio of about 1:1, and wherein Compound N-33 is present as an (R)(R) enantiomer and as an (S)(R) enantiomer in a ratio of about 1:1. (3) Example 58, wherein the stereochemistry is substantially similar to the stereochemistry described in Example 28 above.

TABLE 1
Exemplary Compounds
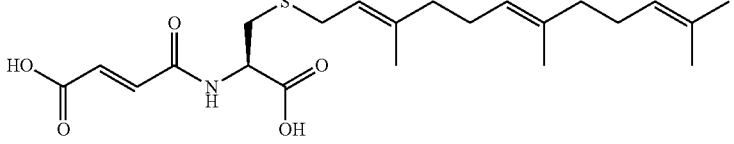 A
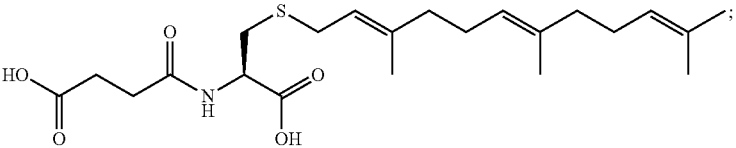 [SMILES: CC(C)=CCC/C(C)=C/CC/C(C)=C/CSC[C@H](NC(=O)CCC(=O)O)C(=O)O] B
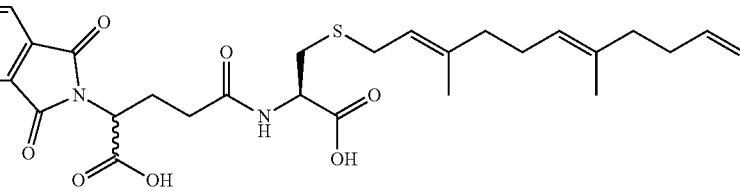 C
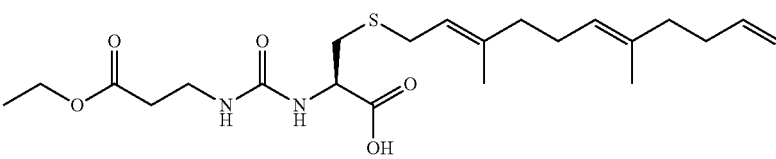 D
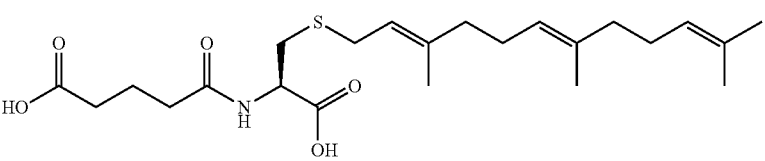 [SMILES: CC(C)=CCC/C(C)=C/CC/C(C)=C/CSC[C@H](NC(=O)CCCC(=O)O)C(=O)O] E
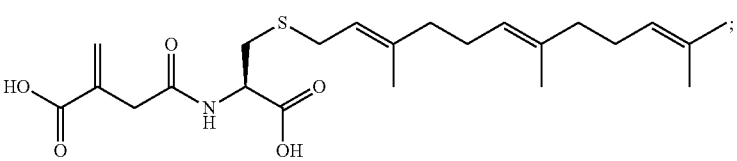 [SMILES: C=C(CC(=O)N[C@@H](CSC/C=C(\C)CC/C=C(\C)CCC=C(C)C)C(=O)O)C(=O)O] F
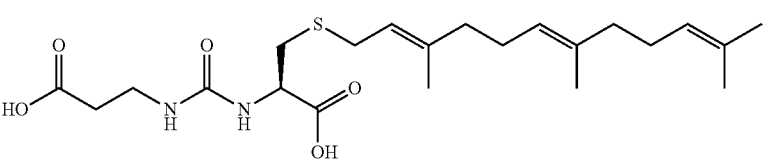 [SMILES: CC(C)=CCC/C(C)=C/CC/C(C)=C/CSC[C@H](NC(=O)NCCC(=O)O)C(=O)O] G
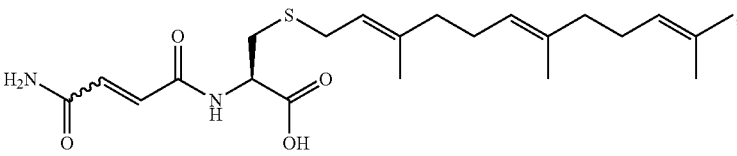 [SMILES: CC(C)=CCC/C(C)=C/CC/C(C)=C/CSC[C@H](NC(=O)C=CC(N)=O)C(=O)O] H
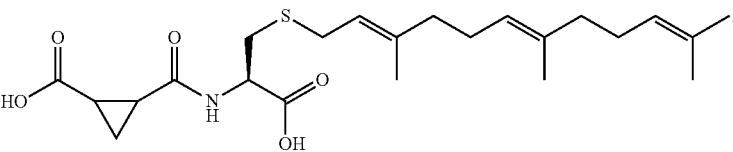 [SMILES: CC(C)=CCC/C(C)=C/CC/C(C)=C/CSC[C@H](NC(=O)C1CC1C(=O)O)C(=O)O] I TABLE 1-continued
Exemplary Compounds
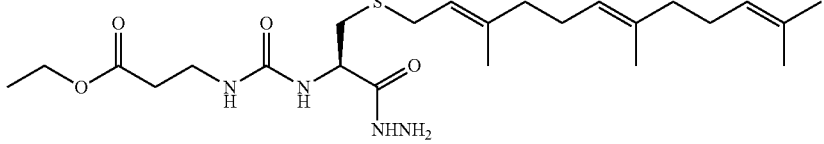 J
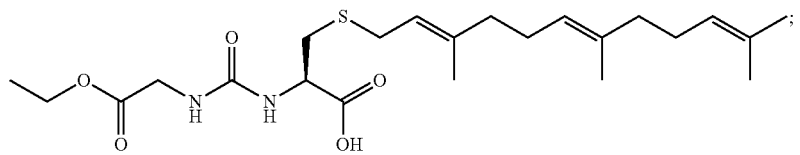 [SMILES: CCOC(=O)CNC(=O)N[C@@H](CSC/C=C(\C)CC/C=C(\C)CCC=C(C)C)C(=O)O] K
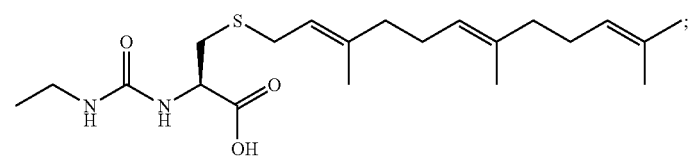 [SMILES: CCNC(=O)N[C@@H](CSC/C=C(\C)CC/C=C(\C)CCC=C(C)C)C(=O)O] L
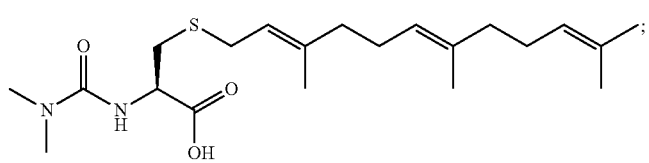 [SMILES: CC(C)=CCC/C(C)=C/CC/C(C)=C/CSC[C@H](NC(=O)N(C)C)C(=O)O] M
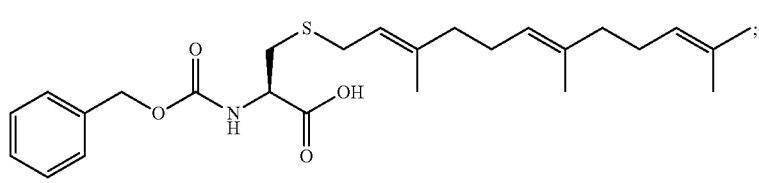 [SMILES: CC(C)=CCC/C(C)=C/CC/C(C)=C/CSC[C@H](NC(=O)OCc1ccccc1)C(=O)O] N-1
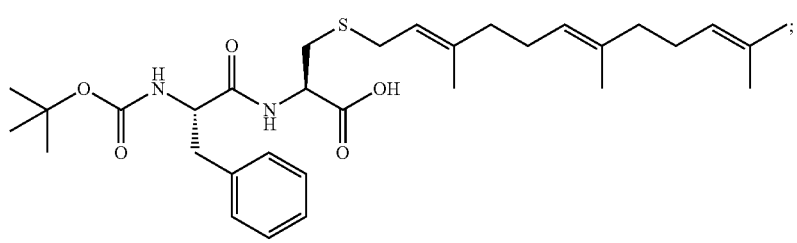 [SMILES: CC(C)=CCC/C(C)=C/CC/C(C)=C/CSC[C@H](NC(=O)[C@H](Cc1ccccc1)NC(=O)OC(C)(C)C)C(=O)O] N-2
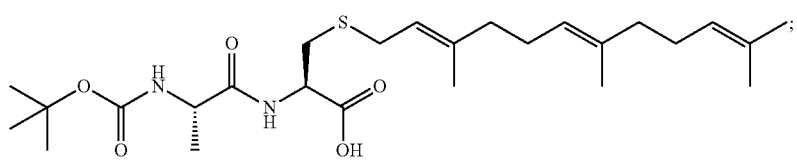 [SMILES: CC(C)=CCC/C(C)=C/CC/C(C)=C/CSC[C@H](NC(=O)[C@H](C)NC(=O)OC(C)(C)C)C(=O)O] N-3
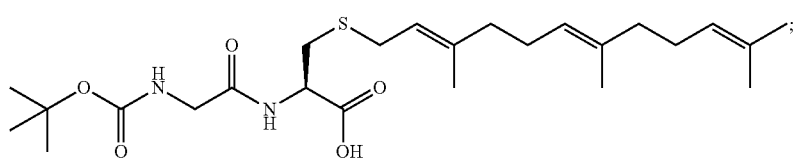 [SMILES: CC(C)=CCC/C(C)=C/CC/C(C)=C/CSC[C@H](NC(=O)CNC(=O)OC(C)(C)C)C(=O)O] N-4

TABLE 1-continued

Exemplary Compounds

| | |
|---|---|
| (structure) | N-5 |
| (structure) | N-6 |
| (structure) | N-7 |
| (structure) | N-8 |
| (structure) | N-9 |
| (structure) | N-10 |
| (structure) | N-11 |
| (structure) | N-12 |

TABLE 1-continued

Exemplary Compounds

N-13 through N-21: chemical structures.

TABLE 1-continued
Exemplary Compounds
N-22
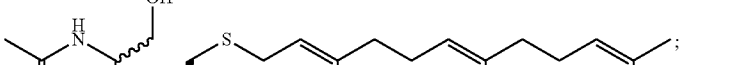
N-23
N-24
N-25
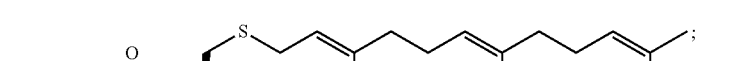
N-26
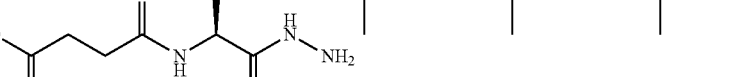
N-27
N-28
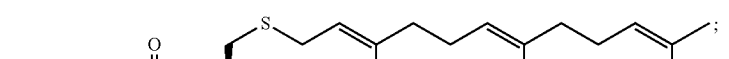
N-29
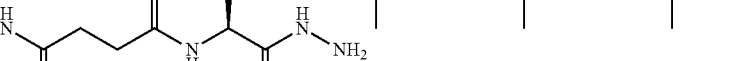
N-30

TABLE 1-continued
Exemplary Compounds
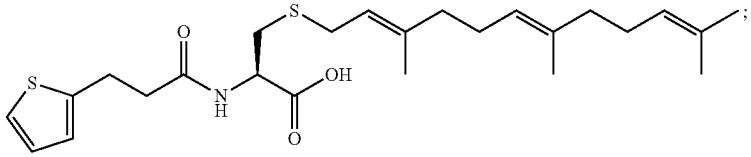 [SMILES: CC(C)=CCC/C(C)=C/CC/C(C)=C/CSC[C@H](NC(=O)CCc1cccs1)C(=O)O] N-31
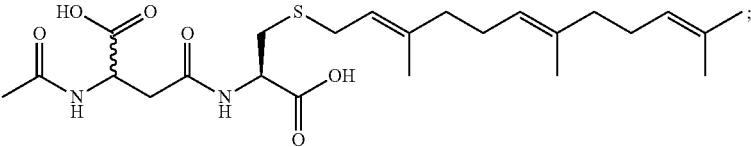 [SMILES: CC(=O)NC(CC(=O)N[C@@H](CSC/C=C(\C)CC/C=C(\C)CCC=C(C)C)C(=O)O)C(=O)O] N-32
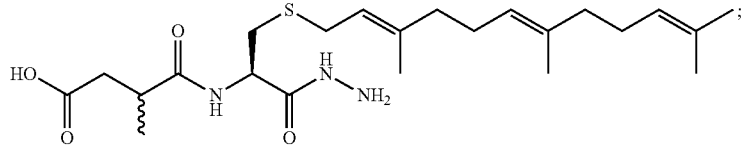 [SMILES: CC(C)=CCC/C(C)=C/CC/C(C)=C/CSC[C@H](NC(=O)C(C)CC(=O)O)C(=O)NN] N-33
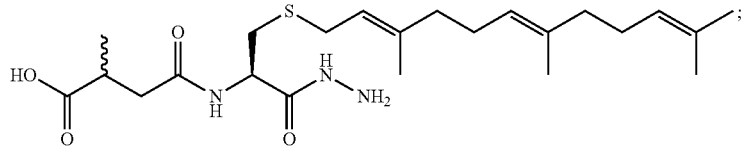 [SMILES: CC(C)=CCC/C(C)=C/CC/C(C)=C/CSC[C@H](NC(=O)CC(C)C(=O)O)C(=O)NN] N-34
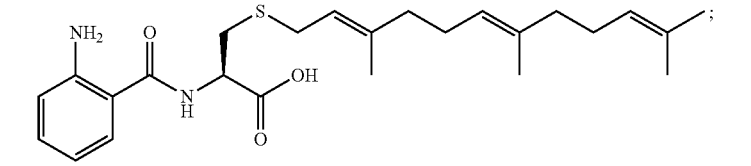 [SMILES: CC(C)=CCC/C(C)=C/CC/C(C)=C/CSC[C@H](NC(=O)c1ccccc1N)C(=O)O] N-35
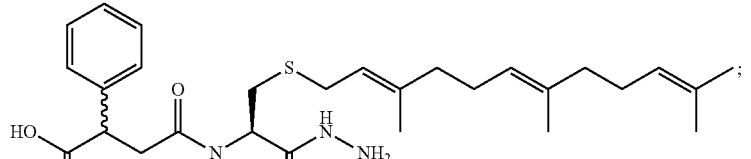 N-36
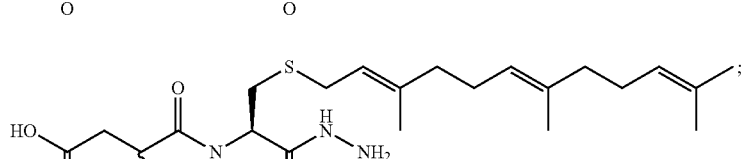 N-37
 N-38

TABLE 1-continued

Exemplary Compounds

| Structure | ID |
|---|---|
| (5-hydroxyindol-3-yl-acetyl-Cys(farnesyl)-OH) | N-39 |
| Ac-Xaa-Cys(farnesyl)-OH | N-40 |
| Ac-Val-Cys(farnesyl)-OH | N-41 |
| Acryloyl-Cys(farnesyl)-OH | N-42 |
| Ac-β-Ala-Cys(farnesyl)-OH | N-43 |
| MeO-succinyl-Cys(farnesyl)-NHNH₂ | N-44 |
| 1-carboxycyclopropanecarbonyl-Cys(farnesyl)-OH | N-45 |
| Ac-Abu-Cys(farnesyl)-OH | N-46 |

TABLE 1-continued

Exemplary Compounds

| | |
|---|---|
| (structure) | N-47 |
| (structure) | N-48 |
| (structure) | N-49 |
| (structure) | N-50 |
| (structure) | N-51 |
| (structure) | N-52 |
| (structure) | N-53 |
| (structure) | N-54 |

TABLE 1-continued

Exemplary Compounds

N-55
N-56
N-57
N-58
N-59
N-60
N-61

TABLE 1-continued
Exemplary Compounds
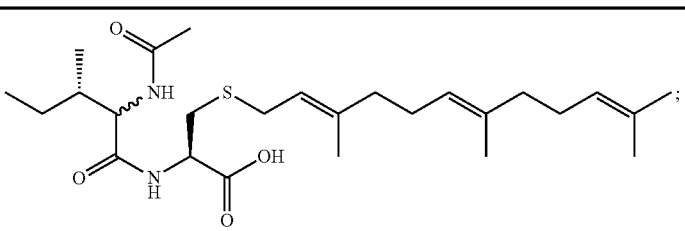 N-62
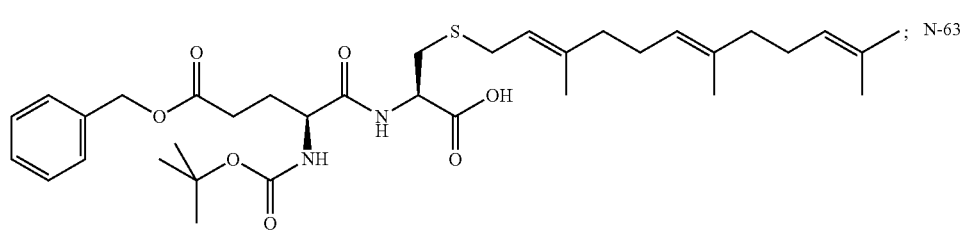 N-63
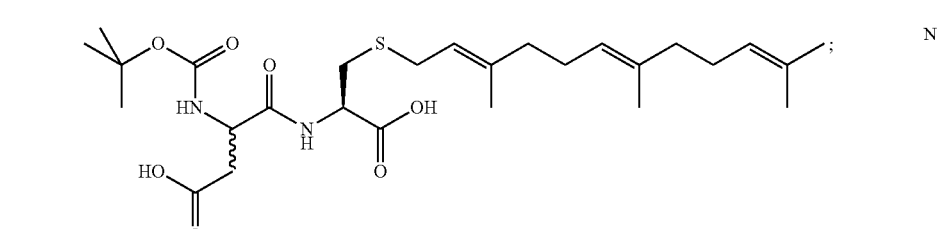 N-64
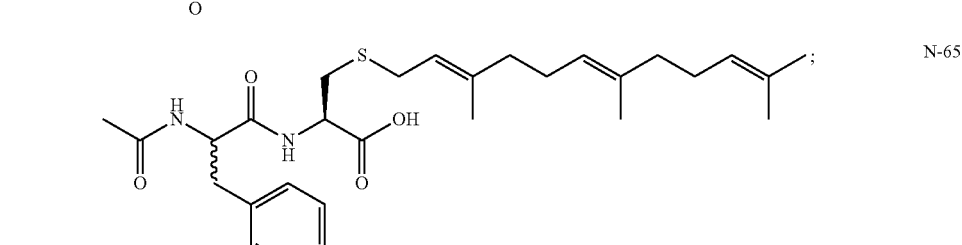 N-65
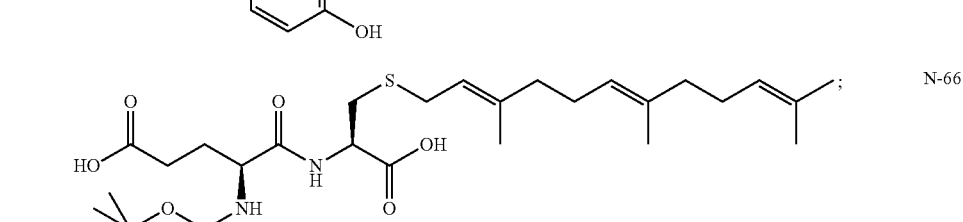 N-66
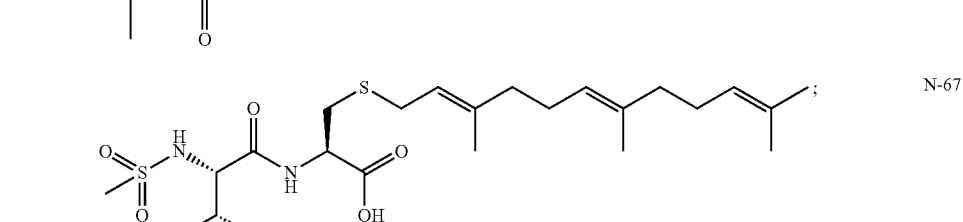 N-67
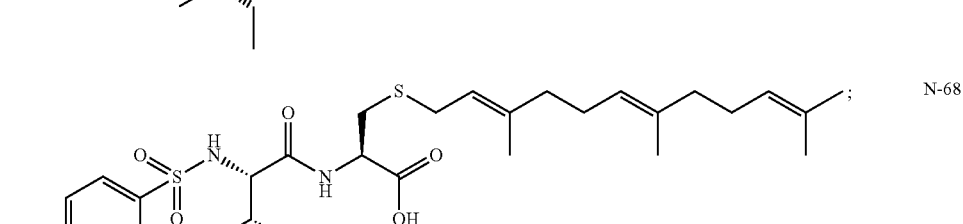 N-68

TABLE 1-continued
Exemplary Compounds
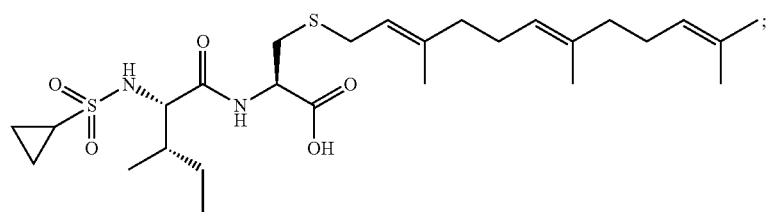 [SMILES: CC[C@H](C)[C@H](NS(=O)(=O)C1CC1)C(=O)N[C@@H](CSC/C=C(\C)CC/C=C(\C)CCC=C(C)C)C(=O)O] N-69
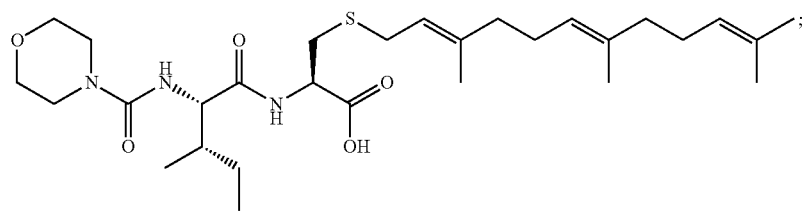 [SMILES: CC[C@H](C)[C@H](NC(=O)N1CCOCC1)C(=O)N[C@@H](CSC/C=C(\C)CC/C=C(\C)CCC=C(C)C)C(=O)O] N-70
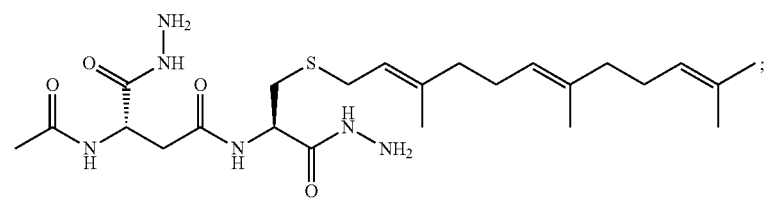 [SMILES: CC(=O)N[C@@H](CC(=O)N[C@@H](CSC/C=C(\C)CC/C=C(\C)CCC=C(C)C)C(=O)NN)C(=O)NN] N-71
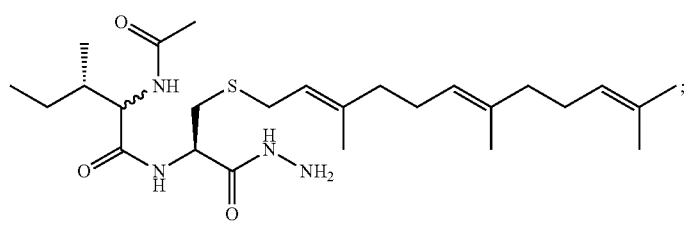 [SMILES: CC[C@H](C)C(NC(C)=O)C(=O)N[C@@H](CSC/C=C(\C)CC/C=C(\C)CCC=C(C)C)C(=O)NN] N-72
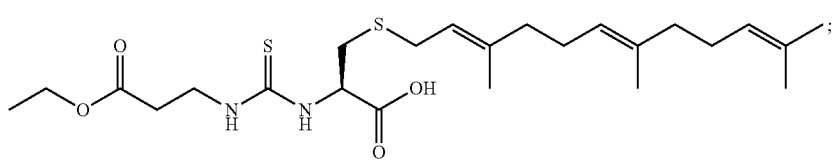 [SMILES: CCOC(=O)CCNC(=S)N[C@@H](CSC/C=C(\C)CC/C=C(\C)CCC=C(C)C)C(=O)O] N-73
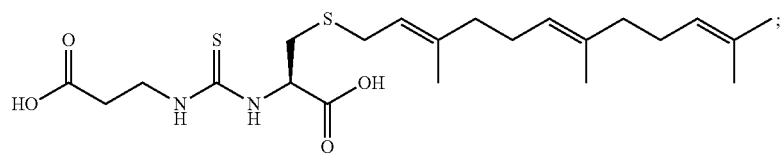 [SMILES: CC(C)=CCC/C(C)=C/CC/C(C)=C/CSC[C@H](NC(=S)NCCC(=O)O)C(=O)O] N-74
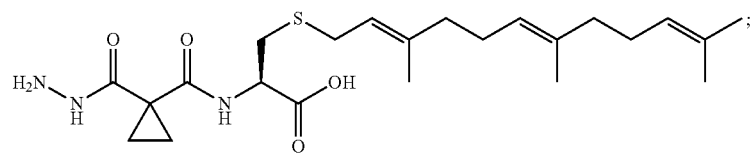 [SMILES: CC(C)=CCC/C(C)=C/CC/C(C)=C/CSC[C@H](NC(=O)C1(C(=O)NN)CC1)C(=O)O] N-75
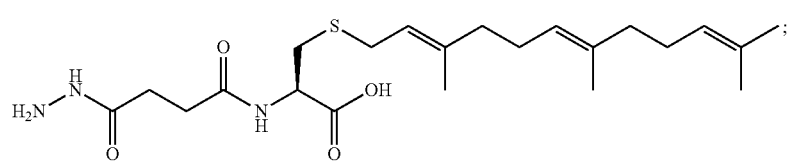 [SMILES: CC(C)=CCC/C(C)=C/CC/C(C)=C/CSC[C@H](NC(=O)CCC(=O)NN)C(=O)O] N-76

TABLE 1-continued

Exemplary Compounds

| Structure | ID |
|---|---|
| (structure) | N-77 |
| (structure) | N-78 |
| (structure) | N-79 |
| (structure) | N-80 |
| (structure) | N-81 |
| (structure) | N-82 |
| (structure) | N-83 |
| (structure) | N-84 |
| (structure) | N-85 |

TABLE 1-continued
Exemplary Compounds
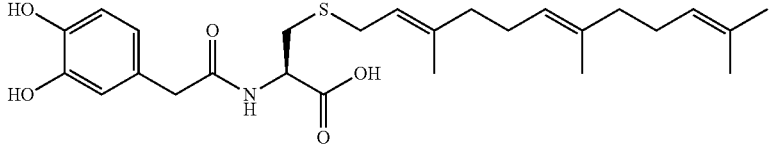 [SMILES: CC(C)=CCC/C(C)=C/CC/C(C)=C/CSC[C@H](NC(=O)Cc1ccc(O)c(O)c1)C(=O)O] N-86
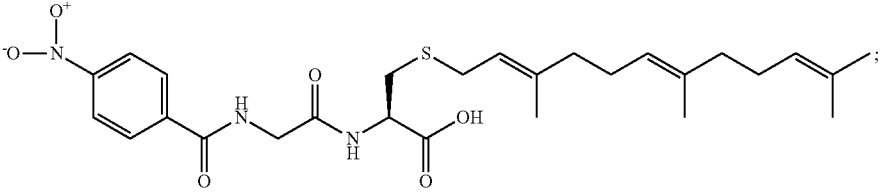 N-87
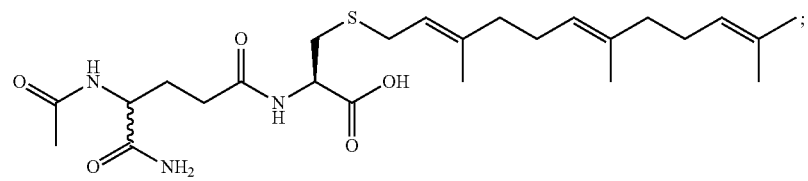 [SMILES: CC(=O)NC(CCC(=O)N[C@@H](CSC/C=C(\C)CC/C=C(\C)CCC=C(C)C)C(=O)O)C(N)=O] N-88
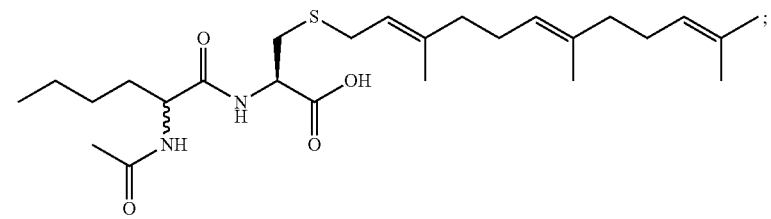 [SMILES: CCCCC(NC(C)=O)C(=O)N[C@@H](CSC/C=C(\C)CC/C=C(\C)CCC=C(C)C)C(=O)O] N-89
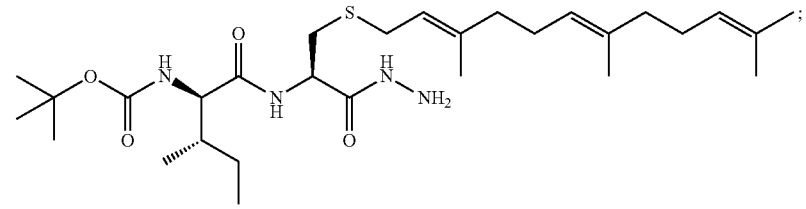 [SMILES: CC[C@H](C)[C@@H](NC(=O)OC(C)(C)C)C(=O)N[C@@H](CSC/C=C(\C)CC/C=C(\C)CCC=C(C)C)C(=O)NN] N-90
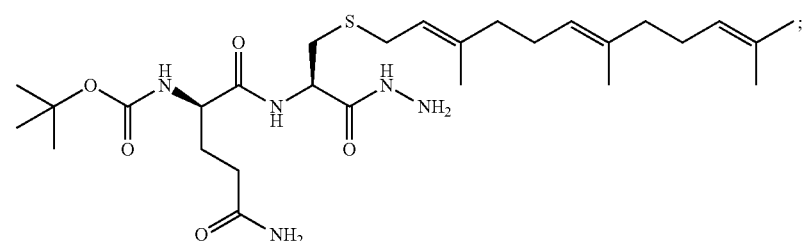 [SMILES: CC(C)=CCC/C(C)=C/CC/C(C)=C/CSC[C@H](NC(=O)[C@@H](CCC(N)=O)NC(=O)OC(C)(C)C)C(=O)NN] N-91
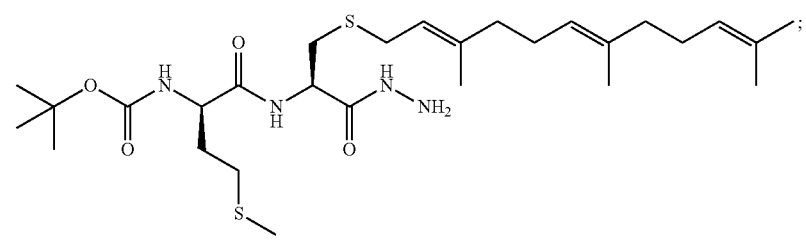 [SMILES: CSCC[C@@H](NC(=O)OC(C)(C)C)C(=O)N[C@@H](CSC/C=C(\C)CC/C=C(\C)CCC=C(C)C)C(=O)NN] N-92

TABLE 1-continued

Exemplary Compounds

| Compound | ID |
|---|---|
| [structure: glutamine-cysteine dipeptide with phenyl urea substituent and farnesyl thioether] | N-93 |
| [structure: glutamine-cysteine dipeptide with ethyl urea substituent and farnesyl thioether] | N-94 |
| [structure: glutamine-cysteine dipeptide with ethyl urea substituent (alternate stereochemistry) and farnesyl thioether] | N-95 |
| [structure: furan-propanoyl-cysteine with farnesyl thioether] | N-96 |
| [structure: 3-nitropropanoyl-cysteine with farnesyl thioether] | N-97 |
| and | |
| [structure: menthyl carbamate of cysteine with farnesyl thioether] | N-98 |

In certain embodiments, the present invention provides any compound depicted in Table 1, above, or a pharmaceutically acceptable salt thereof.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In some embodiments, the $R^1$ group of Formulae I and/or I' comprises one or more deuterium atoms. Mixtures of isomeric forms may be separated and/or purified by techniques as would be known to one skilled in this art, including but not limited to column chromatography.

Compounds of Formulae I, I' and/or Ia may be provided according to the present invention in any of a variety of useful forms, for example as pharmaceutically acceptable salts, as particular crystal forms, etc. In some embodiments, prodrugs of one or more compounds of the present invention are provided. Various forms of prodrugs are known in the art, for example as discussed in Bundgaard (ed.), *Design of Prodrugs*, Elsevier (1985); Widder et al. (ed.), *Methods in Enzymology*, vol. 4, Academic Press (1985); Kgrogsgaard-Larsen et al. (ed.); *"Design and Application of Prodrugs", Textbook of Drug Design and Development*, Chapter 5, 113-191 (1991); Bundgaard et al., *Journal of Drug Delivery Reviews*, 8:1-38 (1992); Bundgaard et al., *J. Pharmaceutical Sciences*, 77:285 et seq. (1988); and Higuchi and Stella (eds.), *Prodrugs as Novel Drug Delivery Systems*, American Chemical Society (1975).

As described above, the present invention provides isoprenyl compounds related in structure to AFC. Like AFC, in certain embodiments, isoprenyl compounds are characterized by an ability to reduce methylation of a protein having a carboxyl-terminal --CAAX motif, wherein C=cysteine, A=any aliphatic amino acid, and X=any amino acid. (See Rando, U.S. Pat. No. 5,202,456). The methylation reaction which is inhibited is part of a series of post-translational modifications involving the --CAAX motif. These modifications include polyisoprenylation of the cysteine of the --CAAX motif (on the sulfur), proteolysis of the carboxyl-terminal three amino acids (--AAX) and methylation of the carboxyl group of cysteine.

In certain embodiments, provided compounds modulate a G-protein signaling cascade. In certain embodiments, provided compounds alter the interactions among polyisoprenylated signal transduction proteins, such as G-proteins and the protein regulatory targets with which they interact, or other intracellular signaling proteins. In certain embodiments, provided compounds modulate the inflammatory response. In certain embodiments, provided compounds inhibit inflammation and are therefore anti-inflammatory. In certain embodiments, provided compounds promote inflammation and are therefore proinflammatory.

In some embodiments, provided compounds modulate levels of inflammatory mediators, such as cytokines induced by G-protein-mediated pathways (e.g., purinergic receptors). In some embodiments, provided compounds inhibit the levels of proinflammatory mediators, such as proinflammatory cytokines. In further embodiments, provided compounds inhibit levels of proinflammatory mediators, such as proinflammatory cytokines induced by G-protein-mediated pathways.

In some embodiments, provided compounds modulate levels of inflammatory mediators, such as cytokines induced by other signal transduction pathways [e.g., pathways involving Toll-like receptors ("TLRs") and TNFα receptors]. In some embodiments, provided compounds inhibit levels of proinflammatory mediators, such as proinflammatory cytokines induced by other signal transduction pathways [e.g., pathways involving Toll-like receptors ("TLRs") and TNFα receptors].

In some embodiments, provided compounds inhibit levels of proinflammatory mediators, such as proinflammatory cytokines that are induced by chemicals such as TPA.

In some embodiments, provided compounds modulate the levels of inflammatory mediators such as cytokines characterized using an Atopic Dermatitis mouse model.

In some embodiments, provided compounds inhibit the levels of proinflammatory mediators such as proinflammatory cytokines characterized using an Atopic Dermatitis mouse model.

In some embodiments, provided compounds modulate the infiltration and accumulation of T-helper lymphocytes. In some embodiments, provided compounds modulate T-helper lymphocytes with CD3+ marker. In some embodiments, provided compounds modulate the infiltration and accumulation of T-helper lymphocytes characterized using a Stat3c psoriasis mouse model. In some embodiments, provided compounds inhibit infiltration and accumulation of T-helper lymphocytes. In some embodiments, provided compounds inhibit infiltration and accumulation of T-helper lymphocytes with CD3+ marker. In some embodiments, provided compounds inhibit infiltration and accumulation of T-helper lymphocytes characterized using a Stat3c psoriasis mouse model.

In some embodiments, provided compounds inhibit methylesterifcation reactions by a specific membrane associated S-adeno sylmethionine-dependent isoprenyl-S-isoprenyl methyltransferase ("ICMT") resulting in carboxy-terminal polyisoprenoid cysteine modifications of a number of key factors in G-protein signaling pathway.

In some embodiments, provided compounds promote inflammation and are therefore pro inflammatory.

In some embodiments, provided compounds inhibit oxidative burst from neutrophils and are therefore anti-oxidants.

In certain embodiments, activity of provided compounds may be characterized using a variety of in vitro or in vivo assays, involving a variety of cell-based or animal-based models. For example, data from exemplary assays for: Edema, Erythema and/or Inhibition of Myeloperoxidase; Inflammatory Cytokines; Stat3c-Psoriasis Mouse Model; Inhibition of Methylesterification Reactions; and Inhibition of Oxidative Burst are each described below.

Edema, Erythema and/or Inhibition of Myeloperoxidase (MPO)

Ability of provided compounds to modulate inflammatory responses may be assessed, for example, using assays that assess edema, erythema, and/or inhibition of myeloperoxidase ("MPO") as described, for example, in Example 79.

In certain embodiments, provided compounds are considered to be inhibitors of inflammation when they show a percent inhibition in an edema assay of at least about 30, 35, 40, 50, 60, 70, 80, 90 or 95%, for example when provided at a dose 0.8 mg/20 In certain embodiments, provided compounds are considered to be inhibitors of inflammation when they show a percent inhibition in an edema assay of at least about 5, 10, 15, 20, 25, 30, 35, 40, 50, 60, 70, or 80%, for example when provided at a dose of 0.2 mg/20 In certain embodiments, provided compounds are considered to be inhibitors of inflammation when they result in an $ED_{50}$ in an edema assay of at least about 0.5, 1, 1.5, 2, 2.5, 3, 3.5, 4, 4.5-fold lower than that observed with AFC. In certain embodiments, provided compounds are considered to be proinflammatory when they show percent inhibition in an edema assay of at least about (−)10, (−)20, (−)30, (−)40, (−)50, (−)55, (−)60, (−)65, (−)70, (−)75, (−)80, (−)85, (−)90 or (−)95%, for example when provided at a dose of 0.8 mg/20 μl.

In certain embodiments, provided compounds are considered to be inhibitors of inflammation when they show a percent inhibition in an erythema assay of at least about 25, 30, 35, 40, 50, 60, 70, 80, 90 or 95%, for example when provided at a dose of 0.8 mg/20 In certain embodiments, provided compounds are considered to be inhibitors of inflammation when they show a percent inhibition in an erythema assay of at least about 5, 10, 15, 20, 25, 30, 35, 40, 50, 60, 70, 80, 90 or 95%, for example when provided at a dose of 0.2 mg/20 In certain embodiments, provided compounds are considered to be inhibitors of inflammation when they result in an $ED_{50}$ in an erythema assay of at least about 0.5, 1, 1.5, 2, 2.5, 3, 3.5, 4, 4.5-fold lower than that observed with AFC. In certain embodiments, provided compounds are considered to be proinflammatory when they show percent inhibition in an erythema assay of at least about (−)10, (−)20, (−)30, (−)40, (−)50, (−)55, (−)60, (−)65, (−)70, (−)75, (−)80, (−)85, (−)90 or (−)95%, for example when provided at a dose of 0.8 mg/20 µl.

In certain embodiments, provided compounds are considered to be inhibitors of inflammation when they show a percent inhibition in an MPO activity assay of at least about 60, 70, 80, 90 or 95%, for example when provided at a dose of 0.8 mg/20 µL. In certain embodiments, provided compounds are considered to be inhibitors of inflammation when they show a percent inhibition in an MPO activity assay of at least about 5, 10, 15, 20, 25, 30, 35, 40, 50, 60, 70, or 80%, for example when provided at a dose of 0.2 mg/20 µL. In certain embodiments, provided compounds are considered to be inhibitors of inflammation when they result in an $ED_{50}$ in an MPO activity assay of at least about 0.5, 1, 1.5, 2, 2.5, 3, 3.5, 4, 4.5, 5, 5.5, 6 or 6.5-fold lower than that observed with AFC. In certain embodiments, provided compounds are considered to be proinflammatory when they show percent inhibition in an MPO activity assay of at least about (−)10, (−)20, (−)30, (−)40, (−)50, (−)55, (−)60, (−)65, (−)70, (−)75, (−)80, (−)85, (−)90 or (−)95%, for example when provided at a dose of 0.8 mg/20 µl.

Inflammatory Cytokines

Ability of provided compounds to modulate inflammatory responses may be assessed for example, using assays that measure the levels of inflammatory cytokines, for example, TNF-α, IL-1β, IL-8/KC, or IL-6, that can be determined using inflammatory models [e.g., TPA-induced mouse ear inflammatory model as described in Example 80; LPS-TLR4-induced cytokine release inflammatory model in Human Microvascular Endothelial cell lines ("HMEC-1") as described in Example 81; ATPγS-purinergic receptor-induced cytokine release inflammatory model in Human Microvascular Endothelial cell lines ("HMEC-1") as described in Example 82; TPA-induced cytokine release inflammatory model in Normal Human Epidermal Keratinocyte cell lines ("NHEK") as described in Example 83; TNFα-induced cytokine release inflammatory model in Human Umbilical Vein Endothelial cell lines ("HUVEC") as described in Example 84; or an Ovalbumin-induced flaky tail Atopic Dermatis mouse model as described in Example 85].

(i) TPA-Induced Mouse Ear Inflammatory Model

In certain embodiments, provided compounds are considered inhibitors of inflammation when they show a percent inhibition of cytokine release in a TPA-induced mouse ear inflammatory model of at least about 5, 10, 15, 20, 25, 30, 35, 40, 45, 50, 55, 60, 65, 70, 75, 80, 85, 90 or 95%, for example when provided at a dosage of 0.25%. In certain embodiments, provided compounds are considered inhibitors of inflammation when they result in an $ED_{50}$ in a TPA-induced mouse ear inflammatory model of at least about 0.01, 0.05, 0.10, 0.15, 0.20, 0.25, 0.30, 0.35 or 0.40 µg cytokine/mouse ear, for example when provided at a dosage of 0.25%. In certain embodiments, provided compounds are considered inhibitors of inflammation when they show a percent inhibition of cytokine release in a TPA-induced mouse ear inflammatory model of at least about 5, 10, 15, 20, 25, 30, 35, 40, 45, 50, 55, 60, 65, 70, 75, 80, 85, 90 or 95%, for example when provided at a dosage of 0.50%. In certain embodiments, provided compounds are considered inhibitors of inflammation when they result in an $ED_{50}$ in a TPA-induced mouse ear inflammatory model of at least about 0.01, 0.05, 0.10, 0.15, 0.20, 0.25, 0.30, 0.35 or 0.40 µg cytokine/mouse ear, for example when provided at a dosage of 0.50%. In certain embodiments, provided compounds are considered inhibitors of inflammation when they show a percent inhibition of cytokine release in a TPA-induced mouse ear inflammatory model of at least about 5, 10, 15, 20, 25, 30, 35, 40, 45, 50, 55, 60, 65, 70, 75, 80, 85, 90 or 95%, for example when provided at a dosage of 1.00%. In certain embodiments, provided compounds are considered inhibitors of inflammation when they result in an $ED_{50}$ in a TPA-induced mouse ear inflammatory model of at least about 0.01, 0.05, 0.10, 0.15, 0.20, 0.25, 0.30, 0.35 or 0.40 µg cytokine/mouse ear, for example, when provided at a dosage of 1.00%.

(ii) LPS-TLR4-induced Cytokine Release Inflammatory Model

In certain embodiments, provided compounds are considered inhibitors of inflammation when they show a percent inhibition of cytokine release in a LPS-TLR4-induced cytokine release model, as determined using HMEC-1 cells of at least about 5, 10, 15, 20, 25, 30, 35, 40, 45, 50, 55, 60, 65, 70, 75, 80, 85, 90 or 95%, for example when provided at a dosage of 0.25%. In certain embodiments, provided compounds are considered inhibitors of inflammation when they result in an $ED_{50}$ in a LPS-TLR4-induced cytokine release model, as determined using HMEC-1 cells, of at least about 0.01, 0.05, 0.10, 0.15, 0.20, 0.25, 0.30, 0.35 or 0.40 µg cytokine/mouse ear, for example when provided at a dosage of 0.25%. In certain embodiments, provided compounds are considered inhibitors of inflammation when they show a percent inhibition of cytokine release in a LPS-TLR4-induced cytokine release model, as determined using HMEC-1 cells, of at least about 5, 10, 15, 20, 25, 30, 35, 40, 45, 50, 55, 60, 65, 70, 75, 80, 85, 90 or 95%, for example when provided at a dosage of 0.50%. In certain embodiments, provided compounds are considered inhibitors of inflammation when they result in an $ED_{50}$ in a LPS-TLR4-induced cytokine release model, as determined using HMEC-1 cells, of at least about 0.01, 0.05, 0.10, 0.15, 0.20, 0.25, 0.30, 0.35 or 0.40 µg cytokine/mouse ear, for example when provided at a dosage of 0.50%. In certain embodiments, provided compounds are considered inhibitors of inflammation when they show a percent inhibition of cytokine release in a LPS-TLR4-induced cytokine release model, as determined using HMEC-1 cells, of at least about 5, 10, 15, 20, 25, 30, 35, 40, 45, 50, 55, 60, 65, 70, 75, 80, 85, 90 or 95%, for example when provided at a dosage of 1.00%. In certain embodiments, provided compounds are considered inhibitors of inflammation when they result in an $ED_{50}$ in a LPS-TLR4-induced cytokine release model, as determined using HMEC-1 cells, of at least about 0.01, 0.05, 0.10, 0.15, 0.20, 0.25, 0.30, 0.35 or 0.40 µg cytokine/mouse ear, for example, when provided at a dosage of 1.00%.

(iii) ATPγS-purinergic Receptor-induced Cytokine Release Inflammatory Model

In certain embodiments, provided compounds are considered inhibitors of inflammation when they show a percent inhibition of cytokine release in an ATPγS-purinergic receptor-induced cytokine release model, as determined using HMEC-1 cells of at least about 5, 10, 15, 20, 25, 30, 35, 40, 45, 50, 55, 60, 65, 70, 75, 80, 85, 90 or 95%, for example when provided at a dosage of 0.25%. In certain embodiments, provided compounds are considered inhibitors of inflammation when they result in an $ED_{50}$ in an ATPγS-purinergic receptor-induced cytokine release model, as determined using HMEC-1 cells, of at least about 0.01, 0.05, 0.10, 0.15, 0.20, 0.25, 0.30, 0.35 or 0.40 µg cytokine/mouse ear, for example when provided at a dosage of 0.25%. In certain embodiments, provided compounds are considered inhibitors of inflammation when they show a percent inhibition of cytokine release in an ATPγS-purinergic receptor-induced cytokine release model, as determined using HMEC-1 cells, of at least about 5, 10, 15, 20, 25, 30, 35, 40, 45, 50, 55, 60, 65, 70, 75, 80, 85, 90 or 95%, for example when provided at a dosage of 0.50%. In certain embodiments, provided compounds are considered inhibitors of inflammation when they result in an $ED_{50}$ in an ATPγS-purinergic receptor-induced cytokine release model, as determined using HMEC-1 cells, of at least about 0.01, 0.05, 0.10, 0.15, 0.20, 0.25, 0.30, 0.35 or 0.40 μg cytokine/mouse ear, for example when provided at a dosage of 0.50%. In certain embodiments, provided compounds are considered inhibitors of inflammation when they show a percent inhibition of cytokine release in an ATPγS-purinergic receptor-induced cytokine release model, as determined using HMEC-1 cells, of at least about 5, 10, 15, 20, 25, 30, 35, 40, 45, 50, 55, 60, 65, 70, 75, 80, 85, 90 or 95%, for example when provided at a dosage of 1.00%. In certain embodiments, provided compounds are considered inhibitors of inflammation when they result in an $ED_{50}$ in an ATPγS-purinergic receptor-induced cytokine release model, as determined using HMEC-1 cells, of at least about 0.01, 0.05, 0.10, 0.15, 0.20, 0.25, 0.30, 0.35 or 0.40 μg cytokine/mouse ear, for example, when provided at a dosage of 1.00%.

(iv) TPA-Induced Cytokine Release Inflammatory Model

In certain embodiments, provided compounds are considered inhibitors of inflammation when they show a percent inhibition of cytokine release in a TPA-induced cytokine release model, as determined using NHEK cells of at least about 5, 10, 15, 20, 25, 30, 35, 40, 45, 50, 55, 60, 65, 70, 75, 80, 85, 90 or 95%, for example when provided at a dosage of 0.25%. In certain embodiments, provided compounds are considered inhibitors of inflammation when they result in an $ED_{50}$ in a TPA-induced cytokine release model, as determined using NHEK cells, of at least about 0.01, 0.05, 0.10, 0.15, 0.20, 0.25, 0.30, 0.35 or 0.40 μg cytokine/mouse ear, for example when provided at a dosage of 0.25%. In certain embodiments, provided compounds are considered inhibitors of inflammation when they show a percent inhibition of cytokine release in a TPA-induced cytokine release model, as determined using NHEK cells, of at least about 5, 10, 15, 20, 25, 30, 35, 40, 45, 50, 55, 60, 65, 70, 75, 80, 85, 90 or 95%, for example when provided at a dosage of 0.50%. In certain embodiments, provided compounds are considered inhibitors of inflammation when they result in an $ED_{50}$ in a TPA-induced cytokine release model, as determined using NHEK cells, of at least about 0.01, 0.05, 0.10, 0.15, 0.20, 0.25, 0.30, 0.35 or 0.40 μg cytokine/mouse ear, for example when provided at a dosage of 0.50%. In certain embodiments, provided compounds are considered inhibitors of inflammation when they show a percent inhibition of cytokine release in a TPA-induced cytokine release model, as determined using NHEK cells, of at least about 5, 10, 15, 20, 25, 30, 35, 40, 45, 50, 55, 60, 65, 70, 75, 80, 85, 90 or 95%, for example when provided at a dosage of 1.00%. In certain embodiments, provided compounds are considered inhibitors of inflammation when they result in an $ED_{50}$ in a TPA-induced cytokine release model, as determined using NHEK cells, of at least about 0.01, 0.05, 0.10, 0.15, 0.20, 0.25, 0.30, 0.35 or 0.40 μg cytokine/mouse ear, for example, when provided at a dosage of 1.00%.

(v) TNFα-induced Cytokine Release Inflammatory Model

In certain embodiments, provided compounds are considered inhibitors of inflammation when they show a percent inhibition of cytokine release in a TNFα-induced cytokine release model, as determined using HUVEC cells of at least about 5, 10, 15, 20, 25, 30, 35, 40, 45, 50, 55, 60, 65, 70, 75, 80, 85, 90 or 95%, for example when provided at a dosage of 0.25%. In certain embodiments, provided compounds are considered inhibitors of inflammation when they result in an $ED_{50}$ in a TNFα-induced cytokine release model, as determined using HUVEC cells, of at least about 0.01, 0.05, 0.10, 0.15, 0.20, 0.25, 0.30, 0.35 or 0.40 μg cytokine/mouse ear, for example when provided at a dosage of 0.25%. In certain embodiments, provided compounds are considered inhibitors of inflammation when they show a percent inhibition of cytokine release in a TNFα-induced cytokine release model, as determined using HUVEC cells, of at least about 5, 10, 15, 20, 25, 30, 35, 40, 45, 50, 55, 60, 65, 70, 75, 80, 85, 90 or 95%, for example when provided at a dosage of 0.50%. In certain embodiments, provided compounds are considered inhibitors of inflammation when they result in an $ED_{50}$ in a TNFα-induced cytokine release model, as determined using HUVEC cells, of at least about 0.01, 0.05, 0.10, 0.15, 0.20, 0.25, 0.30, 0.35 or 0.40 μg cytokine/mouse ear, for example when provided at a dosage of 0.50%. In certain embodiments, provided compounds are considered inhibitors of inflammation when they show a percent inhibition of cytokine release in a TNFα-induced cytokine release model, as determined using HUVEC cells, of at least about 5, 10, 15, 20, 25, 30, 35, 40, 45, 50, 55, 60, 65, 70, 75, 80, 85, 90 or 95%, for example when provided at a dosage of 1.00%. In certain embodiments, provided compounds are considered inhibitors of inflammation when they result in an $ED_{50}$ in a TNFα-induced cytokine release model, as determined using HUVEC cells, of at least about 0.01, 0.05, 0.10, 0.15, 0.20, 0.25, 0.30, 0.35 or 0.40 μg cytokine/mouse ear, for example when provided at a dosage of 1.00%.

(vi) Ovalbumin-induced Flaky Tail Atopic Dermatis Mouse Model

In certain embodiments, provided compounds are considered inhibitors of inflammation when they show a percent inhibition of cytokine release in an Ovalbumin-induced Atopic Dermatitis mouse model, of at least about 5, 10, 15, 20, 25, 30, 35, 40, 45, 50, 55, 60, 65, 70, 75, 80, 85, 90 or 95%, for example when provided at a dosage of 0.25%. In certain embodiments, provided compounds are considered inhibitors of inflammation when they result in an $ED_{50}$ in an Ovalbumin-induced Atopic Dermatitis mouse model, of at least about 0.01, 0.05, 0.10, 0.15, 0.20, 0.25, 0.30, 0.35 or 0.40 μg cytokine/mouse ear, for example when provided at a dosage of 0.25%. In certain embodiments, provided compounds are considered inhibitors of inflammation when they show a percent inhibition of cytokine release in an Ovalbumin-induced Atopic Dermatitis mouse model, of at least about 5, 10, 15, 20, 25, 30, 35, 40, 45, 50, 55, 60, 65, 70, 75, 80, 85, 90 or 95%, for example when provided at a dosage of 0.50%. In certain embodiments, provided compounds are considered inhibitors of inflammation when they result in an $ED_{50}$ in a an Ovalbumin-induced Atopic Dermatitis mouse model, of at least about 0.01, 0.05, 0.10, 0.15, 0.20, 0.25, 0.30, 0.35 or 0.40 μg cytokine/mouse ear, for example when provided at a dosage of 0.50%. In certain embodiments, provided compounds are considered inhibitors of inflammation when they show a percent inhibition of cytokine release in an Ovalbumin-induced Atopic Dermatitis mouse model, of at least about 5, 10, 15, 20, 25, 30, 35, 40, 45, 50, 55, 60, 65, 70, 75, 80, 85, 90 or 95%, for example when provided at a dosage of 1.00%. In certain embodiments, provided compounds are considered inhibitors of inflammation when they result in an $ED_{50}$ in an Ovalbumin-induced Atopic Dermatitis mouse model, of at least about 0.01, 0.05, 0.10, 0.15, 0.20, 0.25, 0.30, 0.35 or 0.40 μg cytokine/mouse ear, for example, when provided at a dosage of 1.00%.

Stat3c-Psoriasis Mouse Model

For example, ability of provided compounds to modulate inflammatory responses may be assessed for example, using assays that measure the levels of CD3+T-helper cells, that can be determined using mouse models, for example, a Stat3c-psoriasis mouse model, as described in Example 86. In certain embodiments, provided compounds are considered inhibitors of the infiltration and accumulation of CD3+ T-helper cells when they show a percent reduction of the number of T-helper cells of at least about 20, 25, 30, 35, 40, 50, 60, 70, 75, 80, 85, 90, 95 or 100%, for example when provided at a concentration of at least 0.3%.

Inhibition of Methylesterification Reactions

For example, ability of provided compounds to inhibit methylesterification reactions by ICMT may be assessed, for example, using assays that measure the reduction of methylated acetyl farnesyl cysteine, an ICMT substrate as described for example in Example 87. In certain embodiments, provided compounds are considered inhibitors of ICMT when they show a percent reduction of methylated acetyl-farnesyl-cysteine, as ICMT substrate of at least about 30, 35, 40, 50, 60, 70, 75, 80, 85, 90, 95 or 100%, for example when provided at a concentration of 25 μM.

Inhibition of Oxidative Burst

For example, ability of provided compounds to inhibit oxidative burst from neutrophils may be assessed, for example, using assays that measure the reduction of superoxide formation, as described for example in Example 88. In certain embodiments, provided compounds are considered inhibitors of oxidative burst from neutrophils when they show a percent reduction of superoxide formation of at least about 30, 35, 40, 50, 60, 70, 75, 80, 85, 90, 95 or 100%, for example when provided at a concentration of 25 μM.

2. Methods of Syntheses

The present invention provides methods of preparing compounds provided herein. As will be appreciated by one of skill in the art, the synthetic methods described herein may be modified without departing from the scope of the present invention. For example, different starting materials and/or different reagents may be used in the inventive synthetic methods.

The present invention provides a process for preparing an N-substituted farnesyl cysteine analog with a terminal carboxylic acid. In certain embodiments, the inventive compounds are prepared as shown in the scheme below.

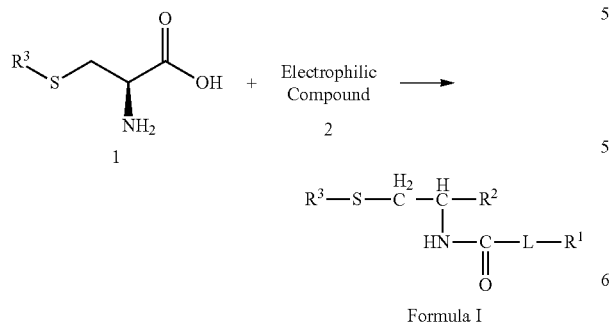

Formula I

To begin, a suitable compound 1 is reacted with a suitable electrophilic compound 2. In certain embodiments, the suitable compound 1 is S-trans, trans-farnesyl-L-cysteine. In certain embodiments, the electrophilic compound 2 is an anhydride. Exemplary anhydrides include succinic anhydride, maleic anhydride, 3-methylenedihydro-2,4-furandione, glutaric anhydride, N-phthaloyl-glutamic anhydride. In certain embodiments, the electrophilic compound 2 is an isocyanate. In certain embodiments, the isocyanate is ethyl-3-isocyanato-propionate. In certain embodiments, the electrophilic compound 2 is an activated ester of an acid. Exemplary activated esters of an acid include maleamic acid, mono-ethyl fumarate and BOC-glutamine. In certain embodiments, the electrophilic compound 2 is an acid chloride. Exemplary acid chlorides include adipoyl chloride, maleyl chloride, and sebacoyl chloride, etc. In certain embodiments, the electrophilic compound 2 is a sulfonyl chloride. Exemplary sulfonyl chlorides include cyclopropane sulfonyl chloride, ethyl 3-(chlorosulfonyl)propanoate, and ethyl 2-(chlorosulfonyl)benzoate, etc. In certain embodiments, the electrophilic compound 2 is an activated acid. Exemplary activated acids include an acid that has been treated with an activating agent. One skilled in the art will be able to identify an appropriate activating agent from exemplary activating agents, including but not limited to the list as defined herein. The reaction is typically performed in the presence of a suitable base to form a compound of formula I. In certain embodiments, the base is $K_2CO_3$. The reaction is typically performed in a suitable solvent. In certain embodiments, the suitable solvent is a mixture of polar, aprotic solvents. In certain embodiments, whether used alone or as part of a mixture, the polar, aprotic solvents include DMF, DCM, NMP and THF.

In the above-described scheme and/or steps, the R', $R^2$, and $R^3$, groups of the various formulae are as described herein.

In some embodiments, the present invention provides processes for preparing exemplary compounds of the present invention (e.g., Compound N-24, Compound N-38, and Compound N-34). In some embodiments, certain compounds of the present invention are prepared according to the scheme below.

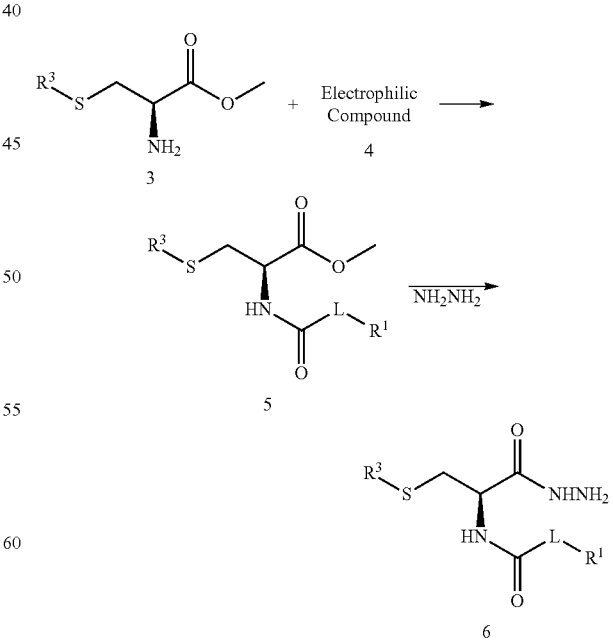

To begin, a suitable compound 3 is reacted with a suitable electrophilic compound 4 to give compound 5. In certain embodiments, the suitable compound 3 is S-trans, trans-farnesyl-L-cysteine methyl ester. Reaction of compound 5 with hydrazine results in compound 6. In certain embodiments, a suitable solvent includes a mixture of polar, aprotic solvents. In certain embodiments, whether used alone or as part of a mixture, the polar, aprotic solvents include, but are not limited to, DMF, DCM, NMP and THF.

In some embodiments, the present invention provides processes for preparing exemplary compounds of the present invention (e.g., Compound N-67, Compound N-68, N-69 and Compound N-70). In some embodiments, certain compounds of the present invention are prepared according to the scheme below.

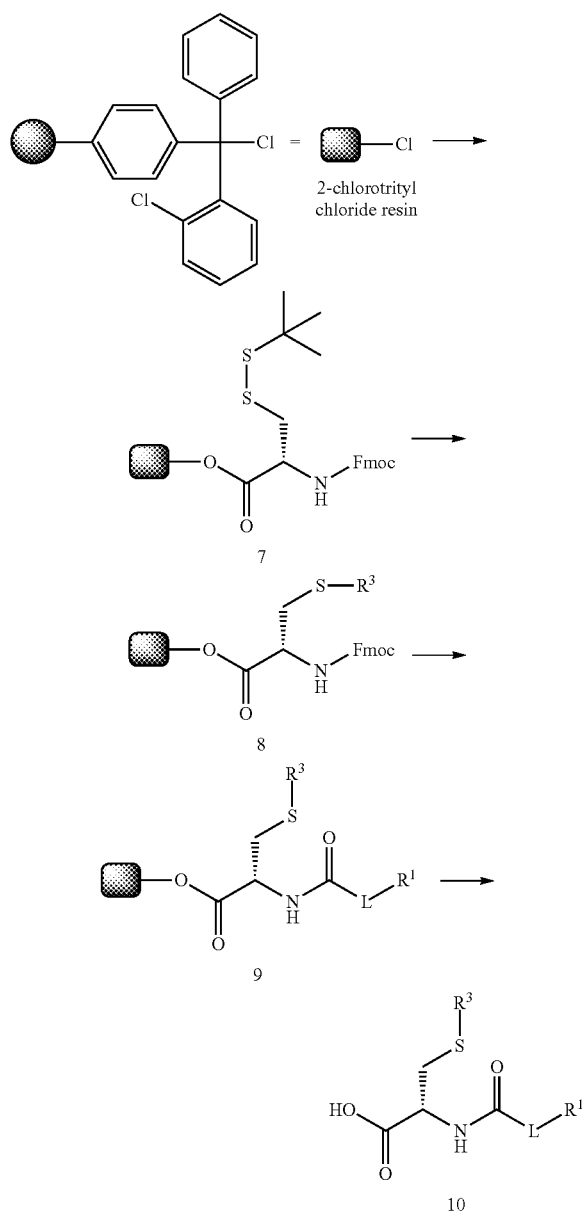

Commercially available 2-chlorotritylchloride resin is coupled to Fmoc-Cys(SStBu)-OH. Reductive removal of the dithio-tert-butyl protecting group from 7 with dithiothreitol is followed by coupling of the desired R³ side chain to the free thiol, using alkyl halide to afford intermediate 8. The Fmoc protecting group is typically removed with 20% piperidine/DMF; followed by coupling an appropriate Fmoc-protected acid with the resulting free amine is accomplished using an activating agent. One skilled in the art will be able to identify an appropriate activating agent, which includes, but is not limited to, the list as defined herein. The Fmoc protecting group is removed with 20% piperidine/DMF. Coupling of the selected N-protecting reagents with the resulting free amine is typically performed in the presence of a suitable base to form a compound of formula 9. In certain embodiments, the base is $K_2CO_3$. The polymer-bound prenylcysteine analog 10 is typically released from the resin using optimized cleavage conditions [e.g., stir 3×1 minute in 1% TFA $CH_2Cl_2$ solution].

In some embodiments, the present invention provides processes for preparing exemplary compounds of the present invention (e.g., Compound N-54, Compound N-32, N-78 and Compound N-77). In some embodiments, certain compounds of the present invention are prepared according to the scheme below.

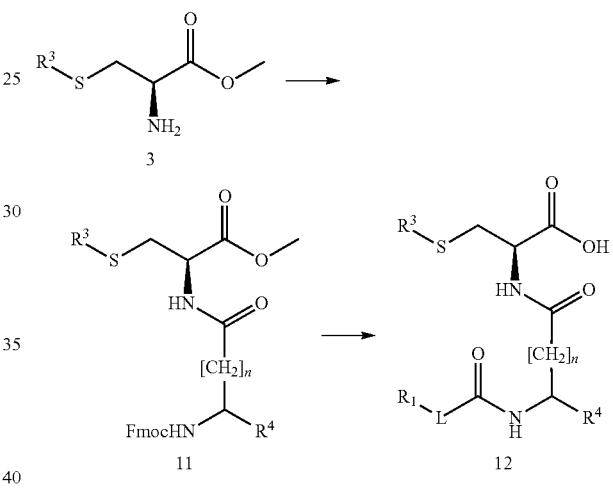

To begin, a suitable compound 3 is reacted with a suitable Fmoc protected amino acid to give a coupled product 11. In certain embodiments, the suitable compound 3 is S-trans, trans-farnesyl-L-cysteine methyl ester. In certain embodiments, the suitable amino acid is an α-amino acid (n=0). In certain embodiments, the suitable amino acid is a β-amino acid (n=1). In certain embodiments, the suitable amino acid is a γ-amino acid (n=2). In certain embodiments, the suitable amino acid is a δ-amino acid (n=3). Deprotection of compound 11 followed by reaction with a suitable electrophilic to afford compound 12. In certain embodiments, the electrophilic compound is an anhydride. In certain embodiments, the electrophilic compound is an isocyanate. In certain embodiments, the isocyanate is ethylisocyanate. In certain embodiments, the electrophilic compound is an anhydride, acid chloride or activated acid. Exemplary anhydrides include acetic anhydride.

3. Compositions and Formulations

The present invention provides compositions comprising isoprenyl compounds as described herein. In some embodiments, provided compositions contain additional components. In some embodiments, all such additional components are pharmaceutically acceptable and provided compositions are pharmaceutical compositions. In some embodiments, all such additional components are cosmetically acceptable and provided compositions are cosmetic compositions. In some embodiments, all such additional components are cosmeceutically acceptable and provided compositions are cosmeceutical compositions.

In some embodiments, pharmaceutical, cosmetic or cosmeceutical compositions of the present invention comprise an isoprenyl compound, a pharmaceutically acceptable inert ingredient (e.g., a carrier) and optionally an additional active ingredient. In certain embodiments, the isoprenyl compound is a compound of Formulae I, I' and/or Ia. In certain embodiments, the isoprenyl compound is a compound of Formulae I, I' and/or Ia. In certain embodiments, the isoprenyl compound is a compound of Formulae I, I' and/or Ia.

In general, one or more compounds of the present invention may be formulated into pharmaceutical compositions that include at least one provided compound of the present invention together with one or more pharmaceutically acceptable carriers, including excipients, such as diluents, binders and the like, and additives, such as stabilizing agents, preservatives, solubilizing agents, and buffers, as desired. Formulation excipients may include polyvinylpyrrolidone, gelatin, hydroxy cellulose, acacia, polyethylene glycol, manniton, sodium chloride and sodium citrate. In some embodiments, inventive compositions contain a pharmaceutically acceptable carrier. In some embodiments, the compositions of the present invention include a cosmetically acceptable carrier. In some embodiments, the compositions of the present invention include a cosmeceutically acceptable carrier.

Pharmaceutical carriers are typically of sufficiently high purity and sufficiently low toxicity to render it suitable for administration to the subject being treated. Pharmaceutical carriers further maintain stability and bioavailability of an active agent (e.g., a isoprenyl compound of the present invention). Pharmaceutical carriers can be liquid or solid and are selected with the planned manner of administration in mind, to provide for the desired bulk, consistency, etc., when combined with an active agent and other components of a given composition.

A carrier in certain compositions according to the present invention may include liquid and, in particular may comprise a buffered, isotonic, aqueous solution.

A carrier, including a pharmaceutically acceptable carrier, may be, or include, an excipient, such as a diluent, binder (e.g., binding agent) and the like, and or an additive, such as a stabilizing agent, preservative, solubilizing agent, and/or buffer as hereafter described. Pharmaceutical carriers include, without limitation, a binding agent (e.g., hydroxypropyl methylcellulose, polyvinylpyrrolidone, or pregelatinised maize starch, etc.); a filler (e.g., calcium hydrogen phosphate calcium sulfate, ethyl cellulose, gelatin, lactose and other sugars, microcrystalline cellulose, pectin, polyacrylates, etc.); a disintegrant (e.g., glycolate, sodium starch, starch, etc.); a lubricant (e.g., colloidal silicon dioxide, corn starch, hydrogenated vegetable oils, polyethylene glycols, magnesium stearate, metallic stearates, silica, sodium benzoate, sodium acetate, stearic acid, talc, etc.); or a wetting agent (e.g., sodium lauryl sulphate, etc.). Additional pharmaceutically acceptable carriers include, for example, petroleum jelly (Vaseline™), and petroleum.

Additional suitable carriers for the compositions of the present invention include, but are not limited to, alcohols, amyloses, animal oil, anti-irritants, chelating agents, colorants, deodorant agents, emulsifiers, fragrances, gelatins, hair conditioning agents, hydroxymethylcelluloses, magnesium stearates moisturizing agents (e.g., humectants), microcrystalline, mineral oil, natural polymers (e.g., collagen, gum arabic, polyols, and xanthanes, and the like), organic, ozocerite wax, and inorganic waxes, paraffin, penetration enhancers, pH adjusting agents, preservatives, propellants, salt solutions, silicic acids, surfactants talcs, solubilizing agents, thickeners, viscous paraffins, and water, and combinations thereof. In some embodiments, isoprenyl compounds of the present invention act as acceptable carrier(s) and/or excipient(s). In certain embodiments, AFC acts as an acceptable carrier and/or excipient. In some embodiments, it may be desirable to use the carriers in cosmetic compositions, as described in the CTFA International Cosmetic Ingredient Dictionary and Handbook, 8th edition, edited by Wenninger and Canterbery, (The Cosmetic, Toiletry, and Fragrance Association, Inc., Washington, D.C., 2000), which is herein incorporated by reference. Also included are the carriers described hereinabove.

In some embodiments, pharmaceutically acceptable carriers of the composition include a sustained release or delayed release carrier. Such carriers can be any material capable of sustained or delayed release of isoprenyl compounds to provide a more efficient administration resulting in less frequent and/or decreased dosage of isoprenyl compounds, ease of handling, and extended or delayed effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes which may enhance the localized delivery of the compounds of the inventive composition within skin layers, may be formed from a variety of phospholipids, such as cholesterol, stearylamines or phosphatidylcholines.

For injection or other liquid administration formulations, water containing at least one or more buffering constituents is commonly utilized, and stabilizing agents, preservatives and solubilizing agents may also be employed. In some embodiments, a provided pharmaceutical composition is or comprises an isotonic solution.

For solid administration formulations, any of a variety of thickening, filler, bulking and carrier additives may be employed, such as starches, sugars, fatty acids and the like. Topical compositions of the present invention can be applied locally to the skin or mucosa and may be in any form including solutions, oils, creams, ointments, gels, lotions, shampoos, milks, cleansers, moisturizers, sprays, skin patches and the like.

For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a provided compound over a period of time. For example, gelatin, sodium carboxymethylcellulose and/or other cellulosic excipients may be included to provide time-release or slower-release formulations, especially for administration by subcutaneous and intramuscular injection.

In practical use, inventive compounds can be combined as the active ingredient in an admixture with a pharmaceutical carrier according to conventional pharmaceutical compounding techniques. Pharmaceutical compositions for the present invention may be formulated for delivery by any of a variety of routes including, for example, oral, parenteral (including intravenous), urethral, vaginal, nasal, topical (e.g., dermal, transdermal), pulmonary, deep lung, inhalation, buccal, sublingual routes, or the like.

In preparing compositions containing isoprenyl compounds for cutaneous administration, such as topical (i.e., local), such compositions can include pharmaceutical carriers (e.g., sterile and non-sterile aqueous solutions, non-aqueous solutions in common solvents such as alcohols, or solutions of isoprenyl compounds in liquid or solid oil bases). Such pharmaceutical carrier solutions also can contain buffers, diluents and other suitable additives.

In preparing compositions containing isoprenyl compounds for parenteral administration (e.g., intramuscular or subcutaneous administration), such compositions can include pharmaceutical carriers (e.g., sterile and non-sterile aqueous solutions, non-aqueous solutions in common solvents such as alcohols, or solutions of isoprenyl compounds in liquid or solid oil bases). Such pharmaceutical carrier solutions also can contain buffers, diluents and other suitable additives.

Representative compositions suitable for oral use include, for example, mouthwash, rinse, oral spray, suspension, dental gel, and the like. Typical oral carriers known in the art may be used in the present invention. The preferred pharmaceutical and/or cosmetic carriers are water, ethanol, and water-ethanol mixtures. The water-ethanol mixtures are generally employed in a weight ratio from about 1:1 to about 20:1, preferably from about 3:1 to about 20:1, and most preferably from about 3:1 to about 10:1, respectively. The pH value of the oral vehicle is generally from about 4 to about 7, and preferably from about 5 to about 6.5. An oral topical vehicle having a pH value below about 4 is generally irritating to the oral cavity and an oral vehicle having a pH value greater than about 7 generally results in an unpleasant mouth feel.

Oral topical inventive compositions may also contain conventional additives normally employed in those products. Conventional additives as described herein include a coloring agents, emulsifiers, fluorine providing compounds, humectants, sweetening agents, and pH adjusting agents, provided that such additives do not interfere with the therapeutic, cosmetically, or cosmeceutically beneficial properties of inventive compositions. Additional ingredients that may be used in compositions of the present invention include fluorine providing compounds, additional active ingredients, new excipients, protectives, and demulcents, as described herein.

Fluorine providing compounds may be fully or slightly water soluble and are characterized by their ability to release fluoride ions or fluoride containing ions in water and by their lack of reaction with other components in the composition. Typical fluorine providing compounds include alkali metal fluorides, inorganic fluoride salts such as water-soluble alkali metal, alkaline earth metal, heavy metal salts, for example, aluminum mono- and di-fluorophosphates, ammonium fluoride, ammonium fluorosilicate, barium fluoride, cuprous fluoride, fluorinated sodium calcium pyrophosphate, potassium fluoride, sodium fluoride, sodium fluorosilicate, sodium fluorozirconate, sodium monofluorophosphate, stannic fluoride, stannous fluoride and zinc fluoride, monofluorophosphates, such as sodium and stannous fluoride, sodium monofluorophosphate, tin fluoride and combinations thereof.

Amounts of fluorine providing compounds present in oral, topical inventive compositions provided herein depend upon the type of fluorine providing compound employed, solubility of the fluorine compound, and the nature of the final oral inventive composition. Amount of fluorine providing compounds used must be a nontoxic amount. In general, fluorine providing compounds when used will be present in an amount up to about 1%, from about 0.001% to about 0.1%, and from about 0.001% to about 0.05%, by weight of oral topical inventive compositions provided herein.

Typical sweetening agents (sweeteners) that are well known in the art include those that are both natural and artificial sweeteners, may be employed. Sweetening agent used may be selected from a wide range of materials including water-soluble sweetening agents, water-soluble artificial sweetening agents, water-soluble sweetening agents derived from naturally occurring water-soluble sweetening agents, dipeptide based sweetening agents, and protein based sweetening agents, including mixtures thereof.

In some embodiments, compositions of the present invention can further include one or more additional ("compatible", as defined herein) active ingredients which are aimed at providing compositions with another pharmaceutical, cosmetic, or cosmeceutical effect, in addition to that provided by an isoprenyl compound of inventive compositions provided herein.

Additional active ingredients according to the present invention include, without limitation, one or more, in any combination, of a protective agent, an emollient, an astringent, an irritant, a keratolytic, a sun screening agent, a sun tanning agent, an antibiotic agent, an antifungal agent, an antiviral agent, an antiprotozoal agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, a hormone, an anti-dandruff agent, an anti-wrinkle agent, an anti-skin atrophy agent, a sclerosing agent, a cleansing agent, a caustic agent and a hypo-pigmenting agent.

In some embodiments, at least one isoprenyl compound of compositions provided herein is an active ingredient.

Compositions according to the present invention, which further include one or more additional active ingredients, can therefore be further efficiently used, in addition to their use as a treatment for an epithelial-related condition, in the treatment of any medical, cosmetic and/or cosmeceutical condition in which applying the additional active ingredient is beneficial.

Protectives as described herein may take the form of dusting powders, adsorbents, mechanical protective agents, and plasters. Dusting powders are relatively inert and insoluble materials that are used to cover and protect epithelial surfaces, ulcers and wounds. Usually, these substances are finely subdivided powders that absorb moisture and can act as a dessicant. The absorption of skin moisture decreases friction and also discourages certain bacterial growth. Some of the materials used as protective adsorbents include bentonite, insoluble salts of bismuth, boric acid, calcium carbonate, (precipitated), cellulose, corn starch, magnesium stearate, talc, titanium dioxide, zinc oxide, and zinc stearate.

In some embodiments, protectives also can be administered to the skin to form an adherent, continuous film that may be flexible or semi-rigid depending on the materials and the formulations as well as the manner in which they are applied. This material may serve several purposes including providing occlusion from the external environment, providing chemical support, and serving as vehicles for other medicaments.

In some embodiments, protectives included in compositions of the present invention are demulcents. Demulcents often are applied to the surface in a viscid, sticky preparation that covers the area readily and may be medicated. A number of chemical substances possess demulcent properties.

In practical use, provided compounds herein can be combined as an active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, dermal, transdermal, pulmonary, deep lung, inhalation, buccal, sublingual, or the like.

In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets. Tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and/or a sweetening agent such as sucrose, lactose or saccharin. Capsules may contain, in addition to materials of the above type, a liquid carrier such as a fatty oil.

In some embodiments, an isoprenyl compound, carrier and, optionally, additional active ingredients are formed into a composition in the form of a solution, emulsion or gel suspension, as will be further described herein.

In some embodiments, an isoprenyl compound, a pharmaceutical or cosmetic carrier and, optionally, one or more additional active ingredients, are in the form of a solution. A solution can be prepared by mixing a solute or dissolved substance (such as a isoprenyl compound of the invention and, optionally, one or more active ingredient(s)) uniformly throughout a solvent carrier such as water or organic solvents, such as the alcohols (e.g. ethanol or isopropanol, acetone).

In some embodiments, the solution is an aqueous solution wherein a provided compound may be appropriately buffered by means of saline, acetate, phosphate, citrate, acetate or other buffering agents, which may be at any physiologically acceptable pH, generally from about pH 4 to about pH 7. Combinations of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, suitable preservatives may be employed, to prevent or limit bacteria and other microbial growth. One such preservative that may be employed is 0.05% benzalkonium chloride.

In some embodiments, inventive compositions comprising an isoprenyl compound, a carrier and other, optional ingredients are provided in the form of an emulsion. Emulsions are a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of two phases will not occur unless a third substance, an emulsifying agent, is incorporated. Thus, a basic emulsion in the context of the present invention typically contains two or more components (e.g., two immiscible liquid carriers, an emulsifying agent, and an isoprenyl compound). In some embodiments a prenyl compound can be an emulsifying agent. Typically, emulsions incorporate an aqueous phase into a non-aqueous phase (or vice versa). However, it is possible to prepare emulsions that are largely non-aqueous, for example, anionic and cationic surfactants of the non-aqueous immiscible system glycerin and olive oil. Exemplary emulsifying agents are described herein.

In some embodiments compositions of the present invention comprise an emulsion including AFC. In some embodiments, non-lipid-based vehicles are useful in an emulsion comprising AFC due to the lipophilic nature of AFC.

In some embodiments, inventive compositions comprising an isoprenyl compound, are provided in the form of gel suspensions, (a semi-solid carrier) or solid carrier to form a paste, powder, ointment, cream, lotion, hydrogel or the like. Exemplary ointments that may be prepared as a gel-suspension include semi-solid preparations intended for external application to the epithelium. Generally, ointment bases are categorized into hydrocarbon bases (oleaginous), which may use white petroleum as a base; adsorption bases (anhydrous), which might use hydrophilic petroleum or anhydrous lanolin; emulsion bases (water and oil type); emulsion bases (oil and water type); and water soluble bases, which often use polyethylene glycol as an ointment base.

Additional isoprenyl compositions of the present invention can be readily prepared using technology known in the art as described in Remington's Pharmaceutical Sciences, $18^{th}$ or $19^{th}$ editions, published by the Mack Publishing Company of Easton, Pa.

It is also possible and contemplated that provided compounds of the present invention may be in a dried and particulate form. In certain embodiments, particles are between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micromilling, spray drying and a quick freeze aerosol followed by lyophilization. With micro-particles, provided compounds may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 μm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

In some embodiments, provided compounds of the present invention may be therapeutically administered by means of an injection, typically a deep intramuscular injection, such as in the gluteal or deltoid muscle, of a time release injectable formulation. In some embodiments, provided compounds of the present invention are formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like. In some embodiments, a provided compound of the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany).

Such formulations may be made, for example, by combining a provided compound of the present invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a time release injectable formulation. The teachings of U.S. Pat. Nos. 4,938,763, 6,432,438, and 6,673,767, and the biodegradable polymers and methods of formulation disclosed therein, are incorporated herein by reference. The formulation may be such that an injection is required on a weekly, monthly or other periodic basis, depending on the concentration and amount of a provided compound, the biodegradation rate of the polymer, and other factors known to those of skill in the art.

In some embodiments, inventive compositions formulated as aqueous suspensions wherein a provided compound is in admixture with excipients additives and/or suitable for the manufacture of aqueous suspensions. Such additives and/or excipients are suspending agents, for example, sodium carboxymethylcellulose, methylcellulose, hydroxy propylmethylcellulose, sodium alginate, polyvinylpyrrolidone, gum tragacanth, and gum acacia; dispersing or wetting agents may be a naturally occurring phosphatide such as lecithin, or condensation products of an alkylene oxide with fatty acids, for example, polyoxyethylene stearate, or condensation products of ethylene oxide with long chain aliphatic alcohols, for example, heptadecaethyl eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions also may contain one or more coloring agents, one or more flavoring agents, and one or more sweetening agents, such as sucrose or saccharin.

In some embodiments, inventive compositions formulated as oily suspensions by suspending a provided compound in a vegetable oil (e.g., *arachis* oil, olive oil, sesame oil, coconut oil, or a mineral oil, such as liquid paraffin). Oily suspensions may contain a thickening agent (e.g., beeswax, hard paraffin or cetyl alcohol). Sweetening agents, such as those described herein, and flavoring agents may be added to provide a palatable oral composition. Such compositions may be preserved by the addition of an antioxidant (e.g., ascorbic acid).

In some embodiments, inventive compositions formulated as dispersible powders and/or granules are suitable for compositions of an aqueous suspension by adding water. Provided compound in such powders and granules is provided in admixture with a dispersing or wetting agent, suspending agent, and one or more preservatives. Suitable dispersing or wetting agents and suspending agents are exemplified by those already mentioned herein. Additional excipients, for example, sweetening, flavoring and coloring agents also may be present.

Compositions of the invention also may be in the form of oil in water emulsions. The oily phase may be a vegetable oil, for example, olive oil or *arachis* oil, or a mineral oil, for example a liquid paraffin, or a mixture thereof. Suitable emulsifying agents may be naturally occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

Compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

4. Administration and Dosage Forms

Provided compounds of the invention of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, antioxidants and other agents known in the art. In general, any route of administration by which provided compounds of the invention are introduced across an epidermal layer of cells may be employed. Administration means may thus include administration through mucous membranes, buccal administration, oral administration, dermal administration, inhalation administration, pulmonary administration, nasal administration, urethral administration, vaginal administration, and the like.

In general, compositions comprising a therapeutically or pharmaceutically effective amount of an inventive composition of provided compounds may be formulated for administration in unit dosage forms.

Oral Administration

Because of their ease of administration, tablets and capsules represent an advantageous oral unit dosage form. If desired, a composition including provided compound of the invention may be coated by standard aqueous or nonaqueous techniques. The amount of active compound, i.e. isoprenyl compounds of the present invention, in such therapeutically useful compositions is such that an effective dosage will be obtained. In another advantageous dosage unit form, sublingual pharmaceutical compositions may be employed, such as sheets, wafers, tablets or the like. An active compound can also be administered intranasally as, for example, by liquid drops or spray.

The tablets, pills, capsules, and the like may also contain a binder as described herein. In some embodiments, binders that may be particularly useful for tablets, pills and capsules, include gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier, such as a fatty oil.

Compositions of the present invention may be in additional forms suitable for oral use, for example, troches, lozenges, pills, aqueous or oily suspensions, solutions, dispersible powders or granules, emulsions, hard or soft capsules, syrups or elixirs, pastes, gels or the like.

A tablet may contain the active ingredient(s) in admixture with non-toxic pharmaceutically acceptable additives and/or excipients which are suitable for the manufacture of tablets. These additives or excipients may be, for example, fillers, wetting agents, inert diluents, such as calcium carbonate, sodium carbonate, lactose, calcium phosphate or sodium phosphate; granulating and noneffervescent disintegrating agents, (e.g., corn starch or alginic acid); binding agents (e.g., starch, gelatin or acacia); and lubricating agents (e.g., magnesium stearate, stearic acid or talc).

A tablet may be prepared by traditional methods such as by compressing or molding a powder or granules containing a provided compound. Compressed tablets may be prepared by compressing, in a suitable machine, the a provided compound in a free-flowing form, such as a powder or granules optionally mixed with a binder, lubricant, inert diluent, and/or surface active/dispersing agent(s). Molded tablets may be made by molding, in a suitable machine, a powdered provided compound moistened with an inert liquid binder.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled delivery. For example, a "delayed release" dosage form releases a product or substance at a time other than promptly after administration. Examples of delayed-release systems include repeat action tablets and capsules, and enteric coated tablets where timed release is achieved by a barrier coating.

Compositions of the present invention also may be formulated for oral use as hard gelatin capsules, where a provided compound is mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

In some embodiments, liquid preparations for oral administration can also be used. Liquid preparations can be in the form of solutions, syrups or suspensions, or a dry product for reconstitution with water or another suitable vehicle before use. Such liquid preparations can be prepared by conventional means with pharmaceutically acceptable additives such as suspending agents, emulsifying agents, non-aqueous vehicles, and preservatives.

Liquid based oral dosage forms, like their solid counterparts, usually contain at least 0.1 mg of a provided compound. One skilled in the art will be able to properly formulate a liquid formulation containing an appropriate amount of a provided compound per fluidic ounce, depending on the additive or carrier selected.

Compositions intended for oral use may be prepared according to any known method, and such compositions may contain one or more excipients selected from the group consisting of sweetening agents, flavoring agents, coloring agents, and preserving agents in order to provide pharmaceutically elegant and palatable compositions. In general, the formulations for oral administration are prepared by uniformly and intimately admixing the active compound, i.e., a provided compound of the present invention or mixtures thereof, with a liquid or finely divided solid excipient, or both, and then, if necessary, shaping the resulting mixture.

Parenteral Administration

Provided compounds of the present invention may also be administered parenterally. Solutions or suspensions of these active peptides may be prepared in water suitably mixed with a surfactant, such as hydroxy-propylcellulose. Dispersions may also be prepared, such as dispersions in glycerol, liquid polyethylene glycols and mixtures thereof in oils. These preparations may optionally contain a preservative to prevent the growth of microorganisms. Lyophilized single unit formulations may also be utilized, which are reconstituted, such as with saline, immediately prior to administration, and thus do not require a preservative.

Pharmaceutical forms suitable for injectable use include, for example, sterile aqueous solutions or dispersions and sterile powders, such as lyophilized formulations, for the extemporaneous preparation of sterile injectable solutions or dispersions. In all cases, the form must be sterile and must be fluid to the extent that it may be administered by syringe. The form must be stable under the conditions of manufacture and storage and may be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Parenterally administered compositions are formulated to allow for injection, either as a bolus or as a continuous infusion. For parenteral application, "parenteral" meaning subcutaneous injections, intravenous, intramuscular, intrasternal injection, or infusion techniques, particularly suitable vehicles consist of solutions, preferably oily or aqueous solutions, as well as suspensions, emulsions, or implants. Formulations for injection can be prepared in unit dosage forms, such as ampules, or in multi-dose units, with added preservatives. The compositions for injection can be in the form of suspensions, solutions, or emulsions, containing either oily or aqueous additives. They may also contain formulatory agents such as suspending agents, stabilizing agents, and/or dispersing agents. A isoprenyl compound may also be presented in powder form for reconstitution with a suitable vehicle before use.

The compositions of the present invention also may be in the form of a sterile injectable aqueous or oleaginous suspension. Injectable compositions, such as sterile injectable aqueous or oleaginous suspensions, may be formulated according to the known art using suitable dispersing or wetting agents and suspending agents. The sterile injectable composition may also be a sterile injectable solution or suspension in a nontoxic parenterally acceptable diluent or solvent, for example, as a solution in 1,3 butanediol. Among the acceptable vehicles and solvents that may be employed are water, Ringer's solution, and isotonic sodium chloride solution. In some embodiments, formulations of the present invention suitable for parenteral administration conveniently comprise sterile aqueous preparations of the active compound, i.e. a isoprenyl compound, which preparations are preferably isotonic with the blood of the intended recipient. Such preparations may conveniently be prepared by admixing the active compound with water or a glycine buffer and rendering the resulting solution sterile and isotonic with the blood.

In addition, sterile, fixed oils are conventionally employed as a solvent or suspending medium. Aqueous suspensions may contain substances which increase the viscosity of the suspension and include, for example, sodium carboxymethyl cellulose, sorbitol and/or dextran. Optionally, the suspension may also contain stabilizers. Alternately, a compound of the present invention can be added to a parenteral lipid solution.

Buccal Administration

Formulations suitable for buccal administration include tablets and lozenges comprising a isoprenyl compound in a flavored base, such as sucrose, acacia or tragacanth; and pastilles comprising the isoprenyl compound in an inert base, such as gelatin and glycerin or sucrose and acacia.

Topical Administration

Formulations of the present invention suitable for topical application to the skin take the form of an ointment, cream, lotion, paste, gel, spray, aerosol, or oil. Additives which may be used include vaseline, lanoline, polyethylene glycols, alcohols, transdermal enhancers, and combinations of two or more thereof.

In some embodiments, formulations suitable for topical application achieve transdermal delivery. Transdermal pharmaceutical devices include patches, occlusive dressings, occlusive formulations, hypodermic sprays, iontophoretic systems, gels and infusion pumps, all of which are well known in the art. A transdermal patch which includes a pharmaceutical may generally include a backing layer impermeable to the pharmaceutical, a reservoir to house the pharmaceutical, and an adhesive cover to be removed upon use of the patch and for adhesion to the skin of a patient.

Formulations suitable for transdermal administration may also be presented as medicated bandages or discrete patches adapted to remain in intimate contact with the epidermis of the recipient for a prolonged period of time. Representative examples of suitable transdermal patches include, for example, those developed by NeuroDerm Ltd (Israel) and/or that used to deliver estradiol, for example, those developed by Novogyne Pharmaceuticals. Formulations suitable for transdermal administration may also be delivered by iontophoresis (passage of a small electric current (~15 mA) to "inject" electrically charged ions into the skin) through the skin. For this, the dosage form typically takes the form of an optionally buffered aqueous solution of the active compound, i.e. a isoprenyl compound.

Formulations suitable for transdermal administration may also be delivered by using an infusion pump connected to a needle that is inserted through the skin, for example, those developed by Medtronic used to deliver insulin. Amounts of compound used in a transdermal device as described herein may vary, depending on many factors including the size of the device and its release characteristics, the amount of the pharmaceutical active agent and the estimated duration of action of the device. Broadly, amounts of compound typically range from about 0.1% to about 10% w/v.

Administration by Inhalation

For administration by inhalation, compositions for use in the present invention can be delivered in the form of an aerosol spray in a pressurized package or as a nebulizer, with use of suitable propellants. In the case of a pressurized aerosol, the dosage unit can be determined by providing a valve to deliver a metered dose in accordance with the invention.

5. Dosage: Therapeutically Effective Amount

The actual quantity of compounds administered to a patient will vary depending on the severity and type of indication, the mode of administration, the particular compound used, the formulation used, and the response desired.

The dosage for treatment is administration, by any of the foregoing means or any other means known in the art, of an amount sufficient to bring about the desired therapeutic effect. Thus, a therapeutically effective amount may be an amount of a compound or pharmaceutical composition that is sufficient to induce a desired effect, including but not limited to an anti-inflammation effect. Those of ordinary skill in the art will appreciate that a therapeutically effective amount may be administered by means of a single dose or multiple doses, and that compositions provided herein may contain a unit dose of a therapeutically effective amount.

In general, provided compounds are highly active. For example, a compound may be administered at about 10 µg/kg to about 100 mg/kg body weight, depending on the specific compound selected, the desired therapeutic response, the route of administration, the formulation and other factors known to those of skill in the art.

5. Dosage: Therapeutically Effective Amount

The actual quantity of compounds administered to a patient will vary depending on the severity and type of indication, the mode of administration, the particular compound used, the formulation used, and the response desired.

The dosage for treatment is administration, by any of the foregoing means or any other means known in the art, of an amount sufficient to bring about the desired therapeutic effect. Thus, a therapeutically effective amount may be an amount of a compound or pharmaceutical composition that is sufficient to induce a desired effect, including but not limited to an anti-inflammation effect. Those of ordinary skill in the art will appreciate that a therapeutically effective amount may be administered by means of a single dose or multiple doses, and that compositions provided herein may contain a unit dose of a therapeutically effective amount.

In general, provided compounds are highly active. For example, a compound may be administered from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of a therapeutic agent per subject body weight per day to obtain a desired therapeutic effect. A desired dosage may be delivered to a subject only once. A desired dosage may be delivered more than three times per day, three times per day, two times per day, once per day, every other day, every third day, every week, every two weeks, every three weeks, every four weeks, every two months, every six months, every twelve months, every two years, every three years, every four years, every five years, every 10 years, or every 20 years. In certain embodiments, the desired dosage may be delivered using multiple administrations (e.g., two, three, four, five, six, seven, eight, nine, ten, eleven, twelve, thirteen, fourteen, fifteen, or more administrations). The skilled artisan will appreciate that certain factors can influence the dosage and timing required to effectively treat a subject, including but not limited to the specific compound selected, the desired therapeutic response, the route of administration, the formulation, the severity of the disease or disorder, previous treatments, the general health and/or age of the subject, other diseases present, and/or other factors known to those of skill in the art.

6. Uses

In certain embodiments, the present invention provides novel isoprenyl compounds, which might themselves be added to or combined with other pharmaceutically active agents, compositions comprising at least one isoprenyl compounds or combination with other pharmaceutically active agents thereof, and/or methods of their preparation or use in the amelioration, treatment or prevention of, for example, certain conditions, diseases or disorders associated with inflammation or the suppression of inflammatory responses.

In certain particular embodiments, the present invention provides anti-inflammatory compounds and compositions described here that inhibit inflammation and are therefore useful in the treatment of diseases, conditions or disorders associated with inflammation. In certain particular embodiments, the present invention provides pro-inflammatory compounds and compositions described herein that promote inflammation and are therefore useful in the treatment of diseases, conditions or disorders associated with the suppression of the inflammatory responses.

In certain embodiments, the present invention provides novel compounds and compositions that modulate inflammation. Although not wishing to be bound by one theory, it is believed that compounds and compositions described herein modulate levels of inflammatory mediators, for example, cytokines. Non-limiting examples of inflammatory mediators modulated by provided compounds and compositions include but are not limited to IL-1α, IL-1β, IL-2, IL-3, IL-4, IL-5, IL-6, IL-7, IL-8, IL-9, IL-10, IL-11, IL-12/IL-23 p40, IL13, IL-17, IL-18, TGF-β, IFN-γ, GM-CSF, Groα, MCP-1 and TNF-α. Although not wishing to be bound by one theory, it is believed that compounds and compositions described herein modulate levels of inflammatory mediators that are associated with a variety of signal transduction pathways. Non-limiting examples of signal transduction pathways that result in release of inflammatory mediators such as cytokines, include but are not limited to G-protein-mediated, PPAR-mediated, Toll-like receptor-mediated, and TNF-α receptor-mediated. Although not wishing to be bound by one theory, it is believed that provided compounds and composition modulate T-helper cell infiltration and accumulation. Although not wishing to be bound by one theory, it is believed that provided compounds and compositions inhibit oxidative burst from neutrophils and are therefore anti-oxidants.

In certain embodiments, the present invention provides novel compounds and compositions that relate to treating or lessening the severity of one or more diseases in which protein inhibitors that modulate the G-protein signaling cascade are known to play a role. Although not wishing to be bound by one theory, it is believed that compounds and compositions described herein inhibit methylesterifcation reactions by a specific membrane associated S-adeno sylmethionine-dependent isoprenyl-S-isoprenyl methyltransferase ("ICMT") resulting in carboxy-terminal polyisoprenoid cysteine modifications of a number of key factors in G-protein signaling pathway. In certain embodiments, provided compounds and compositions alter the interactions among polyisoprenylated signal transduction proteins, such as G-proteins and the protein regulatory targets with which they interact, or other intracellular signaling proteins.

In certain embodiments, such compounds are administered in vitro. In certain embodiments such compounds are administered in vivo.

Another aspect of the present invention is directed to methods of treating, preventing, or ameliorating inflammation by administering an effective amount of a provided compound.

In some embodiments, one or more inventive compounds, alone or together with one or more other pharmaceutically active agents, is used to whiten skin. In some such embodiments, an isoprenyl compound is applied topically.

In general, the actual quantity of provided compounds of the invention administered to a patient will vary depending on the severity and type of indication, the mode of administration, the particular compound used, the formulation used, and the response desired.

The dosage for treatment is administration, by any of the foregoing means or any other means known in the art, of an amount sufficient to bring about the desired therapeutic effect. Thus, an effective amount includes an amount of a provided compound (or mixture of provided compounds) or pharmaceutical composition of this invention that is sufficient to induce a desired effect, including specifically an anti-inflammation effect or a proinflammatory effect depending on the diseases, disorders, conditions, syndromes, and the like, being treated, prevented or promoted.

In general, the provided compounds of the present invention are highly active. For example, a provided compound can be administered at about 10 µg/kg to about 50 mg/kg body weight, depending on the specific provided compound selected, the desired therapeutic response, the route of administration, the formulation and other factors known to those of skill in the art.

Methods (A) Antiinflammatory

Specifically, the present invention relates to a method of treating or lessening the severity of inflammatory diseases or disorders selected from inflammation (acute or chronic), inflammatory diseases or disorders (e.g., asthma, autoimmune diseases, and COPD including emphysema, chronic bronchitis and small airways disease, etc.), inflammatory responses of the immune system, skin diseases (e.g., reducing acute skin irritation for patients suffering from rosacea, atopic dermatitis, seborrheic dermatitis, psoriasis), irritable bowel syndrome (e.g., Chron's disease and ulcerative colitis, etc.), Neurodegenerative Disorders (Parkinson's disease, Alzheimer's disease, Huntington's disease, Dementia pugilistica, Pick's disease, Guam parkinsonism dementia complex, Fronto-temporal dementia, Cortico-basal degeneration, Pallido-pontal-nigral degeneration, Progressive supranuclear palsy, Dementia with Lewy bodies (DLB), and multiple system atrophy (MSA)), as well as inflammation associated with spinal cord injury to promote nerve regeneration and inhibition of rejection of genetically engineered cells by the immune system during in vivo gene therapy, wherein the method comprises administering to a patient in need thereof a composition of the present invention.

In some embodiments, the provided compounds of the present invention are capable of effectively inhibiting inflammatory responses. Thus, provided compounds are inhibitors of edema, erythema and myeloperoxidase and are therefore useful for treating one or more disorders associated with inflammatory diseases or disorders as described herein. In particular, the present invention encompasses the finding that certain compounds having superior in vivo activity than other compounds in the same class. For example, relative to AFC, compound A has improved edema inhibition, improved erythema inhibition and improved MPO (myeloperoxidase) inhibition. Therefore, such compounds are administered to a subject suffering from or susceptible to one or more inflammatory diseases or disorders.

In some embodiments, the provided anti-inflammatory compounds of the present invention are capable of effectively inhiting inflammatory responses by decreasing the levels or production of inflammatory mediators such as inflammatory cytokines, for example TNF IL-1α, IL-1β, IL-2, IL-3, IL-4, IL-5, IL-6, IL-7, IL-8, IL-9, IL-10, IL-11, IL-12/IL-23 p40, IL13, IL-17, IL-18, TGF-β, IFN-γ, GM-CSF, Groα, MCP-1 and TNF-α. Thus, provided anti-inflammatory compounds are inhibitors of proinflammatory cytokines and are therefore useful in treating one or more disorders associated with inflammatory diseases, conditions or disorders described herein. In particular, the present invention encompasses the finding that certain compounds have superior activity, as measured by percent inhibition of levels or production of proinflammatory cytokines in animal and cell-based inflammatory models, than other compounds in the same class. Therefore, such compounds are administered to a subject suffering from or susceptible to one or more inflammatory diseases, conditions or diseasess.

In some embodiments, the treatment of inflammatory diseases or disorders is achieved using compounds without having the side effects of corticosteroids or NSAIDS.

In some embodiments, the provided compounds of the present invention are capable of effective inhibiting oxidative burst response from neutrophils. Thus, provided compounds are inhibitors of oxidative burst response and are therefore useful in the treatment or amelioration of symptoms relating to oxidative damage caused by chemical or environmental factor (e.g., UV damage on the skin). In particular, the present invention encompasses the finding that certain compounds have superior activity, as measured by percent reduction in superoxide formation, than other compounds in the same class. Therefore, such compounds are administered to a subject suffering from conditions associated with oxidative damage. In some embodiments, combinations of such sun screening agents with isoprenyl compounds provided herein exhibit anti-oxidant effects (e.g., inhibition of superoxide formation).

(B) Immune Stimulatory

In some embodiments, certain compounds of the present invention are capable of promoting inflammatory responses, and are therefore proinflammatory. Thus, provided proinflammatory compounds are promoters of edema, erythema and myeloperoxidase (a marker for neutrophil infiltration) and are therefore useful for treating one or more disorders associated with the suppression of inflammatory responses as described herein. Therefore, such compounds are administered to a subject suffering from or susceptible to one or more diseases, conditions or disorders associated with suppression of inflammatory responses.

In some embodiments, the present invention relates to a method of treating or lessening the severity of diseases, conditions or disorders associated with the suppression of inflammatory responses selected from for example, treatment of secondary bacterial or viral infections inflicting subjects with acquired immune deficiency syndrome (AIDS), suppression of systemic inflammatory response syndromes following severe burn injuries and cardiac surgeries and also the side-effect of a number of drugs, for example thalidomide.

(C) Skin Conditions

In some embodiments, provided herein is a method for treating or preventing a skin condition, the method comprising the step of topically applying onto a surface of a subject, including a human, in need thereof, an effective amount of a composition comprising at least one isoprenyl compound, a carrier and optionally an additional active ingredient. In another aspect, provided herein is a method for treating or preventing a skin condition, the method comprising the step of topically applying onto a surface of a subject, including a human, in need thereof, at least 0.1 mg of a compound of Formula I. In a further embodiment, provided herein is a method of promoting healthy skin in a subject, including a human, in need thereof, the method comprising the step of topically applying onto a surface of a subject, including a human, in need thereof, an effective amount of a composition comprising at least one isoprenyl compound, a carrier and optionally an additional active ingredient. In a further aspect, provided herein is a method of promoting healthy skin in a subject, including a human, in need thereof, the method comprising the step of topically applying onto a surface of a subject, including a human, in need thereof, at least 0.1 mg of a compound of Formula I'.

In a further embodiment, the present invention provides a method for treating or preventing inflammation in a subject, including a human, in need thereof, comprising the step of administering an effective amount of a composition comprising at least one isoprenyl compound, a carrier and optionally an additional active ingredient. In a further aspect, the present invention provides a method for treating or preventing inflammation in a subject, including a human, in need thereof, comprising the step of administering at least 0.1 mg of a compound of Formula I'.

In certain embodiments, the present invention provides uses of provided compounds and/or compositions in the treatment or prevention of diseases or conditions associated with suppression of inflammatory responses. In certain embodiments, the present invention provides a composition for treating or preventing conditions associated with suppression of the inflammatory responses, in a subject, including a human, in need of treatment thereof, that comprises of at least one isoprenyl compound, a carrier and optionally, an additional active ingredient. In a further embodiment, provided herein is a method for treating or preventing a disease or condition associated with suppression of inflammatory responses, in a subject, including a human, in need thereof, the method comprising the step of administering an effective amount of a composition comprising at least one isoprenyl compound, a carrier and optionally an additional active ingredient. In a further aspect, provided herein is a method for treating or preventing a disease or condition associated with suppression of inflammatory responses, in a subject, including a human, in need thereof, the method comprising the step of administering at least 0.1 mg of a compound of Formula I'.

Exemplary diseases, disorders or conditions (e.g., rosacea, psoriasis, atopic dermatitis and seborrhic dermatitis) that may be treated with compounds of Formulae I, I', and/or or Ia, in accordance with the present invention are addressed individually below.

Rosacea

Rosacea is a chronic, inflammatory skin disorder that afflicts about 14 million people in the US (FoxAnalytics, *The Dermatology Market Outlook to* 2011, B.I. LTD, Editor: London, UK, p. 201; Crandall, M. A. *Market Intelligence Report*, K. Information, Editor, 2008: New York. p 359). With peak onset between the ages of 51 and 60, its incidence will grow substantially in the years ahead. The condition is characterized by a constellation of symptoms that include central facial erythema, telangiectasias, papules, granulomatous nodules, phyma formation and ocular changes. Flares and remissions occur without rationale. There are no known cures for rosacea. Exemplary cytokines associated with rosacea may include TNFα, ILβ, IL-6, IL-8, MCP-1 and Groα.

Psoriasis

Psoriasis is a chronic inflammatory skin disease affecting ~125 million people worldwide and approximately 2-3% of the general population in the US and Europe (Crandall, M. A. *Market Intelligence Report*, K. Information, Editor, 2008: New York. P. 359; Naldi, L., *Curr. Drug Targets Inflamm. Allergy*, 2004, 3: 121-128). Although the pathogenesis of psoriasis has not been fully elucidated, recent advances demonstrate targeting key mediators of inflammation as a promising therapeutic approach (Numerof et al., *BioDrugs*, 2006, 20: 93-103; Menter et al., *J. Am. Acad. Dermatol.*, 2009, 60: 643-659). Direct therapeutic approaches include using antibodies or soluble receptors (i.e., biologics) to directly neutralize the specific cytokine of interest. However, biologic cytokine-derived therapies are expensive to produce, require sustained high blood levels in order to develop significant skin levels, may induce the production of neutralizing antibodies (leading to a diminished response to therapy), and must be administered by injection. Topical treatments have largely been ineffective, so market growth has been driven by systemic agents that have serious potential side effects. Corticosteroids remain the cornerstone of current topical treatment, but they are far from ideal. Long-term steroid use brings safety concerns ranging from issues of systemic absorption to cutaneous atrophy and its various clinical presentations. Today's US market for psoriasis treatments is greatly underserved, as only 60% of sufferers are being treated (Horn et al., *J. Am. Acad. Dermatol.* 2007, 57: 957-962).

Psoriasis can be conceived in simple terms, as a self reinforcing loop, in which deregulated inflammatory activity stimulates the epidermal Stat3c signaling pathway in the epidermis resulting in epidermal hyperplasia. The affected keratinocytes secrete cytokines which simulate the immune system, including T-helper cell (THc) infiltration and accumulation. Cytokines from the activated immune cells positively feedback on to the epidermal Stat3c pathway maintaining and amplifying the pathophysiology. Inhibition of THc infiltration and accumulation would decrease Stat3c expression and the onset of psoriasis. Exemplary cytokines associated with psoriasis may include TNFα, IL1α, ILβ, IL-2, IL-6, IL-8, IL-12, MCP-1, Groα and IFNγ.

In some embodiments, compounds of the present invention show a surprising inhibition of T-helper cell infiltration and accumulation.

Inflammatory Cytokines and Psoriasis

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, wherein cytokine levels and/or activity (e.g., TNF-α levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-α levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-β levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-2 levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-6 levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-8 levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-12 levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, wherein cytokine levels and/or activity (e.g., IFN-γ levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, wherein cytokine levels and/or activity (e.g., MCP-1 levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, wherein cytokine levels and/or activity (e.g., Gro-α levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a isoprenyl compound of Formulae I, I' and/or in described classes and subclasses thereof, having an activity in the inhibition of (more than about 20%) of levels of CD3+T-helper cells, determined using a K5.Stat3c psoriasis mouse model.

Atopic Dermatitis

Atopic dermatitis, or eczema, is characterized by chromic inflammation and irritation of the skin. Its causes are varied but immunological in nature. In the US, prevalence is 10% to 20% in children and 1% to 3% in adults. Topical dermatitis is caused by exposure to substances such as poison ivy, detergents and cosmetics that trigger allergic skin reactions. According to present theories, Atopic dermatitis is thought to be caused by skin barrier defects that lead to increased exposure to substances such as allergens exposed by inhalation or ingestion. When dermatitis occurs, corticosteroids are the primary treatment. Atopic dermatitis, however, disproportionately affects children, and long-term steroid use in this population raises safety concerns. Exemplary cytokines associated with atopic dermatitis include but are not limited to TNFα, IL1β, IL-6, IL-8, MCP-1, Groα, IL-4, IL-5, IL-10, IL-13, IL-17 and IFNγ.

Inflammatory Cytokines and Atopic Dermatitis

According to one aspect, the present invention provides methods of treating, ameliorating, controlling, or preventing inflammatory skin conditions such as atopic dermatitis comprising administering to a subject in need thereof a dosage form comprising at least about 0.1 mg of a isoprenyl compound of Formulae I, I' and/or in described classes and subclasses thereof, wherein cytokine levels and/or activity (e.g., TNF-α levels and/or activity) are reduced by more than about 20% (e.g., as determined using a ovalbumin-challenged ft/ft atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-α levels and/or activity) are reduced by more than about 20% (e.g., as determined using a ovalbumin-challenged ft/ft atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-β levels and/or activity) are reduced by more than about 20% (e.g., as determined using a ovalbumin-challenged ft/ft atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-2 levels and/or activity) are reduced by more than about 20% (e.g., as determined using a ovalbumin-challenged ft/ft atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-6 levels and/or activity) are reduced by more than about 20% (e.g., as determined using a ovalbumin-challenged ft/ft atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-8 levels and/or activity) are reduced by more than about 20% (e.g., as determined using a ovalbumin-challenged ft/ft atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a isoprenyl compound of Formulae I, I' and/or in described classes and subclasses thereof, wherein cytokine levels and/or activity (e.g., IL-12 levels and/or activity) are reduced by more than about 20% (e.g., as determined using a ovalbumin-challenged ft/ft atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a isoprenyl compound of Formulae I, I' and/or in described classes and subclasses thereof, wherein cytokine levels and/or activity (e.g., IFN-γ levels and/or activity) are reduced by more than about 20% (e.g., as determined using a ovalbumin-challenged ft/ft atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a isoprenyl compound of Formulae I, I' and/or in described classes and subclasses thereof, wherein cytokine levels and/or activity (e.g., MCP-1 levels and/or activity) are reduced by more than about 20% (e.g., as determined using a ovalbumin-challenged ft/ft atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a isoprenyl compound of Formulae I, I' and/or in described classes and subclasses thereof, wherein cytokine levels and/or activity (e.g., Gro-α levels and/or activity) are reduced by more than about 20% (e.g., as determined using a ovalbumin-challenged ft/ft atopic dermatitis mouse model).

Seborrhic Dermatitis

Seborrheic dermatitis, commonly called dandruff, is a disease that causes redness, itchiness, and flaking of the skin. It affects the scalp, face, trunk, and particularly the sebum-gland rich areas of the skin, usually causing the skin to look inflamed and scaly.

Seborrheic dermatitis most often occurs in adults from 30 to 60 years of age and is more common in men than in women. Although the exact cause is not known, those afflicted with seborrhoeic dermatitis often have an unfavorable epidermic response caused by infections. Seborrheic dermatitis has also been linked to neurologic disorders such as Parkinson's disease and epilepsy. The treatment of seborrheic dermatitis depends on its location on the body. Treatment also depends on the person's age. Dandruff is often treated with a shampoo that contains salicylic acid, the prescription medicine selenium sulfide, zinc pyrithione, ketoconazole or coal tar. Steroid lotions may be used in adolescents and adults. Exemplary cytokines associated with seborrhic dermatitis include but are not limited to TNFα, ILβ, IL-6, IL-8, MCP-1, and Groα.

Inflammatory Cytokines and Rosacea, Psoriasis, Atopic Dermatitis and Seborrhic Dermatitis As described herein, the present invention provides methods of treating ameloriating, controlling, or preventing inflammatory skin conditions (e.g., rosacea, psoriasis, atopic dermatitis and seborrhic dermatitis).

In some embodiments, the present invention provides methods of treating ameloriating, controlling, or preventing inflammatory skin conditions (e.g., rosacea, psoriasis, atopic dermatitis and seborrhic dermatitis) by administering a compound and/or composition of Formula I, provided that at least 0.1 mg of the compound is administered. In certain embodiments, the present invention provides methods of treating ameloriating, controlling, or preventing inflammatory skin conditions (e.g., rosacea, psoriasis, atopic dermatitis and seborrhic dermatitis) by administering a compound and/or composition of Formulae I, I' and/or in described classes and subclasses thereof, provided that at least 2 mg of the compound is administered.

According to one aspect, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein inflammatory activity (e.g., MPO activity) is reduced by more than about 30% (e.g., as determined using an MPO activity assay).

According to one aspect, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein inflammatory activity (e.g., MPO activity) is reduced by more than about 60% (e.g., as determined using an MPO activity assay).

According to one aspect, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein inflammatory activity (e.g., erythema activity) is reduced by more than about 30% (e.g., as determined using an erythema activity assay).

According to one aspect, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein inflammatory activity (e.g., edema activity) is reduced by more than about 30% (e.g., as determined using an edema activity assay).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., TNF-α, levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-1β levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-8 levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-6 levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., MCP-1 levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., Gro$\alpha$ levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., TNF-$\alpha$ levels and/or activity) are reduced by more than about 20% (e.g., as determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-1$\beta$ levels and/or activity) are reduced by more than about 20% (e.g., as determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-8/KC levels and/or activity) are reduced by more than about 20% (e.g., as, determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-6 levels and/or activity) are reduced by more than about 20% (e.g., as determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., MCP-1 levels and/or activity) are reduced by more than about 20% (e.g., as determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., Gro-$\alpha$ levels and/or activity) are reduced by more than about 20% (e.g., as determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., TNF-$\alpha$ levels and/or activity) are reduced by more than about 20% (e.g., as determined using an ATP$\gamma$S-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-1$\beta$ levels and/or activity) are reduced by more than about 20% (e.g., as determined using an ATP$\gamma$S-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-8/KC levels and/or activity) are reduced by more than about 20% (e.g., as determined using an ATP$\gamma$S-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-6 levels and/or activity) are reduced by more than about 20% (e.g., as determined using an ATP$\gamma$S-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., MCP-1 levels and/or activity) are reduced by more than about 20% (e.g., as determined using an ATPγS-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., Gro-α levels and/or activity) are reduced by more than about 20% (e.g., as determined using an ATPγS-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., TNF-α levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-1β levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-8/KC levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-6 levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., MCP-1 levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., Gro-α levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., TNF-α levels and/or activity) are reduced by more than about 20% (e.g., as determined using a TNFα-induced cytokine release inflammatory model in HUVEC cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-1β levels and/or activity) are reduced by more than about 20% (e.g., as determined using a TNFα-induced cytokine release inflammatory model in HUVEC cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity are reduced by more than about 20%, such as IL-8/KC, determined using a TNFα-induced cytokine release inflammatory model in HUVEC cell line.

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., IL-6 levels and/or activity) are reduced by more than about 20% (e.g., as determined using a TNFα-induced cytokine release inflammatory model in HUVEC cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., MCP-1 levels and/or activity) are reduced by more than about 20% (e.g., as determined using a TNFα-induced cytokine release inflammatory model in HUVEC cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a isoprenyl compound of Formulae I, I' and/or in described classes and subclasses thereof, wherein cytokine levels and/or activity (e.g., Gro-α levels and/or activity) are reduced by more than about 20% (e.g., as determined using a TNFα-induced cytokine release inflammatory model in HUVEC cell line).

Sun Screen (Protection from UV Damage)

Oxidative stresses caused by environmental insults such as ultraviolet ("UV") rays from the sun, cigarette smoke exposure, consumption of foods with high saturated fat and environmental pollutants as well as the natural process of aging, contributing to the generation of free radicals and reactive oxygen species ("ROS"), stimulate inflammatory responses, especially in the skin (Pilla et al. Intl J. Cosm. Sci. 2005 v27 p17-34). High levels of ROS contribute to adverse effects on the skin including erythema, edema, photoaging and skin cancer (Trouba et al. Antioxid. Redox Signal 2002 v4 p665-673). Neutrophil infiltration during inflammatory responses is associated with increased oxygen consumption and generation of ROS. Extracellular inflammatory agonists such as fMLP bind to GPCRs such as formyl peptide receptors ("FPR"), to trigger the oxidative burst response (i.e., the rapid rapid release of ROS).

In certain embodiments, the present invention provides methods of treating, ameloriating, controlling, or preventing UV damage to especially the skin of a subject, in need thereof, by administering a compound and/or composition of Formula I, provided that at least 0.1 mg of the compound. In certain embodiments, the present invention provides methods of treating, ameloriating, controlling, or preventing UV damage to especially the skin of a subject, in need thereof, by administering a compound and/or composition of Formula I, provided that at least 2 mg of the compound is administered.

According to one aspect, the present invention provides methods of treating, ameliorating, controlling, or preventing UV damage to especially the skin of a subject, in need thereof, comprising administering to a subject in need thereof a dosage form comprising at least about 0.1 mg of a isoprenyl compound of Formulae I, I' and/or in described classes and subclasses thereof, having an activity in the inhibition of more than about 20% of superoxide formation.

7. Combination Therapy

It is contemplated that a provided compound can be used in combination with other drugs or therapeutic agents.

In some embodiments, isoprenyl compounds as described herein are administered in combination with one or more other agents intended to treat the same condition, or disease. As used herein, additional therapeutic agents that are normally administered to treat a particular disease, or condition, are known as "appropriate for the disease, or condition, being treated."

For example, in some embodiments, compounds of the present invention, or a pharmaceutically acceptable composition thereof, are administered in combination with other anti-inflammatory agents to treat inflammatory diseases and/or disorders. Examples of known anti-inflammatory agents include, but are not limited to, dexamethasone, indomethacin and clobetasol.

In some embodiments, isoprenyl compounds of the present invention are administered in combination with one or more other pharmaceutically active agents intended to treat a different disease, disorder, or condition. For example, in some embodiments, it may be desirable to administer an inventive compound in order to reduce inflammation while concurrently administering a different pharmaceutically active agent in order to achieve a different biological result.

To give but one example, it is known that transdermal administration of pharmaceutically active agents often causes skin irritation at the site of delivery. Indeed, it is not uncommon that a skin irritating agent (e.g., SDS) be administered prior to or concurrent with application of a transdermal device such as, for example, a transdermal patch, in order to facilitate the delivery. Applicants have found that addition or co-administration of a isoprenyl compound as described herein in combination with transdermal administration of another pharmaceutically active agent can reduce inflammation and/or irritation associated with the transdermal administration of the other pharmaceutically active agent.

It is also known that single or chronic injections of a pharmaceutically active agent may sometimes result in inflammation, whether due to the identity of the pharmaceutically active agent (i.e., as an irritant) or to the mode of delivery. The present invention contemplates co-administration of one or more compounds of the present invention, in order to reduce inflammation associated with single or chronic injection of a pharmaceutically active agent.

Exemplary pharmaceutically active agents whose delivery, whether transdermally or by injection, may cause skin irritation include levadopa, pro-drug forms of levadopa, insulin, estradiol, estrogen, progesterone, progestins, progestogen, testosterone, nicotine, nitroglycerin, cholinesterase inhibitors, stimulants, antidepressants, and analgesics.

To give another example, application of certain agents such as, for example, hair relaxants, which commonly are or contain basic agents (e.g., NaOH), can cause skin irritation (e.g., irritation and/or inflammation of the scalp). According to the present invention, one or more isoprenyl compounds can be administered together with such a hair relaxant (or other agent) to reduce skin irritation and/or inflammation.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

EXAMPLES

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all classes, subclasses and species of each of these compounds, disclosed herein.

The AFC compounds, including S-trans, trans-farnesyl-L-cysteine, utilized as starting materials may be synthesized according to methods known in the art or synthesized by the methods disclosed in Brown et al., *J Am Chem Soc*, 1991, 113: 3176-3177, the disclosure of which is incorporated by reference herein. Other starting materials such as S-trans, trans-farnesyl-L-cysteine methyl ester, may be synthesized according to methods known in the art or synthesized by the methods disclosed in Troutman et al., *Bioconjugate Chem*, 2005, 16: 1209-1217.

The following general experimental procedures were used for Examples 1-78 as described below. Proton Nuclear Magnetic Resonance ($^1$H-NMR) spectroscopy was recorded on a Bruker 500 MHz spectrometer, dimethyl sulfoxide (DMSO-d6), methanol (CD$_3$OD) or chloroform (CDCl$_3$) was used as $^1$H-NMR solvent. The residual proton absorption of the deuterated solvent was used as the internal standard. All $^1$H-NMR chemical shift are reported as δ values in the parts per million (ppm). The splitting pattern abbreviations are as follows: s, singlet; d, doublet; t, triplet; q, quartet; br, broad; m, multiplet; dd, doublet of doublet; dt, doublet of triplets. The HPLC analysis was done using a phenomenex luna C$_{18}$(2) 50×4.6 mm column. The mobile phase is 60% water, 40% acetonitrile containing 0.05% trifluoroacetic acid at 2 mL per minute flow rate for the first 2.5 minutes, followed by a gradient to 100% acetonitrile containing 0.05% TFA over 10 minutes. The eluent is observed at 214 nm.

Example 1

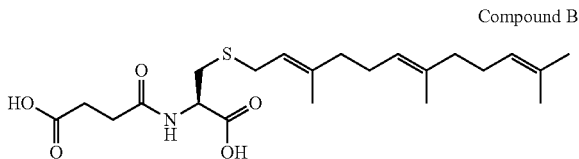 [SMILES: CC(C)=CCC/C(C)=C/CC/C(C)=C/CSC[C@H](NC(=O)CCC(=O)O)C(=O)O]

Compound B

Synthesis of (4-((R)-1-carboxy-2-((2E,6E)-3,7,11-trimethyldodeca-2,6,10-trienylthio)ethylamino)-4-oxobutanoic acid)(Compound B): To a solution of S-trans, trans-farnesyl-L-cysteine (500 mg, 1.54 mmol) in THF, a first portion of K$_2$CO$_3$ (2 mmol) was added and the resultant solution was cooled to 5° C. with vigorous stirring. To this stirred solution was added succinic anhydride (308 mg, 3.1 mmol) dropwise while maintaining the pH at 9.0-10.0 with another portion of K$_2$CO$_3$ (4 mmol). The mixture was stirred at room temperature for 2 h, HPLC analysis showed completion of the reaction. The pH of the reaction mixture then adjusted to 2.0 by the addition of 2 N HCl solution. The acidic solution was extracted three times with 10 mL of ethyl acetate. The combined organic extract was washed with water, brine and dried over Na$_2$SO$_4$, the solvent was removed on rotary evaporator to afford crude Compound B, which was further purified by preparative HPLC (535 mg, 82%) to yield Compound B. $^1$H-NMR (500 MHz, CDCl$_3$): δ 1.59 (s, 6H), 1.66 (s, 6H), 2.05 (m, 8H), 2.60 (m, 2H), 2.48 (m, 2H), 2.86 (dd, 1H), 2.94 (dd, 1H), 3.10 (dd, 1H), 3.12 (dd, 1H), 4.68 (dd, 1H), 5.06 (m, 2H), 5.20 (t, 1H). $^{13}$C-NMR (125 MHz, CDCl$_3$): δ 16.0, 16.1, 17.7, 25.7, 26.5, 26.7, 29.4, 29.8, 30.5, 32.6, 39.6, 39.7, 52.2, 119.3, 123.8, 124.3, 131.3, 135.4, 140.3, 173.4, 174.2, 176.8; ES-MS: mass calcd for Chemical Formula: C$_{22}$H$_{35}$NO$_5$S 425.6. Found (M+Na) m/z 448.

Example 2

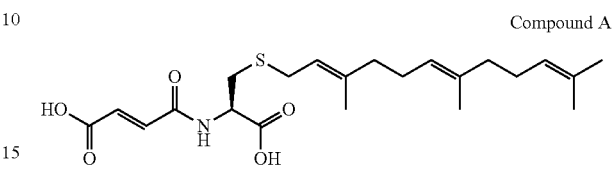

Compound A

Synthesis of ((E)-4-((R)-1-carboxy-2-((2E,6E)-3,7,11-trimethyldodeca-2,6,10-trienylthio)ethylamino)-4-oxobut-2-enoic acid)(Compound A): A solution of S-trans, trans-farnesyl-L-cysteine (500 mg, 1.54 mmol) in THF and a first portion of K$_2$CO$_3$ (3 mmol) was cooled to 5° C. with vigorous stirring. To this stirred solution was added maleic anhydride (302 mg, 3.07 mmol) portionwise while maintaining the pH at 9.0-10.0 with another portion of K$_2$CO$_3$ (3 mmol). The mixture was stirred at room temperature for 3 h, HPLC analysis showed completion of the reaction. The pH of the reaction mixture then adjusted to 2.0 by the addition of 2 N HCl solution. The acidic solution was extracted three times with 15 mL of ethyl acetate. The combined organic extract was washed with water, brine and dried over Na$_2$SO$_4$ and then concentrated to afford crude Compound A, which was further purified by preparative HPLC (552 mg, 85%) to yield Compound A. $^1$H-NMR (500 MHz, CD$_3$OD): δ 1.50 (bs, 6H), 1.57 (s, 3H), 1.59 (s, 3H), 1.85-2.10 (m, 8H), 2.68 (dd, J=6.5, 14.5, 1H), 2.95 (dd, J=4.5, 14.0 Hz, 1H), 3.07 (dd, J=7.0, 13.0 Hz, 1H), 3.17 (dd, J=8.5, 13.5 Hz, 1H), 4.59 (dd, J=4.5, 8.5), 4.97-5.02 (m, 2H), 5.12 (t, J=7.5, 1H), 6.21 (d, J=13.0 Hz, 1H), 6.47 (d, J=13.0 Hz, 1H). $^{13}$C-NMR (125 MHz, CDCl$_3$): δ 16.2, 16.3, 17.8, 25.3, 26.0, 27.4, 27.8, 30.3, 33.3, 40.8, 40.9, 54.0, 121.5, 125.1, 125.5, 132.1, 133.3, 134.4, 136.3, 140.7, 167.7, 168.0, 172.9; ES-MS: mass calcd for Chemical Formula: C$_{22}$H$_{33}$NO$_5$S 423.6. Found (M+Na) m/z 446.

Example 3

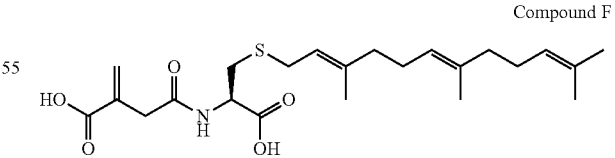

Compound F

Synthesis of (4-((R)-1-carboxy-2-((2E,6E)-3,7,11-trimethyldodeca-2,6,10-trienylthio)ethylamino)-2-methylene-4-oxobutanoic acid)(Compound F): S-trans, trans-Farnesyl-L-cysteine (500 mg, 1.54 mmol) was dissolved in mixture of THF and a first portion of K$_2$CO$_3$ (3 mmol) and the resulting solution was cooled to 5° C. with vigorous stirring. To this stirred solution was added 3-methylenedihydro-2,5-furandione (302 mg, 3.07 mmol) portionwise while maintaining the pH at 9.0-10.0 with another portion of $K_2CO_3$ (3 mmol). The mixture was stirred at room temperature for 3 h. HPLC analysis showed completion of the reaction. The pH of the reaction mixture then adjusted to 2.0 by the addition of 2 N HCl solution. The acidic solution was extracted three times with 15 mL of ethyl acetate. The combined organic extract was washed with water, brine and dried over $Na_2SO_4$, the solvent was removed under reduced pressure to afford crude Compound F, which was further purified by preparative HPLC (552 mg, 82%) to yield Compound F. $^1$H-NMR (500 MHz, $CDCl_3$): δ 1.59 (s, 6H), 1.67 (s, 3H), 1.68 (s, 3H), 2.05 (m, 8H), 2.88 (dd, J=6.5, 14.0, 1H), 2.95 (dd, J=6.5, 14.0, 1H), 3.17-3.15 (m, 2H), 3.36 (d, J=14 Hz, 1H), 4.77 (dd, J=6, 12.5 Hz, 1H), 5.09 (bt, 2H), 5.22 (t, J=7.5 Hz, 1H), 5.93 (s, 1H), 6.46 (s, 1H). $^{13}$C-NMR (125 MHz, $CDCl_3$): δ 16.0, 16.2, 17.7, 25.7, 26.7, 29.9, 32.8, 39.6, 39.7, 40.2, 52.0, 119.4, 123.7, 131.3, 132.0, 135.4, 140.3, 170.3, 171.5, 176.0; ES-MS: mass calcd for Chemical Formula: $C_{23}H_{35}NO_5S$ 437.6. Found (M+Na) m/z 446.

Example 4

Compound E

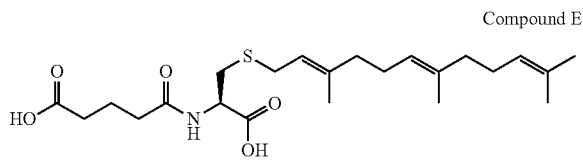 [SMILES: CC(C)=CCC/C(C)=C/CC/C(C)=C/CSC[C@H](NC(=O)CCCC(=O)O)C(=O)O]

Synthesis of (5-((R)-1-carboxy-2-((2E,6E)-3,7,11-trimethyldodeca-2,6,10-trienylthio)ethylamino)-5-oxopentanoic acid) (Compound E): S-trans, trans-Farnesyl-L-cysteine (500 mg, 1.54 mmol) was dissolved in mixture of THF (6 mL) and first portion of $K_2CO_3$ (3 mmol) and the resulting solution was cooled to 5° C. with vigorous stirring. To this stirred solution glutaric anhydride (263 mg, 2.30 mmol) was added slowly while maintaining the pH at 9.0-9.5 with another portion of $K_2CO_3$ (3 mmol). The mixture was stirred at RT for 3 h, TLC showed completion of the reaction. The pH of the reaction mixture then adjusted to 2.0 by the addition of 2 N hydrochloric acid. The acidic solution was extracted with ethyl acetate (10 mL×3). The combined organic extract was washed with water, brine and dried over $Na_2SO_4$, the solvent was removed on rotary evaporator to afford crude Compound E, which was further purified by preparative HPLC (459 mg, 68%) to yield Compound E. $^1$H-NMR (500 MHz, $CD_3OD$): δ 1.60 (s, 6H), 1.70 (s, 3H), 1.72 (s, 3H), 2.02-1.95 (m, 4H), 2.15-2.05 (m, 4H), 2.32 (t, 2H), 2.40 (t, 2H), 2.75 (m, 2H), 3.05 (dd, 1H), 3.15 (dd, 1H), 3.30 (d, 2H), 4.60 (dd, 1H), 5.14 (t, 2H), 5.25 (t, 1H). $^{13}$C-NMR (125 MHz, $CD_3OD$): δ 16.1, 17.7, 18.4, 22.2, 26.3, 27.4, 27.7, 35.7, 40.6, 53.3, 121.5, 125.2, 125.4, 131.8, 136.1, 140.1, 173.7, 175.3, 177.6; ES-MS: mass calcd for Chemical Formula: $C_{23}H_{37}NO_5S$ 439.6. Found (M+Na) m/z 462.3.

Example 5

Compound C

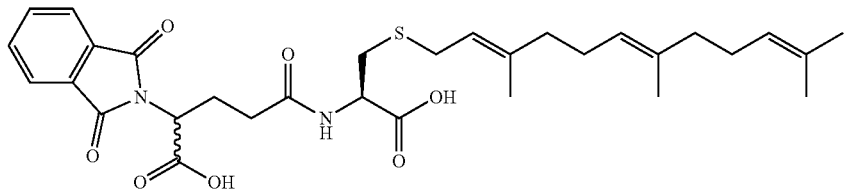

Synthesis of a mixture of (R)-5-((R)-1-carboxy-2-((2E,6E)-3,7,11-trimethyldodeca-2,6,10-trienylthio)ethylamino)-2-(1,3-dioxoisoindolin-2-yl)-5-oxopentanoic acid)(Compound C-1) and (S)-5-((R)-1-carboxy-2-((2E,6E)-3,7,11-trimethyldodeca-2,6,10-trienylthio)ethylamino)-2-(1,3-dioxoisoindolin-2-yl)-5-oxopentanoic acid) (Compound C-2):

S-trans, trans-Farnesyl-L-cysteine (500 mg, 1.54 mmol) was dissolved in mixture of THF (6 mL) and first portion of $K_2CO_3$ (3 mmol) and the resulting solution was cooled to 5° C. with vigorous stirring. To this stirred solution was added N-phthaloyl-DL-glutamic anhydride (599 mg, 2.31 mmol) as portionwise while maintaining the pH at 9.0-10.0 with another portion of $K_2CO_3$ (2 mmol). The mixture was stirred at RT for 3 h, TLC/HPLC showed completion of the reaction. The pH of the reaction mixture was adjusted to 2.0 by adding 2 N HCl solution. The acidic solution was extracted three times with 15 mL of ethyl acetate. The combined organic extract was washed with water, brine and dried over $Na_2SO_4$, and concentrated to afford a crude mixture. The resulting mixture was further purified by preparative HPLC (734 mg, 82%) to yield a mixture of Compound C-1 (the R-R isomer) and Compound C-2 (the S-R isomer), wherein the ratio of C-1 to C-2 is 1:1. $^1$H-NMR (500 MHz, $CDCl_3$): δ 1.50 (s, 3H), 1.52 (s, 3H), 1.55 (s, 1.5H), 1.56 (s, 1.5H), 1.60 (s, 3H), 1.86-1.98 (m, 8H), 2.33-2.56 (m, 4H), 2.75 (dd, J=5.0, 15.0 Hz, 1H), 2.93 (dd, J=5.0, 15.0 Hz, 1H), 3.03-3.13 (m, 2H), 4.63 (dd, J=5.0, 10.0 Hz, 1H), 4.92-5.00 (m, 2H), 5.10 (dd, J=5.0, 15.0 Hz, 1H), 6.87 (d, J=5.0 Hz, 0.5H), 6.99 (d, J=5.0 Hz, 0.5H), 7.63-7.65 (m, 2H), 7.74-7.77 (m, 2H), 9.30 (broad, 2H). $^{13}$C-NMR (125 MHz, $CDCl_3$): δ 16.06, 16.17, 16.19, 17.76, 25.20, 25.41, 25.78, 26.48, 26.73, 29.74, 29.76, 32.48, 32.63, 32.79, 32.93, 39.66, 39.72, 51.13, 51.19, 51.90, 52.11, 119.38, 123.76, 123.81, 124.36, 131.38, 131.60, 131.61, 134.39, 134.45, 135.31, 135.34, 140.18, 140.21, 167.78, 167.91, 172.55, 172.72, 173.17, 173.35, 174.46, 174.62; ES-MS: mass calcd for Chemical Formula: $C_{31}H_{40}N_2O_7S$ 584.72. Found (M+) m/z 585.3, (M+Na) m/z 607.3.

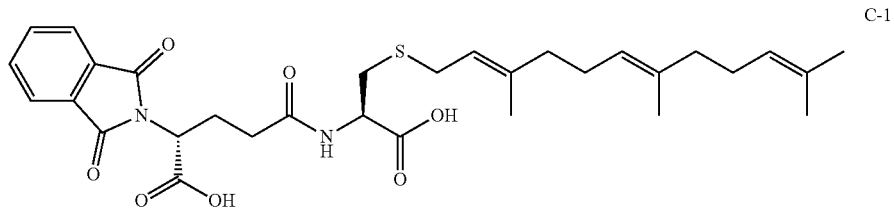

[(R)-(R) isomer]  C-1

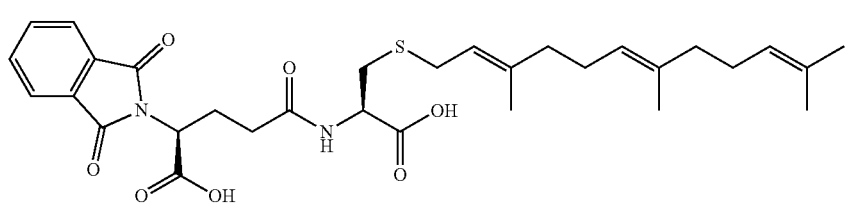

[(S)-(R) isomer]  C-2

Example 5a

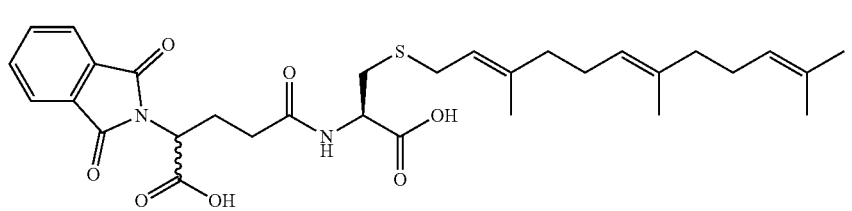

Compound C

Alternate Synthesis of a mixture of (R)-5-((R)-1-carboxy-2-((2E,6E)-3,7,11-trimethyldodeca-2,6,10-trienylthio)ethyl-amino)-2-(1,3-dioxoisoindolin-2-yl)-5-oxopentanoic acid) (Compound C-1) and (S)-5-((R)-1-carboxy-2-((2E,6E)-3,7,11-trimethyldodeca-2,6,10-trienylthio)ethylamino)-2-(1,3-dioxoisoindolin-2-yl)-5-oxopentanoic acid) (Compound C-2): To a solution of S-trans, trans-farnesyl-L-cysteine (325 mg, 1 mmol) and racemic mixture of N-phthaloyl-glutamic anhydride, i.e. N-phthaloyl-DL-glutamic anhydride (259 mg, 1 mmol) in $CH_2Cl_2$ (10 mL) was added N,N-diisopropyl-ethyl-amine (0.87 mL, 5 mmol). The solution was stirred at room temperature for 2 h. The reaction was quenched with 1N HCl (10 mL) and the pH was adjusted to 2.0-3.0. The mixtures were extracted with ethyl acetate (15 mL×3). The organic layer was dried over $Na_2SO_4$ and concentrated in vacuo and the residue was purified by preparative HPLC (311 mg, 53%) to yield a mixture of Compound C-1 and Compound C-2, identical to the isomeric mixture obtained in Example 5, wherein the ratio of C-1 to C-2 is 1:1.

$^1$H-NMR (500 MHz, $CDCl_3$): δ 1.50 (s, 3H), 1.52 (s, 3H), 1.55 (s, 1.5H), 1.56 (s, 1.5H), 1.60 (s, 3H), 1.86-1.98 (m, 8H), 2.33-2.56 (m, 4H), 2.75 (dd, J=5.0, 15.0 Hz, 1H), 2.93 (dd, J=5.0, 15.0 Hz, 1H), 3.03-3.13 (m, 2H), 4.63 (dd, J=5.0, 10.0 Hz, 1H), 4.92-5.00 (m, 2H), 5.10 (dd, J=5.0, 15.0 Hz, 1H), 6.87 (d, J=5.0 Hz, 0.5H), 6.99 (d, J=5.0 Hz, 0.5H), 7.63-7.65 (m, 2H), 7.74-7.77 (m, 2H), 9.30 (broad, 2H). $^{13}$C-NMR (125 MHz, $CDCl_3$): δ 16.06, 16.17, 16.19, 17.76, 25.20, 25.41, 25.78, 26.48, 26.73, 29.74, 29.76, 32.48, 32.63, 32.79, 32.93, 39.66, 39.72, 51.13, 51.19, 51.90, 52.11, 119.38, 123.76, 123.81, 124.36, 131.38, 131.60, 131.61, 134.39, 134.45, 135.31, 135.34, 140.18, 140.21, 167.78, 167.91, 172.55, 172.72, 173.17, 173.35, 174.46, 174.62; ES-MS: mass calcd for Chemical Formula: $C_{31}H_{40}N_2O_7S$ 584.72. Found (M+) m/z 585.3, (M+Na) m/z 607.3.

Example 5b

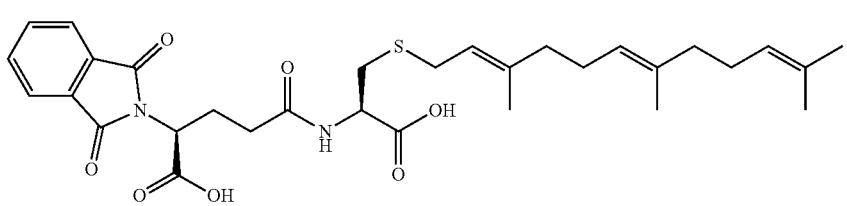

Compound C-2

Synthesis of ((S)-5-((R)-1-carboxy-2-((2E,6E)-3,7,11-trimethyldodeca-2,6,10-trienylthio)ethylamino)-2-(1,3-dioxoisoindolin-2-yl)-5-oxopentanoic acid)(Compound C-2): To a solution of S-trans, trans-farnesyl-L-cysteine (325 mg, 1 mmol) and N-phthaloyl-L-glutamic anhydride (259 mg, 1 mmol) in $CH_2Cl_2$ (10 mL) was added N,N-diisopropyl-ethyl-amine (0.87 mL, 5 mmol). The solution was stirred at room temperature for 2 h. The reaction was quenched with 1N HCl (10 mL) and the pH was adjusted to 2.0-3.0. The mixtures were extracted with ethyl acetate (15 mL×3). The organic layer was dried over $Na_2SO_4$ and concentrated in vacuo and the residue was purified by preparative HPLC (350 mg, 60%) to yield Compound C-2, which is identical to the S-R stereoisomer of the Compound C racemate in Examples 5 and 5a. $^1$H-NMR (500 MHz, $CDCl_3$): δ 1.50 (s, 3H), 1.52 (s, 3H), 1.55 (s, 3H), 1.60 (s, 3H), 1.86-1.98 (m, 8H), 2.33-2.43 (m, 2H), 2.54-2.57 (m, 2H), 2.78 (dd, J=5.0, 15.0 Hz, 1H), 2.91 (dd, J=5.0, 15.0 Hz, 1H), 3.06 (dd, J=5.0, 10.0 Hz, 1H), 3.14 (dd, J=5.0, 10.0 Hz, 1H), 4.65 (dd, J=5.0, 10.0 Hz, 1H), 4.96 (t, J=5.0 Hz, 1H), 5.00 (m, 2H), 5.11 (t, J=5.0 Hz, 1H), 6.79 (d, J=10.0 Hz, 1H), 7.63-7.65 (m, 2H), 7.74-7.76 (m, 2H), 8.00 (broad, 2H). $^{13}$C-NMR (125 MHz, $CDCl_3$): δ 16.06, 16.18, 17.76, 25.19, 25.78, 26.47, 26.73, 29.77, 32.59, 32.79, 39.65, 39.72, 51.10, 51.85, 119.37, 123.76, 123.80, 124.36, 131.39, 131.62, 134.40, 135.36, 140.24, 167.75, 172.78, 173.05, 174.51; ES-MS: mass calcd for Chemical Formula: $C_{31}H_{40}N_2O_7S$ 584.72. Found (M+) m/z 585.3, (M+Na) m/z 607.3.

Example 6

Synthesis of ((R,14E,18E)-15,19,23-trimethyl-4,8-dioxo-3-oxa-12-thia-7,9-diazatetracosa-14,18,22-triene-10-carboxylic acid)(Compound D): S-trans, trans-Farnesyl-L-cysteine (325 mg, 1 mmol) and N,N-diisopropyl-ethyl-amine (650 mg, 5 mmol) were mixed in $CH_2Cl_2$ (10 mL). Ethyl-3-isocyanato-propionate (143, 1 mmol) was added to the reaction mixture. The reaction solution was stirred at room temperature overnight and the solvent was removed by rotary evaporation. The remaining residue was dissolved in ethyl acetate (100 mL) and washed with 1 N HCl solution (50 mL×2). The ethyl acetate solution was dried over $Na_2SO_4$ and concentrated to a crude reaction mixture. The resulting mixture was purified by HPLC (200 mg, 43%) to yield Compound D. $^1$H-NMR (500 MHz, MeOH-$d_4$): δ 1.28 (t, J=7.5 Hz, 3H), 1.62 (s, 3H), 1.63 (s, 3H), 1.69 (s, 3H), 1.70 (s, 3H), 1.98 (m, 2H), 2.06 (m, 6H), 2.52 (t, J=6.5 Hz, 2H), 2.79 (dd, J=7.0, 14.0 Hz, 1H), 2.93 (dd, J=4.5, 13.5 Hz, 1H), 3.17 (dd, J=7.5, 13.5 Hz, 1H), 3.28 (dd, J=8.5, 13.5 Hz, 1H), 3.41 (t, J=6.5 Hz, 3H), 4.16 (q, J=7.5 Hz, 2H), 4.50 (dd, J=4.5, 6.5 Hz, 1H), 5.11 (m, 2H), 5.23 (t, J=7.5 Hz, 1H). $^{13}$C-NMR (125 MHz, MeOH-$d_4$): δ 14.6, 16.1, 16.2, 17.8, 26.0, 27.4, 27.8, 30.5, 34.4, 35.9, 36.7, 40.8, 40.9, 54.0, 61.7, 121.7, 125.1, 125.5, 132.1, 136.3, 140.5, 160.2, 173.8, 175.0; ES-MS: mass calcd for Chemical Formula: $C_{24}H_{40}N_2O_5S$ 468.7. Found (M+Na) m/z 491.3.

Example 7

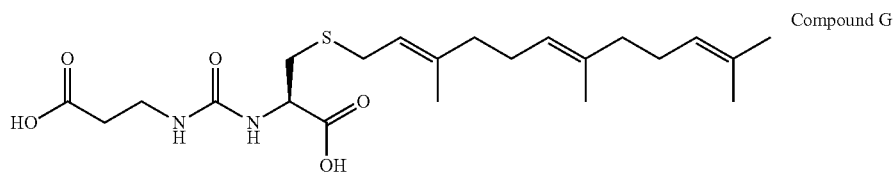

Compound G

Synthesis of ((R)-2-(3-(2-carboxyethyl)ureido)-3-((2E,6E)-3,7,11-trimethyldodeca-2,6,10-trienylthio)propanoic acid) (Compound G): In a 100 mL round bottom flask, Compound D of Example 6 (100 mg, 0.21 mmol) was dissolved in THF (10 mL). LiOH (500 mg, 20 mmol) in water (5 mL) was added to the reaction solution. The reaction mixture was stirred at room temperature overnight. Ethyl acetate (100 mL) was added to the reaction mixture. The reaction mixture was acidified by 1 N HCl solution (pH=4.0). The organic portion was separated and dried over $Na_2SO_4$, concentrated and purified by HPLC (40 mg, 41%) to yield Compound G. $^1$H-NMR (500 MHz, MeOH-$d_4$): δ 1.62 (bs, 6H), 1.69 (s, 3H), 1.70 (s, 3H), 1.99 (m, 2H), 2.08 (m, 6H), 2.51 (t, J=6.5 Hz, 2H), 2.79 (dd, J=7.0, 14.0 Hz, 1H), 2.93 (dd, J=4.5, 8.1 Hz, 1H), 3.17 (dd, J=7.0, 13.0 Hz, 1H), 3.28 (dd, J=9.0, 15.0 Hz, 1H), 3.40 (t, J=6.5 Hz, 3H), 4.50 (dd, J=5.0, 6.5 Hz, 1H), 5.11 (m, 2H), 5.23 (t, J=7.5 Hz, 1H). $^{13}$C-NMR (125 MHz, MeOH-$d_4$): δ 16.1, 16.2, 17.8, 26.0, 27.4, 27.8, 30.5, 34.4, 35.7, 36.8, 40.8, 40.9, 54.1, 121.7, 125.2, 125.5, 132.1, 136.3, 140.5, 160.3, 175.1, 175.7; ES-MS: mass calcd for Chemical Formula: $C_{22}H_{36}N_2O_5S$ 440.6. Found (M+Na) m/z 463.3.

Example 8

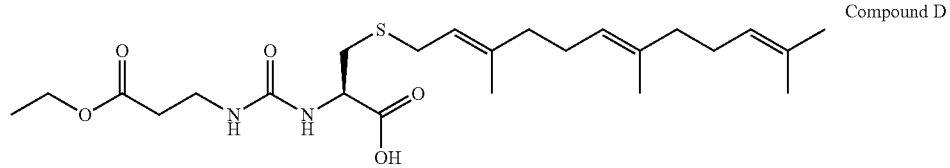 [SMILES: CCOC(=O)CCNC(=O)N[C@@H](CSC/C=C(\C)CC/C=C(\C)CCC=C(C)C)C(=O)O]

Compound D

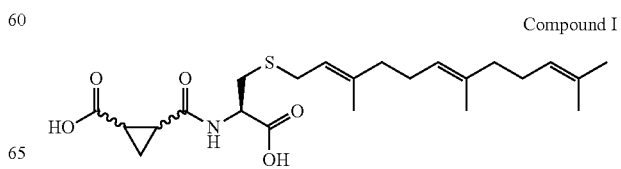

Compound I

Synthesis of Compound I as a mixture of ((1R,2S)-2-((R)-1-carboxy-2-((2E,6E)-3,7,11-trimethyldodeca-2,6,10-trienylthio)ethylcarbamoyl)cyclopropanecarboxylic acid) (Compound I-1) and ((1S,2R)-2-((R)-1-carboxy-2-((2E,6E)-3,7,11-trimethyldodeca-2,6,10-trienylthio)ethylcarbamoyl) cyclopropanecarboxylic acid) (Compound I-2): In a 100 mL round bottom flask, S-trans, trans-farnesyl-L-cysteine (325 mg, 1 mmol) and N,N-diisopropyl-ethyl-amine (650 mg, 5 mmol) were mixed in $CH_2Cl_2$ (10 mL). 3-oxabicyclo[3.1.0]hexane-2,4-dione (112 mg, 1.0 mmol) was added to the reaction mixture. The reaction solution was stirred at room temperature overnight and the solvent was removed by rotary evaporation. The remaining residue was dissolved in ethyl acetate (100 mL) and washed with 1 N HCl solution (10 mL). The ethyl acetate solution was dried over $Na_2SO_4$ to afford a concentrated crude mixture. The crude mixture was purified by preparative HPLC (250 mg, 57%) to yield mixture of Compound I-1 and Compound I-2, wherein the ratio of I-1 to 1-2 is 1:1. $^1$H-NMR (500 MHz, $CD_3OD$): δ 1.32 (m, 1H), 1.56 (m, 1H), 1.62 (bs, 6H), 1.69 (s, 3H), 1.71 (s, 3H), 1.97 (t, J=7.0 Hz, 2H), 2.04-2.22 (m, 8H), 2.73-2.78 (m, 1H), 2.95-3.00 (m, 1H), 3.13-3.18 (m, 1H), 3.25-3.33 (m, 1H), 4.60 (m, 1H), 5.09 (m, 2H), 5.19 (t, J=7.5 Hz, 1H). $^{13}$C-NMR (125 MHz, $CDCl_3$): δ 12.5, 12.6, 16.2, 16.3, 17.8, 22.6, 22.8, 24.1, 24.2, 26.0, 27.4, 27.8, 30.2, 33.4, 33.5, 40.8, 40.9, 53.6, 121.6, 125.1, 125.5, 132.1, 136.2, 140.5, 172.3, 173.7, 173.9, 174.5; ES-MS: mass calcd for Chemical Formula: $C_{23}H_{35}NO_5S$ 437.6. Found (M+Na) m/z 460.3.

cosa-13,17,21-triene-9-carboxylic acid) (Compound N-55): In a 100 mL round bottom flask, N-Boc-L-serine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture. The reaction mixture was stirred at room temperature overnight and the $CH_2Cl_2$ was removed by rotary evaporation. The remaining residue was dissolved in ethyl acetate (50 mL). The resulting organic solution was washed with an $NH_4Cl$ saturated solution (50 mL), dried over $Na_2SO_4$, and concentrated to afford a crude mixture. The crude mixture was purified by preparative HPLC (51 mg, 10%) to yield Compound N-55. $^1$H-NMR (500 MHz, $CD_3OD$): δ 1.47 (s, 9H), 1.62 (bs, 6H), 1.69 (s, 3H), 1.71 (s, 3H), 1.99 (t, J=7 Hz, 2H), 2.05-2.22 (m, 6H), 2.81 (dd, J=7.5, 14 Hz, 1H), 3.01 (dd, J=4, 14.5 Hz, 1H), 3.17 (dd, J=7, 13 Hz, 1H), 3.27 (dd, J=8, 12.5 Hz, 1H), 3.33 (bs, 2H), 3.74-3.80 (m, 2H), 4.22 (t, J=5 Hz, 1H), 4.63 (dd, J=5, 7.5 Hz, 1H), 5.11 (m, 2H), 5.23 (t, J=7.5 Hz, 1H). $^{13}$C-NMR (125 MHz, $CDCl_3$): δ 16.2, 16.3, 17.8, 26.0, 27.4, 27.8, 28.7, 30.4, 33.6, 40.8, 40.9, 53.3, 58.0, 59.6, 63.4, 80.9, 121.6, 125.2, 125.5, 132.1, 136.3, 140.6, 157.8, 173.0, 173.8; ES-MS: mass calcd for Chemical Formula: $C_{26}H_{44}N_2O_6S$ 512.7. Found (M+Na) m/z 535.4.

Example 10

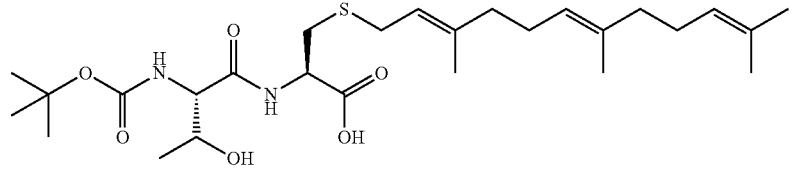

Compound N-56

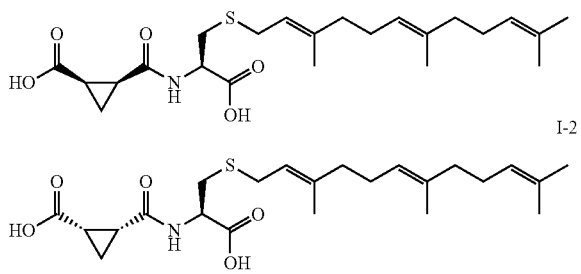

Example 9

Synthesis of ((6S,9R,13E,17E)-6-((S)-1-hydroxyethyl)-2,2,14,18,22-pentamethyl-4,7-dioxo-3-oxa-11-thia-5,8-diazatricosa-13,17,21-triene-9-carboxylic acid)(Compound N-56): In a 100 mL round bottom flask, N-Boc-L-threonine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by Compound N-55

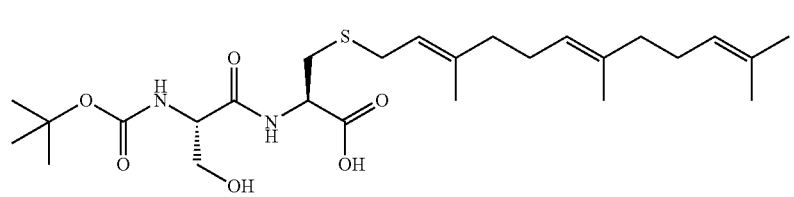

Synthesis of ((6S,9R,13E,17E)-6-(hydroxymethyl)-2,2,14,18,22-pentamethyl-4,7-dioxo-3-oxa-11-thia-5,8-diazatripreparative HPLC (145 mg, 28%) to yield Compound N-56. $^1$H-NMR (500 MHz, $CD_3OD$): δ 1.21 (d, J=6 Hz, 3H), 1.48

(s, 9H), 1.62 (bs, 6H), 1.69 (s, 3H), 1.71 (s, 3H), 1.99 (t, J=7.5 Hz, 2H), 2.05-2.22 (m, 6H), 2.82 (dd, J=7.5, 14 Hz), 3.01 (dd, J=5, 13.5 Hz, 1H), 3.17 (dd, J=7, 13.5 Hz, 1H), 3.29 (dd, J=8.5, 13.5 Hz, 1H), 3.33 (bs, 2H), 4.09-4.16 (m, 2H), 4.65 (dd, J=5, 7 Hz, 1H), 5.11 (m, 2H), 5.23 (t, J=7.5 Hz, 1H). $^{13}$C-NMR (125 MHz, CDCl$_3$): δ 16.2, 16.3, 17.8, 19.9, 26.0, 27.4, 27.8, 28.6, 30.4, 33.5, 40.8, 40.9, 53.4, 61.3, 63.0, 68.7, 80.8, 121.6, 125.15, 125.5, 132.12, 136.26, 140.6, 157.9, 173.2, 173.6; ES-MS: mass calcd for Chemical Formula: $C_{27}H_{46}N_2O_6S$ 526.7. Found (M+Na) m/z 549.4.

Example 11

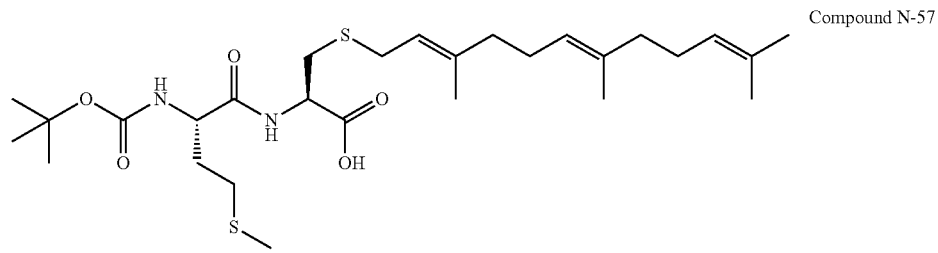 [SMILES: CSCC[C@H](NC(=O)OC(C)(C)C)C(=O)N[C@@H](CSC/C=C(\C)CC/C=C(\C)CCC=C(C)C)C(=O)O]

Compound N-57

Synthesis of ((6S,9R,13E,17E)-2,2,14,18,22-pentamethyl-6-(2-(methylthio)ethyl)-4,7-dioxo-3-oxa-11-thia-5,8-diazatricosa-13,17,21-triene-9-carboxylic acid)(Compound N-57): In a 100 mL round bottom flask, N-Boc-L-methionine (1.0 mmol), coupling reagent (520 mg of PBOP or 380 mg of HATU, 1 mmol) and N,N-diisopropyl-ethyl-amine (650 mg, 5 mmol) were mixed in CH$_2$Cl$_2$ (10 mL). The reaction mixture was stirred at room temperature for 30 minutes. S-trans, trans-Farnesyl-L-cysteine (325 mg, 1 mmol) was added to the reaction mixture. The reaction mixture was stirred at room temperature overnight. CH$_2$Cl$_2$ was removed by rotary evaporation. The resulting residue was dissolved in ethyl acetate (50 mL). The organic solution was washed with an NH$_4$Cl saturated solution (50 mL), dried over Na$_2$SO$_4$, and concentrated to afford a crude mixture. The crude mixture was purified by preparative HPLC (290 mg, 52%) to yield Compound N-57. $^1$H-NMR (500 MHz, CDCl$_3$): δ 1.47 (s, 9H), 1.62 (bs, 6H), 1.69 (s, 3H), 1.72 (s, 3H), 1.90-1.93 (m, 1H), 1.99 (t, J=7.5 Hz, 2H), 2.03-2.16 (m, 8H), 2.50-2.68 (m, 2H), 2.80 (dd, J=8, 14 Hz, 1H), 3.02 (dd, J=4.5, 14 Hz, 1H), 3.18 (dd, J=7, 13 Hz, 1H), 3.27 (dd, J=8, 13 Hz, 1H), 3.25 (dd, J=5, 8 Hz, 1H), 4.60 (dd, J=4.5, 8, 1H), 5.10-5.15 (m, 2H), 5.24 (t, J=7.5, 1H). $^{13}$C-NMR (125 MHz, CDCl$_3$): δ 15.3, 16.2, 16.3, 17.8, 26.0, 27.4, 27.8, 28.8, 30.3, 31.0, 33.0, 33.4, 40.8, 40.9, 53.3, 55.1, 80.8, 121.6, 125.2, 125.5, 132.1, 136.3, 140.6, 157.8, 173.6, 174.6; ES-MS: mass calcd for Chemical Formula: $C_{28}H_{48}N_2O_5S_2$ 556.3. Found (M+Na) m/z 279.2.

Example 12

Synthesis of ((6S,9R,13E,17E)-6-isobutyl-2,2,14,18,22-pentamethyl-4,7-dioxo-3-oxa-11-thia-5,8-diazatricosa-13,17,21-triene-9-carboxylic acid)(Compound N-58): In a 100 mL round bottom flask, N-Boc-L-leucine (1.0 mmol), coupling reagent (520 mg of PBOP or 380 mg of HATU, 1 mmol) and N,N-diisopropyl-ethyl-amine (650 mg, 5 mmol) were mixed in CH$_2$Cl$_2$ (10 mL). The reaction mixture was stirred at room temperature for 30 minutes. S-trans, trans-farnesyl-L-cysteine (325 mg, 1 mmol) was added to the reaction mixture. The reaction mixture was stirred at room temperature overnight, the CH$_2$Cl$_2$ was removed by rotary evaporation. The resulting residue was dissolved in ethyl acetate (50 mL). The organic solution was washed with an NH$_4$Cl saturated solution (50 mL), dried over Na$_2$SO$_4$, and concentrated to afford a crude mixture. The crude mixture was purified by preparative HPLC (200 mg, 37%) to yield Compound N-58. $^1$H-NMR (500 MHz, CDCl$_3$): δ 0.95 (d, J=6.5 Hz, 3H), 0.98 (d, J=6.5 Hz, 3H), 1.47 (s, 9H), 1.62 (bs, 6H), 1.51-1.59 (m, 1H), 1.69 (s, 3H), 1.72 (s, 3H), 1.99 (t, J=7.5 Hz, 2H), 2.05-2.14 (m, 8H), 2.79 (dd, J=7.5, 14.2, 1H), 3.00 (dd, J=4.8, 13.9 Hz, 1H), 3.17 (dd, J=7.6, 13.0 Hz, 1H), 3.25 (dd, J=8.2, 12.9 Hz, 1H), 4.15 (dd, J=5.4, 9.8 Hz, 1H), 4.60 (dd, J=4.9, 8.0 Hz, 1H), 5.09-5.25 (m, 2H), 5.23 (t, J=7.6 Hz, 1H). $^{13}$C-NMR (125 MHz, CDCl$_3$): δ 16.2, 16.3, 17.8, 22.0, 23.5, 25.9, 27.4, 27.8, 28.8, 30.4, 33.6, 40.8, 40.9, 42.3, 53.3, 54.6, 80.6, 121.6, 125.2, 125.5, 132.1, 136.2, 140.6, 157.8, 173.6, 175.6; ES-MS: mass calcd for Chemical Formula: $C_{29}H_{50}N_2O_5S$ 538.3. Found (M+Na) m/z 561.4.

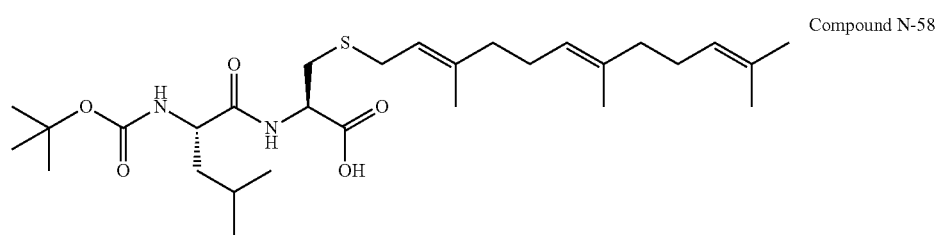 [SMILES: CC(C)=CCC/C(C)=C/CC/C(C)=C/CSC[C@H](NC(=O)[C@H](CC(C)C)NC(=O)OC(C)(C)C)C(=O)O]

Compound N-58

Example 13

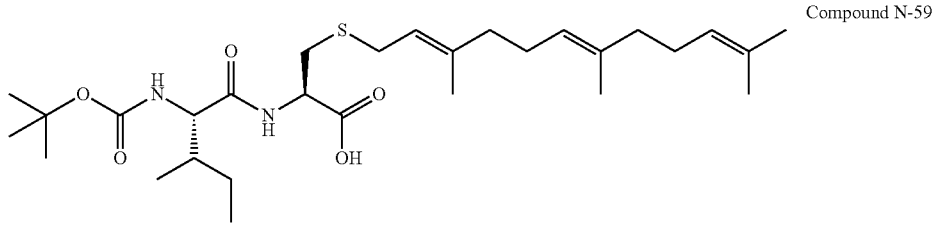 [SMILES: CCC(C)[C@H](NC(=O)OC(C)(C)C)C(=O)N[C@@H](CSC/C=C(\C)CC/C=C(\C)CCC=C(C)C)C(=O)O]

Compound N-59

Synthesis of ((6S,9R,13E,17E)-6-(R)-sec-butyl-2,2,14,18,22-pentamethyl-4,7-dioxo-3-oxa-11-thia-5,8-diazatricosa-13,17,21-triene-9-carboxylic acid)(Compound N-59): In a 100 mL round bottom flask, N-Boc-L-isoleucine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and was stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (210 mg, 39%) to yield Compound N-59. $^1$H-NMR (500 MHz, $CDCl_3$): δ 0.92 (t, J=7.4 Hz, 3H), 0.97 (d, J=6.9 Hz, 3H), 1.19 (m, 1H), 1.47 (s, 9H), 1.61 (m, 1H), 1.62 (bs, 6H), 1.69 (s, 3H), 1.72 (s, 3H), 1.82 (m, 1H), 1.99 (t, J=7.5 Hz, 2H), 2.05-2.14 (m, 8H), 2.78 (dd, J=8.0, 14.0, 1H), 3.01 (dd, J=4.9, 14.0 Hz, 1H), 3.18 (dd, J=7.4, 13.1 Hz, 1H), 3.27 (dd, J=8.4, 13.1 Hz, 1H), 4.00 (d, J=7.3 Hz, 1H), 4.62 (dd, J=4.9, 8.0 Hz, 1H), 5.10-5.17 (m, 2H), 5.24 (t, J=7.4 Hz, 1H). $^{13}$C-NMR (125 MHz, $CDCl_3$): δ 11.6, 16.0, 16.2, 16.3, 17.9, 25.8, 26.0, 27.5, 27.8, 28.8, 30.4, 33.6, 38.5, 40.8, 40.9, 53.4, 60.7, 80.6, 121.6, 125.2, 125.5, 132.1, 136.3, 140.5, 157.9, 173.6, 174.4; ES-MS: mass calcd for Chemical Formula: $C_{29}H_{50}N_2O_5S$ 538.3. Found (M+Na) m/z 561.4.

Example 14

Synthesis of ((R)-2-((S)-1-(tert-butoxycarbonyl)pyrrolidine-2-carboxamido)-3-((2E,6E)-3,7,11-trimethyldodeca-2,6,10-trienylthio)propanoic acid)(Compound N-8): In a 100 mL round bottom flask, N-Boc-L-proline (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture. The reaction mixture was stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (232 mg, 44%) to yield Compound N-8. $^1$H-NMR (500 MHz, $CDCl_3$): δ 1.46 (s, 9H), 1.62 (bs, 6H), 1.69 (s, 3H), 1.72 (s, 3H), 1.89 (bs, 1H), 1.98 (t, J=7.5 Hz, 2H), 2.05-2.14 (m, 6H), 2.24-2.26 (m, 1H), 2.79 (dd, J=8.0, 14.0, 1H), 3.03 (bd, J=13.0 Hz, 1H), 3.15 (dd, J=7.5, 13.0 Hz, 1H), 3.27 (dd, J=8.0, 13.0 Hz, 1H), 3.40 (m, 1H), 3.66 (bs, 1H), 4.28 (bs, 1H), 4.60 (dd, J=4.9, 8.0 Hz, 1H), 5.11-5.14 (m, 2H), 5.24 (t, J=7.4 Hz, 1H). $^{13}$C-NMR (125 MHz, $CDCl_3$): δ 16.2, 16.3, 17.8, 24.2, 24.5, 25.3, 25.9, 27.4, 27.8, 28.7, 30.1, 30.4, 30.7, 31.1, 32.5, 33.5, 40.8, 40.9, 47.9, 48.3, 53.1, 53.4, 61.4, 61.9, 81.4, 81.7, 121.5, 125.1, 125.5, 132.1, 136.3, 140.5, 156.2, 173.6, 175.8; ES-MS: mass calcd for Chemical Formula: $C_{28}H_{46}N_2O_5S$ 522.3. Found (M+Na) m/z 545.3.

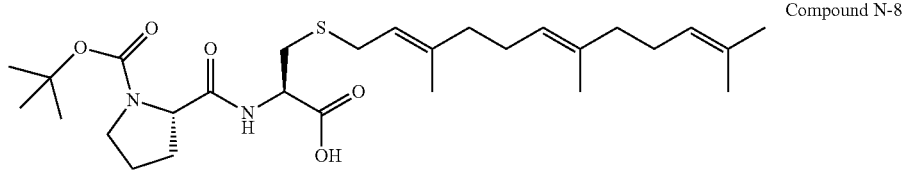 [SMILES: CC(C)=CCC/C(C)=C/CC/C(C)=C/CSC[C@H](NC(=O)[C@@H]1CCCN1C(=O)OC(C)(C)C)C(=O)O]

Compound N-8

Example 15

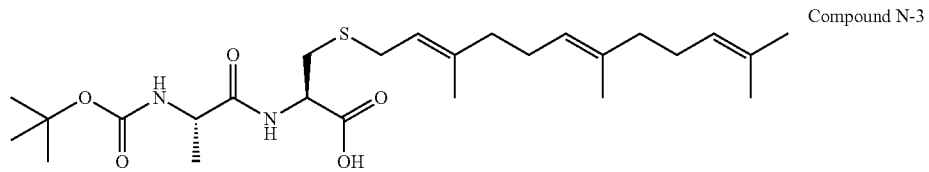 [SMILES: CC(C)=CCC/C(C)=C/CC/C(C)=C/CSC[C@H](NC(=O)[C@H](C)NC(=O)OC(C)(C)C)C(=O)O]

Compound N-3

Synthesis of (((6S,9R,13E,17E)-2,2,6,14,18,22-hexamethyl-4,7-dioxo-3-oxa-11-thia-5,8-diazatricosa-13,17,21-triene-9-carboxylic acid)(Compound N-3): In a 100 mL round bottom flask, N-Boc-L-alanine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (170 mg, 35%) to yield Compound N-3. $^1$H-NMR (500 MHz, $CDCl_3$): δ 1.37 (bt, 3H), 1.44 (s, 9H), 1.60 (bs, 6H), 1.68 (bs, 6H), 1.99 (t, J=8.2 Hz, 2H), 2.04-2.10 (m, 6H), 2.89 (dd, J=6.3, 13.9 Hz, 1H), 3.01 (dd, J=7.5, 14.1 Hz, 1H), 3.14-3.24 (m, 2H), 4.31-4.39 (m, 1H), 4.74-4.77 (m, 1H), 5.08-5.10 (m, 2H), 5.23 (t, J=7.5 Hz, 1H). $^{13}$C-NMR (125 MHz, $CDCl_3$): δ 16.1, 16.2, 17.8, 18.6, 19.1, 25.7, 26.5, 26.7, 28.5, 30.0, 33.0, 33.1, 39.7, 49.7, 49.8, 51.7, 51.8, 51.9, 76.8, 77.0, 77.3, 80.5, 80.7, 119.6, 123.8, 124.3, 131.3, 135.3, 140.1, 155.7, 155.9, 173.0, 173.1; ES-MS: mass calcd for Chemical Formula: $C_{26}H_{44}N_2O_5S$ 496.7. Found (M+Na) m/z 519.4.

Example 16

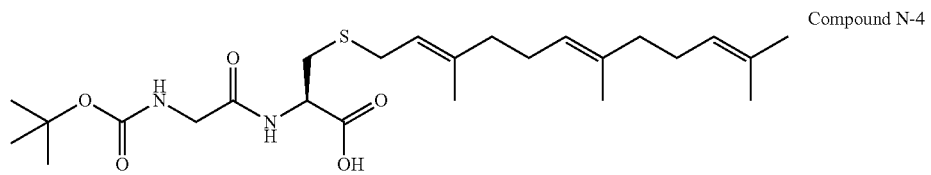 [SMILES: CC(C)=CCC/C(C)=C/CC/C(C)=C/CSC[C@H](NC(=O)CNC(=O)OC(C)(C)C)C(=O)O]

Compound N-4

Synthesis of ((R,13E,17E)-2,2,14,18,22-pentamethyl-4,7-dioxo-3-oxa-11-thia-5,8-diazatricosa-13,17,21-triene-9-carboxylic acid)(Compound N-4): In a 100 mL round bottom flask, N-Boc-L-glycine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes, S-trans, trans-farnesyl-L-cysteine (325 mg, 1 mmol) was added and the reaction mixture was stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (78 mg, 18%) to yield Compound N-4. $^1$H-NMR (500 MHz, $CDCl_3$): δ 1.45 (s, 9H), 1.60 (bs, 6H), 1.67 (s, 3H), 1.68 (s, 3H), 1.97 (t, J=7.5 Hz, 2H), 2.01-2.15 (m, 6H), 2.85 (bd, J=13 Hz, 1H), 3.01 (bd, J=13 Hz, 1H), 3.14-3.23 (m, 2H), 3.81 (d, J=16.5 Hz, 1H), 4.01 (d, J=12 Hz, 1H), 4.77 (m, 1H), 5.09 (m, 2H), 5.30 (1H). $^{13}$C-NMR (125 MHz, $CDCl_3$): δ 16.0, 16.1, 17.7, 25.7, 26.5, 26.7, 28.4, 30.0, 32.9, 39.7, 39.7, 43.8, 51.7, 80.7, 119.5, 123.8, 124.3, 131.4, 135.4, 140.1, 156.3, 169.8, 172.9; ES-MS: mass calcd for Chemical Formula: $C_{25}H_{42}N_2O_5S$ 482.3. Found (M+Na) m/z 505.1.

Example 17

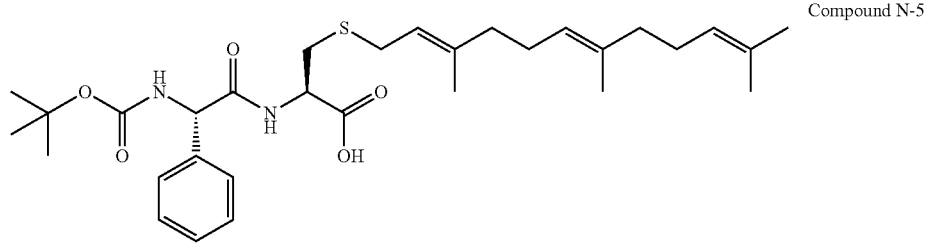

Compound N-5

(6S,9R,13E,17E)-2,2,14,18,22-pentamethyl-4,7-dioxo-6-phenyl-3-oxa-11-thia-5,8-diazatricosa-13,17,21-triene-9-carboxylic acid Synthesis of ((6S,9R,13E,17E)-2,2,14,18,22-pentamethyl-4,7-dioxo-6-phenyl-3-oxa-11-thia-5,8-diazatricosa-13,17,21-triene-9-carboxylic acid)(Compound N-5): In a 100 mL round bottom flask, N-Boc-L-phenylglycine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes and S-trans, trans-farnesyl-L-cysteine (325 mg, 1 mmol) was added. The reaction mixture was stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (118 mg, 21%) to yield Compound N-5. $^1$H-NMR (500 MHz, $CD_3OD$): δ 1.47 (s, 9H), 1.62 (s, 6H), 1.69 (s, 6H), 1.99 (t, J=7.0 Hz, 2H), 2.03-2.13 (m, 6H), 2.81 (dd, J=8.1, 13.9 Hz, 1H), 3.01 (dd, J=6.8, 12.1 Hz, 1H), 3.16 (dd, J=7.6, 13.2 Hz, 1H), 3.26 (dd, J=8.5, 13.4 Hz), 4.62 (bt, J=5.5), 5.09-5.12 (m, 2H), 5.22 (t, J=7.9 Hz, 1H), 7.29-7.37 (m, 3H), 7.46 (d, J=7.3 Hz, 2H). $^{13}$C-NMR (125 MHz, $CD_3OD$): δ 16.2, 16.3, 25.9, 27.3, 27.8, 28.7, 30.3, 33.4, 33.5, 40.8, 40.9, 53.6, 59.9, 81.1, 121.6, 125.2, 125.5, 128.6, 129.1, 129.7, 132.1, 136.3, 139.1, 140.5, 158.3, 173.0, 173.4; ES-MS: mass calcd for Chemical Formula: $C_{31}H_{46}N_2O_5S$ 558.8. Found (M+Na) m/z 581.4.

Synthesis of ((R,14E,18E)-2,2,15,19,23-pentamethyl-4,8-dioxo-3-oxa-12-thia-5,9-diazatetracosa-14,18,22-triene-10-carboxylic acid)(Compound N-6): In a 100 mL round bottom flask, N-Boc-L-beta-alanine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (171 mg, 35%) to yield Compound N-6. $^1$H-NMR (500 MHz, $CD_3OD$): δ 1.45 (s, 9H), 1.60 (s, 3H), 1.61 (s, 3H), 1.69 (s, 3H), 1.72 (s, 3H), 1.99 (t, J=7.6 Hz, 2H), 2.01-2.15 (m, 6H), 2.47 (t, J=6.8 Hz, 2H), 2.73 (dd, J=8.8, 13.9 Hz, 1H), 3.01 (dd, J=4.6, 14.0 Hz, 1H), 3.16 (dd, J=7.3, 13.2 Hz, 1H), 3.28 (dd, J=8.4, 13.4 Hz, 1H), 3.33 (m, 2H), 4.61 (dd, J=4.6, 9.0 Hz, 1H), 5.10-5.22 (m, 2H), 5.24 (t, J=7.7 Hz, 1H). $^{13}$C-NMR (125 MHz, $CD_3OD$): δ 16.2, 16.3, 17.8, 25.9, 27.4, 27.8, 28.8, 30.2, 33.5, 37.0, 38.0, 40.8, 40.9, 53.3, 80.2, 121.6, 125.1, 125.5, 132.1, 136.3, 140.6, 158.3, 174.0; ES-MS: mass calcd for Chemical Formula: $C_{26}H_{44}N_2O_5S$ 496.7. Found (M+Na) m/z 519.3.

Example 18

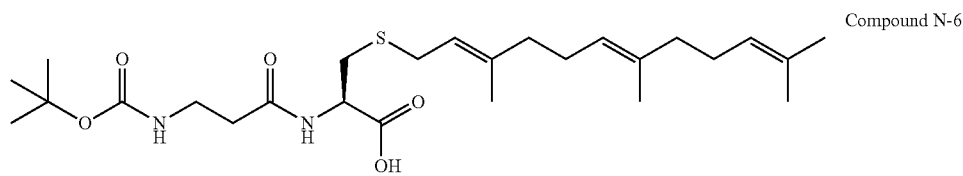 [SMILES: CC(C)=CCC/C(C)=C/CC/C(C)=C/CSC[C@H](NC(=O)CCNC(=O)OC(C)(C)C)C(=O)O]

Compound N-6

Example 19

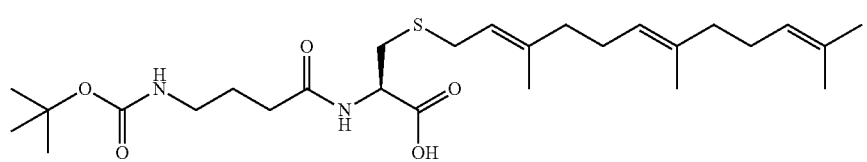

Compound N-7

Synthesis of ((R,15E,19E)-2,2,16,20,24-pentamethyl-4,9-dioxo-3-oxa-13-thia-5,10-diazapentacosa-15,19,23-triene-11-carboxylic acid)(Compound N-7): In a 100 mL round bottom flask, N-Boc-L-aminobutanoic acid (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (142 mg, 32%) to yield Compound N-7. $^1$H-NMR (500 MHz, $CD_3OD$): δ 1.46 (s, 9H), 1.62 (s, 3H), 1.63 (s, 3H), 1.69 (s, 3H), 1.72 (s, 3H), 1.77-1.80 (m, 2H), 1.99 (t, J=7.5 Hz, 2H), 2.01-2.15 (m, 6H), 2.31 (t, J=7.5 Hz, 2H), 2.73 (dd, J=9.0, 13.9 Hz, 1H), 3.02 (dd, J=4.5, 14.0 Hz, 1H), 3.11 (t, J=6.8 Hz, 2H), 3.17 (dd, J=7.3, 13.2 Hz, 1H), 3.29 (dd, J=8.4, 13.2 Hz, 1H), 4.60 (dd, J=4.6, 9.0 Hz, 1H), 5.10-5.22 (m, 2H), 5.24 (t, J=7.8 Hz, 1H). $^{13}$C-NMR (125 MHz, $CD_3OD$): δ 16.2, 16.3, 17.8, 25.9, 27.3, 27.4, 27.8, 28.8, 30.2, 33.5, 34.1, 40.7, 40.8, 40.9, 53.3, 80.0, 121.6, 125.1, 125.5, 132.1, 136.3, 140.5, 158.6, 174.0, 175.7; ES-MS: mass calcd for Chemical Formula: $C_{27}H_{46}N_2O_5S$ 410.3. Found (M+Na) m/z 533.3.

Example 20

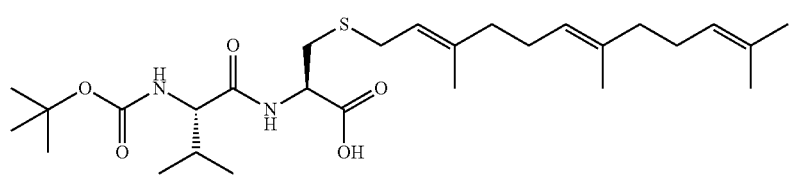

Compound N-9

Synthesis of ((6S,9R,13E,17E)-6-isopropyl-2,2,14,18,22-pentamethyl-4,7-dioxo-3-oxa-11-thia-5,8-diazatricosa-13,17,21-triene-9-carboxylic acid)(Compound N-9): In a 100 mL round bottom flask, N-Boc-L-valine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (276 mg, 53%) to yield Compound N-9. $^1$H-NMR (500 MHz, $CD_3OD$): δ 0.95 (d, J=6.5 Hz, 3H), 0.99 (d, J=6.5 Hz, 3H), 1.21 (m, 1H), 1.47 (s, 9H), 1.62 (bs, 6H), 1.69 (s, 3H), 1.71 (s, 3H), 1.99 (t, J=7.5 Hz, 2H), 2.05-2.15 (m, 8H), 2.78 (dd, J=8.5, 14.0, 1H), 3.00 (dd, J=4.5, 14.0 Hz, 1H), 3.16 (dd, J=7.5, 13.2 Hz, 1H), 3.27 (dd, J=8.4, 13.2 Hz, 1H), 3.95 (d, J=6.5 Hz, 1H), 4.61 (dd, J=4.8, 8.0 Hz, 1H), 5.10-5.14 (m, 2H), 5.51 (t, J=7.4 Hz, 1H). $^{13}$C-NMR (125 MHz, $CDCl_3$): δ 16.2, 16.3, 17.8, 18.4, 19.8, 25.9, 27.4, 27.8, 28.8, 30.3, 32.2, 33.5, 40.8, 40.9, 53.3, 61.5, 80.6, 121.6, 125.2, 125.5, 132.1, 136.3, 140.5, 157.9, 173.6, 174.4; ES-MS: mass calcd for Chemical Formula: $C_{28}H_{48}N_2O_5S$ 524.7. Found (M+Na) m/z 547.4.

Example 21

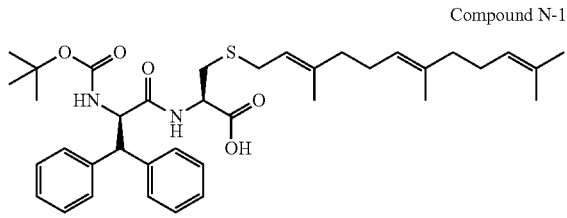

Compound N-12

Synthesis of ((6R,9R,13E,17E)-6-benzhydryl-2,2,14,18,22-pentamethyl-4,7-dioxo-3-oxa-11-thia-5,8-diazatricosa-13,17,21-triene-9-carboxylic acid)(Compound N-12): In a 100 mL round bottom flask, N-Boc-D-diphenyl-alanine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (306 mg, 68%) to yield Compound N-12.

¹H-NMR (500 MHz, CD₃OD): δ 1.33 (s, 9H), 1.62 (s, 3H), 1.63 (s, 3H), 1.65 (s, 3H), 1.69 (s, 3H), 1.99 (t, J=7.0 Hz, 2H), 2.03-2.16 (m, 8H), 2.39 (dd, J=6.5, 14.0 Hz, 1H), 2.52 (dd, J=6.5, 14.0 Hz, 1H), 2.96-3.05 (m, 2H), 4.28-4.36 (m, 1H), 4.37 (s, 1H), 5.01 (d, J=11.0 Hz, 1H), 5.10-5.20 (m, 2H), 7.15-7.38 (m, 10H). ¹³C-NMR (125 MHz, CDCl₃): δ 16.2, 16.3, 26.0, 27.4, 27.8, 28.6, 30.3, 33.2, 40.7, 40.9, 53.3, 53.4, 55.1, 58.6, 80.6, 121.5, 125.2, 125.5, 127.7, 127.9, 129.4, 129.6, 129.7, 132.1, 136.3, 140.3, 142.4, 142.5, 157.4, 173.1, 173.5; ES-MS: mass calcd for Chemical Formula: C₃₈H₅₂N₂O₅S 648.4. Found (M+Na) m/z 671.2.

Example 22

Synthesis of ((6S,9R,13E,17E)-6-cyclohexyl-2,2,14,18,22-pentamethyl-4,7-dioxo-3-oxa-11-thia-5,8-diazatricosa-13,17,21-triene-9-carboxylic acid((Compound N-60): In a 100 mL round bottom flask, N-Boc-L-cyclohexyl-Glycine (1.0 mmol), coupling reagent (520 mg of PBOP or 380 mg of HATU, 1 mmol) and N,N-diisopropyl-ethyl-amine (650 mg, 5 mmol) were mixed in CH₂Cl₂ (10 mL). The reaction mixture was stirred at room temperature for 30 minutes. S-trans, trans-farnesyl-L-cysteine (325 mg, 1 mmol) was added to the reaction mixture and stirred at room temperature overnight. CH₂Cl₂ was removed by rotary evaporation. The resulting residue was dissolved in ethyl acetate (50 mL). The organic solution was washed with an NH₄Cl saturated solution (50 mL), dried over Na₂SO₄, and concentrated to Compound N-49

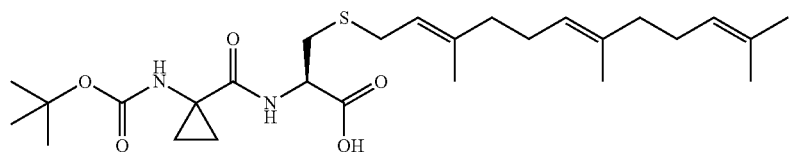

Synthesis of ((R)-2-(1-(tert-butoxycarbonylamino)cyclopropanecarboxamido)-3-((2E,6E)-3,7,11-trimethyldodeca-2,6,10-trienylthio)propanoic acid)(Compound N-49): In a 100 mL round bottom flask, N-Boc-amino-cyclopropionic acid (1.0 mmol), coupling reagent (520 mg of PBOP or 380 mg of HATU, 1 mmol) and N,N-diisopropyl-ethyl-amine (650 mg, 5 mmol) were mixed in CH₂Cl₂ (10 mL). The reaction mixture was stirred at room temperature for 30 minutes. S-trans, trans-farnesyl-L-cysteine (325 mg, 1 mmol) was added to the reaction mixture and stirred at room temperature overnight. CH₂Cl₂ was removed by rotary evaporation. The resulting residue was dissolved in ethyl acetate (50 mL). The organic solution was washed with an NH₄Cl saturated solution (50 mL), dried over Na₂SO₄, and concentrated to afford a crude mixture. The crude mixture was purified by preparative HPLC (158 mg, 31%) to yield Compound N-49. ¹H-NMR (500 MHz, CD₃OD): δ 1.05-1.08 (m, 2H), 1.41-1.46 (m, 2H), 1.49 (s, 9H), 1.62 (s, 3H), 1.63 (s, 3H), 1.69 (s, 3H), 1.70 (s, 3H), 1.99 (t, J=8.2 Hz, 2H), 2.05-2.16 (m, 6H), 2.92 (dd, J=5.5, 13.5 Hz, 1H), 3.01 (dd, J=7.5, 14.0 Hz, 1H), 3.16 (dd, J=7.5, 13.0 Hz, 1H), 3.27 (dd, J=8.5, 13.0 Hz, 1H), 4.61 (bs, 1H), 5.12 (dd, J=7.5, 15.5 Hz, 2H), 5.23 (t, J=7.5 Hz, 1H). ¹³C-NMR (125 MHz, CDCl₃): δ 16.1, 16.3, 17.8, 25.9, 27.4, 27.8, 30.7, 33.7, 40.8, 40.9, 53.7, 53.8, 121.6, 125.1, 125.5, 132.1, 136.3, 140.6, 158.1, 173.6; ES-MS: mass calcd for Chemical Formula: C₂H₄₄N₂O₅S 508.7. Found (M+Na) m/z 531.4.

afford a crude mixture. The crude mixture was purified by preparative HPLC (260 mg, 58%) to yield Compound N-60. ¹H-NMR (500 MHz, CD₃OD): δ 1.05-1.30 (m, 6H), 1.47 (s, 9H), 1.61-1.77 (m, 5H), 1.62 (bs, 6H), 1.69 (s, 3H), 1.76 (s, 3H), 1.99 (t, J=7.5 Hz, 2H), 2.06-2.17 (m, 8H), 2.78 (dd, J=8.0, 14.0, 1H), 3.01 (dd, J=5.0, 14.0 Hz, 1H), 3.18 (dd, J=7.5, 13.0 Hz, 1H), 3.27 (dd, J=8.0, 13.0 Hz, 1H), 3.96 (d, J=6.5 Hz, 1H), 4.61 (dd, J=5.0, 8.0 Hz, 1H), 5.12 (dd, J=8.0, 17.0 Hz, 2H), 5.24 (t, J=7.5 Hz, 1H). ¹³C-NMR (125 MHz, CD₃OD): δ 16.2, 16.3, 17.8, 26.0, 27.1, 27.2, 27.3, 27.5, 27.8, 28.8, 33.5, 40.8, 40.9, 41.8, 53.3, 61.0, 62.5, 80.6, 121.6, 125.2, 125.5, 132.1, 136.3, 140.5, 157.9, 173.6, 174.3; ES-MS: mass calcd for Chemical Formula: C₃₁H₅₂N₂O₅S 564.8. Found (M+Na) m/z 587.4.

Example 24

Compound N-50

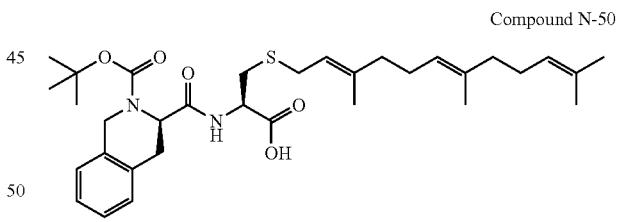

Synthesis of ((R)-2-((R)-2-(tert-butoxycarbonyl)-1,2,3,4-tetrahydroisoquinoline-3-carboxamido)-3-((2E,6E)-3,7,11-

Example 23

Compound N-60

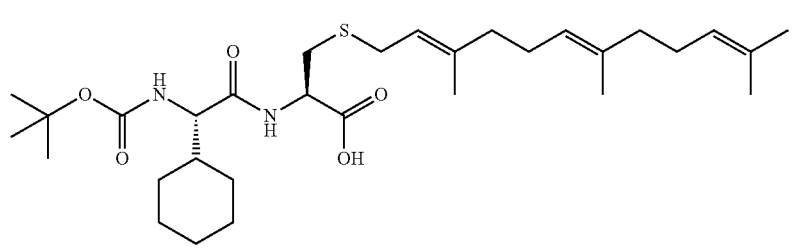

trimethyldodeca-2,6,10-trienylthio)propanoic acid)(Compound N-50): In a 100 mL round bottom flask, N-Boc-(R)-1,2,3,4-tetrahydroisoquinoline-3-carboxylic acid (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (250 mg, 48%) to yield Compound N-50. $^1$H-NMR (500 MHz, $CD_3OD$): δ 1.33 (s, 9H), 1.61 (bs, 6H), 1.68 (bs, 6H), 1.69-1.73 (m, 2H), 1.99 (t, J=7.5 Hz, 2H), 2.06-2.17 (m, 8H), 2.73 (dd, J=7.5, 14.0, 1H), 2.87 (dd, J=5.0, 14.0 Hz, 1H), 3.16 (dd, J=7.5, 13.0 Hz, 1H), 3.25 (dd, J=8.0, 13.0 Hz, 1H), 3.25-3.30 (m, 2H), 3.73 (dd, J=5.5, 14.0 Hz, 1H), 4.55-4.61 (m, 2H), 5.12 (dd, J=8.0, 17.0 Hz, 1H), 5.20 (t, J=7.5 Hz, 1H), 7.39-7.88 (m, 3H), 8.20-8.24 (m, 1H). $^{13}$C-NMR (125 MHz, $CD_3OD$): δ 16.2, 16.3, 17.9, 26.0, 27.4, 27.8, 28.1, 28.7, 30.4, 30.5, 30.9, 33.4, 36.6, 37.9, 40.8, 40.9, 53.3, 56.9, 57.7, 121.5, 124.8, 125.1, 125.5, 126.5, 126.6, 127.3, 128.6, 128.7, 128.8, 129.3, 129.9, 132.1, 133.5, 134.7, 135.5, 136.3, 140.6, 157.5, 173.7, 174.2; ES-MS: mass calcd for Chemical Formula: $C_{33}H_{48}N_2O_5S$ 584.8. Found (M+Na) m/z 607.4.

Example 25

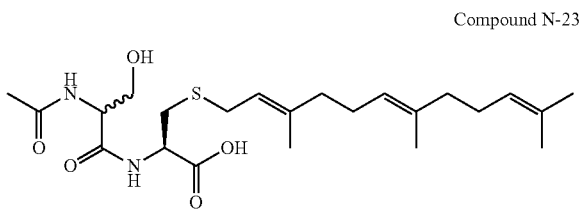 [SMILES: CC(=O)NC(CO)C(=O)N[C@@H](CSC/C=C(\C)CC/C=C(\C)CCC=C(C)C)C(=O)O]

Compound N-23

Synthesis of a mixture of ((R)-2-((S)-2-acetamido-3-hydroxypropanamido)-3-((2E,6E)-3,7,11-trimethyldodeca-2,6,10-trienylthio)propanoic acid) and ((R)-2-((R)-2-acetamido-3-hydroxypropanamido)-3-((2E,6E)-3,7,11-trimethyldodeca-2,6,10-trienylthio)propanoic acid)) (Compound N-23): In a 100 mL round bottom flask, N-acetyl-L-serine (1.0 mmol), coupling reagent (520 mg of PBOP or 380 mg of HATU, 1 mmol) and N,N-diisopropylethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (160 mg, 35%) to yield a 1:1 ratio mixture of R-R and S-R isomers of Compound N-23, similar to Compound C in Examples 5 and 5a. $^1$H-NMR (500 MHz, $CD_3OD$): δ 1.50 (s, 6H), 1.57 (s, 3H), 1.58 (s, 3H), 1.85-2.03 (m, 11H), 2.72-2.79 (m, 1H), 2.87-2.96 (m, 1H), 3.07-3.14 (m, 2H), 3.65-3.69 (m, 1H), 3.70-3.77 (m, 1H), 4.33 (dd, J=5.0, 10.0 Hz, 1H), 4.40 (dd, J=5.0, 10.0 Hz, 1H), 4.98-5.02 (m, 2H), 5.14 (dd, J=5.0, 15.0 Hz, 1H). $^{13}$C-NMR (125 MHz, $CD_3OD$): δ 16.12, 16.28, 17.79, 22.61, 22.71, 25.95, 27.52, 27.80, 30.74, 30.78, 35.19, 35.25, 40.79, 40.90, 55.57, 55.94, 56.87, 57.17, 63.18, 63.37, 121.78, 121.80, 125.24, 125.48, 132.09, 136.15, 140.03, 140.11, 171.84, 171.91, 173.35, 173.54, 177.14, 177.15; ES-MS: mass calcd for Chemical Formula: $C_{23}H_{38}N_2O_5S$ 454.62. Found (M+) m/z 455.3, (M+Na) m/z 477.3.

Example 26

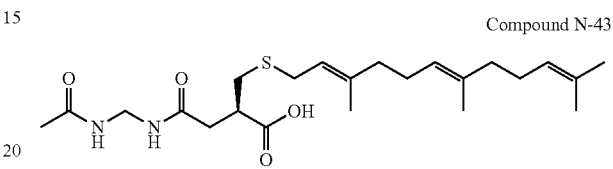

Compound N-43

Synthesis of ((R)-2-(3-acetamidopropanamido)-3-((2E,6E)-3,7,11-trimethyldodeca-2,6,10-trienylthio)propanoic acid)(Compound N-43): In a 100 mL round bottom flask, N-acetyl-DL-beta-alanine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and was stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (250 mg, 57%) to yield Compound N-43. $^1$H-NMR (500 MHz, $CD_3OD$): δ 1.50 (s, 6H), 1.57 (s, 3H), 1.60 (s, 3H), 1.83 (s, 3H), 1.86-1.89 (m, 2H), 1.95-2.05 (m, 6H), 2.38 (t, J=6.5 Hz, 2H), 2.63 (dd, J=9.0, 14.0 Hz, 1H), 2.92 (dd, J=4.0, 14.0 Hz, 1H), 3.06 (dd, J=7.0, 13.0 Hz, 1H), 3.21 (m, 1H), 3.36 (m, 2H), 4.50 (dd, J=4.0, 9.0 Hz, 1H), 4.98-5.03 (m, 2H), 5.13 (t, J=7.5 Hz, 1H), 5.61 (d, J=10.0 Hz, 1H), 6.17 (d, J=17.0 Hz, 1H), 6.28 (dd, J=10.0, 17.0 Hz, 1H). $^{13}$C-NMR (125 MHz, $CD_3OD$): δ 16.16, 16.25, 17.81, 22.66, 25.96, 27.40, 27.79, 30.11, 33.37, 36.41, 37.07, 40.80, 40.89, 53.31, 121.56, 125.13, 125.46, 132.12, 136.28, 140.58, 173.41, 173.83, 174.01; ES-MS: mass calcd for Chemical Formula: $C_{23}H_{38}N_2O_4S$ 438.62. Found (M+) m/z 439.3, (M+Na) m/z 461.2.

Example 27

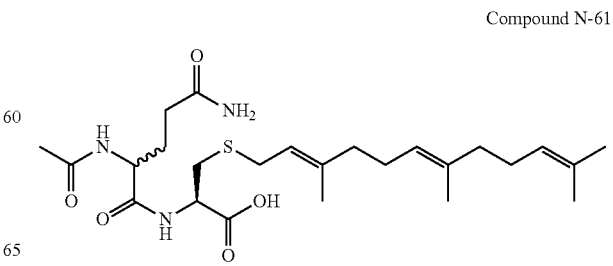

Compound N-61

Synthesis of a mixture of ((R)-2-((R)-2-acetamido-5-amino-5-oxopentanamido)-3-((2E,6E)-3,7,11-trimethyldodeca-2,6,10-trienylthio)propanoic acid) and ((R)-2-((S)-2-acetamido-5-amino-5-oxopentanamido)-3-((2E,6E)-3,7,11-trimethyldodeca-2,6,10-trienylthio)propanoic acid) (Compound N-61): In a 100 mL round bottom flask, N-acetyl-L-glutamine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture. The reaction mixture was stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (155 mg, 31%) to yield a 1:1 ratio mixture of R-R and S-R isomers of Compound N-61, similar to Compound C racemate in Examples 5 and 5a. $^1$H-NMR (500 MHz, $CD_3OD$): δ 1.62 (s, 6H), 1.69 (s, 3H), 1.70 (s, 3H), 1.98-2.12 (m, 13H), 2.35 (t, J=5.0 Hz, 2H), 2.86 (m, 1H), 3.03 (m, 1H), 3.20-3.24 (m, 2H), 4.43-4.46 (m, 2H), 5.12-5.13 (m, 2H), 5.26 (m, 1H). $^{13}$C-NMR (125 MHz, $CD_3OD$): δ 16.12, 16.29, 16.30, 22.54, 22.65, 25.95, 27.54, 27.80, 29.22, 29.25, 30.70, 30.78, 32.71, 32.77, 35.35, 35.46, 40.80, 40.90, 54.37, 54.44, 55.38, 55.70, 121.77, 121.82, 125.25, 125.48, 132.09, 136.15, 140.01, 140.09, 172.78, 172.88, 173.21, 173.34, 177.10, 177.12, 177.99, 178.03; ES-MS: mass calcd for Chemical Formula: $C_{25}H_{41}N_3O_5S$ 495.68. Found (M+) m/z 496.4, (M+Na) m/z 518.4.

Example 28

Compound N-62

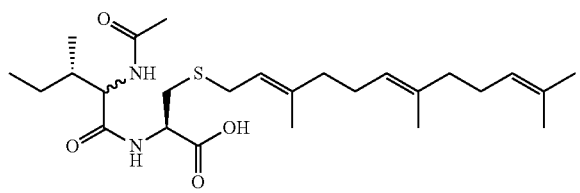

Synthesis of a mixture of ((R)-2-((2S,3S)-2-acetamido-3-methylpentanamido)-3-((2E,6E)-3,7,11-trimethyldodeca-2,6,10-trienylthio)propanoic acid and (R)-2-((2R,3S)-2-acetamido-3-methylpentanamido)-3-((2E,6E)-3,7,11-trimethyldodeca-2,6,10-trienylthio)propanoic acid) (Compound N-62): In a 100 mL round bottom flask, N-acetyl-L-isoleucine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (220 mg, 46%) to yield a mixture of Compound N-62a (the S—S-R enantiomer) and Compound N-62b (the S-R-R enantiomer), wherein the ratio of N-62a to N-62b is 1:1. $^1$H-NMR (500 MHz, $CD_3OD$): δ 0.80-0.86 (m, 6H), 1.06-1.33 (m, 3H), 1.50 (s, 6H), 1.57 (s, 3H), 1.60 (s, 3H), 1.79-2.01 (m, 11H), 2.71-2.77 (m, 1H), 2.87-2.94 (m, 1H), 3.09-3.11 (m, 2H), 4.17-4.43 (m, 2H), 4.99-5.00 (m, 2H), 5.26 (t, J=10.0 Hz, 1H). $^{13}$C-NMR (125 MHz, $CD_3OD$): δ 11.68, 12.14, 15.00, 16.13, 16.28, 17.80, 22.52, 22.58, 25.86, 25.96, 27.48, 27.52, 27.53, 27.80, 30.80, 30.88, 35.51, 35.56, 38.02, 38.31, 40.80, 40.90, 55.37, 55.62, 57.97, 59.80, 121.83, 121.88, 125.23, 125.48, 132.08, 136.14, 139.92, 140.02, 172.89, 173.01, 173.39, 173.46, 176.84, 177.09; ES-MS: mass calcd for Chemical Formula: $C_{26}H_{44}N_2O_4S$ 480.70. Found (M+) m/z 481.4, (M+Na) m/z 503.4.

N-62a

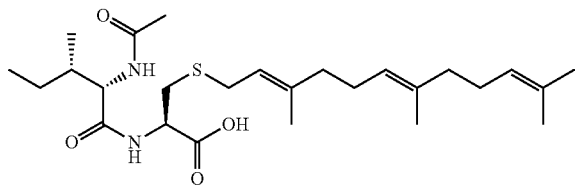

[(S)—(S)—(R) isomer]

N-62b

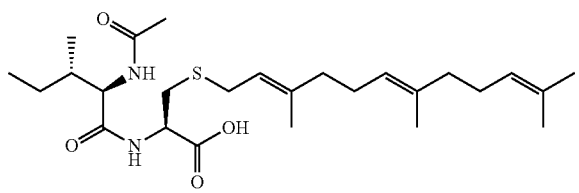

[(S)—(R)—(R) isomer]

Example 29

Compound N-63

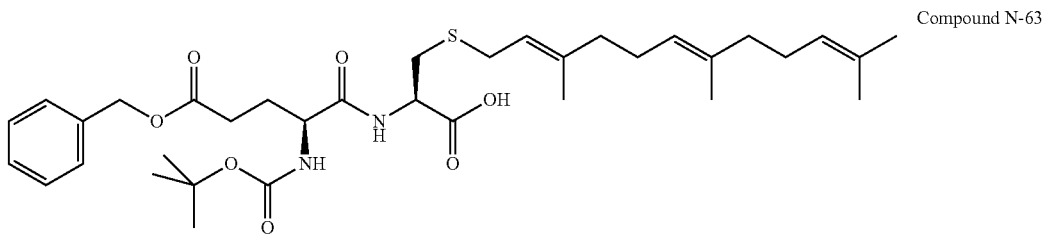 [SMILES: CC(C)=CCC/C(C)=C/CC/C(C)=C/CSC[C@H](NC(=O)[C@H](CCC(=O)OCc1ccccc1)NC(=O)OC(C)(C)C)C(=O)O]

Synthesis of ((R)-2-((S)-5-(benzyloxy)-2-(tert-butoxycarbonylamino)-5-oxopentanamido)-3-((2E,6E)-3,7,11-trimethyldodeca-2,6,10-trienylthio)propanoic acid)(Compound N-63): In a 100 mL round bottom flask, N-Boc-L-glutamic acid-benzyl-ester (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (182 mg, 28%) to yield Compound N-63. $^1$H-NMR (500 MHz, $CDCl_3$): δ 1.44 (s, 9H), 1.62 (s, 6H), 1.67 (s, 3H), 1.70 (s, 3H), 1.97-2.07 (m, 10H), 2.52-2.55 (m, 2H), 2.90 (dd, J=5.0, 15.0 Hz, 1H), 3.01 (dd, J=5.0, 15.0 Hz, 1H), 3.18-3.25 (m, 2H), 4.32 (dd, J=10.0, 15.0 Hz, 1H), 4.74 (m, 1H), 5.11-5.12 (m, 2H), 5.14 (s, 2H), 5.23 (t, J=10.0 Hz, 1H), 5.50 (d, J=10.0 Hz, 1H), 7.22 (d, J=10.0 Hz, 1H), 7.34-7.38 (m, 5H). $^{13}$C-NMR (125 MHz, $CDCl_3$): δ 15.99, 16.18, 17.74, 25.72, 26.50, 26.73, 27.85, 28.32, 29.90, 32.84, 39.73, 52.02, 53.61, 66.70, 80.44, 119.49, 123.68, 124.31, 128.34, 128.61, 131.38, 135.25, 135.62, 140.01, 155.76, 171.70, 173.27, 173.51, 207.33; ES-MS: mass calcd for Chemical Formula: $C_{35}H_{52}N_2O_7S$ 644.86. Found (M+) m/z 645.4, (M+Na) m/z 667.5.

Example 30

Compound N-64

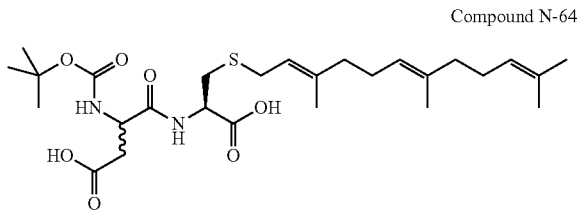 [SMILES: CC(C)=CCC/C(C)=C/CC/C(C)=C/CSC[C@H](NC(=O)C(CC(=O)O)NC(=O)OC(C)(C)C)C(=O)O]

Synthesis of a mixture of ((R)-3-(tert-butoxycarbonylamino)-4-((R)-1-carboxy-2-((2E,6E)-3,7,11-trimethyldodeca-2,6,10-trienylthio)ethylamino)-4-oxobutanoic acid and (S)-3-(tert-butoxycarbonylamino)-4-((R)-1-carboxy-2-((2E,6E)-3,7,11-trimethyldodeca-2,6,10-trienylthio)ethylamino)-4-oxobutanoic acid)(Compound N-64): In a 100 mL round bottom flask, N-Boc-L-glutamic acid (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (136 mg, 17%) to yield a 1:1 ratio mixture of R-R and S-R isomers of Compound N-64, similar to Compound C racemate in Examples 5 and 5a. $^1$H-NMR (500 MHz, $CDCl_3$): δ 1.36 (s, 9H), 1.53 (s, 6H), 1.59 (s, 3H), 1.61 (s, 3H), 1.88-2.03 (m, 10H), 2.77-2.86 (m, 1H), 2.94-2.97 (m, 1H), 3.11-3.17 (m, 2H), 4.45 (m, 1H), 4.63 (m, 1H), 5.01-5.03 (m, 2H), 5.12-5.15 (m, 1H), 5.89-5.90 (m, 1H), 7.33 (m, 1H), 8.70 (broad, 2H). $^{13}$C-NMR (125 MHz, $CDCl_3$): δ 15.00, 15.13, 16.68, 24.71, 25.43, 25.67, 27.29, 28.70, 28.79, 28.85, 31.43, 36.68, 38.62, 38.67, 49.38, 51.36, 79.65, 79.85, 118.23, 118.33, 122.69, 123.27, 130.33, 134.31, 134.34, 134.37, 139.32, 154.89, 170.77, 172.68, 172.79; ES-MS: mass calcd for Chemical Formula: $C_2H_{44}N_2O_7S$ 540.71. Found (M+Na) m/z 563.4.

Example 31

Compound N-65

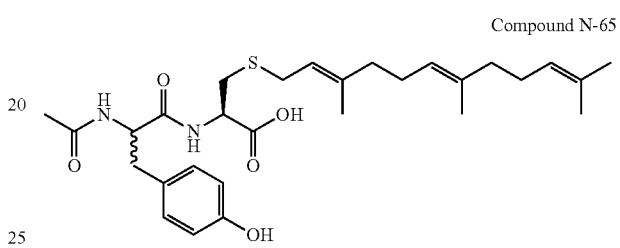

Synthesis of a mixture of ((R)-2-((S)-2-acetamido-3-(4-hydroxyphenyl)propanamido)-3-((2E,6E)-3,7,11-trimethyldodeca-2,6,10-trienylthio)propanoic acid and (R)-2-((R)-2-acetamido-3-(4-hydroxyphenyl)propanamido)-3-((2E,6E)-3,7,11-trimethyldodeca-2,6,10-trienylthio)propanoic acid)(Compound N-65): In a 100 mL round bottom flask, N-acetyl-DL-tyrosine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture. The reaction mixture was stirred at room temperature overnight. $CH_2Cl_2$ was removed by rotary evaporation. The resulting residue was dissolved in ethyl acetate (50 mL). The organic solution was washed with $NH_4Cl$ saturated solution (50 mL), dried over $Na_2SO_4$, and concentrated to afford a crude mixture. The crude mixture was purified by preparative HPLC (230 mg, 43%) to yield a 1:1 ratio mixture of R-R and S-R isomers of Compound N-65, similar to Compound C racemate in Examples 5 and 5a. $^1$H-NMR (500 MHz, $CD_3OD$): δ 1.50 (s, 6H), 1.56 (s, 3H), 1.59 (s, 3H), 1.79-1.80 (m, 3H), 1.87-88 (m, 2H), 1.96-2.03 (m, 8H), 2.57-2.80 (m, 1H), 2.87 (m, 1H), 2.96-3.13 (m, 2H), 4.43-4.48 (m, 1H), 4.52-4.55 (m, 1H), 5.00-5.01 (m, 2H), 5.11 (m, 1H), 6.59 (d, J=8.0 Hz, 2H), 6.97 (d, J=8.0 Hz, 2H). $^{13}$C-NMR (125 MHz, $CD_3OD$): δ 16.26, 16.29, 17.82, 22.43, 25.97, 27.42, 27.79, 30.18, 30.29, 33.38, 33.43, 38.21, 38.46, 40.80, 40.89, 53.21, 53.49, 56.12, 56.17, 116.13, 116.16, 121.55, 121.59, 125.15, 125.47, 129.06, 129.12, 131.33, 131.36, 132.11, 136.26, 140.54, 157.24, 157.30, 173.08, 173.65, 173.70, 173.82; ES-MS: mass calcd for Chemical Formula: $C_{29}H_{42}N_2O_5S$ 530.72. Found (M+) m/z 531.3, (M+Na) m/z 553.3.

Example 32

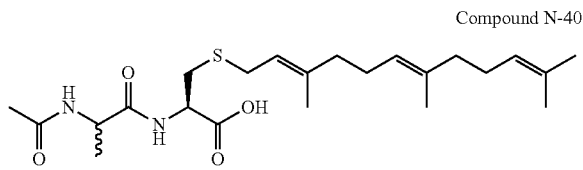 [SMILES: CC(=O)NC(C)C(=O)N[C@@H](CSC/C=C(\C)CC/C=C(\C)CCC=C(C)C)C(=O)O]

Compound N-40

Synthesis of a mixture of ((R)-2-((S)-2-acetamidopropanamido)-3-((2E,6E)-3,7,11-trimethyldodeca-2,6,10-trienylthio)propanoic acid and (R)-2-((R)-2-acetamidopropanamido)-3-((2E,6E)-3,7,11-trimethyldodeca-2,6,10-trienylthio)propanoic acid)(Compound N-40): In a 100 mL round bottom flask, N-acetyl-DL-alanine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-Farnesyl-L-cysteine (325 mg, 1 mmol) was added to the reaction mixture. The reaction mixture was stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (220 mg, 50%) to yield a 1:1 ratio mixture of R-R and S-R isomers of Compound N-40, similar to Compound C racemate in Examples 5 and 5a. $^1$H-NMR (500 MHz, $CD_3OD$): δ 1.27 (t, J=6.5 Hz, 3H), 1.50 (s, 6H), 1.57 (s, 3H), 1.59 (s, 3H), 1.86-2.03 (m, 11H), 2.62-2.69 (m, 1H), 2.86-2.91 (m, 1H), 3.04-3.05 (m, 1H), 3.15 (m, 1H), 4.32-4.34 (m, 1H), 4.46-4.47 (m, 1H), 4.99-5.01 (m, 2H), 5.11 (m, 1H). $^{13}$C-NMR (125 MHz, $CD_3OD$): δ 16.14, 16.23, 17.79, 18.10, 18.37, 22.42, 25.94, 27.41, 27.78, 30.13, 30.28, 33.35, 33.57, 40.79, 40.88, 50.30, 53.08, 53.43, 121.57, 121.60, 125.15, 125.45, 132.11, 140.54, 173.75; ES-MS: mass calcd for Chemical Formula: $C_{23}H_{38}N_2O_4S$ 438.62. Found (M+) m/z 439.2.

Example 33

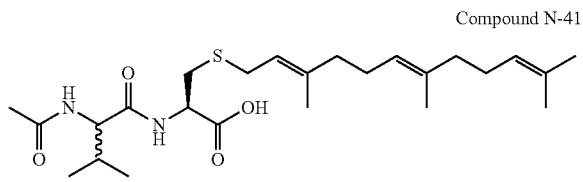 [SMILES: CC(=O)NC(C(=O)N[C@@H](CSC/C=C(\C)CC/C=C(\C)CCC=C(C)C)C(=O)O)C(C)C]

Compound N-41

Synthesis of a mixture of ((R)-2-((S)-2-acetamido-3-methylbutanamido)-3-((2E,6E)-3,7,11-trimethyldodeca-2,6,10-trienylthio)propanoic acid and (R)-2-((R)-2-acetamido-3-methylbutanamido)-3-((2E,6E)-3,7,11-trimethyldodeca-2,6,10-trienylthio)propanoic acid)(Compound N-41): In a 100 mL round bottom flask, N-acetyl-DL-valine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-Farnesyl-L-cysteine (325 mg, 1 mmol) was added to the reaction mixture. The reaction mixture was stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (250 mg, 54%) to yield a 1:1 ratio mixture of R-R and S-R isomers of Compound N-41, similar to Compound C racemate in Examples 5 and 5a. $^1$H-NMR (500 MHz, $CD_3OD$): δ 1.27 (m, 6H), 1.50 (s, 6H), 1.57 (s, 3H), 1.59 (s, 3H), 1.87-2.03 (m, 12H), 2.61-2.67 (m, 1H), 2.86-2.89 (m, 1H), 3.05-3.06 (m, 1H), 3.13-3.15 (m, 1H), 4.21 (dd, J=6.5, 16.0 Hz, 1H), 4.47-4.48 (m, 1H), 4.99-5.03 (m, 2H), 5.13 (t, J=8.0 Hz, 1H). $^{13}$C-NMR (125 MHz, $CD_3OD$): δ 16.16, 17.82, 18.45, 18.62, 19.75, 19.93, 22.47, 25.97, 27.42, 27.79, 30.09, 30.24, 32.09, 33.28, 33.42, 40.80, 40.89, 53.20, 53.43, 60.00, 60.03, 121.56, 121.60, 125.13, 125.15, 125.46, 132.11, 136.26, 140.52, 173.25, 173.32, 173.67, 173.71, 173.74; ES-MS: mass calcd for Chemical Formula: $C_{25}H_{42}N_2O_4S$ 466.68. Found (M+) m/z 467.3.

Example 34

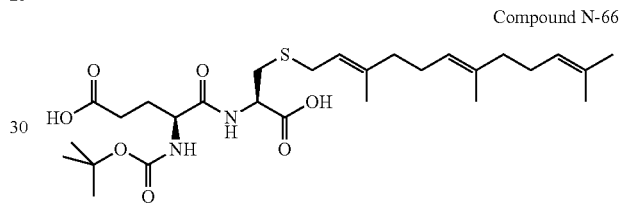

Compound N-66

Synthesis of ((S)-4-(tert-butoxycarbonylamino)-5-((R)-1-carboxy-2-((2E,6E)-3,7,11-trimethyldodeca-2,6,10-trienylthio)ethylamino)-5-oxopentanoic acid)(Compound N-66): In a 100 mL round bottom flask, to a solution of (S)-5-(benzyloxy)-2-(tert-butoxycarbonylamino)-5-oxopentanoic acid (674 mg, 2 mmol) and benzotriazol-1-yl-oxytripyrrolidinophosphonium hexafluorophosphate (PyBop, 1040 mg, 2 mmol) and in THF (5 mL) was added N,N-diisopropyl-ethyl-amine (1.04 mL, 6 mmol) dropwise. After 10 min, S-trans, trans-farnesyl-L-cysteine (650 mg, 2 mmol) was added slowly. The solution was stirred at room temperature for 4 h. The reaction was quenched by 1 N HCl and pH of the solution was adjusted to 3.0. The mixture was extracted by ethyl acetate (15 mL×3). The organic layer was dried over $Na_2SO_4$ and concentrated in vacuo. Half of the residue was used directly for next step to afford crude Compound N-66. To this crude Compound N-66 obtained above dissolved in MeOH (1 mL), was added 5 N NaOH (2 mL, 10 mmol). The reaction was left at room temperature for 10 min. The reaction was quenched by 1 N HCl and pH of the solution was adjusted to 2.0. The mixture was extracted by ethyl acetate (15 mL×3). The organic layer was dried over $Na_2SO_4$ and concentrated in vacuo. The residue was then further purified by preparative HPLC (164 mg, 30%) to yield Compound N-66. $^1$H-NMR (500 MHz, $CDCl_3$): δ 1.45 (s, 9H), 1.62 (s, 6H), 1.68 (s, 3H), 1.70 (s, 3H), 1.95-2.09 (m, 10H), 2.46-2.54 (m, 2H), 2.91 (dd, J=5.0, 15.0 Hz, 1H), 3.04 (dd, J=5.0, 15.0 Hz, 1H), 3.17-3.25 (m, 2H), 4.56 (dd, J=10.0, 15.0 Hz, 1H), 4.77-4.81 (m, 1H), 5.12 (m, 2H), 5.23 (t, J=10.0 Hz, 1H), 5.64 (d, J=10.0 Hz, 1H), 7.66 (d, J=10.0 Hz, 1H), 8.40 (broad, 2H). $^{13}$C-NMR (125 MHz, $CDCl_3$): δ 16.06, 16.15, 17.75, 25.77, 26.52, 26.74, 28.01, 28.33, 29.73, 29.89, 32.60, 39.70, 39.74, 52.22, 52.95, 80.91, 119.57, 123.83, 124.35, 131.38, 135.34, 140.04, 156.06, 172.18, 174.00, 177.16; ES-MS: mass calcd for Chemical Formula: $C_{28}H_{46}N_2O_7S$ 554.74. Found (M+Na) m/z 577.4.

Example 35

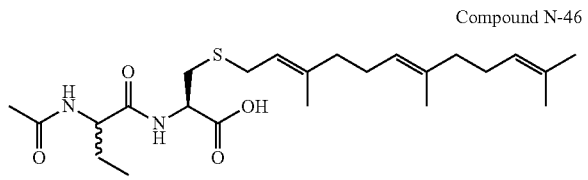 [SMILES: CCC(NC(C)=O)C(=O)N[C@@H](CSC/C=C(\C)CC/C=C(\C)CCC=C(C)C)C(=O)O]

Compound N-46

Synthesis of a mixture of ((R)-2-((S)-2-acetamidobutanamido)-3-((2E,6E)-3,7,11-trimethyldodeca-2,6,10-trienylthio)propanoic acid and (R)-2-((R)-2-acetamidobutanamido)-3-((2E,6E)-3,7,11-trimethyldodeca-2,6,10-trienylthio)propanoic acid)(Compound N-46): In a 100 mL round bottom flask, to a solution of N-acetyl-DL-2-amino-n-butyric acid (174 mg, 1.2 mmol) and 4-(4,6-dimethoxy-1,3,5-triazin-2yl)-4-methylmorpholinium chloride (DMTMM, 332 mg, 1.2 mmol) in $CH_2Cl_2$ (5 mL) was added N,N-diisopropyl-ethyl-amine (0.52 mL, 3 mmol) dropwise. After 10 min, S-trans, trans-farnesyl-L-cysteine (325 mg, 1 mmol) was added slowly. The solution was stirred at room temperature overnight. The mixture was diluted with ethyl acetate (60 mL) and washed by 0.5 N HCl (15 mL×1), $H_2O$ (15 mL×2) and brine (15 mL×2). The organic layer was dried over $Na_2SO_4$ and concentrated in vacuo. The residue was purified by preparative HPLC (290 mg, 64%) to yield a 1:1 ratio mixture of R-R and S-R isomers of Compound N-46, similar to Compound C racemate in Examples 5 and 5a. $^1$H-NMR (500 MHz, $CD_3OD$): δ 0.86 (m, 3H), 1.50 (s, 6H), 1.57 (s, 3H), 1.60 (s, 3H), 1.72-2.03 (m, 13H), 2.61-2.68 (m, 1H), 2.87-2.89 (m, 1H), 3.04 (m, 1H), 3.12-3.21 (m, 1H), 4.21-4.25 (m, 1H), 4.45-4.48 (m, 1H), 4.99-5.01 (m, 2H), 5.13 (t, J=7.5 Hz, 1H). $^{13}$C-NMR (125 MHz, $CD_3OD$): δ 10.62, 10.70, 16.16, 16.25, 17.81, 22.46, 25.96, 26.56, 26.68, 27.42, 27.79, 30.11, 30.27, 33.31, 33.52, 40.80, 40.89, 53.11, 53.42, 56.02, 56.07, 121.56, 121.60, 125.13, 125.46, 132.11, 136.26, 136.27, 140.54, 173.28, 173.32, 173.69, 174.26, 174.31; ES-MS: mass calcd for Chemical Formula: $C_{24}H_{40}N_2O_4S$ 452.65. Found (M+) m/z 453.3, (M+Na) m/z 475.2.

The following general experimental procedures for loading Fmoc-cysteine-(S-farnesyl) on resin were used for Examples 36-39 as described below. 2-Chlorotrityl chloride resin (loading efficiency=1.01 mmol/g, 1.0 g, 1.0 mmol) was placed in a 50 mL peptide synthesis vessel (Polypropylene syringe from Torviq, Niles, Mich.) under Nitrogen. To this was added anhydrous $CH_2Cl_2$ (20 mL). The resin was shacked in 5 min and solvent was removed. In a separate vial, Fmoc-Cys(StBu)-OH (1.1 g, 2.6 mmol) and 2,4,6-collidine (290 mg, 2.8 mmol) were dissolved in anhydrous $CH_2Cl_2$ (20 mL). This solution was transferred to the resin. The mixture was gently agitated for 3 h. Then, 1% solution of 2,4,6-collidine in MeOH (20 mL) was then added, and the mixture was agitated for an additional 10 min. The mixture was drained, and the resin was washed MeOH, $CH_2Cl_2$, and DMF. Dithiothreitol (1.1 g, 6.7 mmol) was dissolved in a diisopropylethylamine/DMF solution (4 mL/20 mL) and added to the resin, and the reaction vessel was gently agitated overnight. The solvent was drained, and the resin washed with $CH_2Cl_2$, and DMF. 2,4,6-Collidine (300 mg, 2.5 mmol) was added to a solution of farnesyl bromide (900 mg, 3.2 mmol) in $CH_2Cl_2$ (20 mL). This reagent solution was added to the resin, and the reaction vessel was gently agitated for 10 h at room temperature. The solvent was then drained, and the resin was washed with DMF and $CH_2Cl_2$.

Example 36

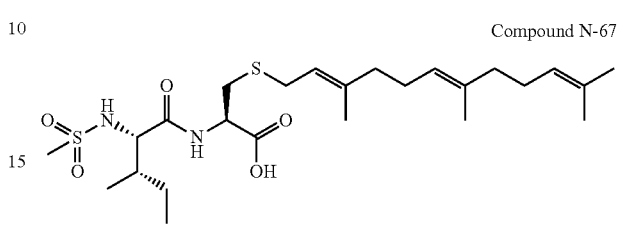

Compound N-67

Synthesis of ((R)-2-((2S,3S)-3-methyl-2-(methylsulfonamido)pentanamido)-3-((2E,6E)-3,7,11-trimethyldodeca-2,6,10-trienylthio)propanoic acid)(Compound N-67): In a 100 mL round bottom flask, 20% solution of piperidine in DMF (10 mL) was added to the farnesylcysteine on the resin (0.5 mmol) and the vessel was agitated for 15 min. The resin was washed with DMF and $CH_2Cl_2$. Fmoc-L-isoleucine (354 mg, 1 mmol), PBOP (502 mg, 1 mmol) and 2,4,6-collidine (242 mg, 2 mmol) were dissolved in DMF (5 mL). The reaction mixture was stirred in 5 min. This solution was added to the resin and agitated for 3 h. The solvent was then drained, and the resin was washed with DMF and $CH_2Cl_2$. 20% solution of piperidine in DMF (10 mL) was added to the farnesylcysteine on the resin (0.5 mmol) and the vessel was agitated for 15 min. The resin was washed with DMF and $CH_2Cl_2$. Methyl sulfonyl chloride (1 mmol) and 2,4,6-collidine (242 mg, 2 mmol) were dissolved in DMF (5 mL). This solution was added to the resin and agitated for 3 h. The solvent was then drained, and the resin was washed with DMF and $CH_2Cl_2$. The resin was treated twice with a 0.5% solution of trifluoroacetic acid in $CH_2Cl_2$ for 5 min. The solution was collected into a round-bottom flask, and the resin was washed twice with anhydrous $CH_2Cl_2$. The solvent was removed by rotary evaporation. The product was purified by preparative HPLC (45 mg, 25%) to yield Compound N-67. $^1$H-NMR (500 MHz, $CD_3OD$): δ 0.94 (t, J=5.0 Hz, 3H), 1.02 (d, J=5.0 Hz, 3H), 1.22 (m, 2H), 1.62 (s, 3H), 1.66 (s, 3H), 1.67 (s, 3H), 1.70 (s, 3H), 1.77-1.82 (m, 1H), 1.99 (t, J=7 Hz, 2H), 2.06-2.17 (m, 6H), 2.74 (dd, J=8.0, 14.0 Hz, 1H), 2.97 (S, 3H), 3.08 (dd, J=5.0, 12.5 Hz, 1H), 3.15 (dd, J=7.0, 13.0 Hz, 1H), 3.30 (dd, J=5.0, 12.0 Hz, 1H), 3.81 (d, J=5.0 Hz, 1H), 4.62 (dd, J=5.0, 10.0 Hz, 1H), 5.10-5.16 (m, 2H), 5.24 (t, J=7.0 Hz, 1H). $^{13}$C-NMR (125 MHz, $CD_3OD$): δ 11.3, 16.0, 16.3, 25.7, 26.0, 27.4, 27.8, 39.2, 40.8, 40.9, 41.3, 52.2, 62.8, 121.5, 125.1, 125.5, 132.1, 136.3, 140.6, 173.6, 174.0; ES-MS: mass calcd for Chemical Formula: $C_{25}H_{44}N_2O_5S_2$ 516.8. Found (M+) m/z 517.

Example 37

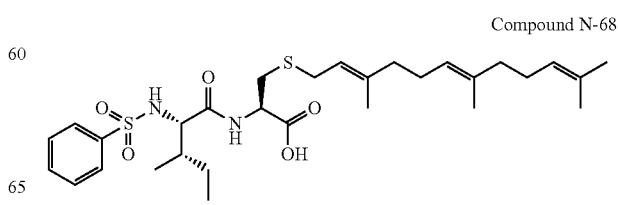

Compound N-68

Synthesis of ((R)-2-((2S,3S)-3-methyl-2-(phenylsulfonamido)pentanamido)-3-((2E,6E)-3,7,11-trimethyldodeca-2,6,10-trienylthio)propanoic acid)(Compound N-68): In a 100 mL round bottom flask, 20% solution of piperidine in DMF (10 mL) was added to the farnesylcysteine on the resin (0.5 mmol) and the vessel was agitated for 15 min. The resin was washed with DMF and $CH_2Cl_2$. Fmoc-L-isoleucine (354 mg, 1 mmol), PBOP (502 mg, 1 mmol) and 2,4,6-collidine (242 mg, 2 mmol) were dissolved in DMF (5 mL). The reaction mixture was stirred in 5 min. This solution was added to the resin and agitated for 3 h. The solvent was then drained, and the resin was washed with DMF and $CH_2Cl_2$. 20% solution of piperidine in DMF (10 mL) was added to the farnesylcysteine on the resin (0.5 mmol) and the vessel was agitated for 15 min. The resin was washed with DMF and $CH_2Cl_2$. Phenyl sulfonyl chloride (1 mmol) and 2,4,6-collidine (242 mg, 2 mmol) were dissolved in DMF (5 mL). This solution was added to the resin and agitated for 3 h. The solvent was then drained, and the resin was washed with DMF and $CH_2Cl_2$. The resin was treated twice with a 0.5% solution of trifluoroacetic acid in $CH_2Cl_2$ for 5 min. The solution was collected into a round-bottom flask, and the resin was washed twice with anhydrous $CH_2Cl_2$. The solvent was removed by rotary evaporation. The product was purified by preparative HPLC (40 mg, 30%) to yield Compound N-68. $^1$H-NMR (500 MHz, $CD_3OD$): δ 0.74 (t, J=7.5 Hz, 3H), 0.80 (d, J=7.0 Hz, 3H), 1.00-1.06 (m, 2H), 1.43-1.48 (m, 1H), 1.50 (s, 3H), 1.51 (s, 3H), 1.57 (s, 3H), 1.58 (s, 3H), 1.87 (t, J=7 Hz, 2H), 1.97-2.07 (m, 6H), 2.45 (dd, J=7.5, 13.5 Hz, 1H), 2.62 (dd, J=7.5, 14.0 Hz, 1H), 2.99 (dd, J=8.0, 13.0 Hz, 1H), 3.06 (dd, J=8.0, 13.0 Hz, 1H), 3.60 (d, J=7.0 Hz, 1H), 4.12 (dd, J=5.5, 7.5 Hz, 1H), 4.99-5.02 (m, 2H), 5.10 (t, J=7.0 Hz, 1H), 7.40-7.50 (m, 3H), 7.73 (d, J=8.0 Hz, 2H). $^{13}$C-NMR (125 MHz, $CD_3OD$): δ 11.4, 15.8, 16.2, 16.3, 17.8, 25.5, 26.0, 27.4, 27.8, 30.4, 33.3, 39.4, 40.8, 40.9, 53.4, 62.4, 121.6, 125.2, 125.5, 128.3, 130.1, 132.1, 133.6, 136.3, 140.5, 142.2, 173.0, 173.5; ES-MS: mass calcd for Chemical Formula: $C_{30}H_{46}N_2O_5S_2$ 578.8. Found (M+) m/z 579.3.

Example 38

Synthesis of ((R)-2-((2S,3S)-2-(cyclopropanesulfonamido)-3-methylpentanamido)-3-((2E,6E)-3,7,11-trimethyldodeca-2,6,10-trienylthio)propanoic acid)(Compound N-69): In a 100 mL round bottom flask, 20% solution of piperidine in DMF (10 mL) was added to the farnesylcysteine on the resin (0.5 mmol) and the vessel was agitated for 15 min. The resin was washed with DMF and $CH_2Cl_2$. Fmoc-L-isoleucine (354 mg, 1 mmol), PBOP (502 mg, 1 mmol) and 2,4,6-collidine (242 mg, 2 mmol) were dissolved in DMF (5 mL). The reaction mixture was stirred in 5 min. This solution was added to the resin and agitated for 3 h. The solvent was then drained, and the resin was washed with DMF and $CH_2Cl_2$. 20% solution of piperidine in DMF (10 mL) was added to the farnesylcysteine on the resin (0.5 mmol) and the vessel was agitated for 15 min. The resin was washed with DMF and $CH_2Cl_2$. Cyclopropyl sulfonyl chloride (1 mmol) and 2,4,6-collidine (242 mg, 2 mmol) were dissolved in DMF (5 mL). This solution was added to the resin and agitated for 3 h. The solvent was then drained, and the resin was washed with DMF and $CH_2Cl_2$. The resin was treated twice with a 0.5% solution of trifluoroacetic acid in $CH_2Cl_2$ for 5 min. The solution was collected into a round-bottom flask, and the resin was washed twice with anhydrous $CH_2Cl_2$. The solvent was removed by rotary evaporation. The product was purified by preparative HPLC (40 mg, 26%) to yield Compound N-69. $^1$H-NMR (500 MHz, $CD_3OD$): δ 0.81 (t, J=7.5 Hz, 3H), 0.86 (d, J=6.5 Hz, 3H), 1.05-1.11 (m, 2H), 1.50 (bs, 6H), 1.42-1.52 (m, 4H), 1.57 (s, 3H), 1.59 (s, 3H), 1.72-1.78 (m, 1H), 1.89 (t, J=7 Hz, 2H), 1.94-2.04 (m, 6H), 2.64 (dd, J=8.0, 13.0 Hz, 1H), 2.87 (dd, J=5.0, 13.0 Hz, 1H), 3.04 (dd, J=7.5, 13.0 Hz, 1H), 3.14 (dd, J=8.5, 13.5 Hz, 1H), 4.20 (d, J=7.5 Hz, 1H), 4.47 (dd, J=5.0, 8.5 Hz, 1H), 4.98-5.03 (m, 2H), 5.11 (t, J=7.5 Hz, 1H), 7.40-7.50 (m, 3H), 7.73 (d, J=8.0 Hz, 2H). $^{13}$C-NMR (125 MHz, $CD_3OD$): δ 11.5, 15.9, 16.2, 16.3, 17.8, 22.5, 25.8, 26.0, 27.4, 27.8, 30.3, 33.3, 38.3, 40.8, 40.9, 53.5, 59.2, 121.6, 125.2, 125.5, 132.1, 136.3, 140.5, 173.2, 173.7, 173.8; ES-MS: mass calcd for Chemical Formula: $C_{27}H_{46}N_2O_5S_2$ 542.8. Found (M+) m/z 543.3.

Compound N-69

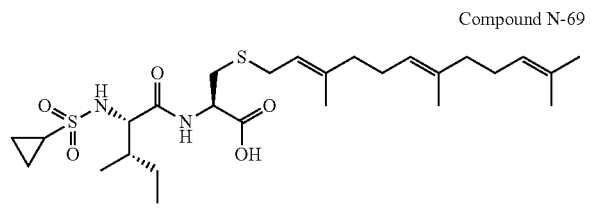 [SMILES: CC[C@H](C)[C@H](NS(=O)(=O)C1CC1)C(=O)N[C@@H](CSC/C=C(\C)CC/C=C(\C)CCC=C(C)C)C(=O)O]

Example 39

Compound N-70

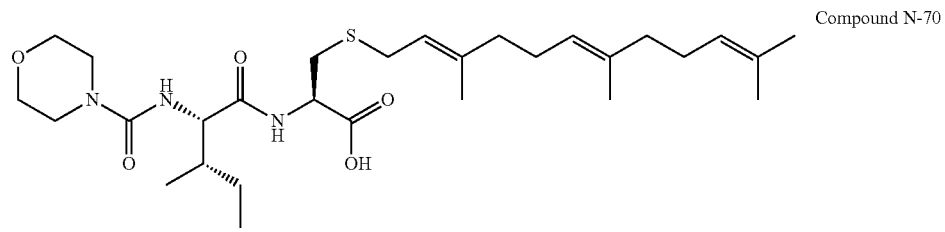 [SMILES: CC[C@H](C)[C@H](NC(=O)N1CCOCC1)C(=O)N[C@@H](CSC/C=C(\C)CC/C=C(\C)CCC=C(C)C)C(=O)O]

Synthesis of ((R)-2-((2S,3S)-3-methyl-2-(morpholine-4-carboxamido)pentanamido)-3-((2E,6E)-3,7,11-trimethyldodeca-2,6,10-trienylthio)propanoic acid)(Compound N-70): In a 100 mL round bottom flask, 20% solution of piperidine in DMF (10 mL) was added to the farnesylcysteine on the resin (0.5 mmol) and the vessel was agitated for 15 min. The resin was washed with DMF and CH$_2$Cl$_2$. Fmoc-L-isoleucine (354 mg, 1 mmol), PBOP (502 mg, 1 mmol) and 2,4,6-collidine (242 mg, 2 mmol) were dissolved in DMF (5 mL). The reaction mixture was stirred in 5 min. This solution was added to the resin and agitated for 3 h. The solvent was then drained, and the resin was washed with DMF and CH$_2$Cl$_2$. 20% solution of piperidine in DMF (10 mL) was added to the farnesylcysteine on the resin (0.5 mmol) and the vessel was agitated for 15 min. The resin was washed with DMF and CH$_2$Cl$_2$. 4-Morpholine carbonyl chloride (1 mmol) and 2,4,6-collidine (242 mg, 2 mmol) were dissolved in DMF (5 mL). This solution was added to the resin and agitated for 3 h. The solvent was then drained, and the resin was washed with DMF and CH$_2$Cl$_2$. The resin was treated twice with a 0.5% solution of trifluoroacetic acid in CH$_2$Cl$_2$ for 5 min. The solution was collected into a round-bottom flask, and the resin was washed twice with anhydrous CH$_2$Cl$_2$. The solvent was removed by rotary evaporation. The product was purified by preparative HPLC (40 mg, 30%) to yield Compound N-70. $^1$H-NMR (500 MHz, CD$_3$OD): δ 0.81 (t, J=7.5 Hz, 3H), 0.86 (d, J=6.5 Hz, 3H), 1.05-1.13 (m, 2H), 1.50 (bs, 6H), 1.57 (s, 3H), 1.59 (s, 3H), 1.72-1.78 (m, 1H), 1.87 (t, J=7 Hz, 2H), 1.94-2.04 (m, 6H), 2.66 (dd, J=7.5, 13.5 Hz, 1H), 2.88 (dd, J=5.0, 14.0 Hz, 1H), 3.05 (dd, J=7.0, 13.5 Hz, 1H), 3.14 (dd, J=8.0, 13.0 Hz, 1H), 3.30 (t, J=5.0 Hz, 2H), 3.55 (t, J=5.0 Hz, 2H), 4.07 (d, J=8.0 Hz, 1H), 4.47 (dd, J=5.0, 8.0 Hz, 1H), 4.98-5.03 (m, 2H), 5.12 (t, J=7.5 Hz, 1H). $^{13}$C-NMR (125 MHz, CD$_3$OD): δ 11.4, 16.0, 16.2, 16.3, 17.8, 26.0, 26.1, 27.4, 27.8, 30.4, 33.6, 38.2, 40.8, 40.9, 45.5, 53.5, 67.6, 121.6, 125.2, 125.5, 132.1, 136.3, 140.5, 159.6, 173.8, 174.9; ES-MS: mass calcd for Chemical Formula: C29H49N3O5S 551.8. Found (M+) m/z 552.4.

Example 40

Compound N-24

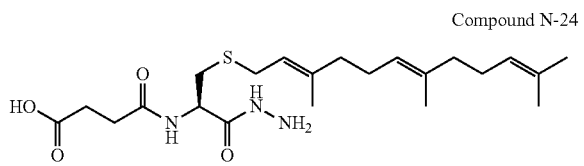 [SMILES: CC(C)=CCC/C(C)=C/CC/C(C)=C/CSC[C@H](NC(=O)CCC(=O)O)C(=O)NN]

Synthesis of (4-((R)-1-hydrazinyl-1-oxo-3-((2E,6E)-3,7,11-trimethyldodeca-2,6,10-trienylthio)propan-2-ylamino)-4-oxobutanoic acid)(Compound N-24): In a 100 mL round bottom flask, to a solution of S-trans, trans-farnesyl-L-cysteine methyl ester (430 mg, 1.27 mmol) in THF (10 mL) was added succinic anhydride (635 mg, 6.34 mmol). The solution was stirred at room temperature overnight. The solvent was removed in vacuo and the residue was dissolved with ethyl acetate (60 mL). The solution was washed by H$_2$O (15 mL×2) and brine (15 mL×1). The organic layer was dried over Na$_2$SO$_4$ and concentrated in vacuo. To the residue obtained above was added hydrazine in THF (1 M hydrazine in THF, 25 mL). The reaction was left at room temperature for 24 h and the solvent was removed in vacuo. The residue was then further purified by preparative HPLC (122 mg, 22%) to yield Compound N-24. $^1$H-NMR (500 MHz, DMSO-d$_6$): δ 1.55 (s, 6H), 1.62 (s, 3H), 1.64 (s, 3H), 1.91-2.06 (m, 8H), 2.36-2.41 (m, 4H), 2.71 (dd, J=5.0, 10.0 Hz, 1H), 3.13-3.17 (m, 3H), 4.39 (dd, J=5.0, 10.0 Hz, 1H), 5.07 (m, 2H), 5.16 (t, J=10.0 Hz, 1H), 8.18 (d, J=10.0 Hz, 1H), 9.27 (s, 1H). $^{13}$C-NMR (125 MHz, DMSO-d$_6$): δ 15.75, 15.79, 17.55, 25.50, 25.85, 26.14, 28.63, 29.17, 29.89, 32.68, 39.90, 39.99, 50.93, 120.15, 123.64, 124.10, 130.65, 134.54, 138.40, 169.30, 170.86, 173.96; ES-MS: mass calcd for Chemical Formula: C$_{22}$H$_{37}$N$_3$O$_4$S 439.61. Found (M+) m/z 440.3, (M+Na) m/z 462.2.

Example 41

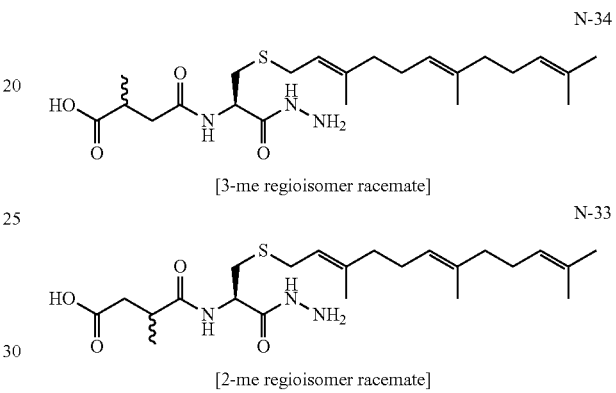

[3-me regioisomer racemate]

[2-me regioisomer racemate]

Synthesis of a mixture of (N-[1-Hydrazinocarbonyl-2-(3,7,11-trimethyl-dodeca-2,6,10-trienylsulfanyl)-ethyl]-3-methyl-succinamic acid)(Compound N-34) and (N-[1-Hydrazinocarbonyl-2-(3,7,11-trimethyl-dodeca-2,6,10-trienylsulfanyl)-ethyl]-2-methyl-succinamic acid)(Compound N-33): In a 100 mL round bottom flask, S-trans, trans-farnesyl-L-cysteine methyl ester (339 mg, 1 mmol) and methylsuccinic anhydride (171 mg, 1.5 mmol) were mixed in CH$_2$Cl$_2$ (5 mL). N,N-diisopropyl-ethyl-amine (0.52 mL, 3 mmol) was added to reaction mixture. The reaction solution was stirred at room temperature overnight. Ethyl acetate (50 mL) was added and then washed with saturated ammonium chloride aqueous solution (20 mL×2), DI water (20 mL×2) and brine (20 mL×2) sequentially. The ethyl acetate solution was dried by Na$_2$SO$_4$ and concentrated in vacuo to yield a crude mixture. The crude mixture was purified by HPLC to yield two fractions. The first fraction was purified as explained in Example 41a. The second fraction collected afforded a 6:4 mixture of the 3-methyl (Compound N-34) and 2-methyl (Compound N-33) regioisomers, wherein each regioisomer is a 1:1 ratio mixture of R-R and S-R isomers (150 mg, 33%). $^1$H-NMR (500 MHz, MeOH-d$_4$): δ 1.04-1.13 (m, 3H), 1.50 (s, 6H), 1.57 (s, 3H), 1.59 (s, 3H), 1.85-1.88 (m, 2H), 1.93-2.03 (m, 6H), 2.21-2.33 (m, 1H), 2.48-2.63 (m, 2H), 2.68-2.82 (m, 2H), 3.05-3.14 (m, 2H), 4.32-4.42 (m, 1H), 4.98-5.02 (m, 1H), 5.12 (t, J=7.5 Hz, 1H). $^{13}$C-NMR (125 MHz, MeOH-d$_4$): δ 16.14, 16.25, 16.27, 17.41, 17.47, 17.80, 17.99, 18.33, 20.05, 23.10, 23.66, 26.30, 26.56, 26.85, 27.43, 27.79, 29.09, 30.12, 30.17, 30.20, 30.82, 33.37, 33.39, 33.50, 33.53, 33.61, 37.40, 37.59, 37.96, 38.03, 38.29, 38.58, 38.84, 39.76, 39.95, 40.08, 40.76, 40.89, 121.23, 121.41, 121.44, 125.14, 132.13, 136.25, 140.54, 140.62, 172.06, 173.93, 174.29, 176.47, 178.93, 179.30; ES-MS: mass calcd for Chemical Formula: $C_{23}H_{39}N_3O_4S$ 453.3. Found (M+) m/z 454.3.

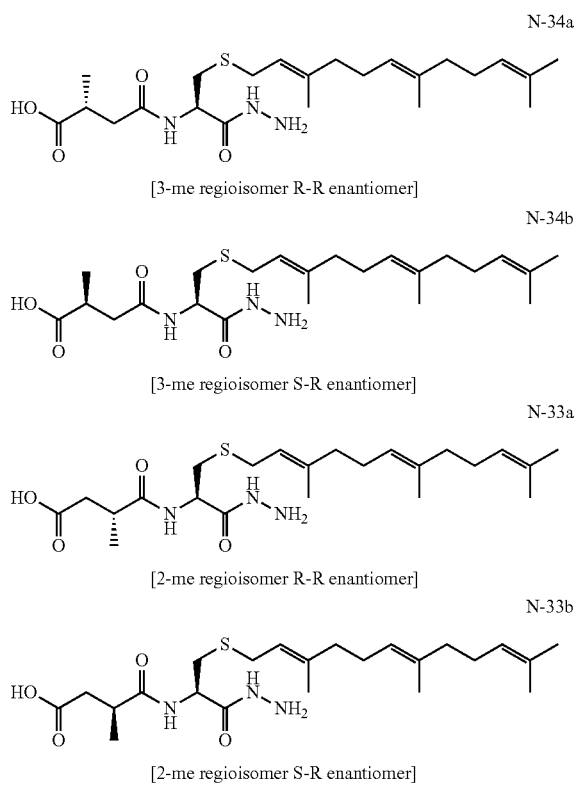

Example 41a

Synthesis of a mixture of (N-[1-Hydrazinocarbonyl-2-(3,7,11-trimethyl-dodeca-2,6,10-trienylsulfanyl)-ethyl]-3-(S)-methyl-succinamic acid) and (N-[1-Hydrazinocarbonyl-2-(3,7,11-trimethyl-dodeca-2,6,10-trienylsulfanyl)-ethyl]-3-(R)-methyl-succinamic acid)(Compound N-34): In a 100 mL round bottom flask, S-trans, trans-farnesyl-L-cysteine methyl ester (339 mg, 1 mmol) and methylsuccinic anhydride (171 mg, 1.5 mmol) were mixed in $CH_2Cl_2$ (5 mL). N,N-diisopropyl-ethyl-amine (0.52 mL, 3 mmol) was added to reaction mixture. The reaction solution was stirred at room temperature overnight. Ethyl acetate (50 mL) was added and then washed with saturated ammonium chloride aqueous solution (20 mL×2), DI water (20 mL×2) and brine (20 mL×2) sequentially. The ethyl acetate solution was dried by $Na_2SO_4$ and concentrated in vacuo to yield a crude mixture. The crude mixture was purified by HPLC to yield two fractions. The second fraction was purified to afford the mixture of regioisomers as explained in Example 41. The first fraction was isolated to yield Compound N-34 (50 mg, 11%): $^1$H-NMR (500 MHz, MeOH-$d_4$): δ 1.05 (d, J=7.0 Hz, 3H), 1.09 (d, J=7.0 Hz, 3H), 1.50 (s, 6H), 1.57 (s, 3H), 1.59 (s, 3H), 1.85-1.88 (m, 2H), 1.94-2.03 (m, 6H), 2.23-2.29 (m, 1H), 2.50-2.64 (m, 2H), 2.70-2.80 (m, 2H), 3.07-3.11 (m, 2H), 4.30-4.34 (m, 1H), 4.98-5.02 (m, 1H), 5.12 (t, J=7.5 Hz, 1H). $^{13}$C-NMR (125 MHz, MeOH-$d_4$): δ 16.13, 16.24, 17.42, 17.79, 17.98, 25.94, 27.43, 27.45, 27.96, 27.79, 30.19, 30.39, 33.36, 33.49, 37.45, 37.99, 38.91, 39.97, 40.76, 40.89, 53.04, 53.34, 121.41, 121.93, 125.14, 125.15, 125.45, 132.12, 136.24, 140.62, 172.06, 173.95, 178.17; ES-MS: mass calcd for Chemical Formula: $C_{23}H_{39}N_3O_4S$ 453.3. Found (M+) m/z 454.3.

Example 42

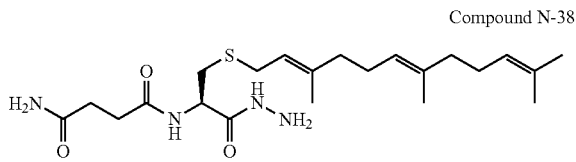 [SMILES: CC(C)=CCC/C(C)=C/CC/C(C)=C/CSC[C@H](NC(=O)CCC(N)=O)C(=O)NN]

Compound N-38

Synthesis of (N1-((R)-1-hydrazinyl-1-oxo-3-((2E,6E)-3,7,11-trimethyldodeca-2,6,10-trienylthio)propan-2-yl)succinamide)(Compound N-38): In a 100 mL round bottom flask, Succinamic acid (140 mg, 1.2 mmol), 2-(7-Aza-1H-benzotriazole-1-yl)-1,1,3,3-tetramethyluronium hexafluorophosphate (1.1 mg, 1.1 mmol) and N,N-diisopropyl-ethyl-amine (0.52 mL, 3 mmol) were mixed in THF (5 mL). The reaction solution was stirred at room temperature for ten minutes. S-trans, trans-Farnesyl-L-cysteine methyl ester (339 mg, 1 mmol) was added to reaction mixture. The reaction solution was stirred at room temperature overnight. Ethyl acetate (50 mL) was added and then washed with saturated ammonium chloride aqueous solution (20 mL×2), DI water (20 mL×2) and brine (20 mL×2) sequentially. The ethyl acetate solution was dried by $Na_2SO_4$ and concentrated in vacuo to afford a crude mixture. The crude mixture obtained was added to 1M $NH_2NH_2$ in THF (10 mL, 10 mmol). The reaction solution was stirred at room temperature overnight. The THF solution was concentrated in vacuo to afford a crude mixture. The crude mixture was purified by HPLC (153 mg, 35%) to yield Compound N-38. $^1$H-NMR (500 MHz, MeOH-$d_4$): δ 1.50 (s, 6H), 1.57 (s, 3H), 1.59 (s, 3H), 1.85-1.88 (m, 2H), 1.93-1.98 (m, 4H), 1.99-2.03 (m, 2H), 2.36-2.49 (m, 4H), 2.71 (dd, J=7.5, 13.5 Hz, 1H), 2.83 (dd, J=5.5, 13.5 Hz, 1H), 3.09 (d, J=8.0 Hz, 2H), 4.37 (t, J=7.5 Hz, 1H), 5.00 (m, 2H), 5.13 (t, J=8.0 Hz, 1H). $^{13}$C-NMR (125 MHz, MeOH-$d_4$): δ 16.13, 16.24, 17.79, 25.94, 27.42, 27.79, 30.22, 31.34, 31.87, 33.59, 40.76, 40.88, 53.19, 121.44, 125.14, 125.46, 132.12, 136.25, 140.58, 171.96, 174.95, 177.38; ES-MS: mass calcd for Chemical Formula: $C_{22}H_{38}N_4O_3S$ 438.3. Found (M+) m/z 439.3.

Example 43

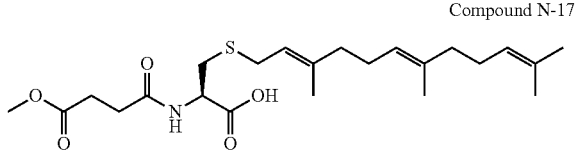 [SMILES: COC(=O)CCC(=O)N[C@@H](CSC/C=C(\C)CC/C=C(\C)CCC=C(C)C)C(=O)O]

Compound N-17

Synthesis of ((R)-2-(4-methoxy-4-oxobutanamido)-3-((2E,6E)-3,7,11-trimethyldodeca-2,6,10-trienylthio)propanoic acid)(Compound N-17): In a 100 mL round bottom flask, mono-methyl succinate (132 mg, 1 mmol), 2-(7-Aza-1H-benzotriazole-1-yl)-1,1,3,3-tetramethyluronium hexafluorophosphate (1.1 mg, 1.1 mmol) and N,N-diisopropyl-ethyl-amine (0.52 mL, 3 mmol) were mixed in THF (5 mL). The reaction solution was stirred at room temperature for ten minutes. S-trans, trans-Farnesyl-L-cysteine (325 mg, 1 mmol) was added to reaction mixture. The reaction solution was stirred at room temperature overnight. Ethyl acetate (50 mL) was added and then washed with saturated ammonium chloride aqueous solution (20 mL×2), DI water (20 mL×2) and brine (20 mL×2) sequentially. The ethyl acetate solution was dried by Na$_2$SO$_4$ and concentrated in vacuo to afford a crude Compound N-17. The crude Compound N-17 was purified by HPLC (110 mg, 25%) to yield Compound N-17. $^1$H-NMR (500 MHz, MeOH-d$_4$): δ 1.50 (s, 6H), 1.57 (s, 3H), 1.58 (s, 3H), 1.85-1.88 (m, 2H), 1.91-1.96 (m, 4H), 1.99-2.03 (m, 2H), 2.46-2.54 (m, 4H), 2.68 (dd, J=7.5, 13.5 Hz, 1H), 2.90 (dd, J=4.5, 13.5 Hz, 1H), 3.09-3.12 (m, 2H), 3.21 (s, 3H), 4.35 (dd, J=4.5, 7.0 Hz, 1H), 4.98-5.02 (m, 2H), 5.14 (t, J=7.5 Hz, 1H). $^{13}$C-NMR (125 MHz, MeOH-d$_4$): δ 16.12, 16.25, 17.79, 25.94, 27.48, 27.79, 30.40, 30.69, 31.73, 35.49, 40.77, 40.89, 52.24, 55.45, 121.82, 125.22, 125.47, 132.08, 136.15, 139.97, 173.57, 174.80, 177.17; ES-MS: mass calcd for Chemical Formula: C$_{23}$H$_{37}$NO$_5$S 439.2. Found (M+Na) m/z 462.2.

Example 44

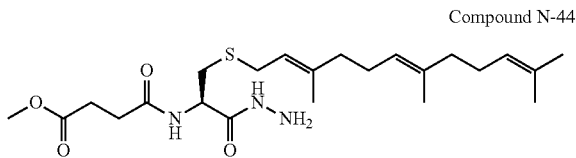 [SMILES: COC(=O)CCC(=O)N[C@@H](CSC/C=C(\C)CC/C=C(\C)CCC=C(C)C)C(=O)NN]

Compound N-44

Synthesis of ((methyl 4-((R)-1-hydrazinyl-1-oxo-3-((2E,6E)-3,7,11-trimethyldodeca-2,6,10-trienylthio)propan-2-ylamino)-4-oxobutanoate))(Compound N-44): In a 100 mL round bottom flask, the crude Compound N-39 (1 mmol) of Example 43, –(7-Aza-1H-benzotriazole-1-yl)-1,1,3,3-tetramethyluronium hexafluorophosphate (1.1 mg, 1.1 mmol) and N,N-diisopropyl-ethyl-amine (0.52 mL, 3 mmol) were mixed in THF (5 mL). The reaction solution was stirred at room temperature for ten minutes. 1 N Hydrazine in THF (2 mL, 2 mmol) was added to reaction mixture. The reaction solution was stirred at room temperature overnight. Ethyl acetate (50 mL) was added and then washed with saturated ammonium chloride aqueous solution (20 mL×2), DI water (20 mL×2) and brine (20 mL×2) sequentially. The ethyl acetate solution was dried by Na$_2$SO$_4$ and concentrated in vacuo to afford a crude mixture, The crude mixture was purified by HPLC (30 mg, 26%) to yield Compound N-44. $^1$H-NMR (500 MHz, MeOH-d$_4$): δ 1.50 (s, 6H), 1.57 (s, 3H), 1.59 (s, 3H), 1.85-1.88 (m, 2H), 1.93-1.98 (m, 4H), 1.99-2.03 (m, 2H), 2.42-2.45 (m, 2H), 2.52-2.54 (m, 2H), 2.54-2.59 (m, 1H), 2.80 (dd, J=6.5, 13.5 Hz, 1H), 3.09 (d, J=8 Hz, 2H), 3.57 (s, 3H), 4.37 (t, J=6.0 Hz, 1H), 4.98-5.01 (m, 2H), 5.12 (t, J=7.5 Hz, 1H). $^{13}$C-NMR (125 MHz, MeOH-d$_4$): δ 16.14, 16.25, 17.80, 25.95, 27.43, 27.79, 30.07, 30.20, 31.24, 33.60, 40.76, 40.89, 52.34, 53.08, 121.43, 125.14, 125.46, 132.13, 136.25, 140.60, 172.00, 174.35, 174.98; ES-MS: mass calcd for Chemical Formula: C$_{23}$H$_{39}$N$_3$O$_4$S 453.3. Found (M+Na) m/z 476.2.

Example 45

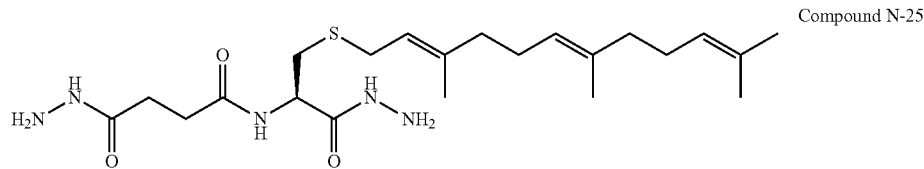 [SMILES: CC(C)=CCC/C(C)=C/CC/C(C)=C/CSC[C@H](NC(=O)CCC(=O)NN)C(=O)NN]

Compound N-25

Synthesis of (4-hydrazinyl-N—((R)-1-hydrazinyl-1-oxo-3-((2E,6E)-3,7,11-trimethyldodeca-2,6,10-trienylthio)propan-2-yl)-4-oxobutanamide)(Compound N-25): In a 100 mL round bottom flask, to a solution of S-trans, trans-farnesyl-L-cysteine methyl ester (339 mg, 1 mmol), benzotriazol-1-yl-oxytripyrrolidinophosphonium hexafluorophosphate (Py-Bop, 624 mg, 1.2 mmol) and 4-methoxy-4-oxobutanoic acid (1.2 mmol) in THF (5 mL) was added N,N-diisopropyl-ethyl-amine (0.52 mL, 3 mmol). The solution was stirred at room temperature overnight. The mixture was diluted with ethyl acetate (60 mL) and washed by 0.5 N HCl (10 mL×1), H$_2$O (15 mL×2) and brine (10 mL×1). The organic layer was dried over Na$_2$SO$_4$ and concentrated in vacuo. The residue was purified by flash chromatography on silica gel with hexanes/ethyl acetate (3/1) as eluent. To the product obtained above was added hydrazine in THF (1 M hydrazine in THF, 48 mL). The reaction was left at room temperature for 64 h and the solvent was removed in vacuo. The residue was then further purified by preparative HPLC (300 mg, 68%) to yield Compound N-25. $^1$H-NMR (500 MHz, CD$_3$OD): δ 1.50 (s, 6H), 1.57 (s, 3H), 1.59 (s, 3H), 1.85-2.03 (m, 8H), 2.35-2.46 (m, 4H), 2.60 (dd, J=10.0, 15.0 Hz, 1H), 2.87 (dd, J=5.0, 15.0 Hz, 1H), 3.08-3.10 (m, 2H), 4.38 (dd, J=5.0, 10.0 Hz, 1H), 4.99-5.01 (m, 2H), 5.16 (t, J=10.0 Hz, 1H). $^{13}$C-NMR (125 MHz, CD$_3$OD): δ 16.14, 16.26, 17.80, 25.95, 27.44, 27.80, 30.06, 30.24, 31.96, 33.58, 40.77, 40.89, 53.28, 121.44, 125.15, 125.47, 132.13, 136.27, 140.59, 171.98, 173.96, 174.88; ES-MS: mass calcd for Chemical Formula: C$_{22}$H$_{39}$N$_5$O$_3$S 453.64. Found (M+) m/z 454.3.

Example 46

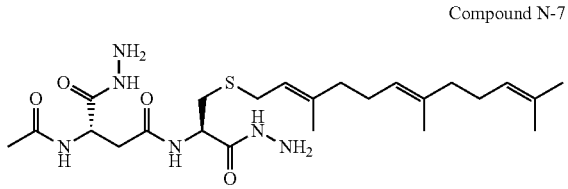

Compound N-71

Synthesis of ((S)-3-acetamido-4-hydrazinyl-N—((R)-1-hydrazinyl-1-oxo-3-((2E,6E)-3,7,11-trimethyldodeca-2,6,10-trienylthio)propan-2-yl)-4-oxobutanamide)(Compound N-71): In a 100 mL round bottom flask, to a solution of S-trans, trans-farnesyl-L-cysteine methyl ester (339 mg, 1 mmol), benzotriazol-1-yl-oxytripyrrolidinophosphonium hexafluorophosphate (PyBop, 624 mg, 1.2 mmol) and N-acetyl-aspartic acid methyl ester (1.2 mmol) in THF (5 mL) was added N,N-diisopropyl-ethyl-amine (0.52 mL, 3 mmol). The solution was stirred at room temperature overnight. The mixture was diluted with ethyl acetate (60 mL) and washed by 0.5 N HCl (10 mL×1), H$_2$O (15 mL×2) and brine (10 mL×1). The organic layer was dried over Na$_2$SO$_4$ and concentrated in vacuo. The residue was purified by flash chromatography on silica gel with hexanes/ethyl acetate (3/1) as eluent. To the product obtained above was added hydrazine in THF (1 M hydrazine in THF, 48 mL). The reaction was left at room temperature for 64 h and the solvent was removed in vacuo. The residue was then further purified by preparative HPLC (330 mg, 65%) to yield Compound N-71. $^1$H-NMR (500 MHz, DMSO-d$_6$): δ 1.56 (s, 6H), 1.62 (s, 3H), 1.63 (s, 3H), 1.81 (s, 3H), 1.91-2.04 (m, 10H), 2.38 (dd, J=10.0, 15.0 Hz, 1H), 2.68-2.72 (m, 1H), 3.12-3.14 (m, 2H), 4.20 (s, 2H), 4.28 (s, 2H), 4.35-4.37 (m, 1H), 4.51-4.52 (m, 1H), 5.06-5.07 (m, 2H), 5.15 (t, J=10.0 Hz, 1H), 7.95 (d, J=10.0 Hz, 1H), 8.13 (d, J=10.0 Hz, 1H), 9.10 (s, 1H), 9.28 (s, 1H). $^{13}$C-NMR (125 MHz, DMSO-d$_6$): δ 15.78, 17.56, 22.67, 25.50, 25.88, 26.14, 28.63, 32.53, 37.80, 48.72, 50.99, 120.07, 123.66, 124.09, 130.65, 134.53, 138.45, 168.94, 168.98, 169.08, 170.10; ES-MS: mass calcd for Chemical Formula: C$_{24}$H$_{42}$N$_6$O$_4$S 510.69. Found (M+) m/z 511.3.

Synthesis of a mixture of ((2R,3S)-2-acetamido-N—((R)-1-hydrazinyl-1-oxo-3-((2E,6E)-3,7,11-trimethyldodeca-2,6,10-trienylthio)propan-2-yl)-3-methylpentanamide) and ((2R,3R)-2-acetamido-N—((R)-1-hydrazinyl-1-oxo-3-((2E,6E)-3,7,11-trimethyldodeca-2,6,10-trienylthio)propan-2-yl)-3-methylpentanamide)(Compound N-72): In a 100 mL round bottom flask, to a solution of S-trans, trans-farnesyl-L-cysteine methyl ester (339 mg, 1 mmol), benzotriazol-1-yl-oxytripyrrolidinophosphonium hexafluorophosphate (PyBop, 624 mg, 1.2 mmol) and N-acetyl-L-isoleucine (1.2 mmol) in THF (5 mL) was added N,N-diisopropyl-ethyl-amine (0.52 mL, 3 mmol). The solution was stirred at room temperature overnight. The mixture was diluted with ethyl acetate (60 mL) and washed by 0.5 N HCl (10 mL×1), H$_2$O (15 mL×2) and brine (10 mL×1). The organic layer was dried over Na$_2$SO$_4$ and concentrated in vacuo. The residue was purified by flash chromatography on silica gel with hexanes/ethyl acetate (3/1) as eluent. To the product obtained above was added hydrazine in THF (1 M hydrazine in THF, 48 mL). The reaction was left at room temperature for 64 h and the solvent was removed in vacuo. The residue was then further purified by preparative HPLC (245 mg, 50%) to yield a 1:1 ratio mixture of RSR and RRR isomers of Compound N-72, similar to the Compound N-62 racemate in Example 28, wherein one of the three chiral centers is racemic and the other two are enantiopure. $^1$H-NMR (500 MHz, CD$_3$OD): δ 0.79-0.87 (m, 6H), 1.05-1.15 (m, 2H), 1.50-1.59 (m, 13H), 1.85-2.01 (m, 11H), 2.57 (m, 1H), 2.75-2.94 (m, 1H), 3.07-3.10 (m, 2H), 4.07-4.16 (m, 1H), 4.36-4.37 (m, 1H), 4.99-5.01 (m, 2H), 5.12 (t, J=10.0 Hz, 1H). $^{13}$C-NMR (125 MHz, CD$_3$OD): δ 11.54, 11.95, 15.27, 15.95, 16.15, 16.25, 16.30, 17.80, 22.32, 22.46, 25.95, 26.01, 27.27, 27.44, 27.46, 27.80, 30.12, 30.19, 30.90, 33.38, 33.66, 37.97, 40.78, 40.89, 52.91, 53.03, 59.29, 59.67, 121.39, 121.41, 125.13, 125.14, 125.46, 126.15, 132.12, 136.27, 140.56, 140.64, 171.70, 171.73, 173.64, 173.72, 173.88, 174.39; ES-MS: mass calcd for Chemical Formula: C$_{26}$H$_{46}$N$_4$O$_3$S 494.73. Found (M+) m/z 495.3.

Example 48

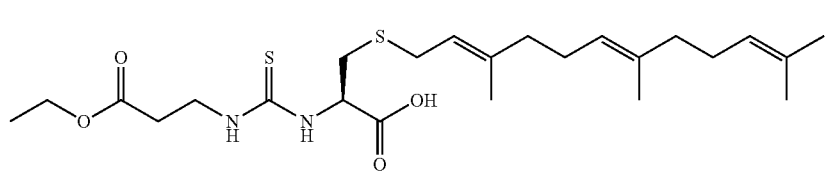

Compound N-73

Synthesis of ((R)-2-(3-(3-ethoxy-3-oxopropyl)thioureido)-3-((2E,6E)-3,7,11-trimethyldodeca-2,6,10-trienylthio)propanoic acid)(Compound N-73): In a 100 mL round bottom flask, to a suspension of ethyl-3-isothiocynato propionate (159 mg, 1 mmol) and S-trans, trans-farnesyl-L-cysteine (325 mg, 1 mmol) in THF (5 mL) was added N,N-diisopropyl-ethyl-amine (0.87 mL, 5 mmol) dropwise. The solution was stirred at room temperature overnight. The mixture was diluted with ethyl acetate (60 mL) and washed by 0.5 N HCl (10 mL×1), H$_2$O (10 mL×1) and brine (10 mL×1). The organic layer was dried over Na$_2$SO$_4$ and concentrated in vacuo. The residue was purified by preparative HPLC (220 mg, 45%) to yield Compound N-73. $^1$H-NMR (500 MHz, CD$_3$OD): δ 1.17 (t, J=5.0 Hz, 3H), 1.50

Example 47

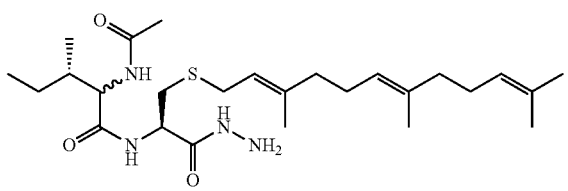

Compound N-72

(s, 3H), 1.51 (s, 3H), 1.57 (s, 3H), 1.59 (s, 3H), 1.86-2.06 (m, 8H), 2.54 (t, J=5.0 Hz, 2H), 2.77 (dd, J=5.0, 15.0 Hz, 1H), 2.95-2.96 (m, 1H), 3.05-3.06 (m, 1H), 3.16-3.20 (m, 1H), 3.68 (broad, 2H), 4.06 (q, J=5.0 Hz, 2H), 5.00-5.01 (m, 2H), 5.09-5.14 (m, 2H). $^{13}$C-NMR (125 MHz, CD$_3$OD): δ 14.65, 16.19, 16.31, 17.83, 25.97, 27.39, 27.80, 30.70, 33.22, 33.91, 34.80, 40.80, 40.90, 57.89, 61.03, 61.71, 61.93, 121.35, 121.70, 125.16, 132.11, 136.24, 140.52, 173.76, 174.47, 210.16; ES-MS: mass calcd for Chemical Formula: C$_{24}$H$_{40}$N$_2$O$_4$S$_2$ 484.72. Found (M+) m/z 485.3, (M+Na) m/z 507.3.

Example 49

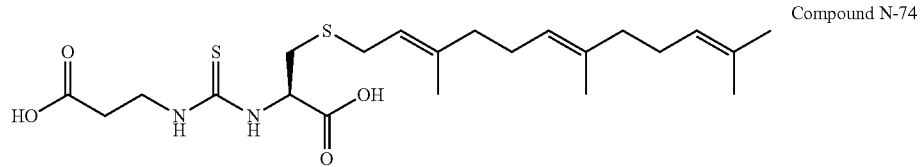 [SMILES: CC(C)=CCC/C(C)=C/CC/C(C)=C/CSC[C@H](NC(=S)NCCC(=O)O)C(=O)O]

Compound N-74

Synthesis of ((R)-2-(3-(2-carboxyethyl)thioureido)-3-((2E,6E)-3,7,11-trimethyldodeca-2,6,10-trienylthio)propanoic acid)(Compound N-74): In a 100 mL round bottom flask, to a suspension of ethyl-3-isothiocynato propionate (1 mmol) and S-trans, trans-farnesyl-L-cysteine (325 mg, 1 mmol) in THF (5 mL) was added N,N-diisopropyl-ethyl-amine (0.87 mL, 5 mmol) dropwise. The solution was stirred at room temperature overnight. The mixture was diluted with ethyl acetate (60 mL) and washed by 0.5 N HCl (10 mL×1), H$_2$O (10 mL×1) and brine (10 mL×1). The organic layer was dried over Na$_2$SO$_4$ and concentrated in vacuo to afford crude Compound N-74. The crude Compound N-74 obtained above was dissolved in THF (3 mL) and a solution of LiOH.H$_2$O (126 mg, 3 mmol) in H$_2$O (2 mL) was added slowly at 0° C. The reaction was left for 4 h. The solution was then diluted with ethyl acetate (60 mL) and washed by 0.5 N HCl (10 mL×1), H$_2$O (10 mL×1) and brine (10 mL×1). The organic layer was dried over Na$_2$SO$_4$ and concentrated in vacuo. The resulting residue was then further purified by preparative HPLC (230 mg, 50%) to yield Compound N-74. $^1$H-NMR (500 MHz, CD$_3$OD): δ 1.50 (s, 3H), 1.51 (s, 3H), 1.57 (s, 3H), 1.59 (s, 3H), 1.86-2.04 (m, 8H), 2.53 (t, J=6.0 Hz, 2H), 2.77 (dd, J=6.5, 14.0 Hz, 1H), 2.94-2.95 (m, 1H), 3.05-3.06 (m, 1H), 3.15-3.17 (m, 1H), 3.67 (broad, 2H), 5.00-5.01 (m, 2H), 5.09-5.14 (m, 2H). $^{13}$C-NMR (125 MHz, CD$_3$OD): δ 16.17, 16.30, 17.81, 25.96, 27.39, 27.79, 30.68, 31.57, 32.81, 33.20, 33.90, 34.56, 37.55, 40.80, 40.89, 57.93, 61.05, 121.34, 121.70, 125.48, 132.11, 136.24, 140.52, 173.76, 174.55, 175.68; ES-MS: mass calcd for Chemical Formula: C$_{22}$H$_{36}$N$_2$O$_4$S$_2$ 456.66. Found (M+) m/z 457.2, (M+Na) m/z 479.2.

Example 50

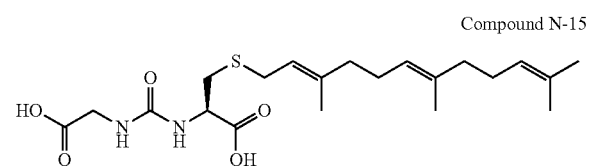 [SMILES: CC(C)=CCC/C(C)=C/CC/C(C)=C/CSC[C@H](NC(=O)NCC(=O)O)C(=O)O]

Compound N-15

Synthesis of ((R)-2-(3-(carboxymethyl)ureido)-3-((2E,6E)-3,7,11-trimethyldodeca-2,6,10-trienylthio)propanoic acid)(Compound N-15): In a 100 mL round bottom flask, to a suspension of ethyl-isocyanate-acetate (1 mmol) and S-trans, trans-L-cysteine (325 mg, 1 mmol) in THF (5 mL) was added N,N-diisopropyl-ethyl-amine (0.87 mL, 5 mmol) dropwise. The solution was stirred at room temperature overnight. The mixture was diluted with ethyl acetate (60 mL) and washed by 0.5 N HCl (10 mL×1), H$_2$O (10 mL×1) and brine (10 mL×1). The organic layer was dried over Na$_2$SO$_4$ and concentrated in vacuo to afford crude Compound N-15. The crude Compound N-15 obtained above was dissolved in THF (3 mL) and a solution of LiOH.H$_2$O (126 mg, 3 mmol) in H$_2$O (2 mL) was added slowly at 0° C. The reaction was left for 4 h. The solution was then diluted with ethyl acetate (60 mL) and washed by 0.5 N HCl (10 mL×1), H$_2$O (10 mL×1) and brine (10 mL×1). The organic layer was dried over Na$_2$SO$_4$ and concentrated in vacuo. The resulting residue was then further purified by preparative HPLC (40 mg, 50%) to yield Compound N-15. $^1$H-NMR (500 MHz, CD$_3$OD): δ 1.62 (bs, 6H), 1.68 (s, 3H), 1.70 (s, 3H), 1.99 (t, J=7 Hz, 2H), 2.06-2.17 (m, 6H), 2.82 (dd, J=7.0, 14.0 Hz, 1H), 2.95 (dd, J=5.0, 13.5 Hz, 1H), 3.18 (dd, J=7.0, 13.0 Hz, 1H), 3.28 (dd, J=5.0, 12.0 Hz, 1H), 3.89 (bs, 2H), 4.50-4.54 (m, 1H), 5.10-5.15 (m, 2H), 5.24 (t, J=7.0 Hz, 1H). $^{13}$C-NMR (125 MHz, CD$_3$OD): δ 16.1, 17.8, 25.9, 27.4, 27.8, 30.6, 34.5, 40.8, 40.9, 42.5, 54.2, 121.7, 125.2, 125.5, 132.1, 136.3, 140.5, 160.1, 174.1, 174.8; ES-MS: mass calcd for Chemical Formula: C$_{21}$H$_{34}$N$_2$O$_5$S 426.6. Found (M+Na) m/z 449.3.

Example 51

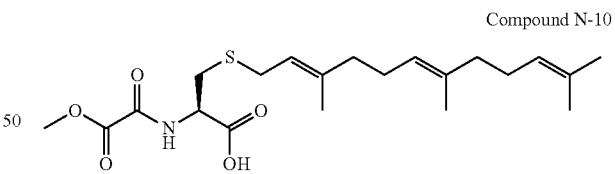

Compound N-10

Synthesis of ((R)-2-(2-methoxy-2-oxoacetamido)-3-((2E,6E)-3,7,11-trimethyldodeca-2,6,10-trienylthio)propanoic acid)(Compound N-10): In a 100 mL round bottom flask, S-trans, trans-Farnesyl-L-cysteine (325 mg, 1 mmol) and N,N-diisopropyl-ethyl-amine (650 mg, 5 mmol) were mixed in CH$_2$Cl$_2$ (10 mL). Methyl chloro oxoacetate (122 mg, 1 mmol) was added to the reaction mixture. The reaction solution was stirred at room temperature overnight. Reaction solvent was removed by rotary evaporation. The remained residue was dissolved in ethyl acetate (100 mL) and washed with an NH$_4$Cl saturated solution (50 mL), dried over Na$_2$SO$_4$ and concentrated to afford a crude mixture. The crude mixture was purified by preparative HPLC (66 mg, 15%) to yield Compound N-10. $^1$H-NMR (500 MHz, CDCl$_3$): δ 1.60 (bs, 6H), 1.66 (s, 3H), 1.67 (s, 3H), 1.97 (t, J=7 Hz, 2H), 2.02-2.15 (m, 6H), 2.95 (dd, J=6.3, 14.2 Hz, 1H), 3.01 (dd, J=4.7, 14.2 Hz, 1H), 3.16-3.27 (m, 2H), 3.93 (bs, 3H), 4.82 (m, 1H), 5.09 (m, 2H), 5.20 (t, J=7.5 Hz, 1H). $^{13}$C-NMR (125 MHz, CDCl$_3$): δ 16.0, 16.2, 17.7, 25.7, 26.4, 26.7, 30.0, 32.5, 39.6, 39.7, 52.0, 53.9, 119.2, 123.7, 124.3, 131.4, 135.5, 140.6, 156.1, 160.2, 173.2; ES-MS: mass calcd for Chemical Formula: C$_{21}$H$_{33}$NO$_5$S 411.6. Found (M+Na) m/z 434.2.

Example 52

Compound N-13

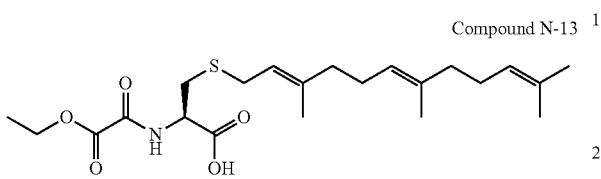

Synthesis of ((R)-2-(2-ethoxy-2-oxoacetamido)-3-((2E, 6E)-3,7,11-trimethyldodeca-2,6,10-trienylthio)propanoic acid)(Compound N-13): In a 100 mL round bottom flask, S-trans, trans-farnesyl-L-cysteine (325 mg, 1 mmol) and N,N-diisopropyl-ethyl-amine (650 mg, 5 mmol) were mixed in CH$_2$Cl$_2$ (10 mL). Ethyl chloro oxoacetate (122 mg, 1 mmol) was added to the reaction mixture. The reaction solution was stirred at room temperature overnight. Reaction solvent was removed by rotary evaporation. The remained residue was dissolved in ethyl acetate (100 mL) and washed with an NH$_4$Cl saturated solution (50 mL), dried over Na$_2$SO$_4$ and concentrated to afford a crude mixture. The crude mixture was purified by preparative HPLC (66 mg, 15%) to yield Compound N-13. $^1$H-NMR (500 MHz, CDCl$_3$): δ 1.40 (t, J=7.0 Hz, 3H), 1.60 (bs, 6H), 1.66 (s, 3H), 1.68 (s, 3H), 1.97 (t, J=7 Hz, 2H), 2.02-2.15 (m, 6H), 2.95 (dd, J=6.5, 14.0 Hz, 1H), 3.02 (dd, J=5.0, 16.0 Hz, 1H), 3.16-3.27 (m, 2H), 4.37 (q, J=7.0 Hz, 2H), 4.81 (m, 1H), 5.09 (m, 2H), 5.19 (t, J=7.5 Hz, 1H). $^{13}$C-NMR (125 MHz, CDCl$_3$): δ 14.0, 16.0, 16.2, 17.7, 25.7, 26.4, 26.7, 30.0, 32.5, 39.6, 39.7, 52.2, 63.6, 119.3, 123.7, 124.3, 131.3, 135.5, 140.5, 156.5, 160.0, 174.1; ES-MS: mass calcd for Chemical Formula: C$_{22}$H$_{35}$NO$_5$S 425.2. Found (M+Na) m/z 448.2.

Example 53

Compound N-19

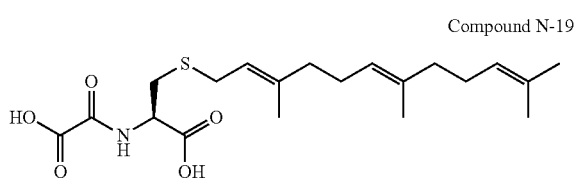 [SMILES: CC(C)=CCC/C(C)=C/CC/C(C)=C/CSC[C@H](NC(=O)C(=O)O)C(=O)O]

Synthesis of ((R)-2-(carboxyformamido)-3-((2E,6E)-3,7,11-trimethyldodeca-2,6,10-trienylthio)propanoic acid) (Compound N-19): In a 100 mL round bottom flask, S-trans, trans-Farnesyl-L-cysteine (325 mg, 1 mmol) and N,N-diisopropyl-ethyl-amine (650 mg, 5 mmol) were mixed in CH$_2$Cl$_2$ (10 mL). Ethyl chloro oxoacetate (122 mg, 1 mmol) was added to the reaction mixture. The reaction solution was stirred at room temperature overnight. Reaction solvent was removed by rotary evaporation. The remained residue was dissolved in ethyl acetate (100 mL) and washed with an NH$_4$Cl saturated solution (50 mL), dried over Na$_2$SO$_4$ and concentrated to afford a crude mixture. The crude reaction mixture and LiOH (126 mg, 3 mmol) were mixed in THF (3 mL) and water (3 mL). The reaction solution was stirred at room temperature for 4 hours. Ethyl acetate (50 mL) was added and then washed with 1N HCl (20 mL×2) and brine (20 mL×2) sequentially. The ethyl acetate solution was dried by Na$_2$SO$_4$ and concentrated in vacuo to afford a crude mixture. The crude mixture was purified by HPLC (60 mg, 16%) to yield Compound N-19. $^1$H-NMR (500 MHz, CD$_3$OD): δ 1.60 (bs, 6H), 1.68 (s, 3H), 1.73 (s, 3H), 1.99 (t, J=7 Hz, 2H), 2.02-2.15 (m, 6H), 2.88 (dd, J=8.5, 14.0 Hz, 1H), 3.08 (dd, J=4.0, 14.0 Hz, 1H), 3.15 (dd, J=5.5, 13.5 Hz, 1H), 3.28 (dd, J=5.5, 13.0 Hz, 1H), 4.64 (dd, J=4.0, 7.5 Hz, 1H), 5.09-5.13 (m, 2H), 5.19 (t, J=7.5 Hz, 1H). $^{13}$C-NMR (125 MHz, CD$_3$OD): δ 16.1, 16.2, 26.0, 27.4, 27.8, 30.2, 33.0, 40.8, 40.9, 53.7, 121.5, 125.1, 125.5, 132.1, 136.3, 140.7, 160.3, 162.4, 173.0; ES-MS: mass calcd for Chemical Formula: C$_{20}$H$_{31}$NO$_5$S 397.5. Found (M+Na) m/z 420.2.

Example 54

Compound N-52

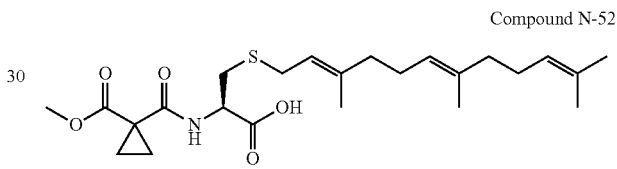

Synthesis of (1-[1-Carboxy-2-(3,7,11-trimethyl-dodeca-2,6,10-trienylsulfanyl)-ethylcarbamoyl]-cyclopropanecarboxylic acid methyl ester)(Compound N-52): In a 100 mL round bottom flask, 1,1-Cyclopropanedicarboxylic acid monomethyl ester (158 mg, 1.1 mmol), 2-(7-Aza-1H-benzotriazole-1-yl)-1,1,3,3-tetramethyluronium hexafluorophosphate (1.1 mg, 1.1 mmol) and N,N-diisopropyl-ethyl-amine (0.52 mL, 3 mmol) were mixed in THF (5 mL). The reaction solution was stirred at room temperature for ten minutes. S-trans, trans-Farnesyl-L-cysteine (325 mg, 1 mmol) was added to reaction mixture. The reaction solution was stirred at room temperature overnight. Ethyl acetate (50 mL) was added and then washed with saturated ammonium chloride aqueous solution (20 mL×2), DI water (20 mL×2) and brine (20 mL×2) sequentially. The ethyl acetate solution was dried by Na$_2$SO$_4$ and concentrated in vacuo to afford crude Compound N-52. The crude Compound N-52 was purified by HPLC (120 mg, 27%) to yield Compound N-52. $^1$H-NMR (500 MHz, MeOH-d$_4$): δ 1.45-1.48 (m, 4H), 1.50 (s, 6H), 1.57 (s, 3H), 1.58 (s, 3H), 1.85-1.89 (m, 2H), 1.93-1.98 (m, 4H), 2.01-2.05 (m, 2H), 2.78-2.91 (m, 2H), 3.06-3.15 (m, 2H), 3.62 (s, 3H), 4.56 (t, J=5.0 Hz, 1H), 4.97-5.02 (m, 2H), 5.12 (t, J=7.5 Hz, 1H). $^{13}$C-NMR (125 MHz, MeOH-d$_4$): δ 9.2, 16.14, 16.20, 17.80, 20.05, 25.95, 27.31, 27.37, 27.78, 30.61, 33.62, 40.74, 40.88, 52.96, 53.97, 121.61, 125.11, 125.45, 132.11, 136.28, 140.59, 170.81, 173.75, 174.39; ES-MS: mass calcd for Chemical Formula: C$_{24}$H$_{37}$NO$_5$S 451.2. Found (M+Na) m/z 474.2.

Example 55

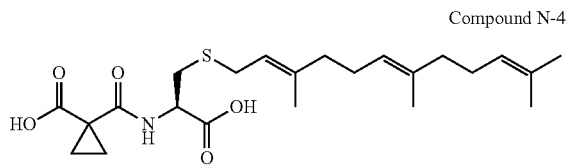

Compound N-45

Synthesis of (1-[1-Carboxy-2-(3,7,11-trimethyl-dodeca-2,6,10-trienylsulfanyl)-ethylcarbamoyl]-cyclopropanecarboxylic acid)(Compound N-45): In a 100 mL round bottom flask, the crude Compound N-52 (1 mmol) of Example 54, and LiOH (126 mg, 3 mmol) were mixed in THF (3 mL) and water (3 mL). The reaction solution was stirred at room temperature for 4 hours. Ethyl acetate (50 mL) was added and then washed with 1N HCl (20 mL×2) and brine (20 mL×2) sequentially. The ethyl acetate solution was dried by $Na_2SO_4$ and concentrated in vacuo to afford a crude mixture. The crude mixture was purified by HPLC (200 mg, 46%) to yield Compound N-45. $^1$H-NMR (500 MHz, MeOH-$d_4$): δ 1.47 (m, 4H), 1.50 (s, 6H), 1.57 (s, 6H), 1.85-1.89 (m, 2H), 1.91-2.06 (m, 6H), 2.78-2.90 (m, 2H), 3.08-3.16 (m, 2H), 3.25 (s, 1H), 4.57 (t, J=5.5 Hz, 1H), 4.97-5.02 (m, 2H), 5.12 (t, J=7.5 Hz, 1H). $^{13}$C-NMR (125 MHz, MeOH-$d_4$): δ 9.2, 16.16, 16.21, 17.81, 20.40, 25.96, 26.59, 27.38, 27.78, 30.66, 33.58, 40.75, 40.88, 53.94, 121.63, 125.12, 125.46, 132.11, 136.28, 140.60, 171.59, 173.70, 175.97; ES-MS: mass calcd for Chemical Formula: $C_{23}H_{35}NO_5S$ 437.2. Found (M+Na) m/z 460.2.

Example 56

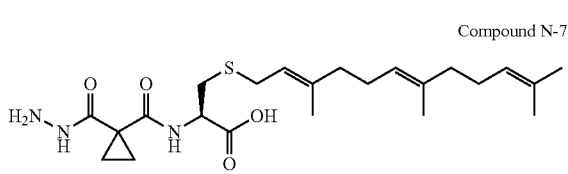

Compound N-75

Synthesis of (2-[(1-Hydrazinocarbonyl-cyclopropanecarbonyl)-amino]-3-(3,7,11-trimethyl-dodeca-2,6,10-trienylsulfanyl)-propionic acid)(Compound N-75): In a 100 mL round bottom flask, the crude Compound N-52 (1 mmol) of Example 54, was added to 1M $NH_2NH_2$ in THF (10 mL, 10 mmol). The reaction solution was stirred at room temperature overnight. The THF solution was concentrated in vacuo to afford a crude mixture. The crude mixture was purified by HPLC (65 mg, 52%) to yield Compound N-75. $^1$H-NMR (500 MHz, MeOH-$d_4$): δ 1.17-1.27 (m, 4H), 1.50 (s, 6H), 1.57 (s, 3H), 1.58 (s, 3H), 1.85-1.88 (m, 2H), 1.91-2.03 (m, 6H), 2.70 (dd, J=9.0, 13.5 Hz, 1H), 3.00 (dd, J=3.5, 13.5 Hz, 1H), 3.06-3.15 (m, 2H), 3.21 (s, 1H), 4.32 (dd, J=3.5, 8.5 Hz, 1H), 4.97-5.02 (m, 2H), 5.14 (t, J=7.5 Hz, 1H). $^{13}$C-NMR (125 MHz, MeOH-$d_4$): δ 9.2, 14.87, 15.72, 16.15, 16.28, 17.82, 25.97, 27.49, 27.80, 30.16, 30.53, 34.90, 40.77, 40.89, 56.22, 121.67, 125.21, 125.47, 132.09, 136.17, 140.11, 171.68, 172.35, 177.58; ES-MS: mass calcd for Chemical Formula: $C_{24}H_{37}N_3O_4S$ 451.2. Found (M+Na) m/z 474.2.

Example 57

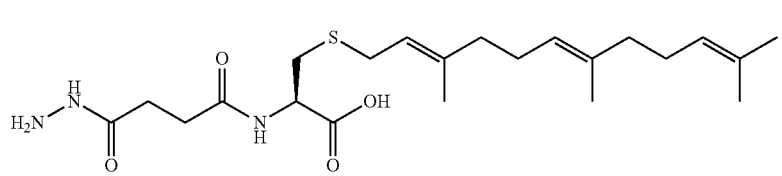

Compound N-76

Synthesis of (2-(3-Hydrazinocarbonyl-propionylamino)-3-(3,7,11-trimethyl-dodeca-2,6,10-trienylsulfanyl)-propionic acid)(Compound N-76): In a 100 mL round bottom flask, the crude Compound N-39 (1 mmol) of Example 43, was added to 1M $NH_2NH_2$ in THF (10 mL, 10 mmol). The reaction solution was stirred at room temperature overnight. The THF solution was concentrated in vacuo to afford a crude mixture. The crude mixture was purified by HPLC (60 mg, 56%) to yield Compound N-76. $^1$H-NMR (500 MHz, MeOH-$d_4$): δ 1.50 (s, 6H), 1.57 (s, 3H), 1.58 (s, 3H), 1.85-1.88 (m, 2H), 1.91-1.96 (m, 4H), 1.99-2.03 (m, 2H), 2.35 (t, J=7.5 Hz, 2H), 2.47 (t, J=7.5 Hz, 2H), 2.68 (dd, J=7.5, 13.5 Hz, 1H), 2.91 (dd, J=4.0, 13.5 Hz, 1H), 3.09-3.12 (m, 2H), 4.33 (dd, J=4.5, 7.5 Hz, 1H), 4.97-5.00 (m, 2H), 5.14 (t, J=7.5 Hz, 1H). $^{13}$C-NMR (125 MHz, MeOH-$d_4$): δ 16.11, 16.26, 17.79, 25.94, 27.50, 27.79, 30.69, 30.74, 32.60, 35.63, 40.78, 40.89, 55.60, 121.80, 125.22, 125.47, 132.08, 136.14, 139.98, 173.73, 174.17, 177.47; ES-MS: mass calcd for Chemical Formula: $C_{22}H_{37}N_3O_4S$ 439.3. Found (M+Na) m/z 462.2.

Example 58

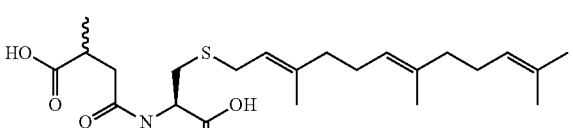

N-22

[3-me regioisomer racemate]

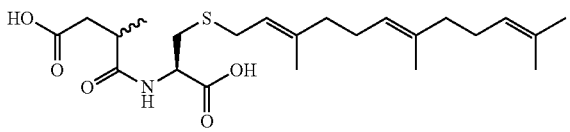

N-21

[2-me regioisomer racemate]

Synthesis of a mixture of (4-((R)-1-carboxy-2-((2E,6E)-3,7,11-trimethyldodeca-2,6,10-trienylthio)ethylamino)-3- methyl-4-oxobutanoic acid) (Compound N-22) and (4-((R)-1-carboxy-2-((2E,6E)-3,7,11-trimethyldodeca-2,6,10-trienylthio)ethylamino)-2-methyl-4-oxobutanoic acid) (Compound N-21): In a 100 mL round bottom flask, to a solution of S-trans, trans-farnesyl-L-cysteine (325 mg, 1 mmol) and N-methyl-succinic-anhydride (1 mmol) in CH$_2$Cl$_2$ (10 mL) was added N,N-diisopropyl-ethyl-amine (0.87 mL, 5 mmol). The solution was stirred at room temperature for 2 h. The reaction was quenched by 1 N HCl (10 mL) and the pH was adjusted to ~0.2.0-3.0. The mixture was extracted with ethyl acetate (15 mL×3). The organic layer was dried over Na$_2$SO$_4$ and concentrated in vacuo. The residue was further purified by preparative HPLC yielding a 6:4 mixture of regioisomeric compounds, N-22 (the 3-methyl isomer) and N-21 (the 2-methyl isomer), wherein each regioisomer is a 1:1 ratio mixture of R-R and S-R isomers, similar to the regioisomeric mixture of compounds N-34 and N-33 in Example 41 (296 mg, 67% yield). $^1$H-NMR (500 MHz, CDCl$_3$): δ 1.14-1.24 (m, 3H), 1.53 (s, 6H), 1.59 (s, 3H), 1.61 (s, 3H), 1.88-2.03 (m, 8H), 2.29-2.66 (m, 2H), 2.72-3.01 (m, 3H), 3.07-3.16 (m, 2H), 4.59 (dd, J=5.0, 10.0 Hz, 0.5H), 4.69 (dd, J=5.0, 10.0 Hz, 0.5H), 5.01 (m, 2H), 5.13 (dd, J=5.0, 15.0 Hz, 1H), 6.52 (m, 0.5H), 6.70 (m, 0.5H), 8.80 (broad, 2H). $^{13}$C-NMR (125 MHz, CDCl$_3$): δ 15.00, 15.12, 15.56, 15.82, 15.98, 16.51, 16.69, 16.84, 24.71, 25.36, 25.39, 25.50, 25.67, 28.74, 28.79, 31.42, 31.47, 31.53, 31.72, 35.04, 35.48, 35.61, 36.59, 36.98, 37.64, 38.40, 38.60, 38.67, 50.50, 50.65, 50.95, 51.02, 117.90, 118.26, 118.29, 122.64, 122.67, 122.71, 123.27, 130.30, 130.35, 134.34, 134.38, 139.26, 139.27, 139.29, 139.33, 170.86, 171.02, 174.01, 174.84, 174.96, 175.23, 175.40, 175.76, 177.16, 179.36, 180.65; ES-MS: mass calcd for Chemical Formula: C$_{23}$H$_{37}$NO$_5$S 439.61. Found (M+) m/z 440.3, (M+Na) m/z 462.3.

Example 58a

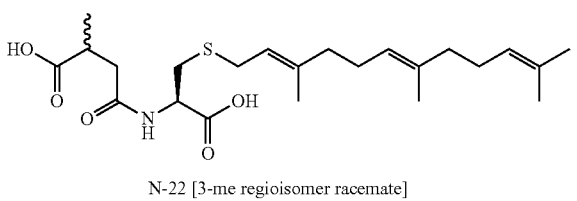

Compound N-22

N-22 [3-me regioisomer racemate]

Synthesis of a mixture of ((S)-4-((R)-1-carboxy-2-((2E,6E)-3,7,11-trimethyldodeca-2,6,10-trienylthio)ethylamino)-3-methyl-4-oxobutanoic acid) and ((R)-4-((R)-1-carboxy-2-((2E,6E)-3,7,11-trimethyldodeca-2,6,10-trienylthio)ethylamino)-3-methyl-4-oxobutanoic acid)(Compound N-22): In a 100 mL round bottom flask, to a solution of S-trans, trans-farnesyl-L-cysteine (325 mg, 1 mmol) and N-methyl-succinic-anhydride (1 mmol) in CH$_2$Cl$_2$ (10 mL) was added N,N-diisopropyl-ethyl-amine (0.87 mL, 5 mmol). The solution was stirred at room temperature for 2 h. The reaction was quenched by 1 N HCl (10 mL) and the pH was adjusted to ~0.2.0-3.0. The mixture was extracted with ethyl acetate (15 mL×3). The organic layer was dried over Na$_2$SO$_4$ and concentrated in vacuo. The residue was further purified by preparative HPLC yielding the 6:4 regioisomeric mixture of Compound N-22 and Compound N-21 in Example 58. This mixture was further purified by preparative HPLC to yield a 1:1 ratio mixture of R-R and S-R isomers of Compound N-22, similar to Compound C racemate in Examples 5 and 5a (135 mg, 31%). $^1$H-NMR (500 MHz, CD$_3$OD): δ 1.10-1.12 (m, 3H), 1.50 (s, 6H), 1.57 (s, 3H), 1.60 (s, 3H), 1.86-2.06 (m, 8H), 2.22-2.28 (m, 1H), 2.55-2.63 (m, 2H), 2.76-2.81 (m, 1H), 2.87-2.92 (m, 1H), 3.02-3.06 (m, 1H), 3.13-3.17 (m, 1H), 4.45-4.50 (m, 1H), 4.98-5.03 (m, 2H), 5.13 (t, J=7.5 Hz, 1H). $^{13}$C-NMR (125 MHz, CD$_3$OD): δ 16.15, 16.24, 17.22, 17.80, 18.41, 25.96, 27.40, 27.79, 30.10, 33.56, 33.65, 37.33, 37.93, 38.57, 40.02, 40.79, 40.89, 53.11, 53.28, 121.60, 125.14, 125.46, 132.12, 136.27, 140.48, 140.50, 173.98, 174.59, 178.25, 179.26; ES-MS: mass calcd for Chemical Formula: C$_{23}$H$_{37}$NO$_5$S 439.61. Found (M+) m/z 440.3, (M+Na) m/z 462.2.

Example 59

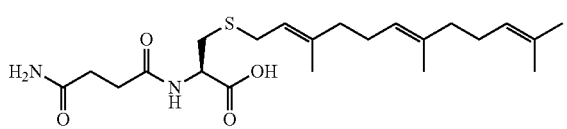

Compound N-26

Synthesis of ((R)-2-(4-amino-4-oxobutanamido)-3-((2E,6E)-3,7,11-trimethyldodeca-2,6,10-trienylthio)propanoic acid)(Compound N-26): In a 100 mL round bottom flask, to a solution of S-trans, trans-farnesyl-L-cysteine methyl ester (339 mg, 1 mmol), 4-(4,6-dimethoxy-1,3,5-triazin-2yl)-4-methylmorpholinium chloride (DMTMM, 332 mg, 1.2 mmol) and 4-amino-4-oxobutanoic acid (140 mg, 1.2 mmol) in CH$_2$Cl$_2$ (5 mL) was added N,N-diisopropyl-ethyl-amine (0.52 mL, 3 mmol). The solution was stirred at room temperature overnight. The mixture was diluted with ethyl acetate (60 mL) and washed sequentially with an NH$_4$Cl saturated solution (10 mL×1), H$_2$O (10 mL×1) and brine (10 mL×1). The organic layer was dried over Na$_2$SO$_4$ and concentrated in vacuo. The resulting residue dissolved in MeOH (3 mL) was added 5 N NaOH (3 mL) at room temperature. The reaction was left at room temperature for 10 min and the pH of the solution was adjusted to 3.0. The mixture was extracted by ethyl acetate (50 mL×1). The organic layer was dried over Na$_2$SO$_4$ and the solvent was removed in vacuo. The residue was then further purified by preparative HPLC (237 mg, 56%) to yield Compound N-26. $^1$H-NMR (500 MHz, CD$_3$OD): δ 1.50 (s, 3H), 1.51 (s, 3H), 1.57 (s, 3H), 1.60 (s, 3H), 1.86-2.04 (m, 8H), 2.40-2.48 (m, 4H), 2.63 (dd, J=5.0, 10.0 Hz, 1H), 2.89 (dd, J=5.0, 15.0 Hz, 1H), 3.02-3.06 (m, 1H), 3.14-3.21 (m, 1H), 4.48 (dd, J=5.0, 10.0 Hz, 1H), 4.98-5.01 (m, 2H), 5.13 (t, J=10.0 Hz, 1H). $^{13}$C-NMR (125 MHz, CD$_3$OD): δ 16.15, 16.24, 17.81, 25.96, 27.41, 27.80, 30.19, 31.67, 31.97, 33.48, 40.80, 40.89, 53.43, 121.61, 125.15, 125.47, 132.12, 136.28, 140.52, 174.10, 174.70, 177.43; ES-MS: mass calcd for Chemical Formula: C$_{22}$H$_{36}$N$_2$O$_4$S 424.60. Found (M+) m/z 425.3.

Example 60

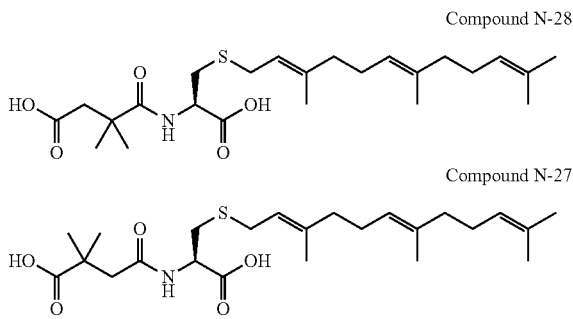

Compound N-28

Compound N-27

Synthesis of a mixture of (4-((R)-1-carboxy-2-((2E,6E)-3,7,11-trimethyldodeca-2,6,10-trienylthio)ethylamino)-3,3-dimethyl-4-oxobutanoic acid) (Compound N-27) and (4-((R)-1-carboxy-2-((2E,6E)-3,7,11-trimethyldodeca-2,6,10-trienylthio)ethylamino)-2,2-dimethyl-4-oxobutanoic acid) (Compound N-28): In a 100 mL round bottom flask, to a solution of S-trans, trans-farnesyl-L-cysteine (325 mg, 1 mmol) and 2,2-dimethylsuccinic anhydride (1 mmol) in $CH_2Cl_2$ (10 mL) was added N,N-diisopropyl-ethyl-amine (0.87 mL, 5 mmol). The solution was stirred at room temperature for 2 h. Then, the reaction was quenched by 1N HCl (10 mL) and pH was adjusted to 2.0~3.0. The mixtures were extracted by ethyl acetate (15 mL×3). The organic layer was dried over $Na_2SO_4$ and concentrated in vacuo. The residue was further purified by preparative HPLC to yield a mixture of regioisomeric compounds Compound N-27 and Compound N-28, wherein the ratio of N-28 to N-27 is 7:3 (386 mg, 85% yield). $^1$H-NMR (500 MHz, $CD_3OD$): δ 1.16-1.23 (m, 6H), 1.50 (s, 6H), 1.57 (s, 3H), 1.60 (s, 3H), 1.86-2.06 (m, 8H), 2.46-2.49 (m, 2H), 2.61 (m, 1H), 2.86 (m, 1H), 3.05-3.06 (m, 1H), 3.13-3.15 (m, 1H), 4.44-4.47 (m, 1H), 4.99-5.01 (m, 2H), 5.13 (t, J=10.0 Hz, 1H). $^{13}$C-NMR (125 MHz, $CD_3OD$): δ 16.16, 16.26, 17.81, 25.80, 25.83, 25.89, 25.96, 27.41, 27.80, 30.15, 30.72, 33.29, 33.45, 40.80, 40.90, 41.67, 41.89, 44.91, 46.19, 53.19, 53.34, 121.59, 121.61, 125.15, 125.47, 132.12, 136.27, 140.48, 140.53, 173.41, 174.92, 179.71, 181.16; ES-MS: mass calcd for Chemical Formula: $C_{24}H_{39}NO_5S$ 453.64. Found (M+) m/z 454.3, (M+Na) m/z 476.2.

Example 61

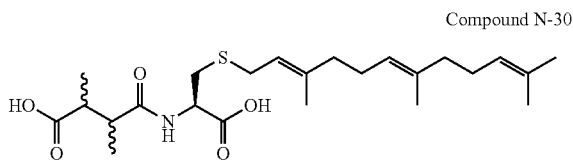

Compound N-30

Synthesis of a mixture of ((2S,3S)-4-((R)-1-carboxy-2-((2E,6E)-3,7,11-trimethyldodeca-2,6,10-trienylthio)ethylamino)-2,3-dimethyl-4-oxobutanoic acid) (Compound N-30a), ((2S,3R)-4-((R)-1-carboxy-2-((2E,6E)-3,7,11-trimethyldodeca-2,6,10-trienylthio)ethylamino)-2,3-dimethyl-4-oxobutanoic acid)(Compound N-30b), ((2R,3R)-4-((R)-1-carboxy-2-((2E,6E)-3,7,11-trimethyldodeca-2,6,10-trienylthio)ethylamino)-2,3-dimethyl-4-oxobutanoic acid) (Compound N-30c) and ((2R,3S)-4-((R)-1-carboxy-2-((2E,6E)-3,7,11-trimethyldodeca-2,6,10-trienylthio)ethylamino)-2,3-dimethyl-4-oxobutanoic acid)(Compound N-30d): In a 100 mL round bottom flask, to a solution of S-trans, trans-farnesyl-L-cysteine (325 mg, 1 mmol) and 2,3-dimethylsuccinic anhydride (1 mmol) in $CH_2Cl_2$ (10 mL) was added N,N-diisopropyl-ethyl-amine (0.87 mL, 5 mmol). The solution was stirred at room temperature for 2 h. Then, the reaction was quenched by 1N HCl (10 mL) and pH was adjusted to 2.0-3.0. The mixtures were extracted by ethyl acetate (15 mL×3). The organic layer was dried over $Na_2SO_4$ and concentrated in vacuo. The residue was further purified by preparative HPLC to yield a mixture of Compound N-30a, Compound N-30b, Compound N-30c and Compound N-30d, wherein the ratio of N-30a:N-30b:N-30c:N-30d is 1:1:1:1 (259 mg, 57%). $^1$H-NMR (500 MHz, $CD_3OD$): δ 1.05-1.10 (m, 6H), 1.50 (s, 3H), 1.51 (s, 3H), 1.57 (s, 3H), 1.60 (s, 3H), 1.86-2.06 (m, 8H), 2.49-2.65 (m, 3H), 2.84-2.88 (m, 1H), 3.06 (m, 1H), 3.13-3.15 (m, 1H), 4.43-4.48 (m, 1H), 4.99-5.02 (m, 2H), 5.11-5.14 (m, 1H). $^{13}$C-NMR (125 MHz, $CD_3OD$): δ 14.26, 14.36, 14.66, 14.92, 16.15, 16.25, 16.27, 16.76, 17.02, 17.21, 17.81, 25.96, 27.41, 27.44, 27.80, 30.02, 30.09, 30.16, 30.72, 33.34, 33.65, 40.80, 40.89, 43.22, 43.33, 43.58, 43.65, 44.52, 44.72, 45.07, 53.06, 53.10, 53.30, 121.58, 121.61, 121.63, 125.14, 125.18, 125.47, 132.12, 136.25, 140.48, 173.88, 174.10, 177.61, 178.13, 178.21, 179.02, 179.07, 179.12; ES-MS: mass calcd for Chemical Formula: $C_{24}H_{39}NO_5S$ 453.64. Found (M+) m/z 454.2, (M+Na) m/z 476.2.

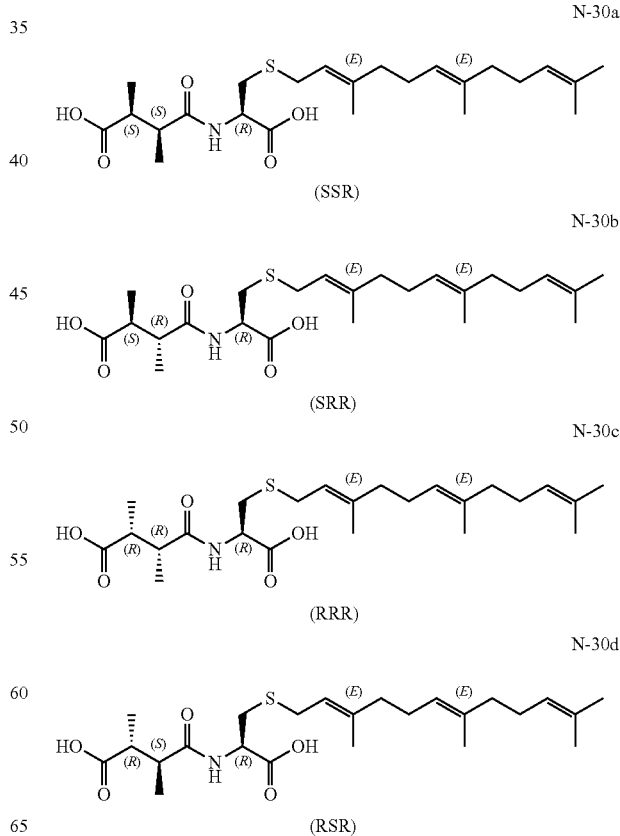

Example 62

Compound N-21

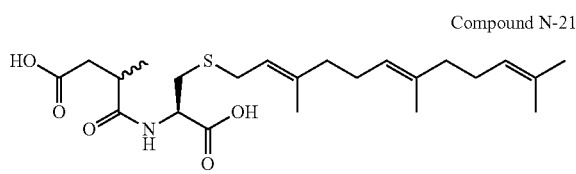 [SMILES: CC(C)=CCC/C(C)=C/CC/C(C)=C/CSC[C@H](NC(=O)C(C)CC(=O)O)C(=O)O]

Synthesis of a mixture of ((S)-4-((R)-1-carboxy-2-((2E,6E)-3,7,11-trimethyldodeca-2,6,10-trienylthio)ethylamino)-3-methyl-4-oxobutanoic acid and (R)-4-((R)-1-carboxy-2-((2E,6E)-3,7,11-trimethyldodeca-2,6,10-trienylthio) ethylamino)-3-methyl-4-oxobutanoic acid)(Compound N-21): In a 100 mL round bottom flask, to a solution of S-trans, trans-farnesyl-L-cysteine methyl ester (339 mg, 1 mmol), 4-(4,6-dimethoxy-1,3,5-triazin-2yl)-4-methylmorpholinium chloride (DMTMM, 332 mg, 1.2 mmol) and (R)-4-methoxy-2-methyl-4-oxobutanoic acid (175 mg, 1.2 mmol) in CH$_2$Cl$_2$ (5 mL) was added N,N-diisopropyl-ethyl-amine (0.52 mL, 3 mmol). The solution was stirred at room temperature for 4 h. The mixture was diluted with ethyl acetate (60 mL) and washed sequentially with an NH$_4$Cl saturated solution (10 mL×1), H$_2$O (10 mL×1) and brine (10 mL×1). The organic layer was dried over Na$_2$SO$_4$ and concentrated in vacuo. The residue was purified by flash chromatography on silica gel with hexanes/ethyl acetate (3/1) as eluent. The product obtained above was dissolved in THF (4 mL) and a solution of LiOH.H$_2$O (203 mg, 4.83 mmol) in H$_2$O (2 mL) was added slowly at 0° C. The reaction was left from 0° C. to room temperature overnight. The solution was then diluted with ethyl acetate (60 mL) and washed with 0.5 N HCl (10 mL×1), H$_2$O (10 mL×1) and brine (15 mL×1). The organic layer was dried over Na$_2$SO$_4$ and concentrated in vacuo. The residue was then further purified by preparative HPLC to yield a 1:1 ratio mixture of R-R and S-R isomers of Compound N-21, similar to Compound C racemate in Examples 5 and 5a (150 mg, 34%). $^1$H-NMR (500 MHz, CD$_3$OD): δ 1.08-1.12 (m, 3H), 1.53 (s, 6H), 1.57 (s, 3H), 1.60 (s, 3H), 1.86-2.05 (m, 8H), 2.23-2.28 (m, 1H), 2.55-2.63 (m, 2H), 2.77-2.78 (m, 1H), 2.85-2.86 (m, 1H), 3.05-3.06 (m, 1H), 3.14-3.18 (m, 1H), 4.44-4.47 (m, 1H), 4.99-5.01 (m, 2H), 5.13 (t, J=10.0 Hz, 1H). $^{13}$C-NMR (125 MHz, CD$_3$OD): δ 16.14, 16.24, 17.22, 17.80, 18.09, 25.95, 27.40, 27.42, 27.79, 30.14, 33.34, 37.40, 37.83, 38.72, 39.95, 40.79, 40.89, 53.35, 53.43, 121.60, 122.62, 125.15, 125.16, 125.46, 132.11, 136.25, 140.48, 140.51, 174.04, 174.08, 175.52, 178.29, 179.26; ES-MS: mass calcd for Chemical Formula: C$_{23}$H$_{37}$NO$_5$S 439.61. Found (M+) m/z 440.3, (M+Na) m/z 462.2.

Example 63

Compound N-51

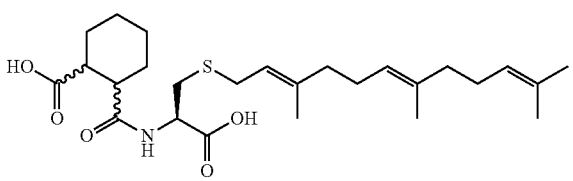

Synthesis of a mixture of stereoisomers ((1S,2R)-2-((R)-1-carboxy-2-((2E,6E)-3,7,11-trimethyldodeca-2,6,10-trienylthio)ethylcarbamoyl)cyclohexanecarboxylic acid)(Compound N-51a) and ((1R,2S)-2-((R)-1-carboxy-2-((2E,6E)-3,7,11-trimethyldodeca-2,6,10-trienylthio)ethylcarbamoyl) cyclohexanecarboxylic acid) (Compound N-51b): In a 100 mL round bottom flask, to a solution of S-trans, trans-farnesyl-L-cysteine (325 mg, 1 mmol) and hexa-hydro-phthalic anhydride (1 mmol) in CH$_2$Cl$_2$ (10 mL) was added N,N-diisopropyl-ethyl-amine (0.87 mL, 5 mmol). The solution was stirred at room temperature for 2 h. Then, the reaction was quenched by 1N HCl (10 mL) and pH was adjusted to 2.0~3.0. The mixtures were extracted by ethyl acetate (15 mL×3). The organic layer was dried over Na$_2$SO$_4$ and concentrated in vacuo. The residue was further purified by preparative HPLC to yield a 7:3 mixture of Compound N-51a and Compound N-51b (352 mg, 73%). $^1$H-NMR (500 MHz, CDCl$_3$): δ 1.18-1.48 (m, 4H), 1.53 (s, 6H), 1.59 (s, 3H), 1.61 (s, 3H), 1.71-1.88 (m, 4H), 1.88-2.00 (m, 8H), 2.79-2.89 (m, 3H), 3.01-3.18 (m, 3H), 4.51-4.77 (m, 1H), 5.01-5.03 (m, 2H), 5.13 (m, 1H), 6.39 (m, 0.5H), 6.52 (d, J=5.0 Hz, 0.5H). $^{13}$C-NMR (125 MHz, CDCl$_3$): δ 15.00, 15.11, 15.18, 16.68, 20.77, 20.78, 21.32, 22.53, 22.94, 23.90, 24.71, 25.38, 25.52, 25.67, 25.69, 27.06, 27.72, 27.94, 28.20, 28.58, 28.65, 28.68, 28.72, 31.45, 31.64, 38.60, 38.65, 38.67, 38.70, 38.80, 40.83, 41.09, 41.27, 42.11, 43.21, 49.61, 50.42, 50.63, 52.79, 118.05, 118.24, 118.29, 122.67, 122.70, 122.77, 123.26, 123.30, 130.28, 130.33, 134.27, 134.34, 134.37, 139.11, 139.27, 139.44, 171.39, 173.68, 173.85, 178.08, 178.12, 178.69; ES-MS: mass calcd for Chemical Formula: C$_{26}$H$_{41}$NO$_5$S 479.67. Found (M+) m/z 480.4, (M+Na) m/z 502.3.

N-51a

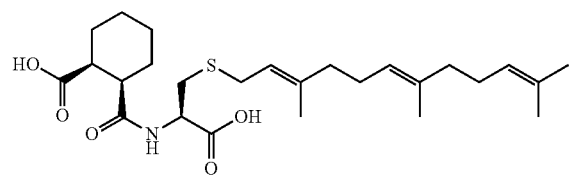

(S-R-R enantiomer)

N-51b

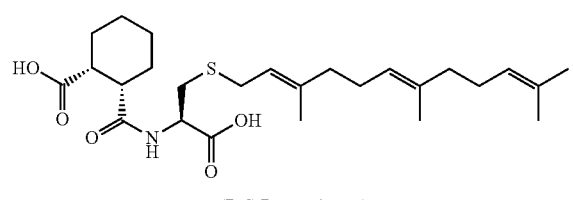

(R-S-R enantiomer)

Example 64

Compound N-42

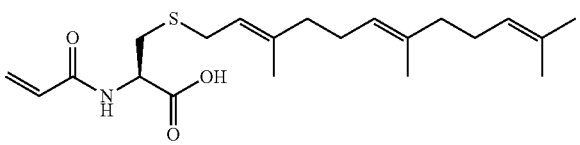

Synthesis of ((R)-2-acrylamido-3-((2E,6E)-3,7,11-trimethyldodeca-2,6,10-trienylthio)propanoic acid)(Compound N-42): In a 100 mL round bottom flask, 3-chloro-propionic acid (1.0 mmol), coupling reagent (520 mg of PBOP or 380 mg of HATU, 1 mmol) and N,N-diisopropyl-ethyl-amine (650 mg, 5 mmol) were mixed in CH$_2$Cl$_2$ (10 mL). The reaction mixture was stirred at room temperature for 30 minutes. S-trans, trans-Farnesyl-L-cysteine (325 mg, 1 mmol) was added to the reaction mixture. The reaction mixture was stirred at room temperature overnight. CH$_2$Cl$_2$ was removed by rotary evaporation. The resulting residue was dissolved in ethyl acetate (50 mL). The organic solution was washed with an NH$_4$Cl saturated solution (50 mL), dried over Na$_2$SO$_4$, and concentrated to afford a crude mixture. The crude mixture was purified by preparative HPLC (120 mg, 32%) to yield Compound N-42. $^1$H-NMR (500 MHz, CD$_3$OD): δ 1.50 (s, 6H), 1.57 (s, 3H), 1.64 (s, 3H), 1.85-1.88 (m, 2H), 1.95-2.06 (m, 6H), 2.67 (dd, J=9.0, 14.0 Hz, 1H), 2.93 (dd, J=4.5, 14.0 Hz, 1H), 3.06 (dd, J=7.0, 13.0 Hz, 1H), 3.20 (dd, J=9.0, 14.0 Hz, 1H), 4.58 (dd, J=4.5, 8.5 Hz, 1H), 4.98-5.03 (m, 2H), 5.13 (t, J=7.5 Hz, 1H), 5.61 (d, J=10.0 Hz, 1H), 6.17 (d, J=17.0 Hz, 1H), 6.28 (dd, J=10.0, 17.0 Hz, 1H). $^{13}$C-NMR (125 MHz, CD$_3$OD): δ 16.16, 16.25, 17.81, 25.96, 27.39, 27.79, 30.16, 33.36, 40.79, 40.89, 53.50, 121.60, 125.14, 125.47, 127.47, 131.65, 132.10, 136.27, 140.55, 168.00, 173.81; ES-MS: mass calcd for Chemical Formula: C$_{21}$H$_{33}$NO$_3$S 379.56. Found (M+Na) m/z 402.2.

Example 65

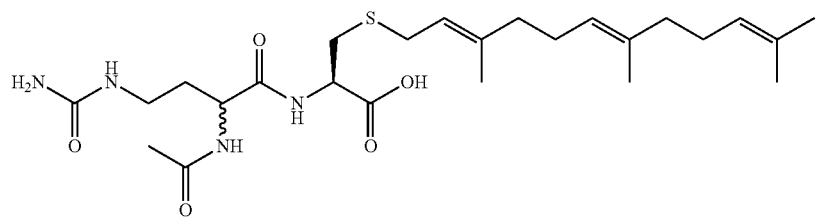

Synthesis of a mixture of ((R)-2-((S)-2-acetamido-4-ureidobutanamido)-3-((2E,6E)-3,7,11-trimethyldodeca-2,6,10-trienylthio)propanoic acid and (R)-2-((R)-2-acetamido-4-ureidobutanamido)-3-((2E,6E)-3,7,11-trimethyldodeca-2,6,10-trienylthio)propanoic acid)(Compound N-77): In a 100 mL round bottom flask, Fmoc-(D,L)-citrulline-OH (1 mmol) was mixed with HATU (380 mg, 1 mmol) and N,N-diisopropyl-ethyl-amine (650 mg, 5 mmol) in DMF (10 mL). After stirring at ambient temperature for 30 min S-trans, trans-farnesyl-L-cysteine methyl ester (340 mg, 1 mmol) was added and the reaction mixture is additionally stirred for 16 hrs. The reaction was quenched by addition of piperidine (10 mL) and stirring for 2 hrs. Then water (10 mL) was added to crush the desired product out of the mixture followed by filtration. The separated product, (2S)-2-[4-(carbamoylamino)-2-aminobutanamido]-3-{[(2E,6E)-3,7,11-trimethyldodeca-2,6,10-trien-1-yl]sulfanyl}propanoic acid (468 mg, 1 mmol) was dissolved in acetic anhydride (3 mL, excess) and reaction was stirred at RT for 2 hrs. Then the excess of acetic anhydride was removed on rotavap, the resulting product was re-suspended in THF (5 mL) and LiOH (saturated aq. solution, 0.25 mL) was added and the resulting mixture stirred for 4 hrs. The mixture was purified by HPLC to yield a 1:1 racemic mixture of R-R and S-R isomers of Compound N-77, similar to Compound C racemate in Examples 5 and 5a (209 mg, 41% yield). $^1$H-NMR (500 MHz, MeOH-d$_4$): δ 1.24-1.61 (m, 9H), 1.63 (br s, 2H), 1.89 (s, 3H), 1.93 (s, 3H), 1.91-2.05 (m, 2H), 2.52-2.55 (m, 1H), 2.81-2.83 (m, 1H), 2.98-3.19 (m, 8H), 4.32 (t, J=4.5 Hz, 1H), 4.46 (t, J=6.5 Hz, 1H), 5.11 (br s, 2H), 5.23 (br s, 1H). $^{13}$C-NMR (125 MHz, MeOH-d$_4$): δ 16.1, 16.2, 23.2, 26.0, 27.4, 27.8, 30.2, 30.3, 33.8, 40.2, 40.3, 48.5, 54.4, 54.5, 121.7, 125.1, 125.5, 132.1, 136.3, 140.5, 162.4, 173.3, 174.5; ES-MS: mass calcd for Chemical Formula: C$_{26}$H$_{44}$N$_4$O$_5$S 524.7. Found (M+) m/z 525.3.

Example 66

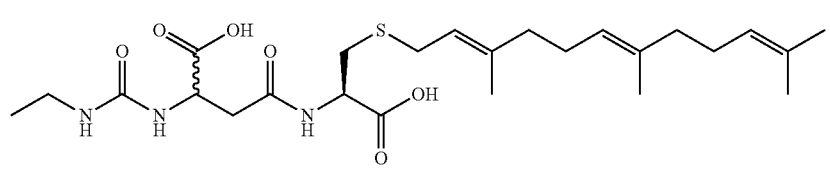

Compound N-77

Synthesis of a mixture of ((S)-4-((R)-1-carboxy-2-((2E,6E)-3,7,11-trimethyldodeca-2,6,10-trienylthio)ethylamino)-2-(3-ethylureido)-4-oxobutanoic acid and (R)-4-((R)-1-carboxy-2-((2E,6E)-3,7,11-trimethyldodeca-2,6,10-trienylthio)ethylamino)-2-(3-ethylureido)-4-oxobutanoic acid) (Compound N-78): In a 100 mL round bottom flask, Fmoc-(D,L)-aspartic acid alpha-methyl ester (1 mmol) was mixed with HATU (380 mg, 1 mmol) and N,N-diisopropyl-ethyl-amine (650 mg, 5 mmol) in DMF (10 mL). After stirring at ambient temperature for 30 min, S-trans, trans-farnesyl-L-cysteine methyl ester (340 mg, 1 mmol) was added and the reaction mixture is additionally stirred for 16 hrs. The reaction was quenched by addition of piperidine (10 mL) and stirring for 2 hrs. Then water (10 mL) was added to crush the desired product out of the mixture followed by filtration. The separated product, 3-{[(1R)-1-carboxy-2-{[(2E,6E)-3,7,11-trimethyldodeca-2,6,10-trien-1-yl]sulfanyl}ethyl]carbamoyl}-2-aminopropanoic acid (440 mg, 1 mmol) was dissolved in ethyl isocyanate (3 mL, excess) and reaction was stirred at RT for 2 hrs. Then the reaction mixture was concentrated on rotavap, the resulting product was re-suspended in THF (5 mL) and LiOH (saturated aq. solution, 0.25 mL) was added and the resulting mixture stirred for 4 hrs. The mixture was purified by HPLC (167 mg, 32% yield) to yield a 1:1 racemic mixture of R-R and S-R isomers of Compound N-78, similar to Compound C racemate in Examples 5 and 5a. $^1$H-NMR (500 MHz, MeOH-d$_4$): δ 0.94 (t, J=7.5 Hz, 3H), 1.61 (s, 6H), 1.63 (s, 6H), 2.55-2.81 (m, 4H), 2.83-2.86 (m, 1H), 3.04 (q, J=7.5 Hz, 2H), 3.14-3.20 (m, 2H), 4.46-4.49 (m, 2H), 5.11 (m, 2H), 5.23 (t, J=7.5, 1H). $^{13}$C-NMR (125 MHz, MeOH-d$_4$): δ 16.1, 16.2, 18.3, 26.2, 27.4, 27.8, 30.5, 34.4, 34.5, 35.8, 38.9, 40.8, 40.9, 54.0, 55.3, 121.5, 125.1, 125.5, 132.1, 136.3, 140.5, 160.4, 172.4, 174.3, 175.6; ES-MS: mass calcd for Chemical Formula: C$_{25}$H$_{41}$N$_3$O$_6$S 511.7. Found (M+) m/z 512.3.

Example 67

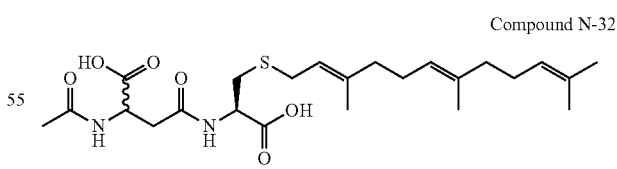

Compound N-32

Compound N-78

Synthesis of ((R)-2-acetamido-4-((R)-1-carboxy-2-((2E,6E)-3,7,11-trimethyldodeca-2,6,10-trienylthio)ethylamino)-4-oxobutanoic acid and (S)-2-acetamido-4-((R)-1-carboxy-2-((2E,6E)-3,7,11-trimethyldodeca-2,6,10-trienylthio)ethylamino)-4-oxobutanoic acid)(Compound N-32): In a 100 mL round bottom flask, Fmoc-(D,L)-aspartic acid alpha-methyl ester (1 mmol) was mixed with HATU (380 mg, 1 mmol) and N,N-diisopropyl-ethyl-amine (650 mg, 5 mmol) in DMF (10 mL). After stirring at ambient temperature for 30 min, S-trans, trans-farnesyl-L-cysteine methyl ester (340 mg, 1 mmol) was added and the reaction mixture is additionally stirred for 16 hrs. The reaction was quenched by addition of piperidine (10 mL) and stirring for 2 hrs. Then water (10 mL) was added to crush the desired product out of the mixture followed by filtration. The separated product, 3-{[(1R)-1-carboxy-2-{[(2E,6E)-3,7,11-trimethyldodeca-2,6,10-trien-1-yl]sulfanyl}ethyl]carbamoyl}-2-aminopropanoic acid (440 mg, 1 mmol) was dissolved in acetic anhydride (3 mL, excess) and reaction was stirred at RT for 2 hrs. Then the excess of acetic anhydride was removed on rotavap, the resulting product was re-suspended in THF (5 mL) and LiOH (saturated aq. solution, 0.25 mL) was added and the resulting mixture stirred for 4 hrs. The mixture was purified by HPLC (322 mg, 67% yield) to yield a 1:1 racemic mixture of R-R and S-R isomers of Compound N-32, similar to Compound C racemate in Examples 5 and 5a. $^1$H-NMR (500 MHz, MeOH-d$_4$): δ 1.29-1.68 (m, 12H), 1.73 (s, 3H), 1.89-1.93 (m, 4H), 2.52-2.55 (m, 4H), 2.81-2.83 (m, 1H), 2.98-3.19 (m, 2H), 4.32 (s, 1H), 4.46 (s, 1H), 5.11 (br s, 2H), 5.23 (br s, 1H). $^{13}$C-NMR (125 MHz, MeOH-d$_4$): δ 16.1, 16.3, 17.8, 22.6, 23.2, 26.0, 27.4, 27.8, 30.2, 30.3, 33.8, 40.2, 40.3, 48.5, 52.4, 121.7, 125.1, 125.5, 132.1, 136.3, 140.5, 162.4, 172.0, 173.2; ES-MS: mass calcd for Chemical Formula: $C_{24}H_{38}N_2O_6S$ 482.6. Found (M+) m/z 483.3.

Example 68

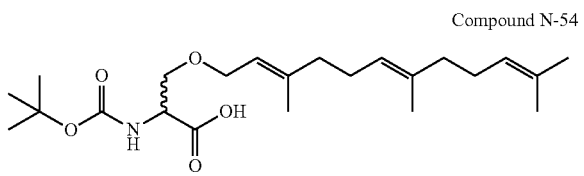 [SMILES: CC(C)=CCC/C(C)=C/CC/C(C)=C/COCC(NC(=O)OC(C)(C)C)C(=O)O]

Compound N-54

Synthesis of racemic mixture of (2-{[(tert-butoxy)carbonyl]amino}-3-{[(2E,6E)-3,7,11-trimethyldodeca-2,6,10-trien-1-yl]oxy}propanoic acid)(Compound N-54): In a 100 mL round bottom flask, N-Boc-(D,L)-serine (410 mg, 2 mmol) was mixed with DMF (anhydrous, 10 mL) and NaH (60% in mineral oil, 100 mg, excess) with vigorous steering at under stream of nitrogen and at room temperature. After 30 min the excessive foaming subsided and trans, trans-farnesyl bromide was added dropwise (284 mg, 1 mmol) over 10 min. The reaction solution was stirred at room temperature overnight then quenched with ammonium chloride (aq. sat., 20 mL) and the product was extracted with ethyl acetate (2×10 mL). The organic layer was dried over magnesium sulfate, concentrated and re-suspended in ethanol (1 mL) to afford a crude mixture. The crude mixture was purified by preparative HPLC (76 mg, 19%) to yield a 1:1 racemic mixture of R and S enantiomers of Compound N-54. $^1$H-NMR (500 MHz, MeOH-d$_4$): δ 1.47 (s, 9H), 1.69 (s, 6H), 1.83 (s, 6H), 2.01 (t, J=6.5 Hz, 2H), 2.07-2.16 (m, 6H), 3.67 (dd, J=7.0, 12.0 Hz, 1H), 5.11-5.14 (m, 2H), 5.23 (t, J=7.5, 1H). $^{13}$C-NMR (125 MHz, MeOH-d$_4$): δ 16.3, 16.7, 17.9, 26.1, 27.4, 27.8, 28.8, 40.8, 40.9, 55.3, 68.5, 70.4, 80.7, 121.8, 125.5, 132.1, 136.3, 141.8, 157.9, 173.9; ES-MS: mass calcd for Chemical Formula: $C_{23}H_{39}NO_5$ 409.6. Found (M+Na) m/z 432.3.

Example 69

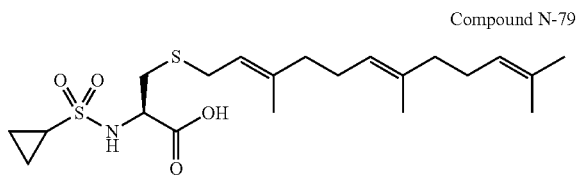 [SMILES: CC(C)=CCC/C(C)=C/CC/C(C)=C/CSC[C@H](NS(=O)(=O)C1CC1)C(=O)O]

Compound N-79

Synthesis of ((R)-2-(cyclopropanesulfonamido)-3-((2E,6E)-3,7,11-trimethyldodeca-2,6,10-trienylthio)propanoic acid)(Compound N-79): In a 100 mL round bottom flask, to a suspension of cyclopropanesulfonyl chloride (169 mg, 1.2 mmol) and S-trans, trans-farnesyl-L-cysteine (325 mg, 1 mmol) in THF (5 mL) was added N,N-diisopropyl-ethyl-amine (0.52 mL, 3 mmol) dropwise. The solution was stirred at room temperature overnight. The mixture was diluted with ethyl acetate (60 mL) and washed by 0.5 N HCl (10 mL×1), H$_2$O (10 mL×2) and brine (10 mL×1). The organic layer was dried over Na$_2$SO$_4$ and concentrated in vacuo. The residue was then further purified by preparative HPLC (50 mg, 12%) to yield Compound N-79. $^1$H-NMR (500 MHz, CD$_3$OD): δ 0.86-0.89 (m, 2H), 0.93-0.96 (m, 2H), 1.50 (s, 3H), 1.51 (s, 3H), 1.57 (s, 3H), 1.61 (s, 3H), 1.86-1.89 (m, 2H), 1.95-1.98 (m, 4H), 2.00-2.04 (m, 2H), 2.43-2.46 (m, 1H), 2.66-2.68 (m, 1H), 2.76-2.79 (m, 1H), 3.09-3.13 (m, 1H), 3.16-3.21 (m, 1H), 4.02 (t, J=5.0 Hz, 1H), 4.99-5.01 (m, 2H), 5.15 (t, J=5.0 Hz, 1H). $^{13}$C-NMR (125 MHz, CD$_3$OD): δ 5.58, 6.28, 16.16, 16.30, 17.81, 25.96, 27.39, 27.80, 30.41, 31.73, 34.88, 40.79, 40.90, 57.75, 121.67, 125.17, 125.47, 132.12, 136.28, 140.55, 174.39; ES-MS: mass calcd for Chemical Formula: $C_{21}H_{35}NO_4S_2$ 429.64. Found (M+) m/z 430.2, (M+Na) m/z 452.2.

Example 70

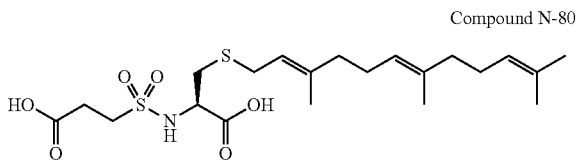 [SMILES: CC(C)=CCC/C(C)=C/CC/C(C)=C/CSC[C@H](NS(=O)(=O)CCC(=O)O)C(=O)O]

Compound N-80

Synthesis of ((R)-2-(2-carboxyethylsulfonamido)-3-((2E,6E)-3,7,11-trimethyldodeca-2,6,10-trienylthio)propanoic acid)(Compound N-80): In a 100 mL round bottom flask, to a solution of methyl 3-(chlorosulfonyl)propanoate (187 mg, 1 mmol) and S-trans, trans-farnesyl-L-cysteine methyl ester (339 mg, 1 mmol) in THF (5 mL) was added N,N-diisopropyl-ethyl-amine (0.52 mL, 3 mmol) dropwise. The solution was stirred at 0° C. for 30 min and then room temperature overnight. The mixture was diluted with ethyl acetate (60 mL) and washed by 0.5 N HCl (10 mL×1), H$_2$O (10 mL×1) and brine (10 mL×1). The organic layer was dried over $Na_2SO_4$ and concentrated in vacuo. The resulting residue was dissolved in THF (3 mL) and a solution of $LiOH.H_2O$ (420 mg, 10 mmol) in $H_2O$ (2 mL) was added slowly at 0° C. The reaction was left at room temperature overnight. The solution was then diluted with ethyl acetate and washed by 0.5 N HCl (10 mL×1), $H_2O$ (10 mL×2) and brine (15 mL×1). The organic layer was dried over $Na_2SO_4$ and concentrated in vacuo. The residue was then further purified by preparative HPLC (100 mg, 22%) to yield Compound N-80. $^1H$-NMR (500 MHz, $CD_3OD$): δ 1.50 (s, 3H), 1.51 (s, 3H), 1.57 (s, 3H), 1.61 (s, 3H), 1.86-1.89 (m, 2H), 1.95-2.00 (m, 4H), 2.01-2.06 (m, 4H), 2.65 (dd, J=8.0, 14.0 Hz, 1H), 2.71-2.76 (m, 2H), 2.84 (dd, J=5.0, 14.0 Hz, 1H), 3.13 (dd, J=7.5, 13.5 Hz, 1H), 3.24-3.29 (m, 1H), 4.05 (dd, J=5.0, 8.0 Hz, 1H), 4.98-5.03 (m, 2H), 5.09-5.14 (t, J=8.0 Hz, 1H). $^{13}C$-NMR (125 MHz, $CD_3OD$): δ 16.15, 16.30, 17.80, 25.95, 27.38, 27.79, 29.56, 30.44, 34.80, 40.78, 40.89, 49.82, 57.51, 121.64, 125.16, 125.46, 132.12, 136.27, 140.62, 174.04, 174.15; ES-MS: mass calcd for Chemical Formula: $C_{21}H_{35}NO_6S_2$ 461.64. Found (M+) m/z 462.2, (M+Na) m/z 484.2.

Example 71

Compound N-81

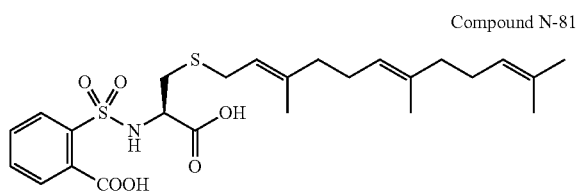 [SMILES: CC(C)=CCC/C(C)=C/CC/C(C)=C/CSC[C@H](NS(=O)(=O)c1ccccc1C(=O)O)C(=O)O]

Synthesis of (2-(N—((R)-1-carboxy-2-((2E,6E)-3,7,11-trimethyldodeca-2,6,10-trienylthio)ethyl)sulfamoyl)benzoic acid)(Compound N-81): In a 100 mL round bottom flask, to a solution of methyl 2-(chlorosulfonyl)benzoate (281 mg, 1.2 mmol) and S-trans, trans-farnesyl-L-cysteine (325 mg, 1 mmol) in THF (5 mL) was added N,N-diisopropyl-ethyl-amine (0.52 mL, 3 mmol) dropwise. The solution was stirred at room temperature for 4 h. The mixture was diluted with ethyl acetate (60 mL) and washed sequentially with an $NH_4Cl$ saturated solution (10 mL×2), $H_2O$ (10 mL×1) and brine (10 mL×1). The organic layer was dried over $Na_2SO_4$ and concentrated in vacuo. The resulting residue was dissolved in THF (3 mL) and a solution of $LiOH.H_2O$ (210 mg, 5 mmol) in $H_2O$ (2 mL) was added slowly at 0° C. The reaction was left at room temperature overnight. The reaction was quenched with 1 N HCl and pH was adjusted to 2.0. The solution was then extracted by ethyl acetate (30 mL×3). The organic layer was dried over $Na_2SO_4$ and concentrated in vacuo. The residue was then further purified by preparative HPLC (290 mg, 57%) to yield Compound N-81. $^1H$-NMR (500 MHz, $CD_3OD$): δ 1.50 (s, 6H), 1.55 (s, 3H), 1.57 (s, 3H), 1.86-1.89 (m, 2H), 1.94-2.02 (m, 6H), 2.71 (dd, J=6.0, 14.0 Hz, 1H), 2.77 (dd, J=5.5, 14.0 Hz, 1H), 3.01-3.08 (m, 2H), 4.10 (t, J=6.0 Hz, 1H), 5.00-5.06 (m, 3H), 7.56-7.62 (m, 2H), 7.84 (d, J=6.5 Hz, 1H), 7.93 (d, J=7.5 Hz, 1H). $^{13}C$-NMR (125 MHz, $CD_3OD$): δ 16.17, 16.28, 17.81, 24.24, 25.96, 27.36, 27.78, 30.52, 34.79, 40.75, 40.89, 57.80, 121.53, 125.14, 125.46, 130.07, 132.13, 132.56, 133.78, 136.28, 140.63, 140.72, 170.16, 173.07; ES-MS: mass calcd for Chemical Formula: $C_{25}H_{35}NO_6S_2$ 509.68. Found (M+Na) m/z 532.1.

Example 72

Compound N-53

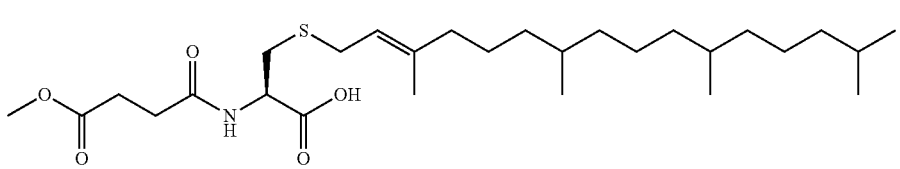

Synthesis of (N-[1-Carboxy-2-(3,7,11,15-tetramethyl-hexadec-2-enylsulfanyl)-ethyl]-succinamic acid methyl ester)(Compound N-53): In a 100 mL round bottom flask, phytol (trans: cis (2:1) isomeric mixture of 34.9 mL, 100 mmol) and triethylamine (1.4 mL, 10 mmol) were added to toluene (100 mL), the reaction mixture was cooled down to −78° C. Phosphorus tribromide (4.7 mL, 50 mmol) was added dropwise. After addition complete, the reaction mixture was warmed up to room temperature and stirred for 4 hours. Water (100 mL) was added dropwise to quench the reaction. Ethyl acetate (200 mL) was added and then washed with water (50 mL×2) and brine (50 mL×2) sequentially. The ethyl acetate solution was dried by $Na_2SO_4$ and concentrated in vacuo. The resulting residue was directly used for the next reaction. L-cysteine hydrochloride monohydrate (1.90 g, 10.73 mmol) and potassium carbonate (2.96 mg, 21.45 mmol) were added to ethanol (40 mL) and water (40 mL), the reaction was stirred at room temperature for 30 min, phytyl bromide (2.56 g, 7.15 mmol) was added. The reaction mixture was stirred at room temperature under argon for 4 hours. The precipitate obtained was washed by water, ethanol and dry in vacuum for 72 hours. White solid obtained was product which was directly used for the next reaction. Mono-methyl succinate (132 mg, 1 mmol), 2-(7-Aza-1H-benzotriazole-1-yl)-1,1,3,3-tetramethyluronium hexafluorophosphate (1 mg, 1.1 mmol) and N,N-diisopropyl-ethyl-amine (0.52 mL, 3 mmol) were mixed in THF (5 mL). The reaction solution was stirred at room temperature for ten minutes. 2-Amino-3-(3,7,11,15-tetramethyl-hexadec-2-enylsulfanyl)-propionic acid (399 mg, 1 mmol) was added to reaction mixture. The reaction solution was stirred at room temperature overnight. Ethyl acetate (50 mL) was added and then washed with saturated ammonium chloride aqueous solution (20 mL×2), DI water (20 mL×2) and brine (20 mL×2) sequentially. The ethyl acetate solution was dried by $Na_2SO_4$ and concentrated in vacuo to afford a crude mixture of 1:1 trans isomers and 1:1 cis isomers of compound N-53, wherein the ratio of trans isomers to cis isomers is 7:3 (200 mg, 40%). $^1H$-NMR (500 MHz, MeOH-$d_4$): δ 0.76-0.79 (m, 12H), 1.00-1.46 (m, 19H), 1.58 and 1.63 (s, 3H), 1.91-1.99 (m, 2H), 2.48-2.52 (m, 4H), 2.60-2.64 (m, 1H), 2.87 (dd, J=4.5, 14.0 Hz, 1H), 3.04-3.07 (m, 1H), 3.14-3.18 (m, 1H), 3.57 (s, 3H), 4.46-4.49 (m, 1H), 5.12 (t, J=7.5 Hz, 1H). $^{13}C$-NMR (125 MHz, MeOH-$d_4$): δ 20.12, 20.17, 20.23, 23.05, 23.14, 23.59, 25.52, 25.94, 25.96, 26.30, 26.31, 26.64, 29.19, 30.20, 30.40, 31.26, 32.87, 33.54, 33.79, 33.82, 33.88, 33.94, 33.97, 37.62, 37.71, 38.41, 38.50, 40.56, 40.95, 52.27, 53.40, 53.53, 121.43, 121.89, 140.87, 141.01; ES-MS: mass calcd for Chemical Formula: $C_{28}H_{51}NO_5S$ 513.3. Found (M+Na) m/z 536.3.

Example 73

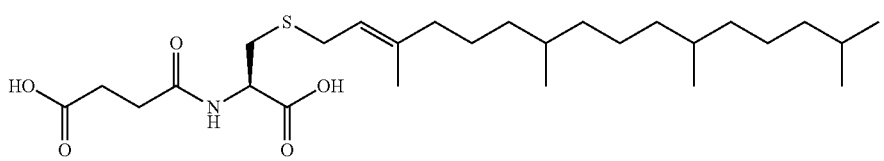

Compound N-48

Synthesis of (N-[1-Carboxy-2-(3,7,11,15-tetramethyl-hexadec-2-enylsulfanyl)-ethyl]-succinamic acid)(Compound N-48): In a 100 mL round bottom flask, phytol (trans: cis (2:1) isomeric mixture of 34.9 mL, 100 mmol) and triethylamine (1.4 mL, 10 mmol) were added to toluene (100 mL), the reaction mixture was cooled down to −78° C. Phosphorus tribromide (4.7 mL, 50 mmol) was added dropwise. After addition complete, the reaction mixture was warmed up to room temperature and stirred for 4 hours. Water (100 mL) was added dropwise to quench the reaction. Ethyl acetate (200 mL) was added and then washed with water (50 mL×2) and brine (50 mL×2) sequentially. The ethyl acetate solution was dried by $Na_2SO_4$ and concentrated in vacuo to afford a crude mixture of 1:1 trans isomers and 1:1 cis isomers of compound N-48, wherein the ratio of trans isomers to cis isomers is 7:3. The crude mixture (1 mmol) and LiOH (126 mg, 3 mmol) were mixed in THF (3 mL) and water (3 mL). The reaction solution was stirred at room temperature for 4 hours. Ethyl acetate (50 mL) was added and then washed with 1N HCl (20 mL×2) and brine (20 mL×2) sequentially. The ethyl acetate solution was dried by $Na_2SO_4$ and concentrated in vacuo to afford a partially purified mixture that was purified by HPLC to yield two fractions.

The first fraction yielded a mixture of 1:1 trans isomers and 1:1 cis isomers of compound N-48, wherein the ratio of trans isomers to cis isomers is 1:1 (50 mg, 20%). $^1$H-NMR (500 MHz, MeOH-$d_4$): δ 0.76-0.79 (m, 12H), 1.00-1.46 (m, 19H), 1.58 and 1.63 (s, 3H), 1.90-1.93 (m, 2H), 2.46-2.49 (m, 4H), 2.62-2.66 (m, 1H), 2.87 (dd, J=4.5, 14.0 Hz, 1H), 3.04-3.07 (m, 1H), 3.14-3.18 (m, 1H), 4.46-4.49 (m, 1H), 5.12 (t, J=7.5 Hz, 1H). $^{13}$C-NMR (125 MHz, MeOH-$d_4$): δ 16.11, 20.13, 20.17, 20.23, 23.06, 23.15, 23.59, 25.53, 25.95, 26.31, 26.65, 29.19, 30.25, 30.29, 30.41, 31.41, 31.44, 32.88, 33.56, 33.79, 33.83, 33.94, 33.98, 37.62, 37.72, 37.92, 38.01, 38.41, 38.47, 38.51, 40.57, 40.96, 53.43, 53.44, 53.56, 121.44, 121.90, 140.86, 141.00, 174.02, 174.05, 174.47, 174.52, 176.17, 176.19; ES-MS: mass calcd for Chemical Formula: $C_{27}H_{49}NO_5S$ 499.3. Found (M+Na) m/z 522.3.

The second fraction yielded a 1:1 mixture of trans isomers of compound N-48 (45 mg, 23%). $^1$H-NMR (500 MHz, MeOH-$d_4$): δ 0.76-0.79 (m, 12H), 1.00-1.46 (m, 19H), 1.58 (s, 3H), 1.90-1.93 (m, 2H), 2.46-2.49 (m, 4H), 2.63 (dd, J=8.5, 13.5 Hz, 1H), 2.87 (dd, J=4.5, 14.0 Hz, 1H), 3.02-3.07 (m, 1H), 3.14-3.18 (m, 1H), 4.46-4.49 (m, 1H), 5.11 (t, J=7.5 Hz, 1H). $^{13}$C-NMR (125 MHz, MeOH-$d_4$): δ 16.10, 16.11, 20.11, 20.16, 20.22, 23.05, 23.14, 25.52, 25.94, 25.95, 26.30, 26.32, 29.19, 30.23, 30.23, 30.28, 31.40, 33.54, 33.55, 33.79, 33.82, 33.94, 33.97, 37.61, 37.71, 38.40, 38.47, 38.50, 38.53, 40.56, 40.95, 53.43, 121.44, 140.87, 174.03, 174.53, 176.19; ES-MS: mass calcd for Chemical Formula: $C_{27}H_{49}NO_5S$ 499.3. Found (M+Na) m/z 522.3.

Example 74

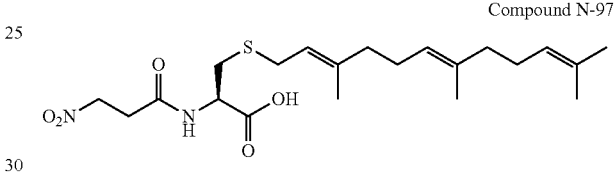

Compound N-97

Synthesis of ((R)-2-(3-nitropropanamido)-3-((2E,6E)-3,7,11-trimethyldodeca-2,6,10-trienylthio)propanoic acid) (Compound N-97): To a solution of 3-nitropropionic acid (143 mg, 1.2 mmol) and 4-(4,6-dimethoxy-1,3,5-triazin-2yl)-4-methylmorpholinium chloride (DMTMM, 332 mg, 1.2 mmol) in $CH_2Cl_2$ (5 mL) was added N,N-diisopropyl-ethyl-amine (0.52 mL, 3 mmol). After stirring for 10 min, S-trans, trans-farnesyl-L-cysteine methyl ester (339 mg, 1.0 mmol) was added slowly. The solution was stirred at room temperature for 4 h and then diluted with ethyl acetate (60 mL). The solution was washed sequentially with an NH4Cl saturated solution (10 mL×1), $H_2O$ (10 mL×1) and brine (10 mL×1). The organic layer was dried over $Na_2SO_4$ and concentrated in vacuo. The residue was purified by flash chromatography on silica gel with hexanes/ethyl acetate (3/1) as eluent. The product (408 mg, 0.93 mmol) obtained above was dissolved in THF (4 mL) and a solution of LiOH.$H_2O$ (117 mg, 2.79 mmol) in $H_2O$ (3 mL) was added slowly at 0° C. The reaction was left at 0° C. for 30 min. The solution was then diluted with ethyl acetate (60 mL) and washed with 0.5 N HCl (10 mL×1), $H_2O$ (10 mL×2) and brine (10 mL×1). The organic layer was dried over $Na_2SO_4$ and concentrated in vacuo. The residue was then further purified by preparative HPLC (288 mg, 68%) to yield Compound N-97. $^1$H-NMR (500 MHz, $CD_3OD$) δ 1.51 (s, 6H), 1.57 (s, 3H), 1.59 (s, 3H), 1.86-1.89 (m, 2H), 1.96-2.04 (m, 6H), 2.64 (dd, J=8.5, 14.0 Hz, 1H), 2.85-2.87 (m, 3H), 3.06-3.07 (m, 1H), 3.18 (dd, J=8.5, 13.5 Hz, 1H), 4.50 (dd, J=5.0, 8.0 Hz, 1H), 4.63 (dd, J=5.0, 11.0 Hz, 2H), 4.99-5.01 (m, 2H), 5.13 (t, J=8.0 Hz, 1H). $^{13}$C-NMR (125 MHz, $CD_3OD$): δ 16.14, 16.22, 17.80, 25.95, 27.40, 27.80, 30.19, 32.80, 33.47, 40.79, 40.87, 53.50, 71.03, 121.56, 125.14, 125.46, 132.12, 136.26, 140.57, 171.55, 173.86; ES-MS: mass calcd for Chemical Formula: $C_{21}H_{34}N_2O_5S$ 426.57. Found (M+1) m/z 427.3, (M+23) m/z 449.3.

Example 75

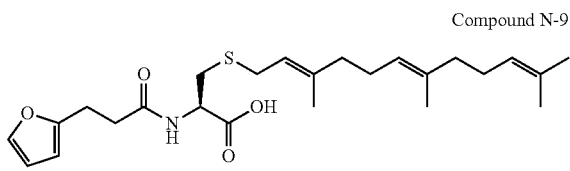 [SMILES: CC(C)=CCC/C(C)=C/CC/C(C)=C/CSC[C@H](NC(=O)CCc1cccs1)C(=O)O]

Compound N-96

Synthesis of ((R)-2-(3-(furan-2-yl)propanamido)-3-((2E,6E)-3,7,11-trimethyldodeca-2,6,10-trienylthio)propanoic acid)(Compound N-96): To a solution of 3-(2-furyl) propionic acid (168 mg, 1.2 mmol) and 4-(4,6-dimethoxy-1,3,5-triazin-2yl)-4-methylmorpholinium chloride (DMTMM, 332 mg, 1.2 mmol) in $CH_2Cl_2$ (5 mL) was added N,N-diisopropyl-ethyl-amine (0.52 mL, 3 mmol). After stirring for 10 min, S-trans, trans-farnesyl-L-cysteine (325 mg, 1 mmol) was added slowly. The solution was stirred at room temperature overnight and then diluted with ethyl acetate (60 mL). The solution was washed by 0.5 N HCl (10 mL×1), $H_2O$ (10 mL×1) and brine (10 mL×1). The organic layer was dried over $Na_2SO_4$ and concentrated in vacuo. The residue was purified by preparative HPLC (333 mg, 74%) to yield Compound N-96. $^1$H-NMR (500 MHz, $CD_3OD$): δ 1.50 (s, 6H), 1.57 (s, 3H), 1.59 (s, 3H), 1.86-1.89 (m, 2H), 1.95-2.06 (m, 6H), 2.51 (t, J=8.0 Hz, 2H), 2.57-2.62 (m, 1H), 2.83-2.869 (m, 3H), 3.05 (dd, J=7.5, 13.5 Hz, 1H), 3.12-3.16 (m, 1H), 4.49 (dd, J=4.5, 8.0 Hz, 1H), 4.99-5.01 (m, 2H), 5.13 (t, J=7.5 Hz, 1H). $^{13}$C-NMR (125 MHz, $CD_3OD$): δ 16.15, 16.24, 17.80, 24.96, 25.95, 27.39, 27.79, 30.11, 33.41, 35.08, 40.79, 40.89, 53.30, 106.28, 111.19, 121.61, 125.14, 125.46, 132.12, 136.27, 140.49, 142.36, 155.72, 174.00, 174.78; ES-MS: mass calcd for Chemical Formula: $C_{25}H_{37}NO_4S$ 447.63. Found (M+1) m/z 448.3, (M+23) m/z 470.2.

Example 76

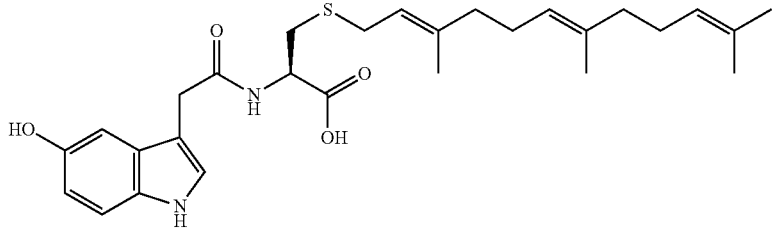

Compound N-39

Synthesis of ((R)-2-(2-(5-hydroxy-1H-indol-3-yl)acetamido)-3-((2E,6E)-3,7,11-trimethyldodeca-2,6,10-trienylthio)propanoic acid)(Compound N-39): In 24 mL vial, 5-hydroxyl indole-3-acetic acid (191 mg, 1.0 mmol), HATU (380 mg, 1 mmol) and N,N-diisopropyl-ethyl-amine (650 mg, 5 mmol) were mixed in THF (10 mL). The reaction mixture was stirred at room temperature for 30 minutes. S-trans, trans-Farnesyl-L-cysteine (325 mg, 1 mmol) was added to the reaction mixture. The reaction mixture was stirred at room temperature overnight. THF was removed by rotary evaporation. The resulting residue was dissolved in ethyl acetate (50 mL). The organic solution was washed with water (50 mL) and brain (50 mL), dried over $Na_2SO_4$, and concentrated to afford a crude mixture. The crude mixture was purified by preparative HPLC (210 mg, 42%) to yield Compound N-39. $^1$H-NMR (500 MHz, $CD_3OD$): δ 1.49 (s, 9H), 1.56 (S, 3H), 1.85-1.98 (m, 6H), 2.62 (dd, J=8.0, 14.0 Hz, 1H), 2.80 (dd, J=4.5, 14.0 Hz, 1H), 2.88 (dd, J=7.0, 13.0 Hz, 1H), 2.98 (dd, J=8.5, 13.0 Hz, 1H), 3.55 (dd, J=6.5, 22.5 Hz, 2H), 4.49 (dd, J=5.0, 8.0 Hz, 1H), 4.98 (bs, 2H), 6.57 (d, J=8.5 Hz, 1H), 6.84 (s, 1H), 7.07 (d, J=6.5 Hz, 2H). $^{13}$C-NMR (125 MHz, $CD_3OD$): δ 16.2, 17.8, 26.0, 27.3, 27.4, 27.8, 28.8, 30.2, 33.3, 33.8, 40.7, 40.9, 53.4, 103.7, 108.2, 112.7, 112.8, 121.5, 125.2, 125.5, 125.8, 129.3, 132.1, 133.0, 136.2, 140.5, 151.5, 173.9, 174.9; ES-MS: mass calcd for Chemical Formula: $C_{28}H_{38}N_2O_4S$ 498.3 (M+). Found (M+1) m/z 499.2.

Example 77

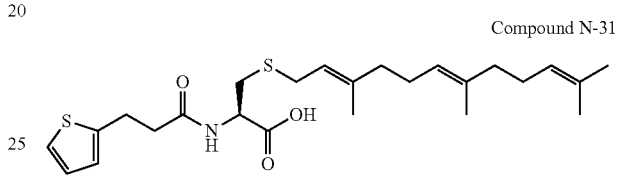

Compound N-31

Synthesis of ((R)-2-(3-(thiophen-2-yl)propanamido)-3-((2E,6E)-3,7,11-trimethyldodeca-2,6,10-trienylthio)propanoic acid)(Compound N-31): To a solution of 3-(2-thienyl) propanoic acid (187 mg, 1.2 mmol) and 4-(4,6-dimethoxy-1,3,5-triazin-2yl)-4-methylmorpholinium chloride (DMTMM, 332 mg, 1.2 mmol) in $CH_2Cl_2$ (5 mL) was added N,N-diisopropyl-ethyl-amine (0.52 mL, 3 mmol). After stirring for 5 min, S-trans, trans-farnesyl-L-cysteine (325 mg, 1 mmol) was added slowly. The solution was stirred at room temperature for 4 h and then diluted with ethyl acetate (60 mL). The solution was washed sequentially with an $NH_4Cl$ saturated solution (15 mL×2), $H_2O$ (10 mL×1) and brine (15 mL×1). The organic layer was dried over $Na_2SO_4$ and concentrated in vacuo. The residue was purified by preparative HPLC (310 mg, 67%) to yield Compound N-31. $^1$H-NMR (500 MHz, $CD_3OD$): δ 1.50 (s, 6H), 1.57 (s, 3H), 1.59 (s, 3H), 1.86-1.89 (m, 2H), 1.96-2.06 (m, 6H), 2.54 (t, J=7.5 Hz, 2H), 2.56-2.61 (m, 1H), 2.87 (dd, J=4.5, 14.0 Hz, 1H), 3.00-3.06 (m, 3H), 3.11-3.15 (m, 1H), 4.49 (dd, J=5.0, 8.5 Hz, 1H), 5.00-5.01 (m, 2H), 5.12 (t, J=7.5 Hz, 1H). $^{13}$C-NMR (125 MHz, $CD_3OD$): δ 16.16, 16.25, 17.81, 25.96, 26.74, 27.40, 27.79, 30.13, 33.42, 38.74, 40.79, 40.89, 53.32, 121.62, 124.36, 125.14, 125.47, 125.75, 127.81, 132.11, 136.27, 140.47, 144.46, 174.98, 174.64; ES-MS: mass calcd for Chemical Formula: $C_{25}H_{37}NO_3S_2$ 463.70. Found (M+23) m/z 486.2.

Example 78

Compound N-35

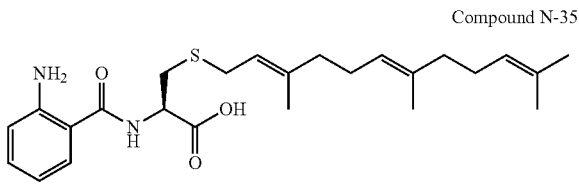 [SMILES: CC(C)=CCC/C(C)=C/CC/C(C)=C/CSC[C@H](NC(=O)c1ccccc1N)C(=O)O]

Synthesis of (2-[(2-aminophenyl)formamido]-3-{[(2E,6E)-3,7,11-trimethyldodeca-2,6,10-trien-1-yl]sulfanyl}propanoic acid)(Compound N-35): Anthranilic acid (137 mg, 1 mmol) is mixed with HATU (380 mg, 1 mmol) and N,N-diisopropyl-ethyl-amine (650 mg, 5 mmol) in DMF (10 mL). After stirring at ambient temperature for 30 min, S-trans, trans-farnesyl-L-cysteine methyl ester (340 mg, 1 mmol) is added and the reaction mixture is additionally stirred for 16 hrs. Then LiOH (saturated aq. solution, 0.25 mL) was added and the resulting mixture stirred for 4 hrs. The mixture was purified by HPLC (107 mg, 24% yield) to yield Compound N-35. $^1$H-NMR (500 MHz, MeOH-d$_4$): δ 1.42 (s, 6H), 1.54 (s, 3H), 1.58 (s, 3H), 1.84-2.07 (m, 8H), 2.76 (dd, J=12.1 Hz, J=14.2 Hz, 1H), 2.93 (s, J=7.4 Hz, J=14.2 Hz, 1H), 3.14 (d, J=12.1 Hz, 2H), 4.32 (t, J=4.5 Hz, 1H), 4.51 (br.s, 2H), 4.59 (t, J=7.5 Hz, 1H), 4.98-5.00 (m, 2H), 5.15 (t, J=12.1 Hz, 1H), 6.55 (t, J=7.4 Hz, 1H), 6.65 (d, J=7.2 Hz, 1H), 7.10 (t, J=7.4 Hz, 1H), 7.41 (d, J=7.4 Hz, 1H). $^{13}$C-NMR (125 MHz, MeOH-d$_4$): δ 16.3, 16.4, 23.3, 25.9, 26.0, 27.7, 27.8, 30.4, 40.7, 40.9, 53.9, 117.1, 117.8, 118.3, 121.4, 125.1, 125.5, 129.3, 132.1, 134.4, 136.2, 140.6, 150.4, 171.6, 175.9; ES-MS: mass calcd for Chemical Formula: $C_{26}H_{44}N_4O_5S$ 444.6. Found (M+Na) m/z 466.3.

Biological Examples

Described below are in vivo assays used to measure the biological activity of provided compounds, including the anti-inflammatory or proinflammatory properties of the compounds, as measured by edema inhibition, erythema inhibition and MPO inhibition.

Example 79

Mouse Model of Inflammation-Edema, Erythema and MPO
Background

The mouse ear model of contact irritation has been established as an appropriate model to determine whether topically applied anti-inflammatories inhibit the development of acute, chemically induced dermal irritation [see Van Arman, C. G. et al., *Clin Pharmacol Ther,* 1974, 16: 900-4; Young et al., *J Invest Dermatol,* 1983, 80: 48-52; Tramposch et al., (Morgan D W, Marshall L A eds), *Birkhäuser Verlag: Basel,* 1999, pp 179-204; and Gordon et al., *J Invest Dermatol,* 2008, 128: 643-54)]. Moreover, the mouse ear model has been used by various groups to identify and compare members of differing classes of anti-inflammatory agents with multiple mechanisms of action (reviewed in Tramposch et al., (Morgan D W, Marshall L A eds), *Birkhäuser Verlag: Basel,* 1999, pp 179-204). The commonly used end points of inflammation are edema (Young et al., *J Invest Dermatol,* 1983, 80: 48-52), (assayed by increase in ear thickness), neutrophil infiltration (which is measured by assaying for the neutrophil marker myeloperoxidase ("MPO") (see Bradley et al., *Blood,* 1982, 60: 618-22) and erythema (skin redness). Using this mouse in vivo model for contact irritation, the present example demonstrates that certain isoprenyl compounds of the present invention, when topically applied exhibit in vivo anti-inflammatory or proinflammatory activities, as evidenced by the effect on the commonly-used inflammatory end-points such as edema, erythema and neutrophil infiltration (MPO neutrophil marker) activities. The example can further be used to identify which structures possess physical or chemical properties critical for inhibiting innate inflammation in the skin.

(a) Protocol—Edema Inhibition

The protocol for inducing in vivo acute contact inflammation on the ears of live mice has been described elsewhere (reviewed in Tramposch et al., (Morgan D W, Marshall L A eds), *Birkhäuser Verlag: Basel,* 1999, pp 179-204). In brief, mice were sedated and their ears were treated with 1.2 µg/20 uL TPA (i.e., tetradecanoylphorbol-13-acetate). After 5 minutes, we dosed these TPA-treated ears with a single 8 µg/20 uL dose, a 2 ug/20 uL dose, or both doses, of the isoprenyl compounds. After 24 hours, the mice were sacrificed and edema was measured by taking micrometer readings of each ear. The percent inhibition of edema was determined by taking the average ear thickness of compound-treated ears and dividing it by the average thickness of 12 ears that only received TPA and subtracting that value from 100%. These values were corrected for the thickness of normal, non TPA-treated mouse ears of littermate controls. Results demonstrating percent inhibition of edema for representative compounds of the present invention are depicted in FIG. 1. ED$_{50}$ values were calculated as described in Gordon et al., *J Invest Derm,* 2008, 128: 643-654. ED$_{50}$ results for AFC and compound A are depicted in FIG. 2.

(b) Protocol—Erythema Inhibition

Another well documented biomarker of skin inflammation is skin redness, termed erythema, which is caused by capillary congestion and dilation in response to various chemical and environmental insults (see Denig, N. I. et al., *Postgrad Med,* 1998; 103: 199-200, 207-8, 212-3). The protocol for measuring erythema inhibition by isoprenyl compounds was developed in-house by utilizing the CR-400 chroma meter from Konica Minolta (http://www.konicaminolta.com/instruments/products/color/colorimeters/cr400-410/index.html). This instrument was used to measure the Δa* redness value from 6 mm biopsy punches taken 24 hours post TPA/compound treatment as described in the edema inhibition section above. The percent inhibition of erythema was determined by taking the average Δa* redness value of compound-treated ears and dividing it by the average Δa* value of 12 ears that only received TPA and subtracting that value from 100%. These values were corrected for the Δa* value of non TPA-treated mouse ears of littermate controls. Results demonstrating percent inhibition of erythema for representative compounds of the present invention are depicted in FIG. 1. ED$_{50}$ values were calculated as described in Gordon et al., *J Invest Derm,* 2008, 128: 643-654. ED$_{50}$ results for AFC and compound A are depicted in FIG. 2.

(c) Protocol—MPO Inhibition

To assay for inhibition of dermal neutrophil infiltration by isoprenyl compounds, a standard method was used (see Bradley et al., *J Invest Dermatol,* 1982,78: 206-209; Young et al., *J Invest Dermatol,* 1983, 80: 48-52; De Young et al, *Agents Actions,* 1989, 26: 335-41; and Rao et al., *Inflammation,* 1993, 17: 723-41). Briefly, we homogenized 6 mm biopsy punches taken from both compound-treated ears as well as TPA-treated and non-treated control groups. We quantitated the levels of MPO by a colorimetric reaction that was measured spectrophotometrically. The percent inhibition of neutrophil infiltration by each isoprenyl compound was determined by comparing the average MPO levels in the presence and absence of these compounds. The calculation for percent inhibition of MPO was determined similar to that as described for calculating the percent edema inhibition. Results demonstrating percent inhibition of MPO for representative compounds of the present invention are depicted in FIG. 1. $ED_{50}$ values were calculated as described in Gordon et al., *J Invest Derm*, 2008, 128: 643-654. $ED_{50}$ results for AFC and compound A are depicted in FIG. 2. Summary of activity ranges determined from an MPO activity assay for compounds in Table 1 are presented in FIG. 3.

Described below are assays used to measure the biological activity of provided compounds, including the anti-inflammatory properties of the compounds, as measured by inhibition of cytokine levels determined using inflammatory models.

Example 80

TPA-Induced Mouse Ear Model of Inflammation—Inhibition of Cytokine Levels

The protocol for inducing acute inflammation in mouse ears has been described elsewhere (reviewed in Tramposch et al., (Morgan D W, Marshall L A eds), *Birkhäuser Verlag: Basel*, 1999, pp 179-204) and similar to the protocol described in Example 79. Using this mouse in vivo model for contact irritation, the present example demonstrates that certain isoprenyl compounds, when topically applied, exhibit in vivo anti-inflammatory activities, in part, by inhibiting the levels of pro-inflammatory cytokines, such as TNF-α and IL-1β, resulting in the observed effects on the inflammatory end-points of edema, erythema and neutrophil infiltration (MPO neutrophil marker) activities, as demonstrated in Example 79. In brief, male Swiss Webster (ICR) mice 10-12 weeks age (Hilltop Lab Animals) were used for these experiments (6 animals per group). Mice received 1.2 μg/20 μl TPA dissolved in acetone [10 μl applied both to the dorsal and ventral surfaces of the mouse ear (20 μl total) using a solvent pipette] to each ear to induce acute irritation. After 5 minutes, Compound A was applied at several concentrations in ethanol. After 24 hours treatment, mice were euthanized and 6-mm punch biopsy specimens were obtained from each ear, snap frozen in liquid nitrogen and stored in −80° C. until use. Ear biopsy specimens were homogenized with HTAB buffer using a Bio-Pulverizer (MP Biomedicals, 2×45 sec at 4 m/s). Samples were centrifuged at 10,000 rpm for 10 min at 4° C. Supernatants were subjected to cytokine profiling by ELISA for the stimulated production of TNF-α and IL-1β using protein standards for quantification. $ED_{50}$ results (μg/ear) for TNF-α and IL-1β, obtained for Compound A using a TPA-induced mouse ear inflammation model are depicted in FIGS. 4A and 4B.

Example 81

Figures 5A, 5B:
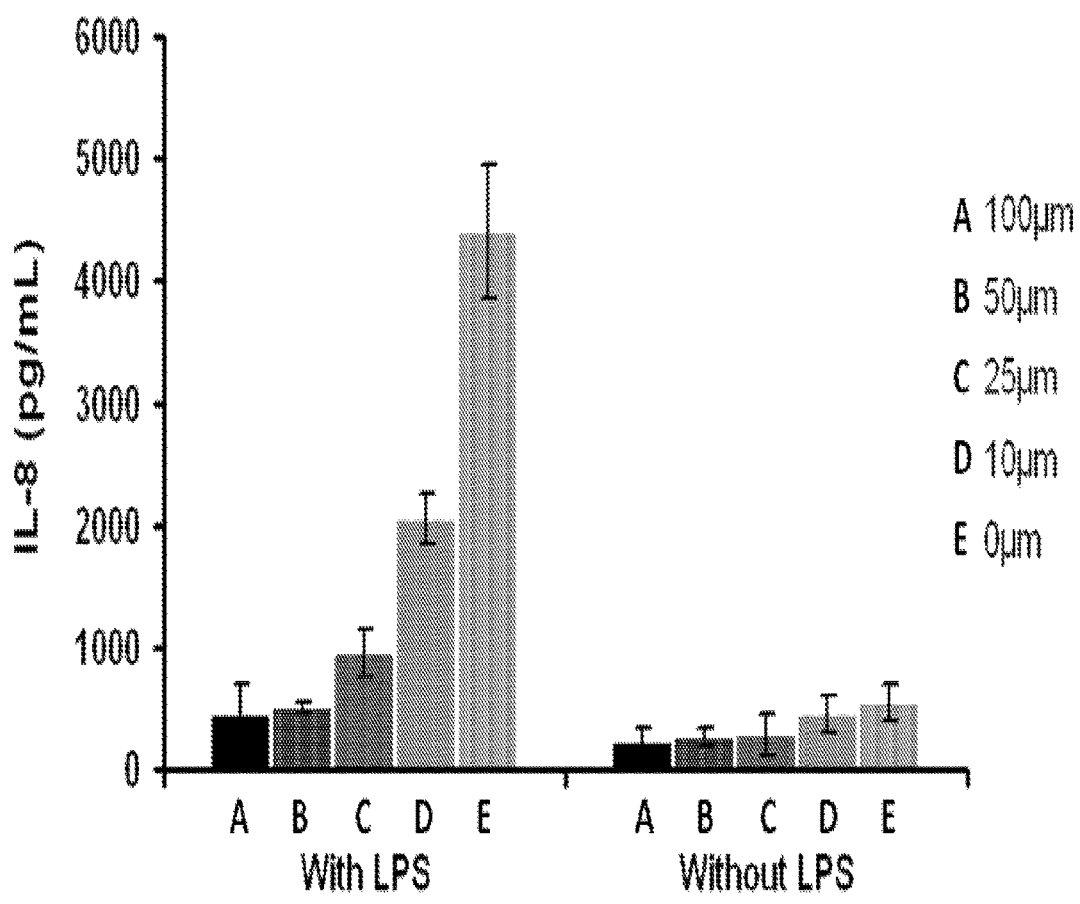
FIG. 5A and FIG. 5B depict bar graphs depicting IL-8 levels (pg/mL) obtained for Compound A in the presence (FIG. 5A panel) and absence (FIG. 5B panel) demonstrating a dose dependent inhibition of LPS-TLR4 induced IL-8 release with, as determined using human microvascular endothelial cell line-1 (HMEC-1) cultures.

LPS-TLR4-induced Inflammation Model in HMEC-1 Cells—Inhibition of Cytokine Levels The activation of Toll-like receptor 4 (TLR4) by lipopolysaccharide (LPS) induces the release of proinflammatory cytokines that are necessary to mediate key immune and inflammatory responses (reviewed in Yong-Chen et al., *Cytokines*, 2008, 42: 145-151). The present example demonstrates that certain isoprenyl compounds of the present invention inhibit TLR4 inflammatory signaling pathways resulting in reduction of proinflammatory cytokine release, for example of IL-8. Human Microvascular Endothelial cells (HMECs) were cultured in EC basal medium (EBM; Cambrex, Walkersville, Md.), supplemented with 0.5% fetal bovine serum (FBS), epidermal growth factor (EGF) (10 ng/mL) hydrocortisone (1 μg/mL) and 100 U/mL penicillin/ 100 μg/mL streptomycin at 37° C. with 5% $CO_2$ (referred to as supplemented media). In order to avoid possible immunomodulating effects of these agents during agonist/antagonist treatments, for some periods, cells were kept in EBM supplemented only with 0.5% FBS and penicillin/streptomycin without EGF or hydrocortisone (referred to as depleted media). Cells were plated at a concentration of $0.25 \times 10^6$ cells/well in supplemented media in 12-well plates. After cells were allowed to adhere (6-8 hours), media was changed to depleted media. After 24 hours, depleted media was removed and fresh depleted media containing various concentrations of Compound A in triplicate was added to the appropriate wells. Two hours later, to induce a pro-inflammatory response, LPS was added (100 μM) in separate wells (in triplicate) (Bender et al., *Exp Dermatol*, 2008, 17: 752-60; and Seiffert et al., *J Invest Dermatol*, 2006, 126: 1017-27). Cell cultures were examined for viability by Trypan blue exclusion and the reduction of 3-(4,5-dimethylthiazol-2-yl)-5-(3-carboxymethoxyphenyl)-2-(4-sulfophenyl)-2H-tetrazolium (MTS assay; Promega, Madison, Wis.) to determine the percentage of viable cells of various treatment concentrations of Compound A. After 6 hours of incubation, supernatants were harvested and assayed by enzyme-linked immunosorbent assays (ELISA) for the stimulated release of IL-8 using appropriate protein standards (BD Pharmigen). IL-8 levels (pg/mL), obtained with Compound A using an LPS-TLR4-induced inflammation model in HMEC-1 cells are depicted in FIGS. 5A and 5B.

Example 82

Figures 6A, 6B:
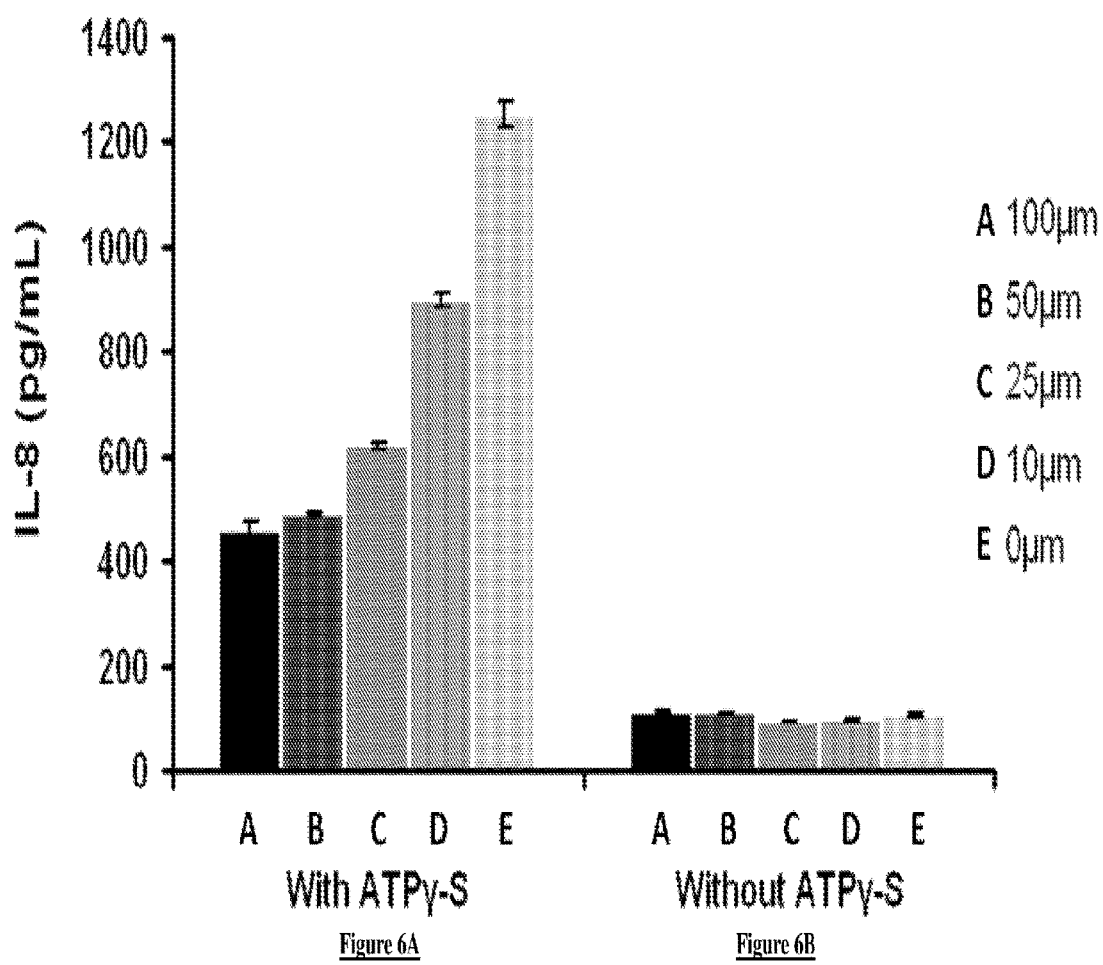
FIG. 6A and FIG. 6B are bar graphs depicting IL-8 levels (pg/mL) obtained for Compound A in the presence (FIG. 6A panel) and absence (FIG. 6B panel) of ATP-γS, demonstrating a dose dependent inhibition of ATP-γS-purinergic receptor-induced IL-8 release, as determined using human microvascular endothelial cell line-1 (HMEC-1) cultures.
Figures 7A, 7B:
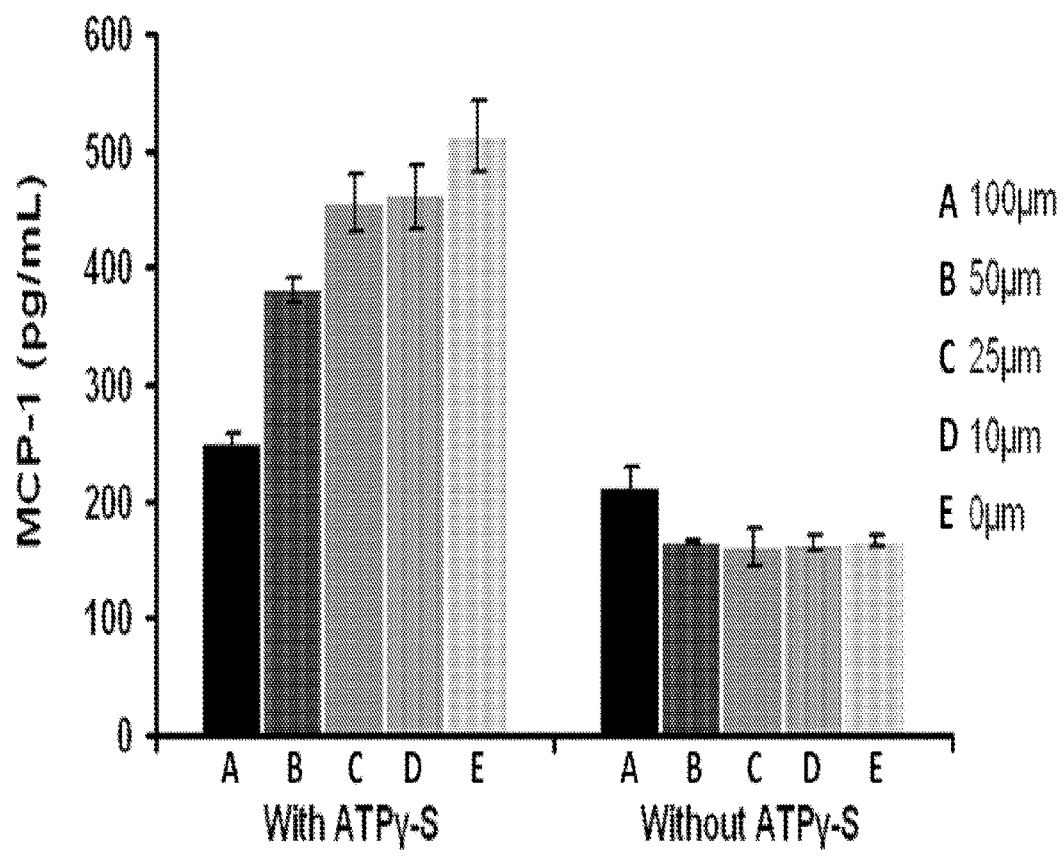
FIG. 7A and FIG. 7B are bar graphs depicting MCP-1 levels (pg/mL) obtained for Compound A in the presence (FIG. 7A panel) and absence (FIG. 7B panel) of ATP-γS, demonstrating a dose dependent inhibition of ATP-γS-purinergic receptor-induced IL-8 release, as determined using human microvascular endothelial cell line-1 (HMEC-1) cultures.

ATPγS-Purinergic Receptor-induced Inflammation Model in HMEC-1 Cells—Inhibition of Cytokine Levels ATP, serving as an extra-cellular signaling molecule, is known to activate purinergic P2 receptors which are expressed on a variety of cells involved in immune and inflammatory responses, including macro- and microvascular endothelial cells (ECs). During the pathophysiology of inflammatory skin disorders, dermal microvascular ECs recruit inflammatory cells, including leukocytes, to the sites of inflammation, such as on the skin, triggered, in part, by the release of proinflammatory mediators, such as IL-6 and MCP-1 (Swerlick et al., *J Invest Dermatol*, 1993, 100: 111S-115S). It has been previously demonstrated that the non-hydrolyzable analog of ATP, i.e., ATPγS induces the production of proinflammatory cytokines in human dermal microcascular endothelial cells through the modulation of the P2 purinergic receptor signaling (Seiffert et al., *J Invest Dermatol*, 2006, 126: 1017-27). The protocol for inducing the production of proinflammatory cytokines in human microvascular endothelial cells (HMECs) with ATPγS, as previously described, serves as a cell-based model for studying the anti-inflammatory activities of test compounds. Using this cell-based model, the present example demonstrates that certain isoprenyl compounds of the present invention exhibit anti-inflammatory activity, as evidenced by the inhibition of ATPγS-induced-purinergic receptor-mediated release of proinflammatory mediators such as IL-8 and MCP-1. HMECs were cultured in EC basal medium (EBM; Cambrex, Walkersville, Md.), supplemented with 0.5% fetal bovine serum (FBS), epidermal growth factor (EGF) (10 ng/mL) hydrocortisone (1 μg/mL) and 100 U/mL penicillin/100 μg/mL streptomycin at 37° C. with 5% $CO_2$ (referred to as supplemented media). In order to avoid possible immunomodulating effects of these agents during agonist/antagonist treatments, for some periods, cells were kept in EBM supplemented only with 0.5% FBS and penicillin/streptomycin without EGF or hydrocortisone (referred to as depleted media). Cells were plated at a concentration of $0.25 \times 10^6$ cells/well in supplemented media in 12-well plates. After cells are allowed to adhere (6-8 hours), media is changed to depleted media. After 24 hours, depleted media was removed and fresh depleted media containing various concentrations of Compound A in triplicate was added to the appropriate wells. Two hours later, to induce a pro-inflammatory response, ATPγS was added (100 μM) in separate wells (in triplicate) (Bender et al., Exp Dermatol, 2008, 17: 752-60; and Seiffert et al., J Invest Dermatol, 2006, 126: 1017-27). Cell cultures were examined for viability by Trypan blue exclusion and the reduction of 3-(4,5-dimethylthiazol-2-yl)-5-(3-carboxymethoxyphenyl)-2-(4-sulfophenyl)-2H-tetrazolium (MTS assay; Promega, Madison, Wis.) to determine the percentage of viable cells of various treatment concentrations of Compound A. After 6 hours of incubation, supernatants were harvested and assayed by enzyme-linked immunosorbent assays (ELISA) for the stimulated release of MCP-1, and IL-8 using appropriate protein standards (BD Pharmigen). IL-8 levels (pg/mL), obtained with Compound A using an ATPγS-purinergic Receptor-induced Inflammation model in HMEC-1 cells are depicted in FIG. 6. MCP-1 levels (pg/mL), obtained with Compound A using an ATPγS-purinergic Receptor-induced Inflammation model in HMEC-1 cells are depicted in FIGS. 7A and 7B.

Example 83

TPA-induced Inflammation Model in NHEK Cells—Inhibition of Cytokine Levels

Figures 8A, 8B:
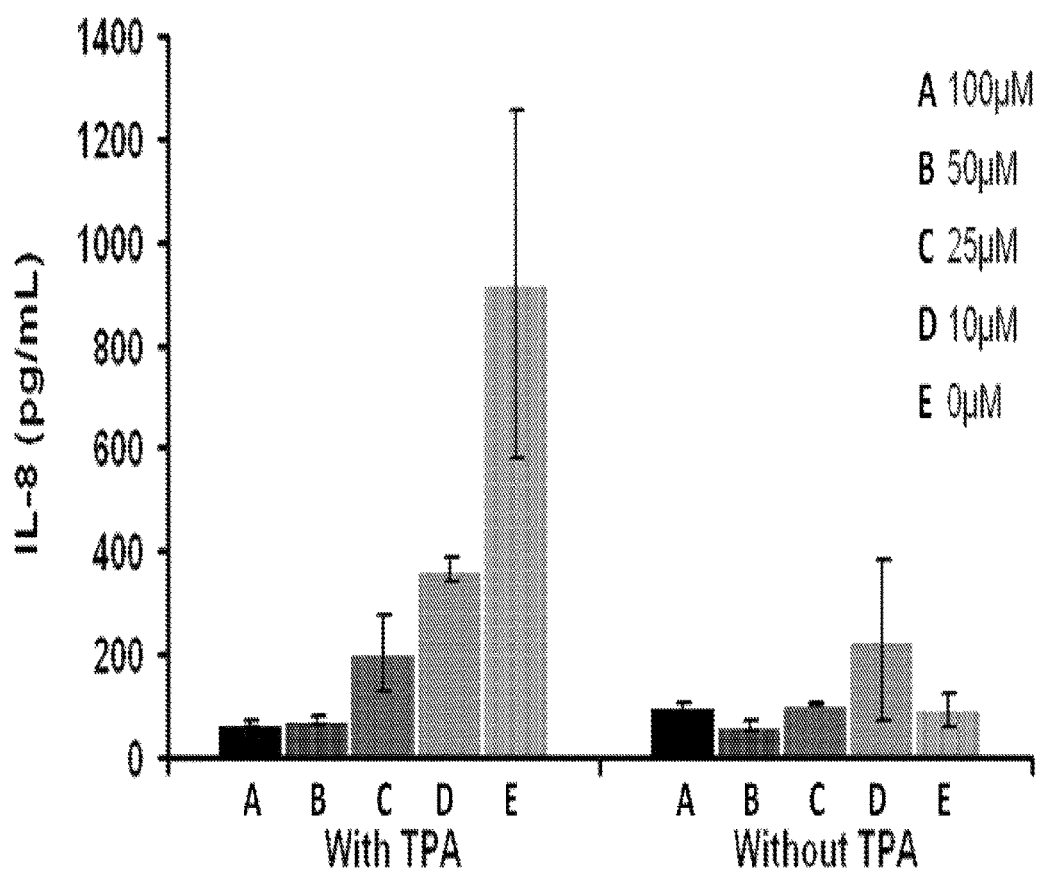
FIG. 8A and FIG. 8B are bar graphs depicting IL-8 levels (pg/mL) obtained for Compound A, demonstrating a dose dependent inhibition of TPA-induced IL-8 release, as determined using Normal Human Epidermal Keratinocyte (NHEK) cell cultures.

The present example demonstrates that certain isoprenyl compounds of the present invention exhibit anti-inflammatory activity, as evidenced by the inhibition of TPA-induced release of proinflammatory mediators such as IL-8, in a human keratinocyte cell line (NHEK), similar to the effect on TPA-induced in vivo mouse ear model of inflammation as described in Example 80. NHEK cells were cultured in keratinocyte growth medium (KGM; Gibco, Carlsbad, Calif.), in a serum-free environment, supplemented with EGF (10 ng/mL), hydrocortisone (1 μg/mL), bovine insulin (5 μg/mL) and human pituitary gland extract (2 mL) at 37° C. with 5% $CO_2$. To avoid any possible modulating effects of these agents during agonist/antagonist treatments, cells were kept in KGM supplemented without EGF or hydrocortisone (depleted medium). Cells were plated at a concentration of $0.25 \times 10^6$ cells/mL in 12 well plates in supplemented media. After the cells were allowed to adhere (6-8 hours), media was changed to depleted media. After 24 hours, the depleted media was removed and fresh depleted media containing various concentrations of Compound A in triplicate was added to appropriate wells. After 8 hours, the media was changed to media without Compound A. After 16 hours, cell viability was determined by Trypan blue exclusion and MTS assay to determine the percent viability of various treatment concentrations of Compound A. Cells were cultured in TPA (5 ng/mL) to induce a pro-inflammatory response and release of IL-8. After 5 hours of incubation, supernatants were harvested and assayed by ELISA for the stimulated release of IL-8. Various concentrations of Compound A were added to tissue culture wells in triplicate 2 hours before addition of TPA as well as cells not exposed to TPA. Cell viability was determined by Trypan blue exclusion and MTS assay 16 hours after stimulation in a duplicate experiment where cells were washed and fresh media added without TPA or Compound A at the end of the stimulation period. IL-8 levels (pg/mL), obtained with Compound A using a TPA-induced inflammation model in NHEK cells are depicted in FIGS. 8A and 8B.

Example 84

Figure 9:
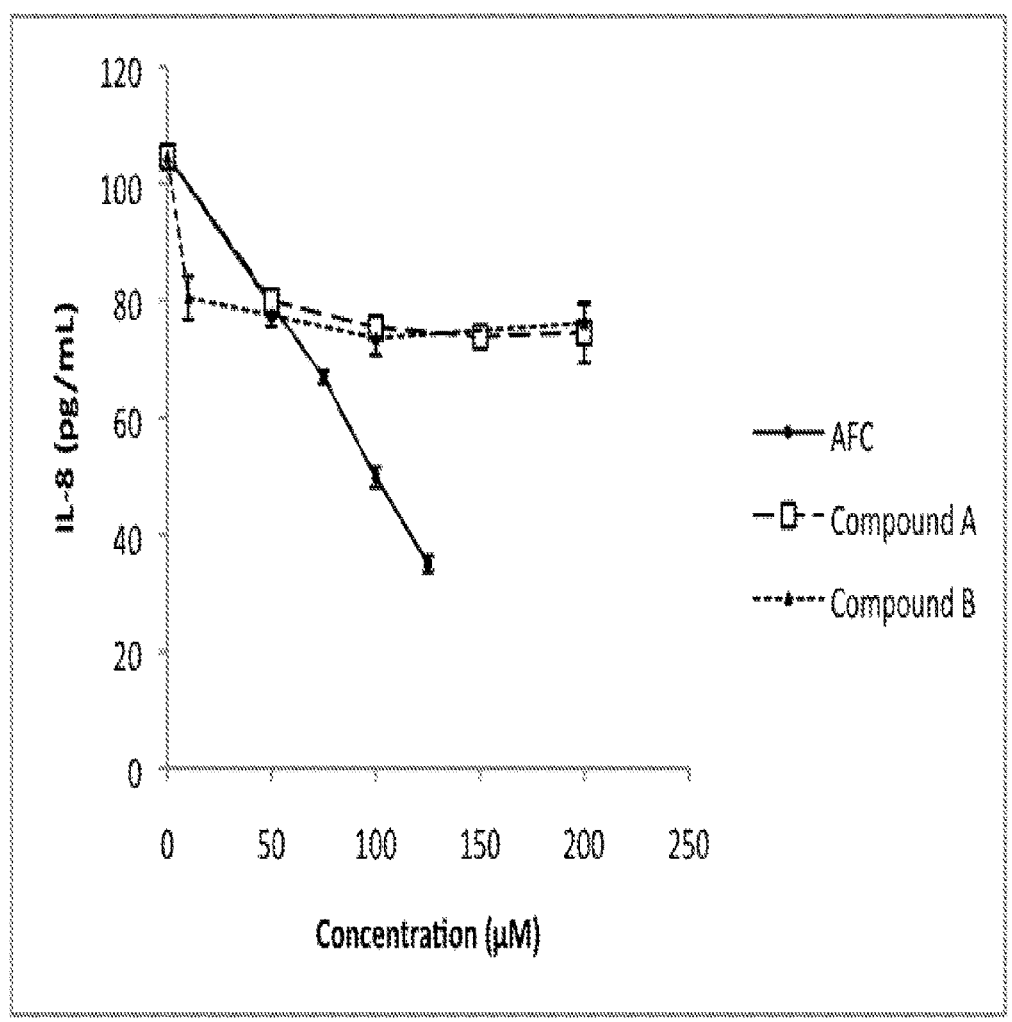
FIG. 9 is a graph depicting IL-8 levels (pg/mL) obtained for AFC, Compound A and Compound B, demonstrating a dose dependent inhibition of TNF-alpha induced IL-8 release, as determined using Human Umbilical Vein Endothelial cell (HUVEC) cultures.

TNFα-induced Inflammation Model in HUVEC Cells—Inhibition of TNFα-induced Cytokine Release TNF-α is a plieotropic cytokine with proinflammatory and immunomodulatory functions. The pathogenic role of TNF-α in inflammation is mediated through the interaction of TNF-α with TNF receptors that in turn result in induction of proinflammatory cytokines, such as TNF-α (itself), IL-8 and others. The present example demonstrates that certain isoprenyl compounds of the present invention exhibit anti-inflammatory activity, as evidenced by the reduction of proinflammatory cytokines such as IL-8, mediated through TNF receptor mediated signaling in human umbilical vein endothelial cells (HUVECs). HUVEC cells were cultured in endothelial growth medium-2 (EGM-2; Lonza; Walkersville, Md.), in a low serum environment (2% FBS), and supplemented with EGM-2 Bullet Kit (Lonza) at 37° C. with 5% $CO_2$. To avoid any possible modulating effects of these agents during agonist/antagonist treatments, cells were kept in EGM-2 supplemented without serum or growth factors (depleted medium). Cells were plated at a concentration of $1 \times 10^5$ cells/mL in 96-well plates in supplemented media. After the cells were allowed to adhere (6-8 hours), media will was changed to depleted media. Twenty-four hours later, media was removed and fresh depleted media containing various concentrations of AFC, Compound A and Compound B in triplicate was added to appropriate wells. After 30 minutes of pre-incubation, cells were stimulated with recombinant Human TNF-α ($1 \times 10^4$ U/mL; Millipore, Billerica, Mass.) to induce a pro-inflammatory response and release of IL-8. After 4 hours of incubation, supernatants were harvested and assayed by ELISA for the stimulated release of IL-8. Cell viability was determined by Trypan blue exclusion and MTS assay to determine the percent viability of various treatment concentrations of AFC, Compound A and Compound B. IL-8 levels (pg/mL), obtained with AFC, Compound A and Compound B using TNF-α-induced inflammation model in HUVEC cells are depicted in FIG. 9.

Example 85

Effects on Ovalbumin-challenged Flaky Tail Mouse Model for Atopic Dermatitis

The flaky tail mouse strain, carries a mutation in the gene for the epidermal protein filaggrin, comparable for the mutation underlying human atopic dermatitis or eczema, and is, therefore, a model for the disease (Fallon et al., Nat Genetics, 2009, 41: 602-608). Topically challenging these mice with ovalbumin results in a atopic dermatitis like condition, exhibiting eczema and increased skin levels of TH2 and the cytokines IL4, IL5 and IL10, usually appearing 4-5 weeks following ovalbumin application. Using this model, the present example demonstrates the effectiveness of isoprenyl compounds of the present invention in inhibiting and/or reducing the various end-points associated with atopic dermatitis. Exemplary end points include but are not limited to skin flakiness, skin levels of TH2 and other cytokines like IL4, IL5 and IL10. The protocol for cutaneous application of Ovalbumin to the intact skin of flaky tail mice has been described elsewhere (Fallon et al., *Nat Genetics,* 2009, 41: 602-608). In brief, the abdomens of 3-5 week ovalbumin-challenged ft/ft mice (6 animals per groups) are shaved 24 hours prior to cutaneous application and suspensions of Ovalbumin (50 µg in 50 µl PBS) are applied to the abdomen according to a strict regimen as described previously (Fallon et al., *Nat Genetics,* 2009, 41: 602-608). Two sets of experiments are conducted: in the first set, the mice are pretreated with the isoprenyl compounds of the present invention prior to and during the application of ovalbumin to study the effects of preventing and inhibiting the development of AD phenotype; and in the second set, the mice are treated with the isoprenyl compounds following 4-5 weeks of ovalbumin treatment when the phenotype appears to study the effects of the compounds in treating the symptoms. For each isoprenyl compound tested, the compound is applied at several concentrations in ethanol to study dose dependent effects. Following each experiment, mice are euthanized and 6-mm punch biopsy specimens from each abdomen are harvested, snap frozen in liquid nitrogen and stored in −80° C. until use. The abdominal skin specimens are homogenized with HTAB buffer using a Bio-Pulverizer (MP Biomedicals, 2×45 sec at 4 m/s). Samples are centrifuged at 10,000 rpm for 10 min at 4° C. Supernatants are subjected to cytokine profiling by ELISA for the levels of TH2, IL4, IL5, and IL10 using protein standards for quantification.

Described below are assays used to measure the biological activity of provided compounds, including the anti-psoriasis properties of the compounds, as measured by inhibition of T-helper lymphocyte infiltration determined using a psoriasis mouse model.

Example 86

K5.Stat3c Mouse Psoriasis Model—Inhibition of Helper-T-lymphocyte Infiltration

The spontaneous and injury induced appearance of plaques having the full psoriatic phenotype in a transgenic mouse constituitively expressing signal transducer and activator of transcription 3 (STAT3C) under regulation of the keratin-5 promoter in basal epidermal keratinocytes ("K5.Stat3c mice") has been recently reported (Sano et al. (2005). *Nat Med* 11(1): 43-9). In addition, the skin from these K5.Stat3c mice when allografted to immunodeficient nude mice do not develop plaques unless they are co-engrafted with activated T-cells, as occurs when human psoriatic skin when grafted to Severe Combined Immunodeficiency (SCID) mice (Wrone-Smith et al., *J Clin Invest,* 1996, 98: 1878-1887; Nickoloff et al., *Am J Pathol,* 1999, 155: 145-158), establishing the necessary interaction between the altered epidermis and the immune system. These CD3+T-helper cells play a critical role in the psoriatic pathogenesis by controlling infiltration of T-lymphocytes. The protocol for studying the CD3+ Helper-T expression using the K5.Stat3c psoriasis mouse model has been previously described (Sano et al., *Nat Med,* 2005, 11: 43-9).

Figure 10:
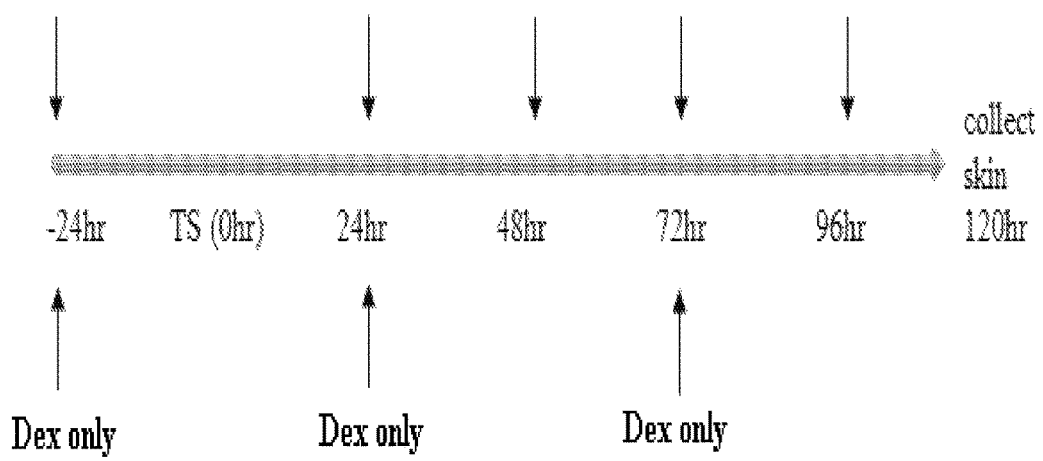
FIG. 10 is a treatment protocol for administering Compound B in a K5.Stat3c psoriasis mouse model.
Figure 11:
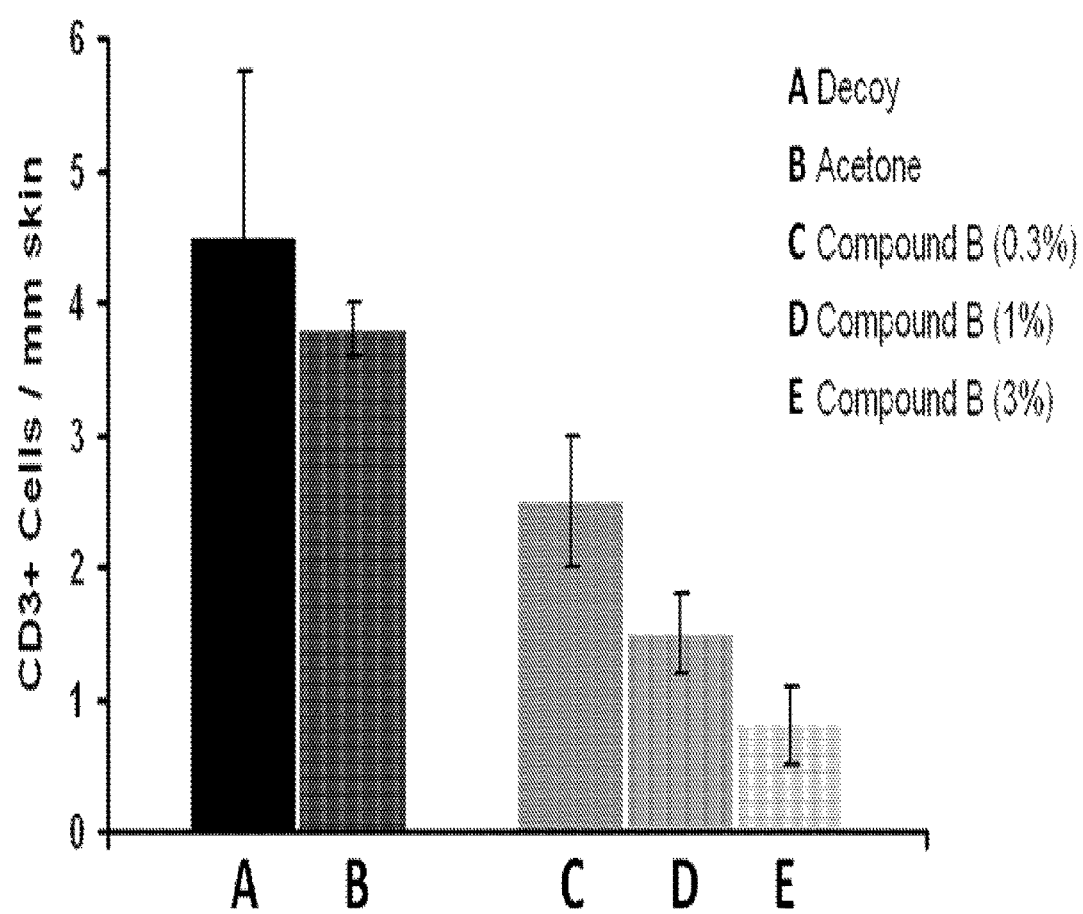
FIG. 11 is a bar graph depicting number of CD3+ cells/mm skin obtained with Compound B, demonstrating a dose dependent inhibition of number of CD3+(Helper-T-lymphocytes), as determined using a transgenic mouse model (K5.Stat3c) for psoriasis.

Using this model, the present invention demonstrates that certain isoprenyl compounds of the present invention, when topically applied, exhibits efficacy in treating psoriasis, as evidenced by the inhibition of T-helper cell infiltration in the K5.Stat3c psoriasis mouse model. Briefly, 5 mice per treatment group were used. Dorsal skin samples of 7-9 wk-old K5.Stat3c mice were shaved 48 hours prior to tape stripping. Mice were then anesthetized with Avertin and received 30 strokes of tape stripping. Compound B, dexamethasone (Dex, positive control) or acetone vehicle control was topically applied to shaved area at indicated times and doses as depicted in FIG. 10. Mice were injected with BrdU 30 minutes prior to sacrifice at day 5, and skin sections collected for histological assessment of dermal inflammatory infiltrates. The dose dependent inhibition in the number of CD3+T-helper cells, obtained with Compound B using the K5.Stat3c psoriasis mouse model are depicted in FIG. 11.

Described below are assays used to measure the biological activity of provided compounds, including the anti-inflammatory properties of the compounds, as measured by inhibition of ICMT.

Example 87

ICMT Inhibition

In the G-protein signaling pathways, for regulatory interactions to occur, many of the signal transduction proteins, including virtually all G-proteins, first must be modified by the post-translational addition of a $C_{15}$ farnesyl or a $C_{20}$ geranylgeranyl polyisoprenoid group in thioether linkage to a cysteine residue located at or near the carboxyl terminus within a so-called CAAX box or related cysteine-containing sequence. Carboxy-terminal polyisoprenoid cysteines that ultimately result from these modifications may be subject to methylesterifcation by a specific membrane associated S-adenosylmethionine-dependent isoprenyl-S-isoprenyl methyltransferase (ICMT). Compounds that can inhibit these enzymatic reactions or otherwise alter the interactions among polyisoprenylated signal transduction proteins, such as G-proteins and the protein regulatory targets with which they interact, or other intracellular signaling proteins, may be used to mitigate leukocyte responses and, theoretically, to treat inflammatory-related conditions. (See e.g., Volker, et al., *Methods Enzymol,* 1995, 250: 216-225).

The present example demonstrates that certain isoprenyl compounds of the present invention exhibit anti-inflammatory activity, as evidenced by the inhibition of the enzymatic activity of ICMT thereby modulating G-protein methylation.

Figure 12:
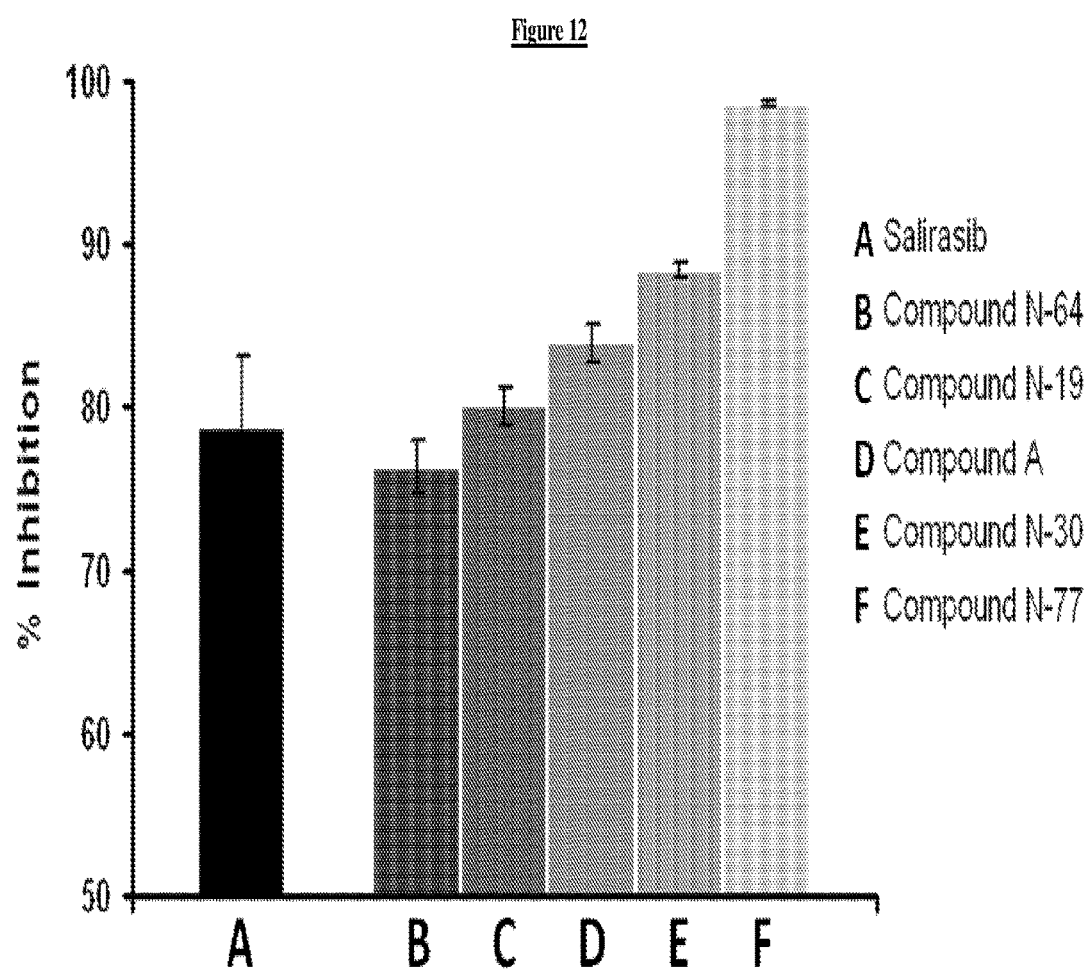
FIG. 12 is a bar graph depicting % inhibition of the G-protein methylating enzyme ICMT obtained for compound N-64, Compound N-19, Compound A, Compound N-30 and Compound N-77, as demonstrated by the % reduction of methylated acetyl-farnesyl-cysteine, an ICMT substrate.

Mouse brain extracts containing ICMT activity were prepared and % inhibition level of [$^3$H]-AFC methylation was determined by the heptane extraction method described previously (Volker et al., Methods, 1: 283-287). Briefly, reaction mixture containing: 5 µl of protein (brain extract~40 µg), 2 µl AFC, 2 µl of IPC analog, 36 µl buffer A, and 5 µl [$^3$H]-SAM (final concentration 10 µM) to a final volume of 50 µl, was mixed and samples vortexed for 15 sec and then incubated for 30 min at 37° C. Reaction was then quenched with 50 µl of 20% Tween20 (vortex for 10 sec). Next 500 µl of heptane was added, the reaction mixture was then vortexed for 10 sec and subsequently spun at 13,000 rpm for 5 min. Next, 250 µl of the top layer was removed and placed in an open-top 1.5 µl centrifuge tube. The open-top tubes were then spun for 30 min in a vacuum centrifuge (Speed Vac Concentrator "Savant RH 4011") to evaporate heptane. The tubes were then placed in 5 mL scintillation vials (containing 3 mL of scintillation fluid (Ecoscint, National Diagnostics). 200 µl of 1 M NaOH were added to each tube to hydrolyze the base-labile AFCME and are immediately covered. The samples were allowed to equilibrate overnight at 37° C., and then the levels of [$^3$H]-MeOH that partitions into the cocktail, were quantified, by liquid scintillation spectrometry (Beckman LS 6500). Percent reduction of ICMT substrate, methylated acetl-farnesylcysteine, obtained with compound N-64, compound N-19, compound A, compound N-30 and compound N-77 are depicted in FIG. 12.

Described below are assays used to measure the biological activity of provided compounds, including the antioxidant properties of the compounds, as measured by inhibition of oxidative burst from neutrophils, as determined by reduction of superoxide formation.

Example 88

Inhibition of Oxidative Burst from Neutrophils

Oxidative stresses caused by environmental insults such as ultraviolet ("UV") rays from the sun, cigarette smoke exposure, consumption of foods with high saturated fat and environmental pollutants as well as the natural process of aging, contributing to the generation of free radicals and reactive oxygen species ("ROS"), stimulate inflammatory responses, especially in the skin (Pilla et al., Intl J Cosm Sci, 2005, 27: 17-34). High levels of ROS contribute to adverse effects on the skin including erythema, edema, photoaging and skin cancer (Trouba et al. Antioxid. Redox Signal 2002 v4 p665-6'73). Neutrophil infiltration during inflammatory responses is associated with increased oxygen consumption and generation of ROS. Extracellular inflammatory agonists such as fMLP bind to GPCRs such as formyl peptide receptors ("FPR") to trigger the oxidative burst response (i.e., the rapid rapid release of ROS). Such oxidative burst responses from neutrophils are also associated with irritable bowel syndrome, including ulcerative colitis (Keshavarzian et al., J Lab Clin Med, 1997, 130: 216-225).

The present invention demonstrates that certain isoprenyl compounds of the present invention exhibit anti-oxidant and anti-inflammatory activities, as evidenced by the inhibition of fMLP-induced GPCR-mediated release of ROS.

Figure 13:
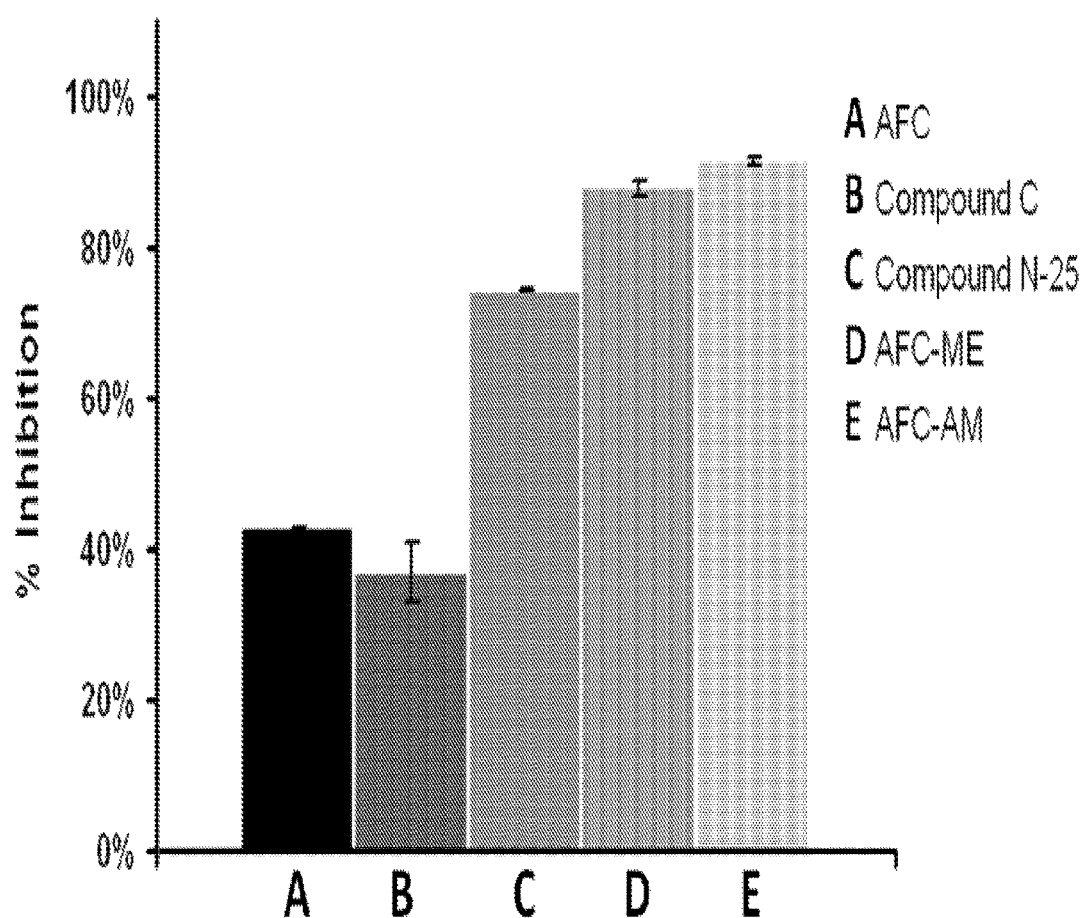
FIG. 13 is a bar graph depicting % inhibition of oxidative burst from neutrophils obtained for AFC, Compound C, Compound N-25, AFC-methyl ester (AFC-ME) and AFC-AcetoxylMethane (AFC-AM), as demonstrated by % reduction of superoxide formation.

The superoxide release assay is based on published protocols (Goldstein et al., J Clin Invest, 1975, 56: 1155-63). Briefly, cells were pre-incubated for 10 min at 37° C. with a mixture of cytochrome c (75 µM final concentration), cytochalasin B (5 µg/mL) with or without SOD (10 µg/mL) and with or without compounds (ranging from 0 to 100 µM). To initiate $O_2^-$ release, fMLP (0.2 µM) was added the cells are incubated for 10 min at 37° C. Samples were then placed on ice for 5 min and subsequently centrifuged at 3,000 rpm at 4° C. The supernatant was then analyzed by spectrophotometric measurement at 550 and 556.5 nm. Percent reduction of superoxide formation, obtained with AFC, compound C, compound N-25, AFC-methyl ester (AFC-ME) and AFC-AcetoxylMethane (AFC-AM) are depicted in FIG. 13.

EQUIVALENTS

Those skilled in the art will recognize, or be able to ascertain using no more than routine experimentation, that while the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any targeting moiety, any disease, disorder, and/or condition, any linking agent, any method of administration, any therapeutic application, etc.) can be excluded from any one or more claims, for any reason, whether or not related to the existence of prior art.

Publications discussed above and throughout the text are provided solely for their disclosure prior to the filing date of the present application. Nothing herein is to be construed as an admission that the inventors are not entitled to antedate such disclosure by virtue of prior disclosure.

We claim:

1. A method of treating a disease or condition in a subject, comprising administering to said subject the compound 4-(1-carboxy-2-((2E,6E)-3,7,11-trimethyldodeca-2.6.10-trienylthio)ethylamino)-4-oxobutanoic acid having the formula

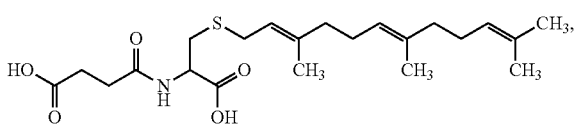 [SMILES: CC(C)=CCC/C(C)=C/CC/C(C)=C/CSCC(NC(=O)CCC(=O)O)C(=O)O]

or a pharmaceutically acceptable salt thereof, wherein said disease or condition is an inflammatory skin disease or condition.

2. The method according to claim 1, wherein said compound is a pharmaceutically acceptable salt of 4-(1-carboxy-2-((2E,6E)-3,7,11-trimethyldodeca-2,6,10-trienylthio)ethylamino)-4-oxobutanoic acid.

3. The method according to claim 2, wherein said pharmaceutically acceptable salt of 4-(1-carboxy-2-((2E,6E)-3,7,11-trimethyldodeca-2,6,10-trienylthio)ethylamino)-4-oxobutanoic acid is an alkali or alkaline earth salt.

4. The method according to claim 3, wherein said pharmaceutically acceptable salt is selected from the group consisting of sodium, lithium, potassium, calcium and magnesium salt.

5. The method according to claim 4, wherein said pharmaceutically acceptable salt is the sodium salt.

6. The method according to claim 1, wherein said compound is 4-((R)- 1-carboxy-2-((2E,6E)-3,7,11-trimethyldodeca-2,6,10-trienylthio)ethylamino)-4-oxobutanoic acid having the formula

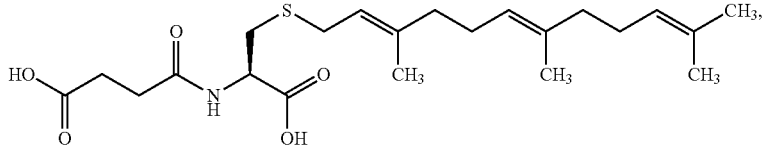 [SMILES: CC(C)=CCC/C(C)=C/CC/C(C)=C/CSC[C@H](NC(=O)CCC(=O)O)C(=O)O]

or a pharmaceutically acceptable salt thereof.

7. The method according to claim 2, wherein said pharmaceutically acceptable salt of 4-(1-carboxy-2-((2E,6E)-3,7,11-trimethyldodeca-2,6,10-trienylthio)ethylamino)-4-oxobutanoic acid is administered to said subject in the form of a pharmaceutical composition.

8. The method according to claim 7, wherein said pharmaceutically acceptable salt of 4-(1-carboxy-2-((2E,6E)-3,7,11-trimethyldodeca-2,6,10-trienylthio)ethylamino)-4-oxobutanoic acid comprising said pharmaceutical composition comprises at least 80% ee of a pharmaceutically acceptable salt of 4-((R)-1-carboxy-2-((2E,6E)-3,7,11-trimethyldodeca-2,6,10-trienylthio)ethylamino)-4-oxobutanoic acid.

9. The method according to claim 8, wherein said pharmaceutically acceptable salt of 4-(1-carboxy-2-((2E,6E)-3,7,11-trimethyldodeca-2,6,10-trienylthio)ethylamino)-4-oxobutanoic acid comprising said pharmaceutical composition comprises at least 85% ee of a pharmaceutically acceptable salt of 4-((R)-1-carboxy-2-((2E,6E)-3,7,11-trimethyldodeca-2,6,10-trienylthio)ethylamino)-4-oxobutanoic acid.

10. The method according to claim 9, wherein said pharmaceutically acceptable salt of 4-(1-carboxy-2-((2E,6E)-3,7,11-trimethyldodeca-2,6,10-trienylthio)ethylamino)-4-oxobutanoic acid comprising said pharmaceutical composition comprises at least 90% ee of a pharmaceutically acceptable salt of 4-((R)-1-carboxy-2-((2E,6E)-3,7,11-trimethyldodeca-2,6,10-trienylthio)ethylamino)-4-oxobutanoic acid.

11. The method according to claim 10, wherein said pharmaceutically acceptable salt of 4-(1-carboxy-2-((2E,6E)-3,7,11-trimethyldodeca-2,6,10-trienylthio)ethylamino)-4-oxobutanoic acid comprising said pharmaceutical composition comprises at least 95% ee of a pharmaceutically acceptable salt of 4-((R)-1-carboxy-2-((2E,6E)-3,7,11-trimethyldodeca-2,6,10-trienylthio)ethylamino)-4-oxobutanoic acid.

12. The method according to claim 11, wherein said pharmaceutically acceptable salt of 4-(1-carboxy-2-((2E,6E)-3,7,11-trimethyldodeca-2,6,10-trienylthio)ethylamino)-4-oxobutanoic acid comprising said pharmaceutical composition comprises at least 97.5% ee of a pharmaceutically acceptable salt of 4-((R)-1-carboxy-2-((2E,6E)-3,7,11-trimethyldodeca-2,6,10-trienylthio)ethylamino)-4-oxobutanoic acid.

13. The method according to claim 7, wherein said pharmaceutical composition is administered to said subject by oral, parenteral, urethral, vaginal, nasal, topical, pulmonary, deep lung, inhalation, buccal, or sublingual administration.

14. The method according to claim 13, wherein said pharmaceutical composition is administered to said subject by oral, parenteral, or topical administration.

15. The method according to claim 13, wherein said pharmaceutical composition is administered to said subject by topical administration.

16. The method according to claim 1, wherein said disease or condition is an inflammatory skin condition.

17. The method according to claim 16, wherein said inflammatory skin condition is selected from rosacea, psoriasis, atopic dermatitis, and seborrhic dermatitis.

18. The method according to claim 2, wherein said disease or condition is an inflammatory skin condition.

19. The method according to claim 18, wherein said inflammatory skin condition is selected from rosacea, psoriasis, atopic dermatitis, and seborrhic dermatitis.

20. The method according to claim 19, wherein said inflammatory skin condition is rosacea.

21. The method according to claim 19, wherein said inflammatory skin condition is psoriasis.

22. The method according to claim 19, wherein said inflammatory skin condition is atopic dermatitis.

23. The method according to claim 19, wherein said inflammatory skin condition is seborrhic dermatitis.

24. The method according to claim 1, wherein said 4-(1-carboxy-2-((2E,6E)-3,7,11-trimethyldodeca-2,6,10-trienylthio)ethylamino)-4-oxobutanoic acid, or a pharmaceutically acceptable salt thereof, is administered to said subject in an amount from about 0.001 mg to about 100 mg per kilogram of subject weight per day.

25. The method according to claim 1, wherein said pharmaceutically acceptable salt of 4-(1-carboxy-2-((2E,6E)-3,7,11-trimethyldodeca-2,6,10-trienylthio)ethylamino)-4-oxobutanoic acid is administered to said subject in an amount from about 0.001 mg to about 100 mg per kilogram of subject weight per day.

26. A method of treating a skin disease or condition in a subject, comprising administering to said subject a pharmaceutical composition comprising the sodium salt of the compound 4-(1-carboxy-2-((2E,6E)-3,7,11-trimethyldodeca-2,6,10-trienylthio)ethylamino)-4-oxobutanoic acid having the formula

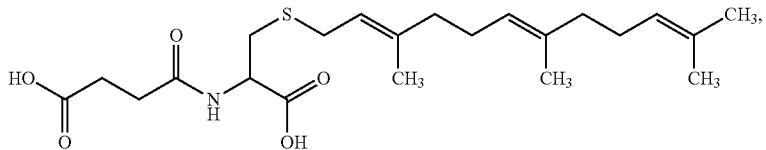 [SMILES: CC(C)=CCC/C(C)=C/CC/C(C)=C/CSCC(NC(=O)CCC(=O)O)C(=O)O]

wherein said disease or condition is an inflammatory skin disease or condition.

27. The method according to claim 26, wherein said pharmaceutical composition comprises the sodium salt of the compound 4-((R)-1-carboxy-2-((2E,6E)-3,7,11-trimethyldodeca-2,6,10-trienylthio)ethylamino)-4-oxobutanoic acid having the formula

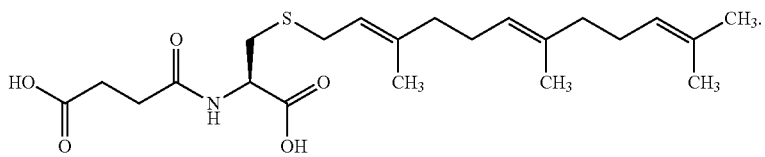 [SMILES: CC(C)=CCC/C(C)=C/CC/C(C)=C/CSC[C@H](NC(=O)CCC(=O)O)C(=O)O]

28. The method according to claim 26, wherein said sodium salt of 4-(1-carboxy-2-((2E,6E)-3,7,11-trimethyldodeca-2,6,10-trienylthio)ethylamino)-4-oxobutanoic acid comprising said pharmaceutical composition comprises at least 80% ee of the sodium salt of 4-((R)-1-carboxy-2-((2E,6E)-3,7,11-trimethyldodeca-2,6,10-trienylthio)ethylamino)-4-oxobutanoic acid.

29. The method according to claim 28, wherein said sodium salt of 4-(1-carboxy-2-((2E,6E)-3,7,11-trimethyldodeca-2,6,10-trienylthio)ethylamino)-4-oxobutanoic acid comprising said pharmaceutical composition comprises at least 85% ee of the sodium salt of 4-((R)-1-carboxy-2-((2E,6E)-3,7,11-trimethyldodeca-2,6,10-trienylthio)ethylamino)-4-oxobutanoic acid.

30. The method according to claim 29, wherein said sodium salt of 4-(1-carboxy-2-((2E,6E)-3,7,11-trimethyldodeca-2,6,10-trienylthio)ethylamino)-4-oxobutanoic acid comprising said pharmaceutical composition comprises at least 90% ee of the sodium salt of 4-((R)-1-carboxy-2-((2E,6E)-3,7,11-trimethyldodeca-2,6,10-trienylthio)ethylamino)-4-oxobutanoic acid.

31. The method according to claim 30, wherein said sodium salt of 4-(1-carboxy-2-((2E,6E)-3,7,11-trimethyldodeca-2,6,10-trienylthio)ethylamino)-4-oxobutanoic acid comprising said pharmaceutical composition comprises at least 95% ee of the sodium salt of 4-((R)-1-carboxy-2-((2E,6E)-3,7,11-trimethyldodeca-2,6,10-trienylthio)ethylamino)-4-oxobutanoic acid.

32. The method according to claim 31, wherein said sodium salt of 4-(1-carboxy-2-((2E,6E)-3,7,11-trimethyldodeca-2,6,10-trienylthio)ethylamino)-4-oxobutanoic acid comprising said pharmaceutical composition comprises at least 97.5% ee of the sodium salt of 4-((R)- 1-carboxy-2-((2E,6E)-3,7,11-trimethyldodeca-2,6,10-trienylthio)ethylamino)-4-oxobutanoic acid.

33. The method according to claim 26, wherein said disease or condition is an inflammatory skin condition.

34. The method according to claim 33, wherein said inflammatory skin condition is selected from rosacea, psoriasis, atopic dermatitis, and seborrhic dermatitis.

35. The method according to claim 34, wherein said inflammatory skin condition is rosacea.

36. The method according to claim 34, wherein said inflammatory skin condition is psoriasis.

37. The method according to claim 34, wherein said inflammatory skin condition is atopic dermatitis.

38. The method according to claim 34, wherein said inflammatory skin condition is seborrhic dermatitis.

39. The method according to claim 27, wherein said disease or condition is an inflammatory skin condition.

40. The method according to claim 39, wherein said inflammatory skin condition is selected from rosacea, psoriasis, atopic dermatitis, and seborrhic dermatitis.

41. The method according to claim 40, wherein said inflammatory skin condition is rosacea.

42. The method according to claim 40, wherein said inflammatory skin condition is psoriasis.

43. The method according to claim 40, wherein said inflammatory skin condition is atopic dermatitis.

44. The method according to claim 40, wherein said inflammatory skin condition is seborrhic dermatitis.

45. The method according to claim 33, wherein said pharmaceutical composition is administered to said subject by oral, parenteral, or topical administration.

46. The method according to claim 45, wherein said pharmaceutical composition is administered to said subject by topical administration.

47. The method according to claim 39, wherein said pharmaceutical composition is administered to said subject by oral, parenteral, or topical administration.

48. The method according to claim 47, wherein said pharmaceutical composition is administered to said subject by topical administration.

49. The method according to claim 26, wherein (a) said sodium salt of 4-(1-carboxy-2-((2E,6E)-3,7,11-trimethyldodeca-2,6,10-trienylthio)ethylamino)-4-oxobutanoic acid comprising said pharmaceutical composition comprises at least 95% ee of the sodium salt of 4-((R)-1-carboxy-2-((2E, 6E)-3,7,11-trimethyldodeca-2,6,10-trienylthio)ethylamino)-4-oxobutanoic acid, and (b) said pharmaceutical composition is administered to said subject by topical administration.

50. The method according to claim 49, wherein said inflammatory skin condition is selected from rosacea, psoriasis, atopic dermatitis, and seborrhic dermatitis.

51. The method according to claim 50, wherein said inflammatory skin condition is rosacea.

52. The method according to claim 50, wherein said inflammatory skin condition is psoriasis.

53. The method according to claim 50, wherein said inflammatory skin condition is atopic dermatitis.

54. The method according to claim 50, wherein said inflammatory skin condition is seborrhic dermatitis.

55. The method according to claim 26, wherein (a) said sodium salt of 4-(1-carboxy-2-((2E,6E)-3,7,11-trimethyldodeca-2,6,10-trienylthio)ethylamino)-4-oxobutanoic acid comprising said pharmaceutical composition comprises at least 97.5% ee of the sodium salt of 4-((R)-1-carboxy-2-((2E,6E)-3,7,11-trimethyldodeca-2,6,10-trienylthio)ethylamino)-4-oxobutanoic acid, and (b) said pharmaceutical composition is administered to said subject by topical administration.

56. The method according to claim 55, wherein said inflammatory skin condition is selected from rosacea, psoriasis, atopic dermatitis, and seborrhic dermatitis.

57. The method according to claim 56, wherein said inflammatory skin condition is rosacea.

58. The method according to claim 56, wherein said inflammatory skin condition is psoriasis.

59. The method according to claim 56, wherein said inflammatory skin condition is atopic dermatitis.

60. The method according to claim 56, wherein said inflammatory skin condition is seborrhic dermatitis.

* * * * *